US006852835B2

(12) United States Patent
Collmer et al.

(10) Patent No.: US 6,852,835 B2
(45) Date of Patent: Feb. 8, 2005

(54) **DNA MOLECULES AND POLYPEPTIDES OF *PSEUDOMONAS SYRINGAE* HRP PATHOGENICITY ISLAND AND THEIR USES**

(76) Inventors: Alan Collmer, 139 Lexington Dr., Ithaca, NY (US) 14850; James R. Alfano, 2407 S. 39$^{th}$ St., Lincoln, NE (US) 68506; Amy O. Charkowski, 4235 Montgomery St., Apt. E, Oakland, CA (US) 94611

( * ) Notice: Subject to any disclaimer, the term of this patent is extended or adjusted under 35 U.S.C. 154(b) by 214 days.

(21) Appl. No.: 09/825,414

(22) Filed: Apr. 3, 2001

(65) Prior Publication Data

US 2002/0083489 A1 Jun. 27, 2002

Related U.S. Application Data

(60) Provisional application No. 60/194,160, filed on Apr. 3, 2000, provisional application No. 60/224,604, filed on Aug. 11, 2000, and provisional application No. 60/249,548, filed on Nov. 17, 2000.

(51) Int. Cl.$^{7}$ .......... C07K 14/21
(52) U.S. Cl. .......... 530/350; 514/12
(58) Field of Search .......... 530/350

(56) References Cited

U.S. PATENT DOCUMENTS

| | | | | |
|---|---|---|---|---|
| 5,939,601 A | * | 8/1999 | Klessig et al. | 800/279 |
| 6,066,451 A | * | 5/2000 | Avraham et al. | 435/6 |
| 6,342,654 B1 | | 1/2002 | Li et al. | |

FOREIGN PATENT DOCUMENTS

| | | |
|---|---|---|
| WO | WO 98/32844 | 7/1998 |

OTHER PUBLICATIONS

Charkowski et al. Phytopathology 87 (6 Suppl.): pS17 (1997).*

Yuan et al. J. Bacteriology, V178, No 21, p. 6399–6402 (1996).*

Charkowski et al. Phytopathology 87 (6 Suppl.): pS17 (1997).*

Yuan et al. J. Bacteriology, V178, No 21, p. 6399–6402 (1996).*

Alfano et al., *Pseudomonas syringae* Hrp Pathogenicity Island has a Tripartite Mosaic Structure Composed of a Cluster of Type III Secretion Genes Bounded by Exchangeable Effector and Conserved Effector Loci that Contribute to Parasitic Fitness and Pathogenicity in Plants, *PNAS* 97(9):4856–4861 (2000).

Charkowski et al., The *Pseudomonas syringae* pv. Tomato HrpW Protein has Domains Similar to Harpins and Pectate Lyases and Can Elicit the Plant Hypersensitive Response and Bind to Pectate, *Journal of Bacteriology* 180(19):5211–5217 (1998).

Preston et al., "The HrpZ Proteins of *Pseudomonas syringae* pvs. *syringae, glycinea*, and *tomato* Are Encoded by An Operon Containing *Yersinia ysc* Homologs and Elicit the Hypersensitive Response in Tomato but Not Soybean," *MPMI* 8(5):717–732 (1995).

Collmer et al., "*Pseudomonas syringae* Hrp Type III Secretion System and Effector Proteins," *PNAS* 97(16):8770–8777 (2000).

Alfano et al., "Evidence That the *Pseudomonas syringae* pv. *Syringae hrp*–Linked *hrmA* Gene Encodes an Avr–Like Protein that Acts in an *hrp*–Dependent Manner Within Tobacco Cells," *MPMI* 10(5):580–588 (1997).

Heu et al., Nucleotide Sequence and Properties of the *hrm*A Locus Associated with the *Pseudomonas syringae* pv. *syringae* 61 *hrp* Gene Cluster, *MPMI* 6(5) 553–564 (1993).

Huang et al., "Characterization of the *hrp* Cluster from *Pseudomonas syringae* pv. *syringae* 61 and Tn*phoA* Tagging of Genes Encoding Exported or Membrane–Spanning Hrp Proteins," *Molecular Plant–Microbe Interactions* 4(5):469–476 (1991).

Shen et al., "Conversion of Compatible Plant–Pathogen Interactions into Incompatible Interactions by Expression of the *Pseudomonas syringae* pv. *syringae* 61 *hrmA* Gene in Transgenic Tobacco Plants," *The Plant Journal* 23(2):205–213 (2000).

van Dijk et al., "The Avr (Effector) Proteins HrmA (HopPsyA) and AvrPto Are Secreted in Culture from *Pseudomonas syringae* Pathovars Via the Hrp (Type III) Protein Secretion System in a Temperature–and pH–Sensitive Manner," *Journal of Bacteriology* 181(16):4790–4797 (1999).

van Dijk et al., "The ShcA Protein is a Molecular Chaperone that Assists in the Secretion of the HopPsyA Effector from the Type III (Hrp) Protein Secretion System of *Pseudomonas syringae*," *Molecular Microbiology* 44(6):1469–1481 (2002).

Alfano et al., "The Type III (Hrp) Secretion Pathway of Plant Pathogenic Bacteria: Trafficking Harpins, Avr Proteins, and Death," *Journal of Bacteriology*, 179(18): 5655–5662 (1997).

(List continued on next page.)

*Primary Examiner*—Robert A. Wax
(74) *Attorney, Agent, or Firm*—Nixon Peabody LLP

(57) ABSTRACT

One aspect of the present invention relates to isolated nucleic acid molecules (i) encoding proteins or polypeptides of *Pseudomonas* CEL and EEL genomic regions, (ii) nucleic acid molecules which hybridize thereto under stringent conditions, or (iii) nucleic acid molecules that include a nucleotide sequence which is complementary to the nucleic acid molecules of (i) and (ii). Expression vectors, host cells, and transgenic plants which include the DNA molecules of the present invention are also disclosed. Another aspect relates to the isolated proteins or polypeptides and compositions containing the same. The nucleic acid molecules and proteins of the present invention can be used to imparting disease resistance to a plant, making a plant hypersusceptible to colonization by nonpathogenic bacteria, causing eukaryotic cell death, and treating cancerous conditions.

11 Claims, 11 Drawing Sheets

OTHER PUBLICATIONS

Bogdanovec et al., "Homology and Functional Similiarity of an hrp–linked Pathogenicity locus, *dspEF*, of *Erwinia amylovoa* and the Avirulence Locus *avrE* of *Pseudomonas syringae* Pathovar Tomato," *Proc. Natl. Acad. Sci.*, 95:1325–1330 (1998).

He et al., "Pseudomonas Syringae pv. Syringae Harpin$_{ss.}$ A Protein That is Secreted via the Hrp Pathway and Elicitis the Hypersensitive Response in Plants," *Cell*, 73:1255–1266 (1993).

Leach et al., "Bacterial Avirulence Genes," *Annu. Rev. of Phytopathol.*, 34:153–179.

Rommens et al., "Intergeneric Transfer anf Functional Expression of the Tomato Disease Resistance Gene *Pto,"* *The Plant Cell*, 7:1537–1544 (1995).

EMBL Accession No. U97505 (1998).

* cited by examiner

Figures 2A-C

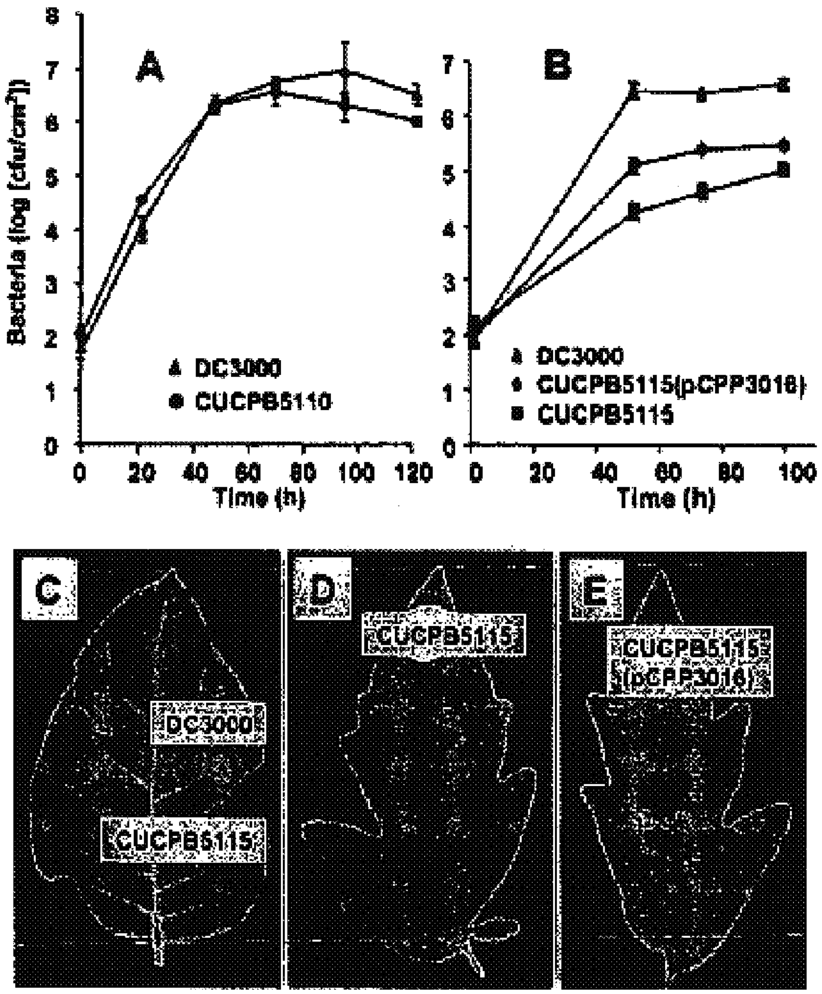
Figures 4A-E
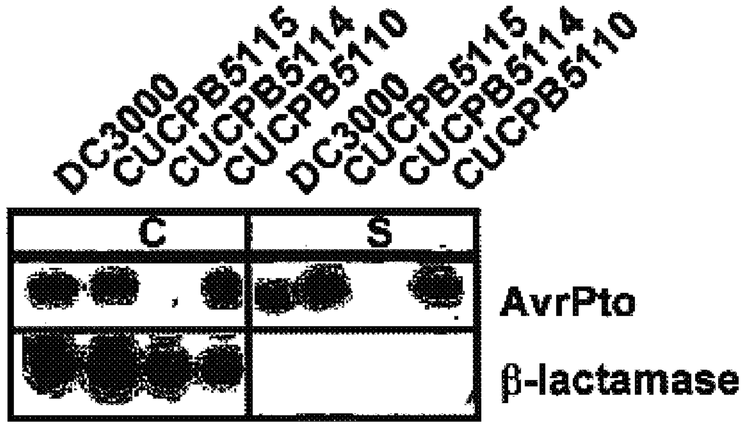
Figure 5

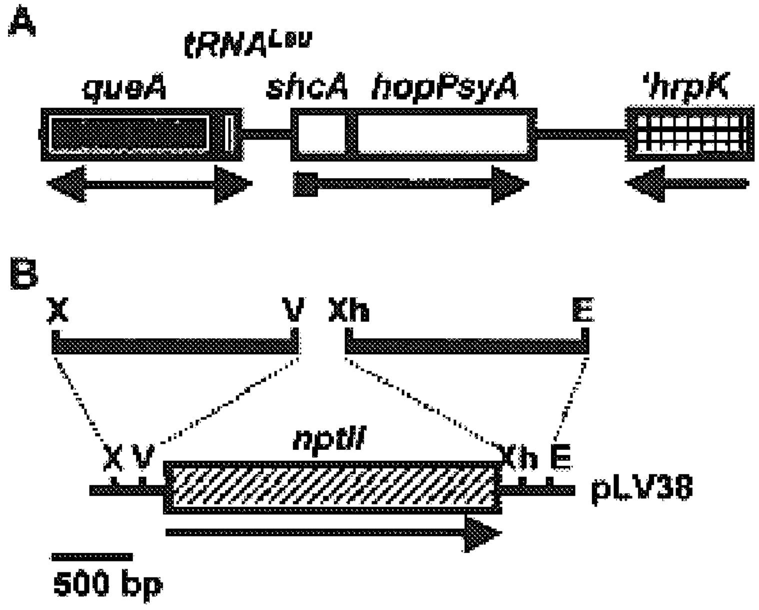
Figures 6A-B
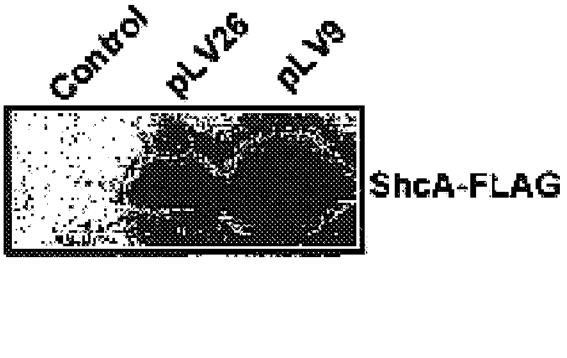
Figure 7

A
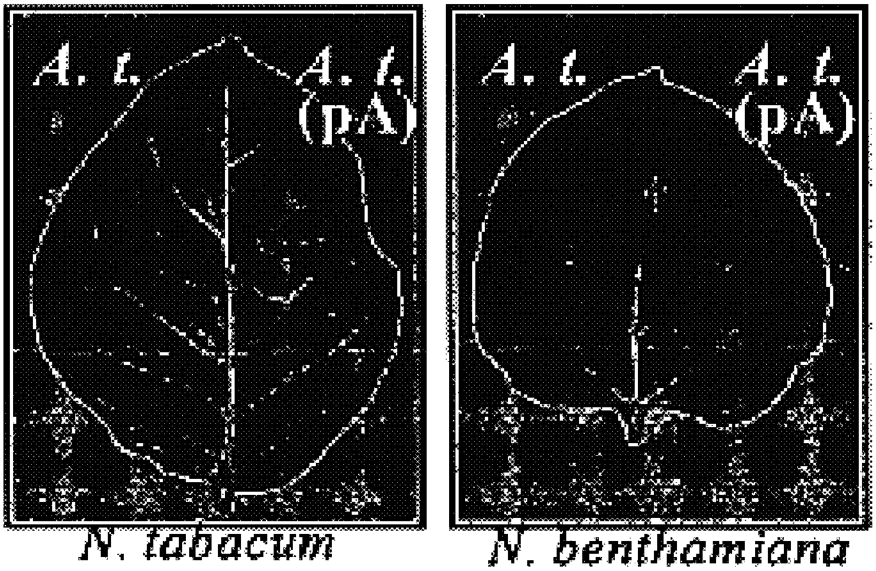
*N. tabacum* cv. Xanthi *N. benthamiana*
B
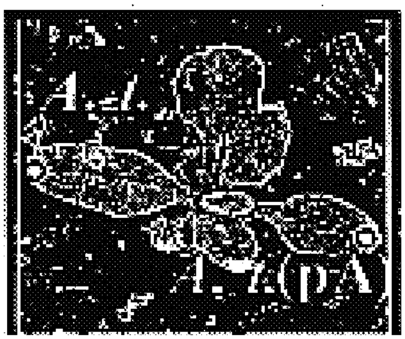
Figures 13A-B

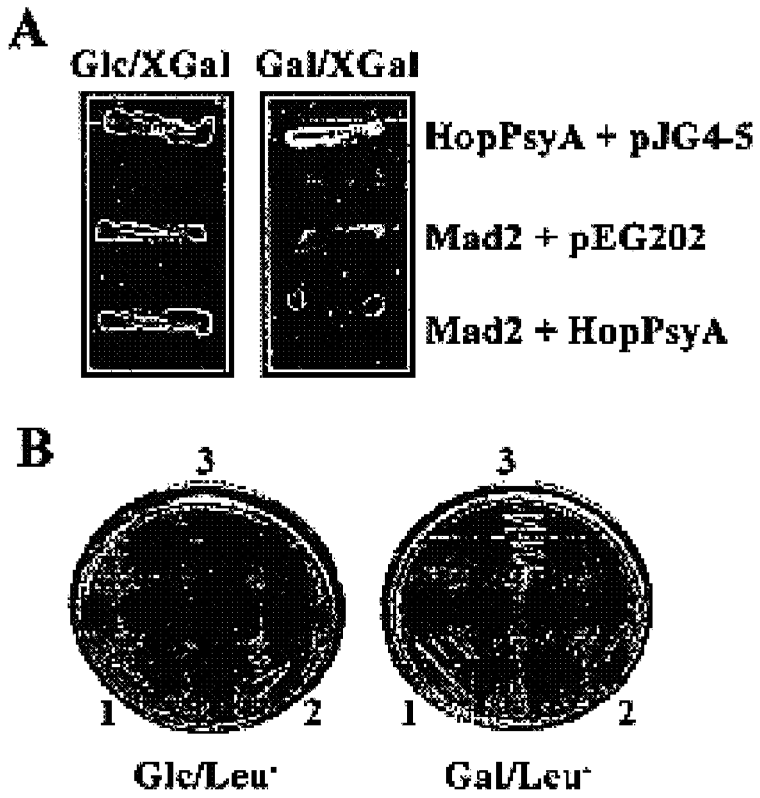
Figures 16A-B

DNA MOLECULES AND POLYPEPTIDES OF *PSEUDOMONAS SYRINGAE* HRP PATHOGENICITY ISLAND AND THEIR USES

This application claims benefit of U.S. Provisional Patent Application Ser. Nos. 60/194,160, filed Apr. 3, 2000, 60/224,604, filed Aug. 11, 2000, and 60/249,548, filed Nov. 17, 2000, which are hereby incorporated by reference in their entirety.

This work was supported by National Science Foundation Grant No. MCB-9631530 and National Research Initiative Competitive Grants Program, U.S. Department of Agriculture, Grant No. 98-35303-4488. The U.S. Government may have certain rights in this invention.

FIELD OF THE INVENTION

The present invention relates to isolated DNA molecules corresponding to the open reading frames in the conserved effector loci and exchangeable effector loci of the *Pseudomonas syringae*, the isolated proteins encoded thereby, and their various uses.

BACKGROUND OF THE INVENTION

The plant pathogenic bacterium *Pseudomonas syringae* is noted for its diverse and host-specific interactions with plants (Hirano and Upper, 1990). A specific strain may be assigned to one of at least 40 pathovars based on its host range among different plant species and then further assigned to a race based on differential interactions among cultivars of the host. In host plants the bacteria typically grow to high population levels in leaf intercellular spaces and then produce necrotic lesions. In nonhost plants or in host plants with race-specific resistance, the bacteria elicit the hypersensitive response (HR), a rapid, defense-associated programmed death of plant cells in contact with the pathogen (Alfano and Collmer, 1997). The ability to produce either of these reactions in plants appears to be directed by hrp (HR and pathogenicity) and hrc (HR and conserved) genes that encode a type III protein secretion pathway and by avr (avirulence) and hop (Hrp-dependent outer protein) genes that encode effector proteins injected into plant cells by the pathway (Alfano and Collmer, 1997). These effectors may also betray the parasite to the HR-triggering R-gene surveillance system of potential hosts (hence the avr designation), and plant breeding for resistance based on such gene-for-gene (avr-R) interactions may produce complex combinations of races and differential cultivars (Keen, 1990). hrp/hrc genes are probably universal among necrosis-causing gram-negative plant pathogens, and they have been sequenced in *P. syringae* pv. *syringae* (Psy) 61, *Erwinia amylovora* Ea321, *Xanthomonas campestris* pv. *vesicatoria* (Xcv) 85-10, and *Ralstonia solanacearum* GMI1000 (Alfano and Collmer, 1997). Based on their distinct gene arrangements and regulatory components, the hrp/hrc gene clusters of these four bacteria can be divided into two groups: I (*Pseudomonas* and *Erwinia*) and II (*Xanthomonas* and *Ralstonia*). The discrepancy between the distribution of these groups and the phylogeny of the bacteria provides some evidence that hrp/hrc gene clusters have been horizontally acquired and, therefore, may represent pathogenicity islands (Pais) (Alfano and Collmer, 1997).

Pais have been defined as gene clusters that (i) include many virulence genes, (ii) are selectively present in pathogenic strains, (iii) have different G+C content compared to host bacteria DNA, (iv) occupy large chromosomal regions, (v) are often flanked by direct repeats, (vi) are bordered by tRNA genes and/or cryptic mobile genetic elements, and (vii) are unstable (Hacker et al., 1997). Some Pais have inserted into different genomic locations in the same species (Wieler et al., 1997). Others reveal a mosaic structure indicative of multiple horizontal acquisitions (Hensel et al., 1999). Genes encoding type III secretion systems are present in Pais in animal pathogenic *Salmonella* spp. and *Pseudomonas aeruginosa* and on large plasmids in *Yersinia* and *Shigella* spp. Genes encoding effectors secreted by the pathway in these organisms are commonly linked to the pathway genes (Hueck, 1998), although a noteworthy exception is sopE, which is carried by a temperate phage without apparent linkage to SPI1 in certain isolates of *S. typhimurium* (Mirold et al., 1999). Three avr/hop genes have already been shown to be linked to the hrp/hrc cluster in *P. syringae*: avrE and several other Hrp-regulated transcriptional units are linked to the hrpR border of the hrp cluster in *P. syringae* pv *tomato* (Pto) DC3000 (Lorang and Keen, 1995); avrPphE is adjacent to hrpY (hrpK) in *Pseudomonas phaseolicola* (Pph) 1302A (Mansfield et al., 1994); and hopPsyA (hrmA) is adjacent to hrpK in Psy 61 (Heu and Hutcheson, 1993). Other *Pseudomonas* avr genes are located elsewhere in the genome or on plasmids (Leach and White, 1996), including a plasmid-borne group of avr genes described as a Pai in Pph 1449B (Jackson et al., 1999).

Because Avr, Hop, Hrp, and Hrc proteins represent promising therapeutic treatments in both plants and animals, it would be desirable to identify other proteins encoded by the Pai's in pathogenic bacteria and identify uses for those proteins.

The present invention overcomes these deficiencies in the art.

SUMMARY OF THE INVENTION

One aspect of the present invention relates to isolated nucleic acid molecules (i) encoding proteins or polypeptides of *Pseudomonas* Conserved Effector Loci ("CEL") and Exchangeable Effector Loci ("EEL") genomic regions, (ii) nucleic acid molecules which hybridize thereto under stringent conditions, or (iii) nucleic acid molecules that include a nucleotide sequence which is complementary to the nucleic acid molecules of (i) and (ii). Expression vectors, host cells, and transgenic plants which include the DNA molecules of the present invention are also disclosed. Methods of making such host cells and transgenic plant are disclosed.

A further aspect of the present invention relates to isolated proteins or polypeptides encoded by the nucleic acid molecules of the present invention. Compositions which contain the proteins are also disclosed.

Yet another aspect of the present invention relates to methods of imparting disease resistance to a plant. According to one approach, this method is carried out by transforming a plant cell with a heterologous DNA molecule of the present invention and regenerating a transgenic plant from the transformed plant cell, wherein the transgenic plant expresses the heterologous DNA molecule under conditions effective to impart disease resistance. According to another approach, this method is carried out by treating a plant with a protein or polypeptide of the present invention under conditions effective to impart disease resistance to the treated plant.

A still further aspect of the present invention relates to a method of making a plant hypersusceptible to colonization by nonpathogenic bacteria. According to one approach, this method is carried out by transforming a plant cell with a heterologous DNA molecule of the present invention and regenerating a transgenic plant from the transformed plant cell, wherein the transgenic plant expresses the heterologous DNA molecule under conditions effective to render the transgenic plant hypersusceptible to colonization by nonpathogenic bacteria. According to an alternative approach, this method is carried out by treating a plant with a protein or polypeptide of the present invention under conditions effective to render the treated plant susceptible to colonization by nonpathogenic bacteria.

Another aspect of the present invention relates to a method of causing eukaryotic cell death by introducing into a eukaryotic cell a cytotoxic *Pseudomonas* protein, where the introducing is performed under conditions effective to cause cell death.

A further aspect of the present invention relates to a method of treating a cancerous condition by introducing a cytotoxic *Pseudomonas* protein into cancer cells of a patient under conditions effective to cause death of cancer cells, thereby treating the cancerous condition.

The benefits of the present invention result from three factors. First, there is substantial and growing evidence that phytopathogen effector proteins have evolved to elicit exquisite changes in eukaryote metabolism at extremely low levels, and at least some of these activities are potentially relevant to mammals and other organisms in addition to plants. For example, ORF5 in the Psy B728a EEL is similar to *Xanthomonas campestris* pv. *vesicatoria* AvrBsT, a phytopathogen protein that appears to have the same active site as its animal pathogen homolog YopJ, which inhibits mammalian MAPKK defense signaling (Orth et al., 2000). Second, the *P. syringae* CEL and EEL regions are enriched in effector protein genes, which makes these regions fertile targets for effector gene bioprospecting. Third, rapidly developing technologies for delivering genes and proteins into plant and animal cells improve the efficacy of protein-based therapies.

BRIEF DESCRIPTION OF THE DRAWINGS

FIG. 2A is a diagram of the EELs of three *P. syringae* strains shown aligned by their hrpK sequences and are compared with the tgt-queA-tRNA$^{Leu}$ locus in Pa PA01. Arrows indicate the direction of transcription, with small boxes denoting the presence of a Hrp box. Shaded regions are conserved, striped regions denote mobile genetic elements, and open boxes denote genes that are completely dissimilar from each other. FIG. 2B is an alignment of the sequences of the DC3000 (DC) (SEQ. ID. No. 85), B728a (B7) (SEQ. ID. No. 86), and 61 (SEQ. ID. No. 87) EELs at the border with tRNA$^{Leu}$, with conserved nucleotides shown in upper case. FIG. 2C is an alignment of the sequences of the DC3000 (DC) (SEQ. ID. No. 88), B728a (B7) (SEQ. ID. No. 89), and 61 (SEQ. ID. No. 90) EELs at the border with hrpK, with conserved nucleotides shown in upper case.

FIGS. 4A–E illustrate the plant interaction phenotypes of Pto mutants carrying deletions of the EEL (CUCPB5110) and CEL (CUCPB5115). FIG. 14A is a graph illustrating growth in tomato of DC3000 and CUCPB5110 (mean and SD). FIG. 14B is a graph illustrating growth in tomato of DC3000, CUCPB5115, and CUCPB5115(pCPP3016) (mean and SD). FIG. 14C is an image showing HR collapse in tobacco leaf tissue 24 h after infiltration with $10^7$ cfu/ml of DC3000 and CUCPB5115. FIG. 14D is an image showing the absence of disease symptoms in tomato leaf 4 days after inoculation with $10^4$ cfu/ml of CUCPB5115. FIG. 14E is an image showing disease symptoms typical of wild-type in tomato leaf 4 days after inoculation with $10^4$ cfu/ml of CUCPB5115(pCPP3016).

FIG. 5 is an image of the immunoblot analysis showing AvrPto secretion by Pto DC3000 derivatives with deletions affecting the three major regions of the Hrp Pai. Bacteria were grown in Hrp-inducing minimal medium at pH 5.5 and 22° C. to an $OD_{600}$ of 0.35 and then separated into cell-bound (C) and supernatant (S) fractions by centrifugation. Proteins were then resolved by SDS-PAGE, blotted, and immunostained with antibodies against AvrPto and β-lactamase as described (Manceau and Harvais, 1997), except that supernatant fractions were concentrated 3-fold relative to cell-bound fractions before loading. Pto DC3000, CUCPB5115 (CEL deletion), CUCPB5114 (hrp/hrc deletion), and CUCPB5110 (EEL deletion) all carried pCPP2318, which expresses β-lactamase without a signal peptide as a cytoplasmic marker.

FIGS. 6A–B illustrate, enlarged as compared to FIG. 1, the organization of the shcA and hopPsyA operon in the EEL of the Hrp Pai of Psy 61. In FIG. 6A, the shcA and hopPsyA are depicted as white boxes. At the border of the Hrp Pai are the tRNA$^{Leu}$ and queA genes depicted as gray boxes. A 5' truncated hrpK gene is represented as a hatched box. The arrows indicate the predicted direction of transcription and the black box denotes the presence of a putative HrpL-dependent promoter upstream of shcA. FIG. 6B illustrates schematically the construction of the deletion mutation in the shcA ORF marker-exchanged into Psy 61. Black bars depict regions that were amplified along with added restriction enzyme sites and each are aligned with the corresponding DNA region represented in FIG. 6A. The striped box depicts the nptII cassette that lacks transcriptional and translational terminators used in making the functionally nonpolar shcA Psy 61 mutant. EcoRI, E; EcoRV, V; XbaI, X; and XhoI, Xh.

FIG. 7 is an image of an immunoblot showing that shcA encodes a protein product. pLV9 is a derivative of pFLAG-CTC in which the shcA ORF is cloned and fused to the FLAG epitope and translation is directed by a vector ribosome binding site (RBS). pLV26 contains an amplified product containing the shcA coding region and its native RBS site. Cultures of *E. coli* DH5α carrying either pFLAG-CTC (Control), pLV9, or pLV26 were grown to an $OD_{600}$ of 0.8 and then 100 μl aliquots were taken, centrifuged, resuspended in SDS-PAGE buffer, and then subjected to SDS-PAGE and immunoblot analysis with anti-FLAG antibodies and secondary antibodies conjugated with alkaline phosphatase.

FIGS. 13A–B illustrate the effects of transgenically expressed HopPsyA on *Nicotiana tabacum* cv. Xanthi, *Nicotiana benthamiana*, and *Arabidopsis thaliana*. FIG. 13A shows *N. tabacum* cv. Xanthi and *N. benthamiana* leaves infiltrated with *Agrobacterium tumefaciens* GV3101 with or without pTA7002::hopPsyA. FIG. 13B illustrates *Arabidopsis thaliana* Col-1 infiltrated with *A. tumefaciens* +/− pTA7002::hopPsyA. For all plants shown in FIGS. 13A–B, 48 h after *Agrobacterium* infiltration, plants were sprayed with the glucocorticoid dexamethasone (DEX). Images were collected 24 h after DEX treatment. A.t.=*Agrobacterium tumefaciens*; pA=pTA7002::hopPsyA.

FIGS. 16A–B illustrate the interaction of HopPsyA and Mad2 in a yeast two-hybrid assay. FIG. 16A illustrates cultures of yeast EGY48 strains containing either pLV24 (pEG202::'hopPsyA) and pJG4-5 (fish-vector), pLV24 and pLV116 (pJG4-5::mad2), or pEG202 (bait vector) and pLV116 on medium containing 5-bromo-4-chloro-3-indolyl-β-D-galactopyranoside (Xgal) to check for β-galactosidase activity with either glucose (Glc) or galactose (Gal). β-galactosidase activity was indicated only in the presence of both HopPsyA and Mad2. FIG. 16B illustrates cultures of the same yeast strains on minimal medium leucine dropout plates with either Glc or Gal sugars. 1=EGY48 (pLV24, pJG4-5); 2=EGY48 (pLV24, pLV116); 3=EGY48 (pEG202, pLV116).

DETAILED DESCRIPTION OF THE INVENTION

Figure 1:
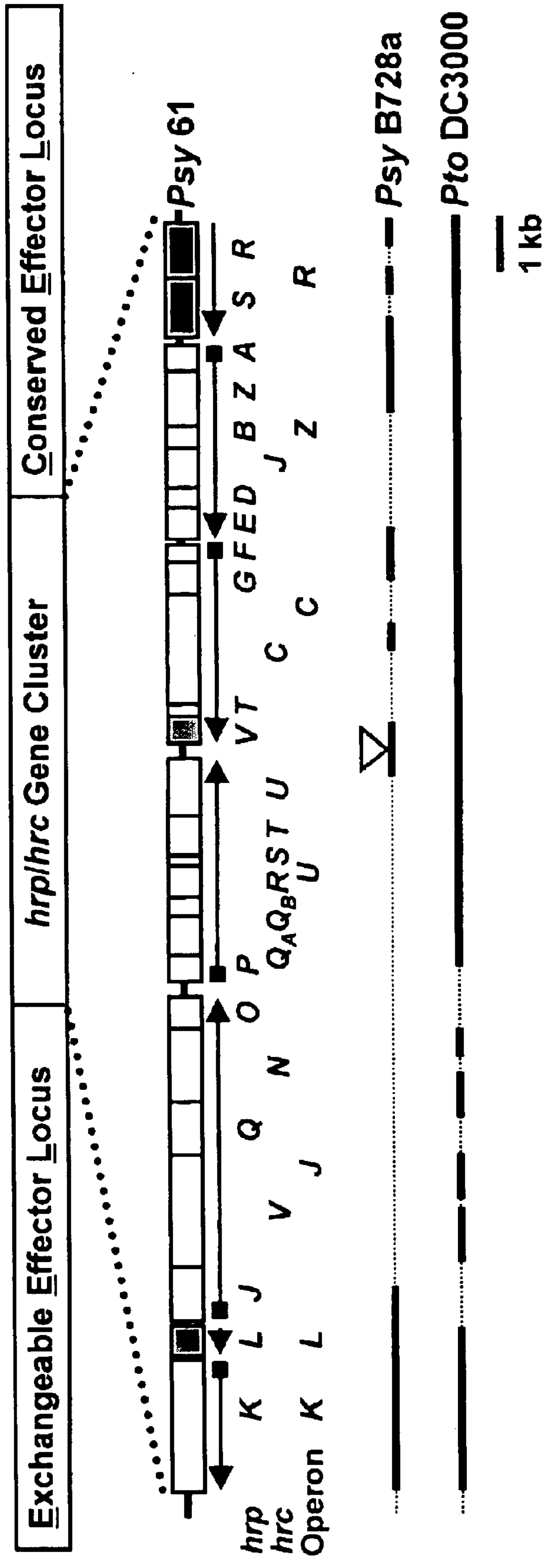
FIG. 1 is a diagram illustrating the conserved arrangement of hrp/hrc genes within the Hrp Pais of Psy 61, Psy B728a, and Pto DC3000. Regions sequenced in B728a and DC3000 are indicated by lines beneath the strain 61 sequence. Known regulatory genes are shaded. Arrows indicate the direction of transcription, with small boxes denoting the presence of a Hrp box. The triangle denotes the 3.6-kb insert with phage genes in the B728a hrp/hrc region.

A DNA molecule which contains the CEL of *Pseudomonas syringae* pv. *tomato* DC3000 has a nucleotide sequence (SEQ. ID. No. 1) as follows:

```
ggtaccgggc tctgtgacgc agagcgtcac gcaaggcatt ccactggagc gtgaggaacg      60
ataatcctga cgacaactat cgtgcgacgc tccgcgtcgg catgccgttc tggacgctct     120
gcgtcctgtc ttgagaggtg cgccaagcgc aaagcacggt aagtatcagg gaggggtgta     180
taggagggtt gcaaggcggg aggtgttcat atcaaggcag tgttcatgaa cccgtcttgc     240
ctgggctcat gaacacgttc ggcttacgcg gtcagtgcat ttcctcgctc aaatggtcca     300
gccctgccag catcaactca tgccggtgga tgtcgtccag gctggcgtag gaacccggtt     360
tttcgttgac cgcgtgccac accacaaagt cgcgtcgtac gtccagaaac aggaagtagt     420
gattgaaacg ctctgactcc ataaaacgtc gttgcagtgc atcacgcagt tgatcgggac     480
gcaacgcgcg gccttctatg tgcaaggcga tcccccaatc atggtgttcg cgccgactga     540
caaacgcgac gccattggcc actggccata ctgctgggct ctgggcggca acctgagcgt     600
aaaatgccga cttttccgtt acctcaatca tttctaatcc tttaactgca cgacagtgta     660
atcccgctca tggtcccggt cgtccagacc ttcgcgcatg tcgggcggcc accaaatgac     720
cagctcgcgg ttgttggagt ccgggcgttt gcaagcgttc cccgcacagc cgtgggtggc     780
acaccctgtc agcgtagcaa acagcaagag caagagcgtt aggctacgaa tcatcatggt     840
ttcgctcccc ggagcagtga cggcctgctt tctttggcca ttttagatat ctgcggctgg     900
cgcacagcga tgtacacctc actttcttca cccggctgca gccatgcatg aggccaggcc     960
gcaacgccga tgacccagcg accgccgcat cggctttcgt cgatacgtac cggcttgtcc    1020
gtgttgttac gcgcaaccac cacagcaaca ccccagtctt ttttgacgaa ccactgcgag    1080
cgctgcccat caagcgtcag accttcgccc ggatcacaca gacttcgtgt ttcaaagggc    1140
agggtctggc cagcgcgcag gccttccggg gcggggccgt cgatcatttg ggtaaagact    1200
ttctggatgt cgccccgcgt tggcagtcgg cctccgtcac gtcgttcctt gatttttcttc   1260
atctggtcat cgacgtcatg gggttgccg ttctgtacat agcgtgctgg attgacctga     1320
tcgccgatca gtcgaggggt cagaatgaac agccgctcgc gctgactcag ttcgcgactg    1380
cgggactgga acagcagctt gccgatatag ggaatgtcgc ccaacagcgg gatcttgtga    1440
atcctgtcat tggcttccag accgtggaag ccgccgatga ccagcgagcc gtgctcggca    1500
atcaccgcct gggtgctgac attgcctcgg cgcacactgg gttgggtgtc attgatcgtc    1560
gacacatcga tctggccatc ctcgatgtcc acgatcattt ggacctgagg cttgccatcg    1620
ttgtccagcg aacgcggaat cacttgaagg ctggtgcccg ccgtgatggg cagaatgtca    1680
gcggcccgct cggaagtggg cgtcaggtat tcggtgcgac tgaggtcgat cactgcaggc    1740
tgattctcca gggtcaggat cgacgggttg gcgatgactg acgcagaacc attgccttca    1800
agcgcatgca attcggcaga aaacttgctg gcgttctgca agaacaacgt tgaactggtg    1860
ccgccatcaa acaggttggc acccacctcc gacgctgccg ggcattgaaa ttccagccga    1920
ctggacagtt cagccagttc attggggtcg atgtcgagaa tgaccgcatc gatttcgatc    1980
aggttgcgcg gaacgtccag ctccttgacc agtttctggt acatggcctt gcgctctggc    2040
aggtcgtaaa tcaatacgga gttgttacgc acatcagcgc ttacgcggat attgccttgc    2100
ctgaggcatg acccttggca gtttttttgc tgttgaagtt caatacgcgg tgcaatgccc    2160
ctgttgcagt gctcccgtat cgataccatt ggagcccagg ttgtaaggca ggccggggcc    2220
gcgacacctg tgctgttggc aacactgctg ccctgccccg ccaacaagtt cacgctgtca    2280
atgctttcgc cacgcgaacg gctttccagc agctcttgaa gaatactggc gacaccggcc    2340
accactaact gctggtcacg gtagcgaata gtccgatcag ccgcgttggc gtatttgagt    2400
```

-continued

```
ggcagcacga caacatcttg cttgtcggcc ttctcgtcgg gcttttcgac tttcttgctg    2460
tagtcgcgca caaactccac gtatttggcc ggaccacgaa ccagaaccac gccttcgtca    2520
ggcagcgagc cccagcccaa acgcttgtca acaagaccga catcggtcag cgccgtttgc    2580
aggtcgtcca ccgcatccgg cgagacttcg atgcgccccg aggtgtgctc gctggaaggg    2640
ctgacataca gcgtgtcgtt atagacgaac cactggaagt ggtattcctg actcagccgc    2700
tcaagaaact cttcagggtt ctgagcacga atacgtccat cgaggtttcc ctggacaggc    2760
gacatgtcga gcgacatacc gaactccctg gcaaagtcag ccagggcagt agacaactcg    2820
gtctgccggg catcataggc gtaggcggtg tgtttccagg cttctggggt gaccgcccac    2880
gtggcaggga tcaccccgat caacaataaa ggcaaccaca ttaaggcctt gcgcatttca    2940
cactcccggt tgccggtgat tgaggatcga acgcccggac aaagtgggcg tcgtgttacg    3000
aatagtggtt tgcatcaggc tgagcatgcc cgcgcgctga ttggccaggc tttccagacg    3060
atcgagcagg tcaccgaggc tgcaggggtt tgccatccag ctgaccagca ctacgcagcg    3120
ggtctgcgga tcgatggcca gcgcgccgtc gcaggcacac gccaggcttg cgccgccctc    3180
gccaagcaag gcttcgagcc gttgcgggtc accggcgtcg tacgggtcga gcagttcgat    3240
actgcaacgc accccgtcgc cgacgaccgc cagccgagca ttggcgtcat cgatccagca    3300
gtccagcggc atcgctggac gctgggcaga ccactggcca acgatctcgg tgaattcact    3360
gaattccatc gatgactgct ttattgatac cgtgcttggc acgcaggcat tcattgacgg    3420
caataccggc gacatcgacc tgctgctggg acatcgtgaa tgcctgcagg tcttcgacgg    3480
tgccactctc ggaggcttcc atcgctgcct ggtccatgtt ggtgtgagca cggctcaccg    3540
aattgtcgag atggcgttgc aagctgttga aactgatcat gtcctggtgc tccagcagaa    3600
gggttcaaac cttgagtgga gcaaacccgc cgagcggttc catcatgcga tcaagtgagt    3660
gcagagagtg tgtatcaggc agcaggctcg acacccagca gccccttgcg caggtctgcc    3720
caagcgatat cgaacgcgcc attggcatcg ctcagacgca agctgtccga ggcgatcgtt    3780
gcatcgcgct tgagttgcca gtgctcggaa aaacggctgt ctgccagcca ctcagccacg    3840
gggtcggcta tttgggggtg aacactgagc gtcgcgaccg cttcattgag ctggctggcg    3900
gccaggtttc tggccagcgc ccgcgcacgt tcggccagcg tggtgtcgtc taacaagtgc    3960
cgcagggatt cactcaacag ttcttctacg gcggtcattg cctgctcctg caacgcctcg    4020
cgctgcacct gaagctcgcc gagaaacgcg ttggcgtttt cccagaactg cgccagcgcc    4080
tgctgctgaa ggtgctcggc tttctcttgc tcaagggcca gtatctgcgt ggcctgctgc    4140
cgcgcgtctg ccaggatgtc gcgcgccagc aggctgtcgg cgatgtcttc gcggcgcaag    4200
atcggttcgc gcagcagcgt agcggccgtc agagcaatac tgcgtttggc gagcatgggc    4260
gtattcctga tgcagagaag ctggttcgga ttcaggcagc cgtgacgcgc cacatgatgg    4320
cctgccataa cgcctgaagt ttgttttcgg gtgccttgcc gggggtgtcg ggcacttcat    4380
tgggcgggca ctccagacac agtcgcgacc agtattgcgg cccaagccag gcgcccagca    4440
gaagacgcgc gtcctcgtgt tcaaactcca gccagacacc ggggcgcagc gctttggtca    4500
acccccagca ccattgaccg tcaggtccgt cgctttcgtt acgggagaag cagatgcact    4560
gcgccaggct tagcgcctgc tcacgctgcg agggcgtcag cgccaaccag cgcagcaccg    4620
gttccgcggg cgctggcggc tgagccgggt caatgcccag actctgcaga aacacgccat    4680
gacggctggc catgagcgca tcgcagtcac tgaccgataa cccacgagcg ttggcgaatc    4740
ggtcatgcca ctccgaatgt gcccactgcc aggggttgca ccaccagtga atccagtgat    4800
```

-continued

```
cctcggcaga aaggctcatc atgcacgtgc cggcagcgtt gaacgaccgc gactgccaaa    4860
cccgatccgt cgcaacagac tggcgcgcca gtcactgcgc accagcagtg caccgatcag    4920
caacaccaac gcaagaccga caggtgccac ccagagcatc aggttccaga acggcaagtt    4980
cgtgctgtcc agcttgaagg gcccgaagct cacccattgc gtggtctctt ggaactctgc    5040
agcaggcaca aacacgatgg aaaacttttt cgaatcgaca gattgcgtgg acataccggg    5100
aatactgctg gcgaccatct gttgaatacg tccgcgcaca ctgtcgggat caagtgcagc    5160
agagtgcttg atgaacaccg cagcagaagc cggttgaaca ggttcgcccg gcgcgatgcg    5220
ctcgggcagc accacatgca ccctggccac aatgactccg tcgatctgcg acagcgtggc    5280
ttcaagttcc tgggacaagg cgtagatgta acgggcacgc tcttcaagcg gcgtcgaaat    5340
caccccttcc ttcttgaaaa tctcccccag cgtggtgcgc gagcgccgag gcagacccgc    5400
agcgtcgagc acgcgcacgg cgcggttcat ttcgctggtg gcgacagtca cgacaacgcc    5460
ggttttctcc agacgtttac gcgcatcgat atgctgatcg gcgaggcgcg ctacgacctc    5520
attggaatcc tgctcggaca agccagtgaa caaatcagtc tcatcactgc agccgccgag    5580
cagcagcatg cacaacagca gcagccctgc gctcagaaaa ttcacggaaa cctctactgc    5640
aggttggtca acttgtcgag cgcctgagcg ctcttgctca cgaccttggt cgtcaacgcc    5700
atttgcaacg agcactgcga caacgcccga ctcatctgca cgatgtctcc aggatcttcg    5760
gtgttcgaca ctttcttcat ctggcgtaat gcttgctgtg aaagcttctc ggtactgccc    5820
agccgctcgg acagcgcact ggctatccgg tcggacaggt gcgacgctgc tggcccgctg    5880
tcagggcgca tcgccgcatt gaataggtcg acatccgcct gaacgggttc ggagccgagc    5940
ccctgatgag cattctgccc aagctccggc gatacacttt tcaaattgct gagttgggaa    6000
atggtcacac tggttctccg tcaggcggct gtcagtcagg ccacagcctg gttagtctgg    6060
ttattggtgc cttgcaacag cgcattgatc agctgagctg ccacttgcgc agcgctcgat    6120
tgcaggtcgg cgccggtgtt gccagcatcc tgaagcgtcg cttccagccc gcgttgacgc    6180
aagccgctca gcagttgacc caggtcctga ttggacacgt tgcccgtcgg gttagccact    6240
ggcgtgccac ctgtcggctg cgtggaattg tcgaccggtg taccaagacc accacccgac    6300
gaaaccgact gcaaaccacg gtcgatgagt tgaccgatca gttgacctac gtcgacgctg    6360
gcattgccat tggccgcggg acctgtgttg gcatcgattg caggattacc cagggagctg    6420
tcactcacgg gcgaacccag accgccgcca ctggtaacgc cactggcatc accttgttgc    6480
tggccgagct gttgaccaat gacgtcgaga gccgaacgaa actgagcggt ttcctgtgca    6540
tccaggccat tgtcttcctt cagctcgttc atccacgagc cgccgtcccg agtagggaac    6600
tgggccttgt tgtcgtccat gaactgggca actttttcca gggtcggcat gtcatcactg    6660
gaaaaggttg ttccgccttc accactcggt gtcagcagat cgtccagcac ggctttgccg    6720
aggccgttca ggacctggct catcagatcg gattgcccgg cacccgcgtc gctgctcaga    6780
ccgccaccga cacccgaacc agaacccgcc ccgccaatgc caccgccacc gccacccgcg    6840
ccgatgccgg cagaggcacc gaaattgtcg ccgagctttt cgtggatcag cttgtcgagc    6900
gatgcagtga tgtcatcgat gctgttagcc gacttgccat ccgcagccat ggccttggcg    6960
agcattttgc cgagcggtga ggtttcatcg agctgcccac tttgggtcag cgcctgaacc    7020
agctgatcga tcacagcctt gagctctttg ctggaagtgc tggtgttggc gctcacatcg    7080
ctgttgagcg acacggggaa caatgatgca gaggtttgca acgaactgat gctgttaagt    7140
gcttgcataa aacgcccatc ccaaggtagc ggcccccctct gatgaggggg caatcagaaa    7200
```

-continued

```
taattagtaa ctgatacctt tagcgttcgt cgctgtggca ctgatcttct tgttggtaga 7260
gtcttctttg ccggcctgga tggcgttgag cacgtccatg gtctgcttct tcattgtttc 7320
ctgggcctgc atcgcgatca gcttcgcgcc gttggcgtcg gactctttac tggccttggc 7380
ttgtgcatca accgacaggc tgtcgccggt gcccaaaaga atgtttttct gaagagtggc 7440
gttggaagca accgtgttga caccctgcaa tgcgccgccg acaccgccaa cggcgctgtt 7500
accaaggttg gtgagtttgg aggttaatcc tgcaaatgcg accatgattt gatgcccctt 7560
aagatttacc agcgtgattg cttggtactc actaggtggc agcagcctgc gatacggttc 7620
cagcgtcttt gcaaaaaatc agatctgcaa ttctttgatg cgtcgataga gcgtacgggc 7680
gtggcagtcc agttccaggc ttaccgaatc caaacaattg tcgtggcgct tgagcgactc 7740
ctgaatcagg gctttttcat caactcgcaa ttgcgatttg agcccacagg ccaagtgctc 7800
ttcgccctgc ggctcggcgc ccagcaaggg gaaacccagc acatggcgtt tggctgcagc 7860
cttgagctca cggatattgc cgggccagtc gtggcccagc agcactttgt gcagcagtgg 7920
gcaaacatcg ggaacgggaa caccgagctc cctcgcggcg gcggccgtaa aacgtgtgaa 7980
caggggaact atgcgatcag actggttacg tagcggagga agcttgagtg tcaggacgtt 8040
caggcgaaaa tacagatcgc gacgaaactg cccccgctcg acggcgtcgt ccagcgagca 8100
ttgggcggag gcgatcacgc agatatccag gttgatcgtc gacgtcgaac ccagccgttc 8160
aagcgctcgg gtttccagca ccctcagcaa tttggcttgc agggccagcg gcatgctatc 8220
gatctcatcc aggtacagcg tgccgccctg cgccgcttcg acataaccga ctctggagcg 8280
atcagcgccg gtgtaggcac cgctgaccac gccgaataac tcgctctcgg cgagggactc 8340
cggaatggcc gcgcaattca tcgccaccag gcgccctttg cgggctgaca tctcatgaat 8400
ccgtcgggca atcgtgtctt tgcccgtgcc ggtctcaccc gatagcagca cgtcgatacc 8460
cagttgcgaa atactttcgg caactatccc cagattcgga acccgctcct cgtccagatc 8520
atcctcaaac ctttcatcaa gactcatccc atgaccccca ggacatcaac gttggataac 8580
cacacctgcg tcacagaccc cggacctcgc agagtatcgg cgctgcaact cccagttcct 8640
tcatgcggtg atacagggtg cgtcttggca actccaactc ctgaagcacc gcgtcgaaat 8700
tgtgcctgtg ccgcttcaag gcatcctgga tgagcatttt ctcgatgatg cgcatttgcg 8760
tgcgcagccc cgtggcaggg tcaagcgctt ccacagggtc ggcgcccagc aaggggaagc 8820
cgagtacgaa gcgcttggct gcagacttca attcgcggat gttgcccggc cagtcgtggc 8880
tgagcagcag ctgcacacgc ccgctgtcca gcgcaggagc gggacgtccg aactcggcag 8940
cgataccctg ggtgaactgg tcgaacaatg gcaggatctg ttcacgacgt ttgcgcaagg 9000
ctggcaagtg aagcgtcagc acgttgagcc gaaaaaacag gtcgcgacgg aaaagtcctt 9060
gttccaccag ttcatccagt ggccgctggg ccgaggcaat gatccgcaga tccaccggga 9120
tgaattcggt cgagcccaga cgctcgatac ctcgactctc caacacacgc agcagtttgg 9180
cctgcaggct caacggcatg ctgtcgattt catccaggta caaggtgcca ccactggagg 9240
cctctatgta gccctcgcga gcccggcata cgccggtgaa tgcaccgttg accacaccga 9300
ataactggct ctctgccagc gactcgggaa tggcggcgca gttcatgccc acaaagggtc 9360
ccgacctgct ggacaactcg tgaatgcggt tggccagtgt gtccttgccg gtgccggttt 9420
ccccgcacaa cagcaagtcc atatccagaa acgcgctatt cattgcaatt tgatgacccg 9480
ctgataatgc agttacgccc caacactctc ggacgtcctt atcgatgcct gtactcatcg 9540
ttgcactctc atggtgggtg gcaagcggag tattaatacc acgtcttaca aggcagaaat 9600
```

-continued

```
atattaattt agttccccgg gaaatgagaa aaagatcaca aagttgagaa ttactatcat      9660
attaatatca ccataccaag acgaccctac cgatagactc aggctcttga gatgattgct      9720
ttaatctatc gttactccaa tgcgaacaag cgcttacagc gtccatgcgc tggctcgccc      9780
cgcaagccat agggcctctc cacacctcaa agcagctgtg atccgggaca agagcaggca      9840
cctttgagca gcaagcgccc caaaatcgcg caatgaaacg caactaactt ctcgtcacta      9900
ctcgagagaa acatataaga cttttccaaa acaactaaag gggtcacaag taaggaagca      9960
gaagaaaacc gaacacacaa aacaagaaaa ccaaacggtt tttagcggcg agcttaaaga     10020
agcgaacaac aataacacga gaaaacaaaa aacagcctga cactaactat ttgcacttta     10080
gaacagtcga taccaaccag cttagttccg ccccacgagc agtcggattt ccgaacaaca     10140
cagaggcttg gatactggca aagcggtcat agccccggtt tttcggcacc actcagtact     10200
ggcatttagt catcatcgca ttcggcaatc cgaacaaaag cccacctgct tagactattt     10260
ccaggcacag ccatctaagg aatcgcggaa aggattcagc gtagcttaat accggaaccg     10320
caggtttagg ttctgtgaac caggcggtta atacgatcga tgatcgcgtg ccatcaccta     10380
gaatgtttct aaatgtgtgt aatctttcac ttacattcgg ctaaaaaagt tcatcaaaat     10440
aatcatatgt agcgctctac atcatatggc taagcgccat ctttagggtc caaaaaacgg     10500
gtaacgctca ataaaagaag ttgtattgag gcagatcaat attgtccgac aacgagaaaa     10560
agcaccaaaa aagtgcgctt ttcaggggtt ttcaatagaa caatcgagta aaaccggggt     10620
tattggcgtg gatcactggc aaaaaccacg acgcgcggcc ccgtaggcag ctcgcgcgga     10680
ccgctgcgat actcgtcgtc atcacgcttg cgaggcgacg aacggtcatc cctgatgcgg     10740
ggcaactgta tccggtttgt aagcggatca ggttccacaa caggtgcgga ttgggcgatc     10800
tctaccgccg gcgctgattc agctgcagga gctggctgta acgcctcagg cgcagtgggc     10860
tgctgagcca ccggcaacgg ctgagccgtt ttgggcgaag gcaggttctc ggctaactgg     10920
gccgactgca cgggcttggg cagcggcgga cgctctgcaa cgcgcactgg acgctcagcc     10980
acaggcgcgg gcgcgggcag acgctcagcc gcccgtttca caatggctga aggggtgacc     11040
agcgggatgc tggcagtcac cggggactca ccggtaatgc gcgcgatgct ggtcgtgagc     11100
acgcgattct gggttttagg tatcagcaga cgtcccggtc catcgaaggt ctttttgcgc     11160
aggaatgccg agttcagccg caacaactgg ccctcatcca cacccgccgt ggccgcgagc     11220
tgggtcaggt ctacggcatg gttaagctcg actacgtcaa aatacggcgt gttggcgacc     11280
ggggtcagtt tcacaccgta ggcattgggg ttgcgcacaa ccattgagag cgccaacagt     11340
ctgggcacgt aatcctgggt ttccttgggt aaattcagat tccagtagtc cacaggcaga     11400
ccacgccgtc ggttggcctc aatcgcccga ccgacggtgc cctcccccgc gttataggcg     11460
gccagcgcca gcagccagtc attattgaac tgatcatgca agcgggtcag gtaatccatc     11520
gccgccttgc tggaggccac cacgtcacgg cgagcgtcgt aggtcgcgct ttgatgcaga     11580
ttgaagctgc gccccgtgga tggaatgaat tgccacaaac ctgccgcagc ggccggagag     11640
ttggccatgg ggttataaga gctttcgatc atcggcagca gtgccagctc cagcggcatg     11700
ttgcgctcgt ccaggcgctc gacaataaaa tgcagataag ggctggcccg gacactggct     11760
cccgtgataa atccgcgatt gctcagcaac cagtcgcgct ggcgagcgat acgctcattc     11820
atgccttggc catcgaccag cctgcagcgc tgggcaaccc gctgccacac gtcctcgccg     11880
ttataaacag gcagatcgga gattttgtct gcagcccgcg aaccttcctt atcatctccc     11940
ccccaataga ccagccccga caccagccgc ggcggacggt cctgacgcgg cggcgaatag     12000
```

-continued

```
tccacagact ggcagcccac acacaaggcg cccatagcga ggactgcgat ttgaacagcg      12060
cgagccagca agcgtgggct cgatacgggg aaggcgacgg cgggcatggg cgggaatgtc      12120
ctgagcgtgt ccaccctacg tggcacgctc gccgttacgg ttccctttttg aaaccgagat     12180
cggcgcacac aacgcattgc tgaatccttt cagccgtaag tttttccgat ggaacccgct      12240
ggcattgcat gccactcatc ctgtgaagga attttcacgt ttggtatcag gcggctatca      12300
gcgataaaat ggacagagag attcaccgtg cagtcaccat cgatccaccg gaacaccgga      12360
agcatcattc agccaaccgt cacccctgac gcacgtgctg caactgacct gcaggaaaga      12420
gccgaacaac ccaggcaacg ctcttcgcac tcgttgagca gtgtcggcaa gcgggcgctg      12480
aaaagcgtcg gtaaattgtt ccagaaatcc aaagcgccgc agcagaaagc tgccacgccg      12540
cccaccgcga aaaacgtcaa gacgccccg cctgcttcaa atgtggctac gcccagaaac       12600
aaagcccgcg aatccggttt ttccaacagc agcccgcaaa atacccatag ggcacccaag      12660
tggattctgc gtaaccaccc caaccaggcg agcagctcgg gcgcgcagac gcatgaaata      12720
cacccggagg cagcccccg taaaaacctg cgcgtaaggt ttgatctgcc gcaagaccgc       12780
cttgagcgca gcccgtcgta cctcgattca gacaacccga tgaccgatga agaagcggtc      12840
gcaaatgcca ctcgccaatt ccggtcacct gacagtcacc tgcagggctc tgacggtacg      12900
cgcatttcaa tgctggccac agatcctgat cagcccagca gctccggcag caaaatcggt      12960
gattcggacg gaccgattcc gccgcgcgag cccatgctgt ggcgcagcaa cggaggccgt      13020
ttcgagctga aagacgaaaa actggttcgc aactcagagc cacaaggcag cattcagctg      13080
gatgccaagg gaaagcctga cttctccacg ttcaatacgc ccggcctggc tccattgctc      13140
gattccattc ttgccacacc caagcaaacc tacctggccc accaaagcaa agacggcgtg      13200
cacgggcacc agttgctaca ggccaacggg cactttctgc acctggcgca agacgacagc      13260
tcgctggccg tgatccgtag cagcaacgaa gcactcctta tagaaggaaa gaaaccaccg      13320
gccgtgaaaa tggagcgtga agacggcaac attcacatcg acaccgccag cggccgcaaa      13380
acccaagagc tcccaggcaa ggcacacatc gctcacatta ccaatgtgct tctcagtcac      13440
gacggcgagc gtatgcgtgt gcatgaggac cgtctctatc agttcgaccc gataagcact      13500
cgctggaaaa taccggaagg cctggaggat accgctttca acagcctgtc cactggcggc      13560
aacggctcgg tttatgcaaa aagtgacgat gccgtggtcg acttgtcgag cccgttcatg      13620
ccgcacgtgg aagtcgaaga cctgcagtca ttttcagtcg cgccggacaa cagagcagcg      13680
ttgctcagcg gcaaaacgac ccaggcgatc ctactgactg acatgagccc ggtgattggc      13740
gggctgacgc cgaaaaaaac caaaggcctt gagctcgacg gcggcaaggc gcaggcggcg      13800
gcggtcggtt tgagtggcga caagctgttt atcgctgaca ctcagggcag actttacagt      13860
gcggaccgta gcgcattcga gggcgatgac ccgaaattga agctgatgcc cgagcaggca      13920
aactttcagc tggaaggcgt gcccctcgga ggccacaacc gcgtcaccgg attcatcaac      13980
ggggacgacg gcggtgttca cgcgctgatc aaaaaccgtc agggcgagac tcactcccac      14040
gctttagacg agcaaagctc aaaactgcaa agcggctgga acctgaccaa tgcgctggta      14100
ctgaacaaca atcgcggcct gaccatgccc ccgccaccca ccgccgctga ccggctcaac      14160
ctcgatcgtg cgggcctggt tggcctgagt gaaggacgca ttcaacgctg ggacgcaacg      14220
ccagaatgct ggaaagacgc aggcataaaa gatatcgatc gcctgcaacg cggcgccgac      14280
agcaatgctt atgtactcaa gggcggcaag ctgcacgcac tcaagattgc ggccgaacac      14340
cccaacatgg cttttgaccg caacacagca ctggcccaga ccgcacgctc gacaaaagtc      14400
```

-continued

```
gaaatgggca aagagatcga aggcctcgac gaccgagtga tcaaagcctt tgcaatggtc      14460
agcaacaaac gcttcgtcgc cctcgatgac cagaacaagc tgaccgccca cagtaaggat      14520
cacaaacccg tcacactcga cattcccggg ctggaaggcg atatcaagag cctgtcgctg      14580
gacgaaaaac acaacctgca cgccctcacc agtaccggcg ggctttactg cctgcccaag      14640
gaagcctggc aatcgacaaa gctgggggac cagttgcgag cccgctggac gccggttgcg      14700
ctgcccggag ggcagccggt aaaggcactt ttcaccaacg acgacaacgt gctcagcgcc      14760
cagatcgaag acgccgaggg caagggtctt atgcagctca aggcaggcca atggcaaagg      14820
ttcgaacagc gcccggtaga agaaaacggt ttgaatgatg tgcactcgcg catcacaggt      14880
tcaaacaaga cctggcgaat tccaaaaacc gggctgacgc tcagaatgga cgtcaataca      14940
ttcgggcgca gcggtgtgga gaaatccaaa aaagccagca ccagcgagtt catccgcgcc      15000
aacatctaca aaaacaccgc agaaacgccc cgctggatga agaacgtagg tgaccatatt      15060
cagcatcgct accagggtcg cctgggtctg aaagaggttt atgaaaccga gtcgatgctg      15120
ttcaagcaac tggagctgat ccatgagtcc gggggaaggc ctccggcacg gggtcaagac      15180
ctgaaagcgc gcatcaccgc actggaagca aaactggggc ctcaaggcgc tacgctggtc      15240
aaggaactgg aaaccctgcg cgacgagctg gaaaatcaca gctacaccgc gctgatgtcg      15300
atcggtcaga gctatggcaa ggcgaaaaac cttaaacagc aggacggcat tctcaaccag      15360
catggcgagc tggccaagcc gtcggtgcgc atgcagtttg gcaagaagct tgctgatctg      15420
ggcacaaagc tcaacttcaa aagctctgga catgacttgg tcaaggagct gcaggatgcc      15480
ttgactcaag tggctccgtc tgctgaaaac cccaccaaaa agttgctcgg cacgctgaag      15540
catcaagggc tgaaactcag ccaccagaaa gccgacatac ctttgggaca gcgccgcgat      15600
gccagcgagg atcatggcct gagcaaagcg cgcctggcgc tggatctggt cacactgaaa      15660
agccttggcg cgctgctcga ccaggtcgaa cagctaccgc cgcaaagcga catagagccg      15720
ttacaaaaaa agctggcgac gctgcgtgat gtgacttacg gcgaaaaccc ggtcaaggtg      15780
gtcacagaca tgggctttac cgataacaaa gcgctggaaa gcggttacga atcggtcaag      15840
acattcctca agtcgttcaa aaaagcggac catgccgtca gcgtcaatat gcgcgcagcc      15900
acaggcagca aggaccaggc cgagctggcc ggaaaattca aaagcatgct caagcaactg      15960
gagcatggcg acgacgaagt cgggctgcag cgcagctacg gagtgaacct caccaccccg      16020
ttcatcattc ttgccgacaa ggctacaggg ctctggccaa cggcaggtgc caccggtaac      16080
cgtaactaca tactcaatgc cgagcgttgc gagggcggcg ttacgctgta cctcattagc      16140
gaaggtgcgg gaaacgtgag cggcggtttc ggtgccggca aagactactg gccgggcttt      16200
tttgacgcaa ataatcctgc acgcagtgtt gatgtcggca acaaccgcac actgaccccc      16260
aactttcgcc tgggcgtgga cgtgaccgcc accgtcgccg ccagccagcg cgccggggtg      16320
gtcttcaatg ttccggatga agacatcgac gcattcgtcg acgacctgtt tgaaggtcag      16380
ttgaatccat tgcaggtgct gaaaaaagca gtggaccatg agagctacga ggctcggcga      16440
ttcaacttcg acctcacggc aggtggaact gccgatatac gcgccggaat aaacctgacc      16500
gaagaccgag acccgaatgc cgaccccaac agcgattcgt tttctgcggt agtgcgcggc      16560
ggattcgctg cgaacatcac cgttaacctg atgacctaca ccgattattc gttgacccag      16620
aaaaacgaca agaccgaact gaaggaaggc ggtaaaaacc gcccgcgctt tttgaataac      16680
gtgacggccg gcgggcagct tcgcgctcag atcggcggca gccacacggc ccccacaggc      16740
acacccgcct ccgccccagg ccccactccc gcatcacaaa cagccgccaa caacttgggc      16800
```

-continued

```
ggagcgctca atttcagtgt ggaaaacagg acggtcaaac ggatcaagtt tcgttacaac      16860
gtcgccaagc cgataacgac tgaaggtctg agcaaattgt cgaagggcct tggggaagcg      16920
ttcctggaca acacgaccaa agcaaaactg gcggagctgg ccgaccctct gaatgcacgc      16980
tacacaggca agaaaccgga tgaggttatt caggcgcaac tcgacgggct tgaagaactg      17040
tttgccgaca taccaccgcc caaagacaac gacaagcagt acaaggcatt gcgcgacttg      17100
aaacgcgcgg cggtcgagca tcgggcatca gccaacaagc acagcgtgat ggacaacgca      17160
cgctttgaaa ccagcaaaac caacctctcc ggcctgtcca gtgaaagcat acttaccaaa      17220
ataatgagtt ccgtgcgcga cgcgagcgcc ccgggcaatg cgacaagagt tgccgaattc      17280
atgcgccagg acccgaaact tcgcgccatg ctcaaggaga tggagggcag tatcgggacg      17340
ctggcacgcg tacggctgga accgaaggac tcactggtcg acaagatcga tgaaggcagc      17400
ctcaacggca ccatgactca aagcgacctc tccagcatgc tggaggatcg caacgagatg      17460
cgcatcaagc gtctggtggt attccacacc gcgacccagg ctgaaaactt cacctcacca      17520
acaccgttgg tcagctataa cagtggagcg aatgtgagcg tcactaaaac actggggcgc      17580
atcaacttcg tttatggcgc agaccaggac aagccgattg gttacacctt cgacggcgaa      17640
ttgtcacgac catcggcatc gctcaaggaa gcggctggcg acttgaagaa agaggggttc      17700
gaactgaaga gctaataacg aaaacagtaa aaaaagcgcc gcattgaagt ggcgcttttt      17760
tattcaagcc tgtaaaaaag cacgcgcttc acgtgcctgg gaaatgaacc cgcgcgtcac      17820
gtcacaaaac gctggctcat cgagtgaggc cagttcacgc tgcgcgcata gacggacatc      17880
tccctgatcg accgcaaacc agcagccatg caagcgcgct acgtcgaagt tcagactcaa      17940
cagacgcagc aaatcggggg ctcgttccgg gcagcggcca atgcggcaat gaaagatgac      18000
catctcactg tgctcgggca attcaatgat cgccgcttcg ttgttctgac cgtcataaag      18060
agcgcatacg ccgttctgca aggtcagtga cgtgccgagc tgggcgccca gagaattgat      18120
gaagcgggcg aaatcgggtt gcgaagtttt catcgtcata gtcctttaag gttaaaacag      18180
catgaagcat gccggacagc aggcgcctgc agcctgtgtc cggcgccggg attaacgcgg      18240
gtcaagcaag ccctcttcaa gtgccctCaa tgcgtcatcg tcttttgtcg gctgcttaag      18300
cgcctcgcgt gctgacgcga ctgcgttcaa cacaccttca tccacgaccc gaaccgtatc      18360
cacggccatc tgggtaggca actgcaatgc gcctcgtccc atgtgatagg cgttttccgc      18420
gactcgtggg ataccgctca acgtgctctt ctggaacgta tgtggcagag actccctgtt      18480
cggatgacgg atgttattca aagcgtctcg gtacggtcca gcataggtgt tgcaccgccc      18540
atgcctgccg ctttcaacgc cttggcttct gcggtaaccg actggttggt gtacaacgtg      18600
gacagatagg acaccgaacc cgtcgctgcc agggccatgt tgcgcaaaat agccccccgca     18660
ctgagcgtgc cacttgcgcc ttcagcctga gcggtcacag gcggcagtgc cgaggtcagt      18720
gcagaactct gaatacccga aagagccttg ctgtagaacg tggtgcgtac cgacggctcg      18780
cgcaggtcca tacctttgag caggtccttt ttcagatcgc tctcggcgcg gtccggggta      18840
aataccggaa ttttgcgccc ttgcgggtcg acataattcg acttcaattg cagcagcgtt      18900
tgcgaactgg cagacaccgc cccgccaaaa ccggatgcca gagctcttgc actcagcgtc      18960
tgcccattga tctggtgaac atcgttgagc atctggcgca cagcctgaga accaccgaag      19020
gcactgtaag ccatcagctc acctaccgga tgggtggacg aaccctgaac cttcttctgg      19080
ttcagcagcg cgcgttcact tttcacgaac gccttgtcct gagcgacttc ctcgggcgtt      19140
tttttgacca gctcaccgtg ttcgcttttc agctcgaagg ggtcaggaat aaccgtattg      19200
```

-continued

```
gtatccacag ccttcattgg caccatgttc aggcgttcgt tgaggccagt cttctgcaag     19260
gcggcctgaa acatcggctt gaccacgctg ttgaccgtct cgtgagcaat gcccgccacc     19320
atcccgatta tcgaagcctt gagcatgttg gcgtcgctgc tggtctcggg aatcgtgtct     19380
cgcagcttgt cgctggtgga caaacgcaca taacccaagt gtgtcattga agacaagaac     19440
tgcggaaccg cagccgcgac aatcggccct gcacctttcc agccacccac cgtgttacgg     19500
gcagtgacga gatcgctgac gacgttgtcc agttgcgtat gtgcggcgac cgaagcaagg     19560
cgcttggcct ccggcgactt gacgaaatcg gcgtgcaaac ctaccagggt ggttttggcg     19620
tcgaccagcg cctgcctgtc agcgtgcaga gactccttgt tgccctgttc ggcatcttgc     19680
agagtgagat ccagcgcact gatgtgctca tccagcgacg cgatgctgtt gctcaggcct     19740
tcgccgattg ccttgcttgc acgaccggcg tattcgccaa gggcagtctg actgacggca     19800
agcgtcgcct tgtccgcttt tgcatgctgg cctaccgttg cgggcgaagc gtcatgcatc     19860
agttgaaagt gctccagttg atcagcgacc gactgagcaa aacccttgat cagttgcccg     19920
acctcggctt tatccggtat ctgacccggc tgggcgaatt tttccagccg ctgctgcaag     19980
tccgagccct gaaactgctt cagttgatag cgctcaggag acaatttctc ggccatgact     20040
tcaaaaggca aaggctcggc ctgcagcaga ctaccgatca acaacgcagc acgcgaactg     20100
atcatcggcg cgccgctgac cggagccgtc ccatgctcag ccttgaaggc ctgcaaaagc     20160
tgtgtgtgtc gagccgcgac attcagccgc gccgcgccgg cagacgagct ttctgtcgcg     20220
tgtgaccctg actgatcggg agtcagcggc ggattcatgc ctgcagtgac tgcatttggg     20280
tgagctgtct gggcgggaac agtatcgtgc tgctggttta cccggctgag tttgacgcca     20340
ccggccccgc cgatccgcga actgatcatt ggaatctccc aggagccgaa aggctctcgc     20400
gtttggctgc tggggcaaca ggttggtccg tcgaggagcc tgcagttgtg gcctgcccca     20460
tgaatccatg ctcgcgccac tctttggcca ggtcggaaaa cgacttcatc aacaacagca     20520
cgccttcggc agaggctcgt tcaagggcca cagagcccat cagcagcaca cgaccggtct     20580
gcgcattaaa ggaaaatgcc gggctgtggg cgcccgcgaa catgtgaaag ttgatgtcca     20640
tcaacgccag caacgcgctc tcacggccgc gcgcgggcaa cgcgcccatg tcaccgtaga     20700
tcagaacggc acggccttcg tcgcggtcct gaaactgcag ggtgaagtcc acttcgctga     20760
ttttgaaatt ggcagattca tagaaacgtt caggtgtgga aatcaggctg agtgcgcaga     20820
tttcgttgat aagggtgtgg tactggtcat tgttggtcat ttcaaggcct ctgagtgcgg     20880
tgcggacgaa taccagtctt cctgctggcg tgtgcacact gagtcgcagg cataggcatt     20940
tcagttcctt gcgttggttg ggcatataaa aaaaggaact tttaaaaaca gtgcaatgag     21000
atgccggcaa aacgggaacc ggtcgctgcg ctttgccact cacttcgagc aagctcaacc     21060
ccaaacatcc acatccctat cgaacggaca gcgatacggc cacttgctct ggtaaaccct     21120
ggagctggcg tcggtccaat tgcccactta gcgaggtaac gcagcatgag catcggcatc     21180
acaccccggc cgcaacagac caccacgcca ctcgattttt cggcgctaag cggcaagagt     21240
cctcaaccaa acacgttcgg cgagcagaac actcagcaag cgatcgaccc gagtgcactg     21300
ttgttcggca gcgacacaca gaaagacgtc aacttcggca cgcccgacag caccgtccag     21360
aatccgcagg acgccagcaa gcccaacgac agccagtcca acatcgctaa attgatcagt     21420
gcattgatca tgtcgttgct gcagatgctc accaactcca ataaaaagca ggacaccaat     21480
caggaacagc ctgatagcca ggctcctttc cagaacaacg gcgggctcgg tacaccgtcg     21540
gccgatagcg gggcggcggg tacaccggat gcgacaggtg gcggcggcgg tgatacgcca     21600
```

-continued

```
agcgcaacag gcggtggcgg cggtgatact ccgaccgcaa caggcggtgg cggcagcggt      21660
ggcggcggca cacccactgc aacaggtggc ggcagcggtg gcacacccac tgcaacaggc      21720
ggtggcgagg gtggcgtaac accgcaaatc actccgcagt tggccaaccc taaccgtacc      21780
tcaggtactg gctcggtgtc ggacaccgca ggttctaccg agcaagccgg caagatcaat      21840
gtggtgaaag acaccatcaa ggtcggcgct ggcgaagtct ttgacggcca cggcgcaacc      21900
ttcactgccg acaaatctat gggtaacgga gaccagggcg aaaatcagaa gcccatgttc      21960
gagctggctg aaggcgctac gttgaagaat gtgaacctgg gtgagaacga ggtcgatggc      22020
atccacgtga aagccaaaaa cgctcaggaa gtcaccattg acaacgtgca tgcccagaac      22080
gtcggtgaag acctgattac ggtcaaaggc gagggaggcg cagcggtcac taatctgaac      22140
atcaagaaca gcagtgccaa aggtgcagac gacaaggttg tccagctcaa cgccaacact      22200
cacttgaaaa tcgacaactt caaggccgac gatttcggca cgatggttcg caccaacggt      22260
ggcaagcagt ttgatgacat gagcatcgag ctgaacggca tcgaagctaa ccacggcaag      22320
ttcgccctgg tgaaaagcga cagtgacgat ctgaagctgg caacgggcaa catcgccatg      22380
accgacgtca aacacgccta cgataaaacc caggcatcga cccaacacac cgagctttga      22440
atccagacaa gtagcttgaa aaaagggggt ggactcgtcg agtccacccc ctttttactg      22500
tttagctaca gctcacagat tgcttacgac cgcataggcc gaaacggtat ttcacttgga      22560
gaagccgccg tgccccccctc ttctatatca gcttcacgag ccgggcgttg acgcaggtta      22620
ttgaccgtat tgcgcaagct ggcgccggta tgggtgatcg cctccccgcc catgtctttg      22680
acggtcttcg ccagtttgac ggtctggtcg gctacgtagc ctgtggtact ggatgcagtc      22740
gatttcaccg tgtcctgtat gaacgactcg gctttttttca ccgcgggatc ggttgtcagc      22800
gcggccgtgg tccagcctgc gaaaacggct gccgaacctg ccaggttggt caactgactg      22860
accgcggcct tggtcgccgg gtcggtgata tttttcgtcg ccatctcctg caacttgcct      22920
accccctgcaa agccacccgc cagggccaga ccgttttggg tcaggctgga cgctgacacc      22980
aggcttctta ccgcacccat tgcgtcggtc gccatatcca gtggcagacc ggccatccgc      23040
ttgccagcgt tgagcgccgc acccgagtag ctggccgatt tgattgcttt ataagcctcg      23100
agccagtcgt tttcttcgct cagttgagcc ttgggctctt tatccttcaa accgagcact      23160
aatgcaccgc cacgctggtg atcacgcgac tgcacactga gcaggcggtt gccaaagcct      23220
gcgttggcag ccagaccacc cgccatcgat acaccaaggt ccacagcacc ctgcacggcg      23280
ggtctggacg ccagtgccgg agccaatacg gtacgtacgg cgttgcgcgc cgagtacgtc      23340
tgaaccgcaa cccccgtgtc cagaacctgt cgagcaaggc ttggcgagtg gcgcttcacc      23400
gaagcggcca tcgcatcgtg gagcctgtcc ggcgaggcgc tcaggtaatg cagatcaccc      23460
gtcgcgcggt ccatcatctt ggtgcccacc tggtccatgg cgcccgacag cgctccggaa      23520
atgagcgggg tcagcggttt gagcggagcc ggcagccaat cgcccttgtt gatcgcaggc      23580
tgcatgtact gaagcaacga ggccatggca aagggcgtcg cccgcaacgc gcctgatgta      23640
gtcgtcgcca atcggtcgag cttttccgcc ttggcgaagg tgtcggcgat ggttgccggg      23700
gtttcccctt cgaagtgcag gcggctggcg cgcgtctcga tcagcgcagt gatctgcgca      23760
ttgtgtacgt caactgcagc ttggccatca gccgaatcgg ccggcggcag tttatgcgca      23820
gcgaacacat gatctgtcag gtaatcggca atcgcattta tctcgcgttg ctgatcggag      23880
ctgacagatc gcacagagct ggaggcaaga gacgcgtcgg acgctgtccg aaagctatcc      23940
gtcgcagtca caggcggttg ttggacgcgt cggttgatgt gcatggaaat tccctctcgt      24000
```

-continued

```
tctacggaag tttgaacagc gcagtgctga agcgggcgtg tccggagcga ctacttgcgt      24060
gaaagcaata cagtgaactg tcgatcaaac agcgccagaa acagcgaaac gtccggtcgt      24120
ccgccggttt aaaaggatcg acgaaggctg tgtggtcccg gatcggttga cggttccact      24180
gaataatctg cgtacgccca ctaccaagga ctgcgccgaa aaatcaccgt cgtttgtgtt      24240
gcagattacg caaattgaaa ttaagcgagc tttaaggatg gcagcgtaag ttcacaacat      24300
ggcttggcgc ttagcgagta agcgccttCt tccaaaccag caaaggagtg ccgcaatgtc      24360
tggtcctttc gagaaaaaat ggcggtgttt cacccgaacc gtgacctacg ttggctggtc      24420
gctgttctgg cttctgctct gggacgtggc cgtcaccgtg gacgtcatgc tgatagaagg      24480
caaaggcatc gacttccccc tgatgcccct cacgttgctt tgctcggcac tgatcgtgct      24540
gatcagcttt cgcaactcga gtgcctataa ccgttggtgg gaagcgcgca ccttgtgggg      24600
cgcaatggtc aacacttcac gcagttttgg ccggcaggta ctgacgctga tcgatggcga      24660
acgggatgac ctcaacaacc ctgtcaaagc catactcttt caacgtcatg tggcttactt      24720
gcgtgccctg cgcgcgcacc tcaaaggcga cgtcaaaaca gcaaaactcg acgggttact      24780
gtcgcccgac gagattcagc gcgccagcca gagcaacaac ttccccaatg acatcctcaa      24840
tggctctgct gcggttatct cgcaagcctt tgccgccggc cagttcgaca gcatccgtct      24900
gacccgcctg gaatcgacca tggtcgatct gtccaactgt cagggcggca tggagcgcat      24960
cgccaacacg ccactgccct accccctacgt ttatttccca cggctgttca gcacgctgtt      25020
ctgcatcctg atgccgctga gcatggtcac caccctgggc tggttcaccc cggcgatctc      25080
cacggtggta ggctgcatgc tgctggcaat ggaccgcatc ggtacagacc tgcaagcccc      25140
gttcggcaac agtcagcacc ggatccgcat ggaagacctg tgcaacacca tcgaaaagaa      25200
cctgcaatcg atgttctctt cgccagagag gcagccgctg ctggctgacc tgaaaagccc      25260
cgtaccgtgg cgcgtggcca acgcatcaat tggcggtctg agcaggcaga aaaacaggtt      25320
aggggaaggc gcgaggctta tcgcaagtga aagtctgctc tgggcaccat ttcgctcagt      25380
tgcagacgtt gctccgtgcc acgccagtgc gtacctacgt cgcgcttgaa cacatcagca      25440
agaaaatggc tcatgttgct gaagctgtct gcctgaacca cgccaaaaag aggatcaaaa      25500
aaatgcagac atccctgact gtcctgatgc agagccatcg catggctatc actcaaaaac      25560
agaagcatct ggtctttacc gggctgcaac actgctttga gatcgcgatc aaggttttcc      25620
agagcaaccg catagtgcgc gtgctgtgct ctgcccagcc cttttccaag tgtcatgccc      25680
aacttgggaa gtgtgtccag aagcataggt gctgcgttct gcaacttgtt tgaataggcc      25740
tgctgctcga tatgctggaa gcccattacc ctgggtagca atgcatcgcc ctgatagtcc      25800
tccagtttgt gaaagaaggc ctcatccgac tgcccttttg cacggctctg acaccaattt      25860
actgatagcc ccagacaagc gtgcccgtcg ccacccgcgc ggccatagtc agcagcaaac      25920
gctctatcat cgatagtttt ttcaaataga aatttgctct ggtgaaacgg gtggacaagc      25980
tgacagccgt gctcttgggc aatctttctt ttggcttcga tgttcgcagt cgcgcctatg      26040
ctgttgtccg ccatagcctt gattctggtc ttgatgtatt gcgtggcgcc gtcacgtaat      26100
gaggcgatag agaccatcag atccggtagc agggtacgca acgaatgaag ctggggttgt      26160
acctgctcgg gactgggaag atcagcggca tcgaccgacg aaaaggaaga gcgcgcatcg      26220
aaaaagacct cttcatgccc ctccaatggg acaaaggcgc ccgccttttc gggatgaaaa      26280
cgggcgaacg catccgacga accgggggcg agtccggaca atgacgaggg cttatcgtgt      26340
tgcgtcttag cggcaacccc tgattgggcg ccagattgct ggatatacat aaaccgccct      26400
```

-continued

```
ctgtcaggtc atgaacgttc gtggggtcag atggacagcc ggtaagaacc gaggctcttt      26460

ctgggcggtt tttccggctt gctcctggcg tcgataatct tccagatagc gctgcaacga      26520

gacggccaat gtgctaattc gcgtcatgag gtgatcaagt ccggtctcat ccagatccgc      26580

cattgagtgc acactgcgca acaacagttc ccttgaatca gggttatagc caagcgcagc      26640

gccacctgtg cgagcaggct ccagattcag cgccattgcc agaatcaaaa tgacgttgtc      26700

ctgcggcatc gtcagccttt cgatctgtgt gaagatgaac aacgaagtgt cctgttctgg      26760

caaccagagc agacactcgc ttccattcgc ggtccttacg ttgtggcgtt gaccctcctg      26820

cgcatcgatg cctcgattgc gcagccactg ataaagccga tcttttgcct cgacaggccg      26880

catggaaatt ccccgctcgt ttaacgatga ttttcctctg tggttcaaga cgtgatgcgg      26940

ttccctttag ggtttgcact aatatcaatg cgattcttgt aaaaatcgac tcgtgagtgc      27000

cgccgatggc aaaggtaacg ggatgggcag cgagtttttg gtaacgttgc cgttgttgca      27060

gggttgaatt tgttgggtga cgttaaaacg aaggaatgta tgcttaaaaa atgcctgcta      27120

ctggttatat caatgtcact tggcggctgc tggagcctga tgattcatct ggacggcgag      27180

cgttgcatct atcccggcac tcgccaaggt tgggcgtggg gaacccataa cggagggcag      27240

agttggccca tacttataga cgtgccgttt tccctcgcgt tggacacact gctgctgccc      27300

tacgacctca ccgcttttct gcccgaaaat cttggcggtg atgaccgcaa atgtcagttc      27360

agtggaggat tgaacgtgct cggttgatcc atatttttac tgcgacagaa gagtgcggcc      27420

ccgacgcttt tggagagcac accagggatt caaacccgcc ttaaaagctt tatatgcgtg      27480

gcatgcacct cgtcaactgc ctgaaagccg caacgtaagt aaaattttgc tccgctcgga      27540

gtatcagtga acaggcgcac ggcgaaaaat tcctgcgccg catgctccac aagtcgattc      27600

accagagtct ttccaaggcc ttgacctctt gatgcgcttg cgacgtataa ccgtcgtagc      27660

ctgcccatat caccccgggc atgcggatca cgcgaaaggc ctccgatacc tgccagagcg      27720

ccgtccagaa gtacgaccat gaggcattca cccttggcct cgaatcgatt ctttccggac      27780

ctccactcct cgatcaagcg ggtaagaaac ctgaagccct ctgctactgc ctcttgctcc      27840

aggatcagaa cctgacaagg caattcagta atgatctgga cttctacctg tttcatctaa      27900

tgacctcatc cacagtggtc ctgcgctggc gaaaacacga gcaggtctgg acagaatgca      27960

tatgcaacag caaaggctgc aaccagtgca caccaccaga accgggttcg acagttaagc      28020

tgatatcatt caagcacctg caagccgagt agaagcacat gaaccgtcgc aagaaaatac      28080

agcaactgtt aaaggctcat gccaagaaag ccagcgctaa actggcaccg gcaaacaaat      28140

ccagctacgt gagcaaggct gatcggttga agctggcggc agagtccggt aacgacccga      28200

tcagttccgt cgaggactga acagcgacgt ttacgcgcca ccggtatggt caggctgttc      28260

attccgatgg agcgtattgc aaggagcctg ttcaacagct cacttacttc gcaaacgagt      28320

actcaccgcc ctgctccagc gcctggcgat acgcaggtct ttcctggcat cgttgtaccc      28380

aggctgcaag gttaggatgc ggctgcagca ttccctgcat tttggcgaat tcgccaatga      28440

agctcatctg aatatccgcg ccactcaatt cgtcgcccag cagataaggc gtcagcccca      28500

gagcttcatt cagatagccc agatagttgg ccagttcaga gtgaatgcgc ggatgcaaag      28560

gcgcgcccgc gtcacccagg cgaccgacgt acaggttgag catcagcggc agaatggccg      28620

aaccttcggc gaagtgcagc cattgtacgt actcatcgta ggtggcgctg gcaggatccg      28680

gttgcaggcg gccgtcgcca tgacggcgga tcaggtaatc gacgatggcg ccagactcga      28740

taaccacatg ggaccgtctt tcgatcaccg ggatttgccc cagcggatga atggccttca      28800
```

-continued

```
gctcaggcgg cgcgaggttg gttttcgggt cgcgctggta gcgttttatc tcgtacggca      28860
ggccaagttc ttcgagtaac cacagaatgc gctgcgaacg tgagttgttc aggtggtgga      28920
caataatcat gtgggtctcc gctgggtgag agtgggatgt ctagaaaaag actgctgggc      28980
cgccgtagag tgccgtgaat cgaatgtcct ctggcgacct cagacgcgtc tgtcggcgca      29040
gagcgctgcc gactcaccgc gaagctgacg ctccactgcc gctttatcga ttaccgacca      29100
aacgccgatt atcttgccat cgctgaatgt gtagaacaca ttttcggaaa aggtgatgcg      29160
ccgtccctgt gtgtcctgcc ccagaaatcg accctgtggc gagcagttga agaccagccg      29220
ggcagcgacc tgtggtgctt caacgaccag caaatcgatc ttgaaacgca agtcggggat      29280
aatcctgacg tcgttttcca gcattgtttt gtagccggaa aggctgatca gctcaccgtt      29340
gtaatgcaca ttgtcatcga cgaagttgcc caactggtgc caactacggt cattcagaca      29400
ggcgatgtaa gcccgatagt gatcggtcag gttcatggcg cgccctcctt caggtgctca      29460
aagcagtcac tgtcaatcat ccagataacc cgcacagttt taacagagtc atagggaact      29520
cgtgcggccg acatcgccct aagcctcaca tctatgtact ggcgcgacgc tggtttcaag      29580
cgaaggactt cagattcatg tcttcaagta gcactacagc agcggctgac acgcaaggtc      29640
ggcaaaacgc ctcgcctaac cgactgattt tcatctccgt acttgtggca accatgggcg      29700
cgctcgcgtt tggttatgac accggtatta tcgncggcgc attgcccttc atgacgctgc      29760
cggccgatca gggcgggctg ggtttgaatg cctacagcga agggatgatc acggcttcgc      29820
tgatcgtcgg tgcagccttc ggctcactgg ccagtggcta tatttccgac cgtttcggac      29880
gacgcctgac cctgcgcctc ctgtcggtgc tgttcatcgc gggtgcgctg ggtacggcca      29940
ttgcgccgtc cattccgttc atggtcgccg cgcgcttcct gctgggtatc gcggtgggtg      30000
gcggctcggc gacggtgccg gtgttcattg ccgaaatcgc cggcccctcg cgtcgtgcgc      30060
ggctggtcag ccgcaacgaa ctgatgatcg tcagcggcca gttgctcgcc tatgtgctca      30120
gcgcggtcat ggccgcgctg ctgcacacgc cgggcatctg gcgctatatg ctggcgatcg      30180
cgatggtgcc gggggtgttg ctgctgatcg gcaccttctt cgtacctcct tcgccgngct      30240
ggctggcgtc caaaggccgt tttgacgaag ctcaggatgt gctggagcaa ctgcgcagca      30300
acaaggacga tgcgcancgt gaagtggacg aaatgaaagc tcatgacgag caggcgcgca      30360
atcgt                                                                  30365
```

Figure 3:
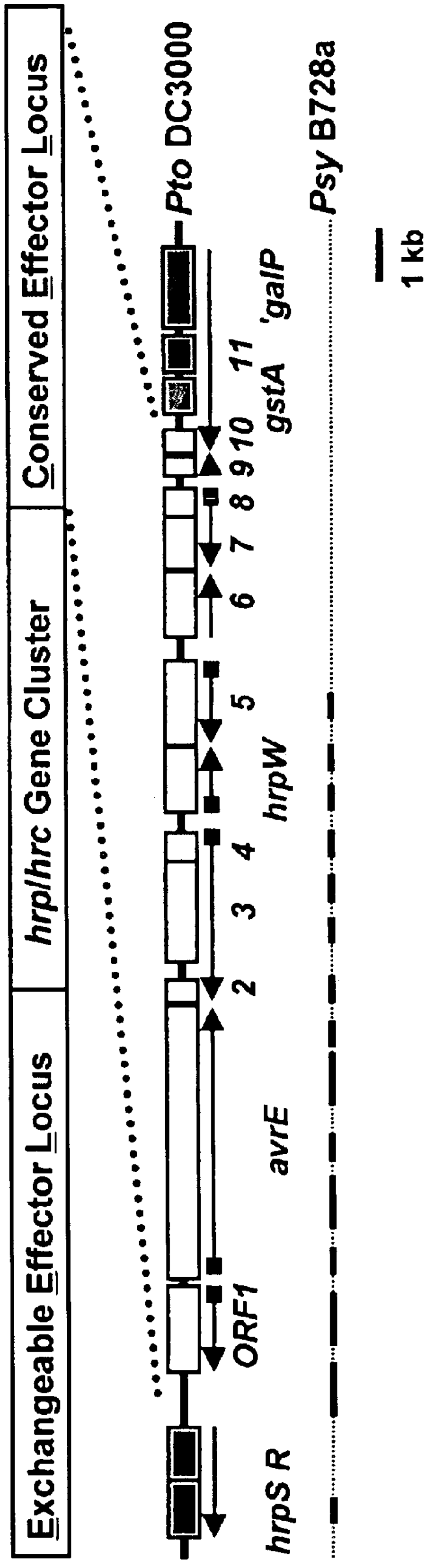
FIG. 3 is a diagram illustrating the Hrp Pai CEL of *P. syringae*. The Pto DC3000 CEL is shown with the corresponding fragments of Psy B728a that were sequenced aligned below. The nucleotide identity of the sequenced fragments in coding regions ranged from 72% to 83%. Arrows indicate the direction of transcription, with small boxes denoting the presence of a Hrp box.

Several undefined nucleotides exist in SEQ. ID. No. 1, however these appear to be present in intergenic regions. The CEL of *Pseudomonas syringae* pv. *tomato* DC3000 contains a number of open reading frames (ORFs). Two of the products encoded by the CEL are HrpW and AvrE, both of which are known. An additional 10 products are produced by ORF1-10, respectively, as shown in FIG. 3. The nucleotide sequences for a number of these ORFs and their encoded protein or polypeptide products are provided below.

The DNA molecule of ORF3 from the *Pseudomonas syringae* pv. *tomato* DC3000 CEL has a nucleotide sequence (SEQ. ID. No. 2) as follows:

```
atgatcagtt cgcggatcgg cggggccggt ggcgtcaaac tcagccgggt aaaccagcag       60
cacgatactg ttcccgccca gacagctcac ccaaatgcag tcactgcagg catgaatccg      120
ccgctgactc ccgatcagtc agggtcacac gcgacagaaa gctcgtctgc cggcgcggcg      180
cggctgaatg tcgcggctcg acacacacag cttttgcagg ccttcaaggc tgagcatggg      240
acggctccgg tcagcggcgc gccgatgatc agttcgcgtg ctgcgttgtt gatcggtagt      300
ctgctgcagg ccgagccttt gccttttgaa gtcatggccg agaaattgtc tcctgagcgc      360
tatcaactga agcagtttca gggctcggac ttgcagcagc ggctggaaaa attcgcccag      420
```

-continued

```
ccgggtcaga taccggataa agccgaggtc gggcaactga tcaagggttt tgctcagtcg    480
gtcgctgatc aactggagca ctttcaactg atgcatgacg cttcgcccgc aacggtaggc    540
cagcatgcaa aagcggacaa ggcgacgctt gccgtcagtc agactgccct tggcgaatac    600
gccggtcgtg caagcaaggc aatcggcgaa ggcctgagca acagcatcgc gtcgctggat    660
gagcacatca gtgcgctgga tctcactctg caagatgccg aacagggcaa caaggagtct    720
ctgcacgctg acaggcaggc gctggtcgac gccaaaacca ccctggtagg tttgcacgcc    780
gatttcgtca agtcgccgga ggccaagcgc cttgcttcgg tcgccgcaca tacgcaactg    840
gacaacgtcg tcagcgatct cgtcactgcc cgtaacacgg tgggtggctg gaaaggtgca    900
gggccgattg tcgcggctgc ggttccgcag ttcttgtctt caatgacaca cttgggttat    960
gtgcgtttgt ccaccagcga caagctgcga gacacgattc ccgagaccag cagcgacgcc   1020
aacatgctca aggcttcgat aatcgggatg gtggcgggca ttgctcacga gacggtcaac   1080
agcgtggtca agccgatgtt tcaggccgcc ttgcagaaga ctggcctcaa cgaacgcctg   1140
aacatggtgc caatgaaggc tgtggatacc aatacggtta ttcctgaccc cttcgagctg   1200
aaaagcgaac acggtgagct ggtcaaaaaa acgcccgagg aagtcgctca ggacaaggcg   1260
ttcgtgaaaa gtgaacgcgc gctgctgaac cagaagaagg ttcagggttc gtccacccat   1320
ccggtaggtg agctgatggc ttacagtgcc ttcggtggtt ctcaggctgt gcgccagatg   1380
ctcaacgatg ttcaccagat caatgggcag acgctgagtg caagagctct ggcatccggt   1440
tttggcgggg cggtgtctgc cagttcgcaa acgctgctgc aattgaagtc gaattatgtc   1500
gacccgcaag ggcgcaaaat tccggtattt accccggacc gcgccgagag cgatctgaaa   1560
aaggacctgc tcaaaggtat ggacctgcgc gagccgtcgg tacgcaccac gttctacagc   1620
aaggctcttt cgggtattca gagttctgca ctgacctcgg cactgccgcc tgtgaccgct   1680
caggctgaag gcgcaagtgg cacgctcagt gcgggggcta ttttgcgcaa catggccctg   1740
gcagcgacgg gttcggtgtc ctatctgtcc acgttgtaca ccaaccagtc ggttaccgca   1800
gaagccaagg cgttgaaagc ggcaggcatg ggcggtgcaa cacctatgct ggaccgtacc   1860
gagacgcttt ga                                                       1872
```

The protein or polypeptide encoded by Pto DC3000 CEL ORF3 has an amino acid sequence (SEQ. ID. No. 3) as follows:

```
Met Ile Ser Ser Arg Ile Gly Gly Ala Gly Gly Val Lys Leu Ser Arg
  1               5                  10                  15

Val Asn Gln Gln His Asp Thr Val Pro Ala Gln Thr Ala His Pro Asn
             20                  25                  30

Ala Val Thr Ala Gly Met Asn Pro Pro Leu Thr Pro Asp Gln Ser Gly
         35                  40                  45

Ser His Ala Thr Glu Ser Ser Ser Ala Gly Ala Ala Arg Leu Asn Val
     50                  55                  60

Ala Ala Arg His Thr Gln Leu Leu Gln Ala Phe Lys Ala Glu His Gly
 65                  70                  75                  80

Thr Ala Pro Val Ser Gly Ala Pro Met Ile Ser Ser Arg Ala Ala Leu
                 85                  90                  95

Leu Ile Gly Ser Leu Leu Gln Ala Glu Pro Leu Pro Phe Glu Val Met
            100                 105                 110

Ala Glu Lys Leu Ser Pro Glu Arg Tyr Gln Leu Lys Gln Phe Gln Gly
        115                 120                 125
```

-continued

```
Ser Asp Leu Gln Gln Arg Leu Glu Lys Phe Ala Gln Pro Gly Gln Ile
    130                 135                 140

Pro Asp Lys Ala Glu Val Gly Gln Leu Ile Lys Gly Phe Ala Gln Ser
145                 150                 155                 160

Val Ala Asp Gln Leu Glu His Phe Gln Leu Met His Asp Ala Ser Pro
                165                 170                 175

Ala Thr Val Gly Gln His Ala Lys Ala Asp Lys Ala Thr Leu Ala Val
            180                 185                 190

Ser Gln Thr Ala Leu Gly Glu Tyr Ala Gly Arg Ala Ser Lys Ala Ile
        195                 200                 205

Gly Glu Gly Leu Ser Asn Ser Ile Ala Ser Leu Asp Glu His Ile Ser
    210                 215                 220

Ala Leu Asp Leu Thr Leu Gln Asp Ala Glu Gln Gly Asn Lys Glu Ser
225                 230                 235                 240

Leu His Ala Asp Arg Gln Ala Leu Val Asp Ala Lys Thr Thr Leu Val
                245                 250                 255

Gly Leu His Ala Asp Phe Val Lys Ser Pro Glu Ala Lys Arg Leu Ala
            260                 265                 270

Ser Val Ala Ala His Thr Gln Leu Asp Asn Val Val Ser Asp Leu Val
        275                 280                 285

Thr Ala Arg Asn Thr Val Gly Gly Trp Lys Gly Ala Gly Pro Ile Val
    290                 295                 300

Ala Ala Ala Val Pro Gln Phe Leu Ser Ser Met Thr His Leu Gly Tyr
305                 310                 315                 320

Val Arg Leu Ser Thr Ser Asp Lys Leu Arg Asp Thr Ile Pro Glu Thr
                325                 330                 335

Ser Ser Asp Ala Asn Met Leu Lys Ala Ser Ile Ile Gly Met Val Ala
            340                 345                 350

Gly Ile Ala His Glu Thr Val Asn Ser Val Val Lys Pro Met Phe Gln
        355                 360                 365

Ala Ala Leu Gln Lys Thr Gly Leu Asn Glu Arg Leu Asn Met Val Pro
    370                 375                 380

Met Lys Ala Val Asp Thr Asn Thr Val Ile Pro Asp Pro Phe Glu Leu
385                 390                 395                 400

Lys Ser Glu His Gly Glu Leu Val Lys Lys Thr Pro Glu Glu Val Ala
                405                 410                 415

Gln Asp Lys Ala Phe Val Lys Ser Glu Arg Ala Leu Leu Asn Gln Lys
            420                 425                 430

Lys Val Gln Gly Ser Ser Thr His Pro Val Gly Glu Leu Met Ala Tyr
        435                 440                 445

Ser Ala Phe Gly Gly Ser Gln Ala Val Arg Gln Met Leu Asn Asp Val
    450                 455                 460

His Gln Ile Asn Gly Gln Thr Leu Ser Ala Arg Ala Leu Ala Ser Gly
465                 470                 475                 480

Phe Gly Gly Ala Val Ser Ala Ser Ser Gln Thr Leu Leu Gln Leu Lys
                485                 490                 495

Ser Asn Tyr Val Asp Pro Gln Gly Arg Lys Ile Pro Val Phe Thr Pro
            500                 505                 510

Asp Arg Ala Glu Ser Asp Leu Lys Lys Asp Leu Leu Lys Gly Met Asp
        515                 520                 525

Leu Arg Glu Pro Ser Val Arg Thr Thr Phe Tyr Ser Lys Ala Leu Ser
    530                 535                 540

Gly Ile Gln Ser Ser Ala Leu Thr Ser Ala Leu Pro Pro Val Thr Ala
```

-continued

```
545                 550                 555                 560

Gln Ala Glu Gly Ala Ser Gly Thr Leu Ser Ala Gly Ala Ile Leu Arg
                565                 570                 575

Asn Met Ala Leu Ala Ala Thr Gly Ser Val Ser Tyr Leu Ser Thr Leu
            580                 585                 590

Tyr Thr Asn Gln Ser Val Thr Ala Glu Ala Lys Ala Leu Lys Ala Ala
        595                 600                 605

Gly Met Gly Gly Ala Thr Pro Met Leu Asp Arg Thr Glu Thr Leu
    610                 615                 620
```

The DNA molecule of ORF4 from the *Pseudomonas syringae* pv. *tomato* DC3000 CEL has a nucleotide sequence (SEQ. ID. No. 4) as follows:

```
atgaccaaca atgaccagta ccacaccctt atcaacgaaa tctgcgcact cagcctgatt       60

tccacacctg aacgtttcta tgaatctgcc aatttcaaaa tcagcgaagt ggacttcacc      120

ctgcagtttc aggaccgcga cgaaggccgt gccgttctga tctacggtga catgggcgcg      180

ttgcccgcgc gcggccgtga gagcgcgttg ctggcgttga tggacatcaa ctttcacatg      240

ttcgcgggcg cccacagccc ggcattttcc tttaatgcgc agaccggtcg tgtgctgctg      300

atgggctctg tggcccttga acgagcctct gccgaaggcg tgctgttgtt gatgaagtcg      360

ttttccgacc tggccaaaga gtggcgcgag catggattca tggggcaggc cacaactgca      420

ggctcctcga cggaccaacc tgttgcccca gcagccaaac gcgagagcct ttcggctcct      480

gggagattcc aatga                                                       495
```

The protein or polypeptide encoded by Pto DC3000 CEL ORF4 has an amino acid sequence (SEQ. ID. No. 5) as follows:

```
Met Thr Asn Asn Asp Gln Tyr His Thr Leu Ile Asn Glu Ile Cys Ala
  1               5                  10                  15

Leu Ser Leu Ile Ser Thr Pro Glu Arg Phe Tyr Glu Ser Ala Asn Phe
             20                  25                  30

Lys Ile Ser Glu Val Asp Phe Thr Leu Gln Phe Gln Asp Arg Asp Glu
         35                  40                  45

Gly Arg Ala Val Leu Ile Tyr Gly Asp Met Gly Ala Leu Pro Ala Arg
     50                  55                  60

Gly Arg Glu Ser Ala Leu Leu Ala Leu Met Asp Ile Asn Phe His Met
 65                  70                  75                  80

Phe Ala Gly Ala His Ser Pro Ala Phe Ser Phe Asn Ala Gln Thr Gly
                 85                  90                  95

Arg Val Leu Leu Met Gly Ser Val Ala Leu Glu Arg Ala Ser Ala Glu
            100                 105                 110

Gly Val Leu Leu Leu Met Lys Ser Phe Ser Asp Leu Ala Lys Glu Trp
        115                 120                 125

Arg Glu His Gly Phe Met Gly Gln Ala Thr Thr Ala Gly Ser Ser Thr
    130                 135                 140

Asp Gln Pro Val Ala Pro Ala Ala Lys Arg Glu Ser Leu Ser Ala Pro
145                 150                 155                 160

Gly Arg Phe Gln
```

The DNA molecule of ORF5 from the *Pseudomonas syringae* pv. *tomato* DC3000 CEL has a nucleotide sequence (SEQ. ID. No. 6) as follows:

```
atgcacatca accgacgcgt ccaacaaccg cctgtgactg cgacggatag ctttcggaca      60
gcgtccgacg cgtctcttgc ctccagctct gtgcgatctg tcagctccga tcagcaacgc     120
gagataaatg cgattgccga ttacctgaca gatcatgtgt tcgctgcgca taaactgccg     180
ccggccgatt cggctgatgg ccaagctgca gttgacgtac acaatgcgca gatcactgcg     240
ctgatcgaga cgcgcgccag ccgcctgcac ttcgaagggg aaaccccggc aaccatcgcc     300
gacaccttcg ccaaggcgga aaagctcgac cgattggcga cgactacatc aggcgcgttg     360
cgggcgacgc cctttgccat ggcctcgttg cttcagtaca tgcagcctgc gatcaacaag     420
ggcgattggc tgccggctcc gctcaaaccg ctgaccccgc tcatttccgg agcgctgtcg     480
ggcgccatgg accaggtggg caccaagatg atggaccgcg cgacgggtga tctgcattac     540
ctgagcgcct cgccggacag gctccacgat gcgatggccg cttcggtgaa gcgccactcg     600
ccaagccttg ctcgacaggt tctggacacg gggttgcgg ttcagacgta ctcggcgcgc      660
aacgccgtac gtaccgtatt ggctccggca ctggcgtcca gacccgccgt gcagggtgct     720
gtggaccttg gtgtatcgat ggcgggtggt ctggctgcca acgcaggctt tggcaaccgc     780
ctgctcagtg tgcagtcgcg tgatcaccag cgtggcggtg cattagtgct cggtttgaag     840
gataaagagc ccaaggctca actgagcgaa gaaaacgact ggctcgaggc ttataaagca     900
atcaaatcgg ccagctactc gggtgcggcg ctcaacgctg gcaagcggat ggccggtctg     960
ccactggata tggcgaccga cgcaatgggt gcggtaagaa gcctggtgtc agcgtccagc    1020
ctgacccaaa acggtctggc cctggcgggt ggctttgcag ggtaggcaa gttgcaggag     1080
atggcgacga aaaatatcac cgacccggcg accaaggccg cggtcagtca gttgaccaac    1140
ctggcaggtt cggcagccgt tttcgcaggc tggaccacgg ccgcgctgac aaccgatccc    1200
gcggtgaaaa aagccgagtc gttcatacag gacacggtga aatcgactgc atccagtacc    1260
acaggctacg tagccgacca gaccgtcaaa ctggcgaaga ccgtcaaaga catgggcggg    1320
gaggcgatca cccataccgg cgccagcttg cgcaatacgg tcaataacct gcgtcaacgc    1380
ccggctcgtg aagctgatat agaagagggg ggcacggcgg cttctccaag tgaaataccg    1440
tttcggccta tgcggtcgta a                                              1461
```

The protein or polypeptide encoded by Pto DC3000 CEL ORF5, now known as HopPtoA, has an amino acid sequence (SEQ. ID. No. 7) as follows:

```
Met His Ile Asn Arg Arg Val Gln Gln Pro Pro Val Thr Ala Thr Asp
  1               5                  10                  15

Ser Phe Arg Thr Ala Ser Asp Ala Ser Leu Ala Ser Ser Ser Val Arg
             20                  25                  30

Ser Val Ser Ser Asp Gln Gln Arg Glu Ile Asn Ala Ile Ala Asp Tyr
         35                  40                  45

Leu Thr Asp His Val Phe Ala Ala His Lys Leu Pro Pro Ala Asp Ser
     50                  55                  60

Ala Asp Gly Gln Ala Ala Val Asp Val His Asn Ala Gln Ile Thr Ala
 65                  70                  75                  80

Leu Ile Glu Thr Arg Ala Ser Arg Leu His Phe Glu Gly Glu Thr Pro
                 85                  90                  95

Ala Thr Ile Ala Asp Thr Phe Ala Lys Ala Glu Lys Leu Asp Arg Leu
```

-continued

```
            100                 105                 110

Ala Thr Thr Thr Ser Gly Ala Leu Arg Ala Thr Pro Phe Ala Met Ala
        115                 120                 125

Ser Leu Leu Gln Tyr Met Gln Pro Ala Ile Asn Lys Gly Asp Trp Leu
    130                 135                 140

Pro Ala Pro Leu Lys Pro Leu Thr Pro Leu Ile Ser Gly Ala Leu Ser
145                 150                 155                 160

Gly Ala Met Asp Gln Val Gly Thr Lys Met Met Asp Arg Ala Thr Gly
                165                 170                 175

Asp Leu His Tyr Leu Ser Ala Ser Pro Asp Arg Leu His Asp Ala Met
            180                 185                 190

Ala Ala Ser Val Lys Arg His Ser Pro Ser Leu Ala Arg Gln Val Leu
        195                 200                 205

Asp Thr Gly Val Ala Val Gln Thr Tyr Ser Ala Arg Asn Ala Val Arg
    210                 215                 220

Thr Val Leu Ala Pro Ala Leu Ala Ser Arg Pro Ala Val Gln Gly Ala
225                 230                 235                 240

Val Asp Leu Gly Val Ser Met Ala Gly Gly Leu Ala Ala Asn Ala Gly
                245                 250                 255

Phe Gly Asn Arg Leu Leu Ser Val Gln Ser Arg Asp His Gln Arg Gly
            260                 265                 270

Gly Ala Leu Val Leu Gly Leu Lys Asp Lys Glu Pro Lys Ala Gln Leu
        275                 280                 285

Ser Glu Glu Asn Asp Trp Leu Glu Ala Tyr Lys Ala Ile Lys Ser Ala
    290                 295                 300

Ser Tyr Ser Gly Ala Ala Leu Asn Ala Gly Lys Arg Met Ala Gly Leu
305                 310                 315                 320

Pro Leu Asp Met Ala Thr Asp Ala Met Gly Ala Val Arg Ser Leu Val
                325                 330                 335

Ser Ala Ser Ser Leu Thr Gln Asn Gly Leu Ala Leu Ala Gly Gly Phe
            340                 345                 350

Ala Gly Val Gly Lys Leu Gln Glu Met Ala Thr Lys Asn Ile Thr Asp
        355                 360                 365

Pro Ala Thr Lys Ala Ala Val Ser Gln Leu Thr Asn Leu Ala Gly Ser
    370                 375                 380

Ala Ala Val Phe Ala Gly Trp Thr Thr Ala Ala Leu Thr Thr Asp Pro
385                 390                 395                 400

Ala Val Lys Lys Ala Glu Ser Phe Ile Gln Asp Thr Val Lys Ser Thr
                405                 410                 415

Ala Ser Ser Thr Thr Gly Tyr Val Ala Asp Gln Thr Val Lys Leu Ala
            420                 425                 430

Lys Thr Val Lys Asp Met Gly Gly Glu Ala Ile Thr His Thr Gly Ala
        435                 440                 445

Ser Leu Arg Asn Thr Val Asn Asn Leu Arg Gln Arg Pro Ala Arg Glu
    450                 455                 460

Ala Asp Ile Glu Glu Gly Gly Thr Ala Ala Ser Pro Ser Glu Ile Pro
465                 470                 475                 480

Phe Arg Pro Met Arg Ser
                485
```

The DNA molecule of ORF6 from the *Pseudomonas syringae* pv. *tomato* DC3000 CEL has a nucleotide sequence (SEQ. ID. No. 8) as follows:

```
atgtctggtc ctttcgagaa aaaatggcgg tgtttcaccc gaaccgtgac ctacgttggc      60
tggtcgctgt tctggcttct gctctgggac gtggccgtca ccgtggacgt catgctgata     120
gaaggcaaag gcatcgactt ccccctgatg cccctcacgt tgctttgctc ggcactgatc     180
gtgctgatca gctttcgcaa ctcgagtgcc tataaccgtt ggtgggaagc gcgcaccttg     240
tggggcgcaa tggtcaacac ttcacgcagt tttggccggc aggtactgac gctgatcgat     300
ggcgaacggg atgacctcaa caaccctgtc aaagccatac tctttcaacg tcatgtggct     360
tacttgcgtg ccctgcgcgc gcacctcaaa ggcgacgtca aaacagcaaa actcgacggg     420
ttactgtcgc ccgacgagat tcagcgcgcc agccagagca acaacttccc caatgacatc     480
ctcaatggct ctgctgcggt tatctcgcaa gcctttgccg ccggccagtt cgacagcatc     540
cgtctgaccc gcctggaatc gaccatggtc gatctgtcca actgtcaggg cggcatggag     600
cgcatcgcca acacgccact gccctacccc tacgtttatt tcccacggct gttcagcacg     660
ctgttctgca tcctgatgcc gctgagcatg gtcaccaccc tgggctggtt caccccggcg     720
atctccacgg tggtaggctg catgctgctg gcaatggacc gcatcggtac agacctgcaa     780
gccccgttcg gcaacagtca gcaccggatc cgcatggaag acctgtgcaa caccatcgaa     840
aagaacctgc aatcgatgtt ctcttcgcca gagaggcagc cgctgctggc tgacctgaaa     900
agccccgtac cgtggcgcgt ggccaacgca tcaattggcg gtctgagcag gcagaaaaac     960
aggttagggg aaggcgcgag gcttatcgca agtgaaagtc tgctctgggc accatttcgc    1020
tcagttgcag acgttgctcc gtgccacgcc agtgcgtacc tacgtcgcgc ttga          1074
```

The protein or polypeptide encoded by Pto DC3000 CEL ORF6 has an amino acid sequence (SEQ. ID. No. 9) as follows:

```
Met Ser Gly Pro Phe Glu Lys Lys Trp Arg Cys Phe Thr Arg Thr Val
  1               5                  10                  15

Thr Tyr Val Gly Trp Ser Leu Phe Trp Leu Leu Leu Trp Asp Val Ala
             20                  25                  30

Val Thr Val Asp Val Met Leu Ile Glu Gly Lys Gly Ile Asp Phe Pro
         35                  40                  45

Leu Met Pro Leu Thr Leu Leu Cys Ser Ala Leu Ile Val Leu Ile Ser
     50                  55                  60

Phe Arg Asn Ser Ser Ala Tyr Asn Arg Trp Trp Glu Ala Arg Thr Leu
 65                  70                  75                  80

Trp Gly Ala Met Val Asn Thr Ser Arg Ser Phe Gly Arg Gln Val Leu
                 85                  90                  95

Thr Leu Ile Asp Gly Glu Arg Asp Asp Leu Asn Asn Pro Val Lys Ala
            100                 105                 110

Ile Leu Phe Gln Arg His Val Ala Tyr Leu Arg Ala Leu Arg Ala His
        115                 120                 125

Leu Lys Gly Asp Val Lys Thr Ala Lys Leu Asp Gly Leu Leu Ser Pro
    130                 135                 140

Asp Glu Ile Gln Arg Ala Ser Gln Ser Asn Asn Phe Pro Asn Asp Ile
145                 150                 155                 160

Leu Asn Gly Ser Ala Ala Val Ile Ser Gln Ala Phe Ala Ala Gly Gln
                165                 170                 175
```

-continued

```
Phe Asp Ser Ile Arg Leu Thr Arg Leu Glu Ser Thr Met Val Asp Leu
            180                 185                 190

Ser Asn Cys Gln Gly Gly Met Glu Arg Ile Ala Asn Thr Pro Leu Pro
        195                 200                 205

Tyr Pro Tyr Val Tyr Phe Pro Arg Leu Phe Ser Thr Leu Phe Cys Ile
    210                 215                 220

Leu Met Pro Leu Ser Met Val Thr Thr Leu Gly Trp Phe Thr Pro Ala
225                 230                 235                 240

Ile Ser Thr Val Val Gly Cys Met Leu Leu Ala Met Asp Arg Ile Gly
                245                 250                 255

Thr Asp Leu Gln Ala Pro Phe Gly Asn Ser Gln His Arg Ile Arg Met
            260                 265                 270

Glu Asp Leu Cys Asn Thr Ile Glu Lys Asn Leu Gln Ser Met Phe Ser
        275                 280                 285

Ser Pro Glu Arg Gln Pro Leu Leu Ala Asp Leu Lys Ser Pro Val Pro
    290                 295                 300

Trp Arg Val Ala Asn Ala Ser Ile Gly Gly Leu Ser Arg Gln Lys Asn
305                 310                 315                 320

Arg Leu Gly Glu Gly Ala Arg Leu Ile Ala Ser Glu Ser Leu Leu Trp
                325                 330                 335

Ala Pro Phe Arg Ser Val Ala Asp Val Ala Pro Cys His Ala Ser Ala
            340                 345                 350

Tyr Leu Arg Arg Ala
        355
```

The DNA molecule of ORF7 from the *Pseudomonas syringae* pv. *tomato* DC3000 CEL has a nucleotide sequence (SEQ. ID. No. 10) as follows:

```
atgtatatcc agcaatctgg cgcccaatca ggggttgccg ctaagacgca acacgataag      60

ccctcgtcat tgtccggact cgccccccggt tcgtcggatg cgttcgcccg ttttcatccc     120

gaaaaggcgg gcgcctttgt cccattggag gggcatgaag aggtcttttt cgatgcgcgc     180

tcttcctttt cgtcggtcga tgccgctgat cttcccagtc ccgagcaggt acaaccccag     240

cttcattcgt tgcgtaccct gctaccggat ctgatggtct ctatcgcctc attacgtgac     300

ggcgccacgc aatacatcaa gaccagaatc aaggctatgg cggacaacag cataggcgcg     360

actgcgaaca tcgaagccaa aagaaagatt gcccaagagc acggctgtca gcttgtccac     420

ccgtttcacc agagcaaatt tctatttgaa aaaactatcg atgatagagc gtttgctgct     480

gactatggcc gcgcgggtgg cgacgggcac gcttgtctgg ggctatcagt aaattggtgt     540

cagagccgtg caaaagggca gtcggatgag gccttctttc acaaactgga ggactatcag     600

ggcgatgcat tgctacccag ggtaatgggc ttccagcata tcgagcagca ggcctattca     660

aacaagttgc agaacgcagc acctatgctt ctggacacac ttcccaagtt gggcatgaca     720

cttggaaaag ggctgggcag agcacagcac gcgcactatg cggttgctct ggaaaacctt     780

gatcgcgatc tcaaagcagt gttgcagccc ggtaaagacc agatgcttct gtttttgagt     840

gatagccatg cgatggctct gcatcaggac agtcagggat gtctgcattt ttttgatcct     900

ctttttggcg tggttcaggc agacagcttc agcaacatga gccattttct tgctgatgtg     960

ttcaagcgcg acgtaggtac gcactggcgt ggcacggagc aacgtctgca actgagcgaa    1020

atggtgccca gagcagactt tcacttgcga taa                                1053
```

The protein or polypeptide encoded by Pto DC3000 CEL ORF7 has an amino acid sequence (SEQ. ID. No. 11) as follows:

```
Met Tyr Ile Gln Gln Ser Gly Ala Gln Ser Gly Val Ala Ala Lys Thr
  1               5                  10                  15

Gln His Asp Lys Pro Ser Ser Leu Ser Gly Leu Ala Pro Gly Ser Ser
             20                  25                  30

Asp Ala Phe Ala Arg Phe His Pro Glu Lys Ala Gly Ala Phe Val Pro
         35                  40                  45

Leu Glu Gly His Glu Glu Val Phe Phe Asp Ala Arg Ser Ser Phe Ser
     50                  55                  60

Ser Val Asp Ala Ala Asp Leu Pro Ser Pro Glu Gln Val Gln Pro Gln
 65                  70                  75                  80

Leu His Ser Leu Arg Thr Leu Leu Pro Asp Leu Met Val Ser Ile Ala
                 85                  90                  95

Ser Leu Arg Asp Gly Ala Thr Gln Tyr Ile Lys Thr Arg Ile Lys Ala
            100                 105                 110

Met Ala Asp Asn Ser Ile Gly Ala Thr Ala Asn Ile Glu Ala Lys Arg
        115                 120                 125

Lys Ile Ala Gln Glu His Gly Cys Gln Leu Val His Pro Phe His Gln
    130                 135                 140

Ser Lys Phe Leu Phe Glu Lys Thr Ile Asp Asp Arg Ala Phe Ala Ala
145                 150                 155                 160

Asp Tyr Gly Arg Ala Gly Gly Asp Gly His Ala Cys Leu Gly Leu Ser
                165                 170                 175

Val Asn Trp Cys Gln Ser Arg Ala Lys Gly Gln Ser Asp Glu Ala Phe
            180                 185                 190

Phe His Lys Leu Glu Asp Tyr Gln Gly Asp Ala Leu Leu Pro Arg Val
        195                 200                 205

Met Gly Phe Gln His Ile Glu Gln Gln Ala Tyr Ser Asn Lys Leu Gln
    210                 215                 220

Asn Ala Ala Pro Met Leu Leu Asp Thr Leu Pro Lys Leu Gly Met Thr
225                 230                 235                 240

Leu Gly Lys Gly Leu Gly Arg Ala Gln His Ala His Tyr Ala Val Ala
                245                 250                 255

Leu Glu Asn Leu Asp Arg Asp Leu Lys Ala Val Leu Gln Pro Gly Lys
            260                 265                 270

Asp Gln Met Leu Leu Phe Leu Ser Asp Ser His Ala Met Ala Leu His
        275                 280                 285

Gln Asp Ser Gln Gly Cys Leu His Phe Phe Asp Pro Leu Phe Gly Val
    290                 295                 300

Val Gln Ala Asp Ser Phe Ser Asn Met Ser His Phe Leu Ala Asp Val
305                 310                 315                 320

Phe Lys Arg Asp Val Gly Thr His Trp Arg Gly Thr Glu Gln Arg Leu
                325                 330                 335

Gln Leu Ser Glu Met Val Pro Arg Ala Asp Phe His Leu Arg
            340                 345                 350
```

The DNA molecule of ORF8 from the *Pseudomonas syringae* pv. *tomato* DC3000 CEL has a nucleotide sequence (SEQ. ID. No. 12) as follows:

```
atgcggcctg tcgaggcaaa agatcggctt tatcagtggc tgcgcaatcg aggcatcgat    60

gcgcaggagg gtcaacgcca caacgtaagg accgcgaatg gaagcgagtg tctgctctgg   120

ttgccagaac aggacacttc gttgttcatc ttcacacaga tcgaaaggct gacgatgccg   180
```

-continued

```
caggacaacg tcattttgat tctggcaatg gcgctgaatc tggagcctgc tcgcacaggt  240

ggcgctgcgc ttggctataa ccctgattca agggaactgt tgttgcgcag tgtgcactca  300

atggcggatc tggatgagac cggacttgat cacctcatga cgcgaattag cacattggcc  360

gtctcgttgc agcgctatct ggaagattat cgacgccagg agcaagccgg aaaaaccgcc  420

cagaaagagc ctcggttctt accggctgtc catctgaccc cacgaacgtt catgacctga  480
```

The protein or polypeptide encoded by Pto DC3000 CEL ORF8 has an amino acid sequence (SEQ. ID. No. 13) as follows:

```
Met Arg Pro Val Glu Ala Lys Asp Arg Leu Tyr Gln Trp Leu Arg Asn
  1               5                  10                  15

Arg Gly Ile Asp Ala Gln Glu Gly Gln Arg His Asn Val Arg Thr Ala
             20                  25                  30

Asn Gly Ser Glu Cys Leu Leu Trp Leu Pro Glu Gln Asp Thr Ser Leu
         35                  40                  45

Phe Ile Phe Thr Gln Ile Glu Arg Leu Thr Met Pro Gln Asp Asn Val
     50                  55                  60

Ile Leu Ile Leu Ala Met Ala Leu Asn Leu Glu Pro Ala Arg Thr Gly
 65                  70                  75                  80

Gly Ala Ala Leu Gly Tyr Asn Pro Asp Ser Arg Glu Leu Leu Leu Arg
                 85                  90                  95

Ser Val His Ser Met Ala Asp Leu Asp Glu Thr Gly Leu Asp His Leu
            100                 105                 110

Met Thr Arg Ile Ser Thr Leu Ala Val Ser Leu Gln Arg Tyr Leu Glu
        115                 120                 125

Asp Tyr Arg Arg Gln Glu Gln Ala Gly Lys Thr Ala Gln Lys Glu Pro
    130                 135                 140

Arg Phe Leu Pro Ala Val His Leu Thr Pro Arg Thr Phe Met Thr
145                 150                 155
```

The DNA molecule of ORF9 from the *Pseudomonas syringae* pv. *tomato* DC3000 CEL has a nucleotide sequence (SEQ. ID. No. 14) as follows:

```
atgcttaaaa aatgcctgct actggttata tcaatgtcac ttggcggctg ctggagcctg   60

atgattcatc tggacggcga gcgttgcatc tatcccggca ctcgccaagg ttgggcgtgg  120

ggaacccata acggagggca gagttggccc atacttatag acgtgccgtt ttccctcgcg  180

ttggacacac tgctgctgcc ctacgacctc accgcttttc tgcccgaaaa tcttggcggt  240

gatgaccgca aatgtcagtt cagtggagga ttgaacgtgc tcggttga               288
```

The protein or polypeptide encoded by Pto DC3000 CEL ORF9 has an amino acid sequence (SEQ. ID. No. 15) as follows:

```
Met Leu Lys Lys Cys Leu Leu Leu Val Ile Ser Met Ser Leu Gly Gly
  1               5                  10                  15

Cys Trp Ser Leu Met Ile His Leu Asp Gly Glu Arg Cys Ile Tyr Pro
             20                  25                  30
```

-continued

```
Gly Thr Arg Gln Gly Trp Ala Trp Gly Thr His Asn Gly Gly Gln Ser
        35                  40                  45

Trp Pro Ile Leu Ile Asp Val Pro Phe Ser Leu Ala Leu Asp Thr Leu
    50                  55                  60

Leu Leu Pro Tyr Asp Leu Thr Ala Phe Leu Pro Glu Asn Leu Gly Gly
65                  70                  75                  80

Asp Asp Arg Lys Cys Gln Phe Ser Gly Gly Leu Asn Val Leu Gly
                85                  90                  95
```

The DNA molecule of ORF10 from the *Pseudomonas syringae* pv. *tomato* DC3000 CEL has a nucleotide sequence (SEQ. ID. No. 16) as follows:

```
atgaaacagg tagaagtcca gatcattact gaattgcctt gtcaggttct gatcctggag   60

caagaggcag tagcagaggg cttcaggttt cttacccgct tgatcgagga gtggaggtcc  120

ggaaagaatc gattcgaggc caagggtgaa tgcctcatgg tcgtacttct ggacggcgct  180

ctggcaggta tcggaggcct ttcgcgtgat ccgcatgccc ggggtgatat gggcaggcta  240

cgacggttat acgtcgcaag cgcatcaaga ggtcaaggcc ttggaaagac tctggtgaat  300

cgacttgtgg agcatgcggc gcaggaattt ttcgccgtgc gcctgttcac tgatactccg  360

agcggagcaa aattttactt acgttgcggc tttcaggcag ttgacgaggt gcatgccacg  420

catataaagc ttttaaggcg ggtttga                                      447
```

The protein or polypeptide encoded by Pto DC3000 CEL ORF10 has an amino acid sequence (SEQ. ID. No. 17) as follows:

```
Met Lys Gln Val Glu Val Gln Ile Ile Thr Glu Leu Pro Cys Gln Val
  1               5                  10                  15

Leu Ile Leu Glu Gln Glu Ala Val Ala Glu Gly Phe Arg Phe Leu Thr
            20                  25                  30

Arg Leu Ile Glu Glu Trp Arg Ser Gly Lys Asn Arg Phe Glu Ala Lys
        35                  40                  45

Gly Glu Cys Leu Met Val Val Leu Leu Asp Gly Ala Leu Ala Gly Ile
    50                  55                  60

Gly Gly Leu Ser Arg Asp Pro His Ala Arg Gly Asp Met Gly Arg Leu
65                  70                  75                  80

Arg Arg Leu Tyr Val Ala Ser Ala Ser Arg Gly Gln Gly Leu Gly Lys
                85                  90                  95

Thr Leu Val Asn Arg Leu Val Glu His Ala Ala Gln Glu Phe Phe Ala
            100                 105                 110

Val Arg Leu Phe Thr Asp Thr Pro Ser Gly Ala Lys Phe Tyr Leu Arg
        115                 120                 125

Cys Gly Phe Gln Ala Val Asp Glu Val His Ala Thr His Ile Lys Leu
    130                 135                 140

Leu Arg Arg Val
145
```

A DNA molecule which contains the EEL of *Pseudomonas syringae* pv. *tomato* DC3000 has a nucleotide sequence (SEQ. ID. No. 18) as follows:

```
ggatccagcg gcgtattgtc gtggcgatgg aacgcgttac ggattttcag cacaccggta      60
tcgatgaaca ggtggccgtt gcgggcgttg cgggtcggca tgacacaatc gaacatatca     120
acgccacggc gcacaccttc gaccagatct tcgggcttgc ctacacccat caagtaacga     180
ggtttgtctg ctggcataag gcccggcagg taatccagca ccttgatcat ctcgtgcttg     240
ggctcgccca ccgacagacc gccaatcgcc aggccgtcaa agccgatctc atccaggcct     300
tcgagcgaac gcttgcgcag gttctcgtgc atgccaccct gaacaatgcc gaacagcgcg     360
gcagtgtttt cgccgtgcgc gaccttggag cgcttggccc agcgcaacga cagctccatg     420
gagacacgtg ctacgtcttc gtcggccggg tacggcgtgc actcatcgaa aatcatcacg     480
acgtccgaac ccaggtcacg ctggacctgc atcgactctt ccgggcccat gaacaccttg     540
gcaccatcga ccggagaggc gaaggtcacg ccctcctcct tgatcttgcg catggcgccc     600
aggctgaaca cctgaaaacc gccagagtcg gtcagaatcg gccctttcca ctgcatgaaa     660
tcgtgcaggt cgccgtggcc cttgatgacc tcggtgcccg gacgcagcca caagtggaag     720
gtgttgccca gaatcatctg cgcaccggtg gcctcgatat cacgcggcaa catgcccttg     780
accgtgccgt aggtgcccac cggcatgaac gccggggtct cgaccacgcc acgcggaaag     840
gtcaggcgac cgcgacgggc cttgccgtcg gtggccaaca actcgaaaga catacgacag     900
gtgcgactca tgcgtgatcc tctggtgccg attcctgtgg ggccgtcggc gcgggattgc     960
gggtgatgaa catggcatca ccgtaactga agaagcggta cccgtgttcg atggccgccg    1020
cgtaggccgc catggtttcg ggataaccgg cgaacgccga aaccagcatc aacagcgtgg    1080
attcaggcaa atgaaaatta gtcaccaggg catcgaccac atgaaacggc cgccccggat    1140
agatgaagat gtcggtgtcg ccgctaaacg gcttcaactg gccatcacgc gcggcactct    1200
ccagcgaacg cacgctggtg gtcccgaccg caatcacccg cccgccccgc gcacggcacg    1260
ccgccacggc atcgaccacg tcctggctga cttccagcca ttcgctgtgc atgtggtgat    1320
cttcgatctg ctcgacacgc accggctgga acgtacccgc gccgacgtgc agagtgacaa    1380
aagcagtctc gacgcccttg gcggcaattg cttccatcaa cggctggtcg aaatgcaggc    1440
cggcagtcgg cgccgccaca gcaccggcgc gctgggcgta aacggtctga taacgctcgc    1500
ggtcggcacc ttcgtccggg cggtctatat aaggaggcaa cggcatatgg ccgacacgat    1560
ccagcaacgg cagcacttct tcggcaaagc gcaactcgaa cagcgcgtca tgccgcgcca    1620
ccatctcggc ctcgccgccg ccatcgatca ggatcgacga gcccggcttt ggcgacttgc    1680
tggcacgcac gtgcgccagc acacgatggc tgtccagcac gcgctcgacc agaatctcca    1740
gcttgccgcc ggacgccttc tgcccgaaca aacgtgcggg aatgacacgg gtattgttga    1800
acaccatcaa gtcgcccgag cgcaaatgct cgagcaaatc ggtgaattga cgatgtgcca    1860
gcgcgcccgt cggcccatca agggtcaaca gacgactgct gcgacgctcg gccaacgggt    1920
gacgagcaat cagggaatcg gggagttcga aggtaaagtc agcgacgcgc atgatcgggt    1980
tcgtttagca gggccgggaa gtttatccgg tttgacggca ttagtaaaaa acctgcgtaa    2040
atccctgttg accaacggaa aactcatcct tatacttcgc cgccattgag ccctgatggc    2100
ggaattggta gacgcggcgg attcaaaatc cgttttcgaa agaagtggga gttcgattct    2160
ccctcggggc accaccattg agaaaagacc ttgaaattca aggtcttttt tttcgtctgg    2220
tggaaagtgg tctgactgag gctgcgatct accccacctg cccggaattg gccgcggagc    2280
gcccaggact gccttccagc gcagagcgtc ggtacccgga tcacacgacc aaggataacg    2340
ctatgaacaa gatcgtctac gtaaaagctt acttcaaacc cattggggag gaagtctcgg    2400
```

-continued

```
ttaaagtacc tacaggcgaa attaaaaagg gctttttcgg cgacaaggaa atcatgaaaa    2460
aagagaccca gtggcagcaa accgggtggt ctgattgtca gatagacggt gaacggctat    2520
cgaaagacgt cgaagacgca gtggcgcaac tcaatgctga cggttatgag attcaaacgg    2580
tattgcctat attgtccggg gcttatgatt atgcgctcaa ataccgatac gaaatacgtc    2640
acaatagaac tgaactaagc ccaggagacc agtcctatgt cttcggctat ggctacagct    2700
tcaccgaagg cgtgacgctg gtggcgaaaa aatttcagtc gtctgcaagc tgaataatag    2760
tgacctcgtg ccacggacgc cgctctgccc cctgatacga aaacgccttc ctcaacaaga    2820
ggcaggcgta ctaacgtgca caagacctgc ccgtatcagc aagcgcaaga cgctcgcctc    2880
cacgaaataa cacggtaggt cgcgttgcta ctttttagcg gcagacggcg tgccgttgta    2940
gttgtcggtg ttgttgtcgt tatcaagatc gcggtcattt ccaccgaaag ccgcatcggt    3000
tttgttgtcg ttgtcgagat ctttgtcgtt accgccaaac gctgcatccg tatggtgatc    3060
gttgtccagg tccttgtcgt tacccccaaa tgccgcgtcg gtgtggtggt cattgtccat    3120
atccttgtcg ttgccgccaa atgccgcgtc agtcacgttg tcgttatcca gatccttgtc    3180
gttgccgcca cacgtggcac cggtgctgtt gtcgttgtcc agatcacaat cgtttacggc    3240
aaatgcaggt agcgaagtgc caatgatcgt cagcgcaagc agaaagccgc cgatctttgc    3300
cgtcaggttt ttatacgcgc gcatcaggtt ttcccggata agtgaaaatg atgaagcaag    3360
ggttactgaa cacgttcgat cagtgactaa aacagtatgt aactgcagcc ttctgcaaga    3420
ccgacagagg tcgaccaaac tgcagcctgt ttcataccca tcaatttcta tagcgaccgt    3480
tcacacgact ctcctaccga tgctgggagt accaaaaaac ttccgcactg cattttttttg    3540
cagtgtcgga tggtttgacc ggttttgggg agaattgctc aaacggagaa cgatgagttt    3600
tttgttgcgt ggcatgctaa tcgatacatt tatcagtgtg tgatgcggta tggcagcttc    3660
atgcctccgt caaatagtgg acgccagtca cgttgcataa aacctgacgt cactccaaaa    3720
aaggctacgc acgaggacat tgctgagatt cggctgggca ttttcgctgt ttacacaggg    3780
atcgagcaga acgcccccat gccagccacc cgttaactca attgtctttt gccctgaaaa    3840
caacaatccc tggcttttcc gatacatagt ccagaaaagg caaatccatc acctttctgt    3900
tttcttttcg tgaagatgca tttcgcaaga cagggccttt atccgtcacg ataaagaaac    3960
cgacgtgtgt cacatccagc ccgggaagcg ggggtgtaaa tgccaatgta atcaccggtg    4020
cgcaggtggc tcaccacctg actgtcgaca aggcggctcg ggatatacgt catgctacgc    4080
tcaaccacag gcaaccctgg cagatagact ttgcctttgg ccctttcatt aaggcgtttt    4140
ctgacactta ccgcaccggg gcttatctgc gcggtaatgt catccgccac agggtatgcc    4200
gttccgtaag cccaatccgt gaaaaagtgc ttgcgattca aaaagtcaac atcgccaccc    4260
ttgtaacgaa cctgaacgag attcctcaca aaatcctgct gcgatgttga tcttcgaaac    4320
gcttcgacgt aatccagata agcaaaacaa tccagacctc tgaagtcgat gactaattgt    4380
tcaggtacat tcgctgagcc caccaacatg tttgagcggt acggtgttcc taaaaacgct    4440
cctgatacaa ggtcgatcag ctgaccttta ttcatataac ttttgttggt gcgggcttcc    4500
agcacagcat ccagtttttt tgaggtgtag gcatccagat ttagtttaac gggtgttttc    4560
atctctgcct gggcaccctg aatatcactt cccggcgccg gccccgaaac cccacaccct    4620
gccaacattg caaaggctaa agcccatagg gtcgtctttt gcatctgatt caccgtaatt    4680
ccaaagcgtc gtcggacctg attgtggctc gcgatacgcg agcaggctgc tccattcctt    4740
cgagatgccg cattggttag ctcaatcacg gcgcactatt taccacgtgt catcggttgc    4800
```

-continued

```
gtcatcggct gggagcatca gttggcaatg cattcgcggt ctcggcctca gcagacgctg    4860
gtagtgccca gagtgcagct gaccagcgtg ccgccatcga ggccgccgca gaggccgccc    4920
agcgatacgg attcgtttgc ggcaggggcc atgcccgcta ttgaatcggc tgactggccc    4980
gtgataaagg cctgatgcct cagtacgcca cctggcttac aggcgggttg cattgcaata    5040
ggtctatacc ttttgcaagg ttaacgaact gtcatcaaaa aacatggaag cacaatcaga    5100
aaaaagacct tgagtttcaa ggtctttttt cgtttggtga aaagtgatct gactcaaccc    5160
gcgatcttac cctcctctac tcgggttggc cgttagcacc caaagctacc ttcctgcgcg    5220
aatgcttgtt tcgttatggg catggcgtga tacaagcggt aggcgtacag caggtccatg    5280
agtctcggga acctgattga gagccgctct gcgctgtacc cccctggcct gagccactgt    5340
tcaaggcaac gcttccctga ccttgagcac cacttagctg ggcgccacca tcggcatgca    5400
ccaaaggcat ttgcagagag aggacagcaa agctggccaa tgcaatgaat tttgttttag    5460
agcagatatc tttaagtttc ataacaacca cctttgttga tcagaattgt tgaagaaatc    5520
atgagtcacg cttatgtgtg gcgactcatc gaaatcggtt ccaatgcaag atgggatttt    5580
tacgtccggc ctatccgctg atggcgatgc tgcggattca cctgatgcag aactggtttg    5640
attacagcga tccggcgatg gaggaagcac tttacgagac aacgatcctg cgccagttcg    5700
cagggttgag tctggatcga atcgccgatg aaaccacgat tctcaatttc cggcgcctgc    5760
tggaaaagca tgagttggca ggcgggattt tgcaggtcat caatggctat ctgggtgatc    5820
gaggtttgat gctgcgccaa ggtatggtgg tcgatgcgac gatcattcat gcgccgagct    5880
cgaccaagaa caaggacggc aaacgcgatc ccgaaatgca tcagacgaag aaaggaaacc    5940
agtatttctt cggcatgaaa gcgcatatcg gcgtcgatgc cgagtcgggt ttagtccata    6000
gcctggtggg tactgcggcg aatgtggcgg acgtgactca ggtcgatcaa ctgctgcaca    6060
gtgaggaaac ctatgtcagc ggtgatgcgg gctacaccgg cgtggacaag cgtgcggagc    6120
atcaggatcg ccagatgatc tggtcaattg cggcacgccc aagccgttat aaaaagcatg    6180
gcgagaaaag tttgatcgca cgggtctatc gcaaaatcga gttcacgaaa gcccagttgc    6240
gggcgaaggt tgaacatccg cttcgcgtga tcaagcgcca gtttggttat acgaaagtcc    6300
ggtttcgcgg gctggctaaa aacaccgcgc aacaggctac tctgtttgcc ttgtcgaacc    6360
tttggatggt gcgaaaacgg ctgctggcga tgggagaggt gcgcctgtaa tgcggaaaaa    6420
cgccttggaa aggtgctgtt tgaaggaaaa tcgatgagtt aacagcgcaa aaacgtctga    6480
ctatctgatc gggcgagttt ttttgaacct caggccatga aggcatcaaa aatcgatgct    6540
tacttcagac cttccttaac ctcagtagcg aggccggata aacgagtccc tttctatgat    6600
gctgtttcca gtaaactgac aaatttcatg cactgccgcc cgcgtgttca agcgctcaga    6660
ccttatagga aagcctcacg tctggattca gcttgccgcc gtagtttttc acattgatat    6720
cgacggtcgc tcgggacttg aggcccagat catcgatcac cagactgcgt accccatgca    6780
actctgccaa ccctgggact ccgtcacagg aagtggcgtg cgttgccccg acaaaagcga    6840
cccacttacc ttccggtttg ctcagcctta ttttttctgc tgcgtagtaa ttcatggctt    6900
gggcacgctt tatctcagct ttctccgggg ccatataggt ggacgttgta tccagcgaga    6960
caacgcgcaa cccggcgtgc ttggccgctt ccaccaaggt ggtgaagtta tatttcgtgt    7020
ggagctcttc cggggcctga tgaccctgac tctgcaaatc gaggtagttt ttcagcctgg    7080
caggcatcgg actgcctttg ggcgcgctca ggtaattatt gagcgccttg tcatgtgact    7140
cggcgcagag gtgctccata aaaagcgtgg tcacgccact ggccttcaag ctcttcatgt    7200
```

-continued

```
tattgatcag ttcacgcttg ctggacgttg aattgtgacc ctcaccaata acaagccccg    7260
gcgcatcacg taacagctcg cgcatgacac cgagactgtc cttgcttttc atcttcgtca    7320
acggcgccag ctcaggtaac ttttgcgcgt tgaaatcatc aaaataacgc gctgccttgg    7380
caatcagttt cttgtcatta ctgtcaggtg cccataaacc cttggacgtc cccagacaac    7440
tgtccatttc aaggtaattg agatttatat gaaggtggtc ccgaccttcc gagacaacaa    7500
cgtcggccag cttgagacct tgagcctcaa ggcgctgttc aagggcgtgc ttgccttctt    7560
gcaacaggat gctcacaaca tttgcagaca gttggctgct tttccccgct gcttttgagg    7620
gtgccagcgc ataggggtgc gggctctcac accagcgcgc gagctcggca agatcgctcg    7680
ccttgaagtt cgtatcctgc aatgctttgc tttgagctga agccgaggtc gaggccacgc    7740
tctggccgcc gtgcacatga ctgctgcctg ctgcgtccgg cttacgcctt ctggtgtgct    7800
ttacgccatc ctttccgcca ggctcctgcc cctcgatttt cagccggata ttttctacct    7860
tcatatccgg atagcgcccg gctggaaagc gcttcaggtc cccagcatt ggagtctctg    7920
gcgcaacgct ggctgctgga gaggaactgg cctgtgaaga tcgggcgcga tcgtttcctg    7980
cagcttgcgc agtgggacgc tcagcttcat aggttggcgg ataatagcct ggagccggtc    8040
caccgacggg tctcatgatt gaatctccgc gtacgaaaaa tagtgccgag cccgggcgtg    8100
acgctgcccg ggccccgaca tttcagtcaa tcaatgcgcc ttcgcaatcc cgaactgatc    8160
aagcaccgga tcaacgttat ggtcgaacgc cttctgcgcc ttatgctttt tcacagcatc    8220
aatgatcatg gaaataccga aacctaccgc cagggcgcca tcgattgccc agccgaccac    8280
tggaatcgcg gcgcctaggg cggcacctgc ggcaaggccg gtggcttcac cggcaaccat    8340
gccgacggcg cgaccgatca tctgtccgcc cagacgccct aggccggctg aggcttcgcg    8400
gcccatcatc ttcgccccgg cgtcgatgcc acctttaatg gcctcggcgc ccatcctcgt    8460
gctgtcgtaa atggcctggg ttgcgccaag cttgtcgcca tgagcgatca ggctggacac    8520
tgaagcaaag cccacgatcg agttgagcgc cttgccgccg acgcccgcct cggcgagctg    8580
agtcaacatg gacggtccgc cctcatcgct tttgccttcc agaagcttgc ggcctttttt    8640
ggagtcttgc agcgtaccca acgtgctgtt catgtagttt tcatgctgat tttcggtgaa    8700
atcaggggc agcacgctgt cgtaaatggc tttctggtta tcggcggttt gcagagactg    8760
gctggcatca gactttttct ggccaagcag ctgcttcagt gcaccgcctt cgctgaagtt    8820
ggtcacgtag gacgtggcaa tcttgtcttg cagatcgggt ttgttttcaa gcacctgatt    8880
ggtagtgggt actttggaat cggggaacag gtctttttgc agttgcaact gggcggacaa    8940
accgctgatg gcgccgctgt aatcggcatt cggattatgt ttgttgacgg ccttgtccgc    9000
cttgtccata tcagtctgca gcgcttgacc gctattgacg tttttcgtct gctcgacgac    9060
tgccttttgc agcgaggcat cactgcggac cagattgcgc tcctgctcgg gaatgctttt    9120
attgaggtac gcttgtacgt caggatcagc ctgtagctgg gaaatccggt cgttcaaacc    9180
ctgctcggtc ttgtcggtgt tgcgcaggct gcgcccggcg ataacgcttt gctgggtctg    9240
ctgcaacttg accatgacgg ccgctttctg tgcaccgctg taagacttgg gtttgtcgaa    9300
tacgtccttg tccagcttgc tgatatcaat cccggccacc gcattgagcg tcgcagaatc    9360
gctgagcatg ctggcgaact ggccgccgtt ggtgggtgcg cttttcttga tccactcact    9420
cagatttttc gcgtcgaaca tcttatcagg gctgtgcgca gccttcttgc gccccgacat    9480
gcccgcttcg tctacctgac ccaaaaagcc tggttgcgac caggtgctgc aggactgttt    9540
gagcgctccg gacaaccctg ggttactttg tgccaacccc ttcaggtctt ctgcgtcgac    9600
```

-continued

```
attaccgtca actttggtct tgtccgctgc atccactgca tgatgtgggt cggcagcaat    9660
cgccagtggc atattggctc gcatcactgc cgcgctgcgc accatttcca gtgactgcgg    9720
gtcagcgtcg gggttgtcct tggtgtagtt ggccaagtcc ttgtcggcac tgtctgcggc    9780
cttttccata ttttttgcga aggtcttgag atctttgttc gtgatcttgc catctgcgtt    9840
gccaccaccc tgagcaacgt ccacggcggt cttcagcgcc gggttggcgt tgatgaaatc    9900
catggccttg ccggcatcgg ggccatcatc acgcgccatc catgccgctg caatcgggcg    9960
attgagctct ttcgccgcct gctcgcgctc ttcgggcggc agatgggcaa ccatcggctc   10020
ccaacgtttc agagcttctg gcgaggagta ttcagaattg tcgagaaagg ctgcgtctgc   10080
ggctttgggg gcgttggaag cgtcggttgc atctgtgttc gtgggagctg cgacctgttc   10140
aaccggagcg gccggggcag tcgcttcagt cggtgaagcc tcggcaggag aatctgcgca   10200
gggttgcggc tggacctgat tattcacatt ggcattggca gctgccccgc cactgccctg   10260
gagcaaaaga gccaggatag acgacgcggt ctgctcggct cctgtcggcg cgccttgcgt   10320
gttgccggcc ggctgaccga actgcacgcc ggcttgccca ccgccaccca caggtgtcgg   10380
caaggctttg gcaagaggcg actcaacagc cagagccagt tcgccaggag tgggttggtt   10440
cacgataacg aagggagaac tggatatacg catggtgagt tgccatccga gagtgagcga   10500
tggcaactgt gtggttgaag gtgcaagttg gttccagaaa aaatgatcga gatcgccatt   10560
caggcgaacg ggtcgatttg ctgcttgagc tgaacccgcg cgcgggacag gcgtgagcga   10620
acggtgccaa tcggcacgcc gaggctgttc gctgtttcct gataattgcc gtccatctcc   10680
agcgacactt ccagcacttt ttgcatgttc gacggcaggc aatcaatggc ctgaatgact   10740
cgcgccagtt gccgatgccc ctctacctga tgactgacat caccgtgccc ttccagctcg   10800
gaatgcactt cgtcttccca gctttcctga tacggctgac gatacatttt gcggaagtga   10860
ttgcggatca ggttcagcgc gatgccacac agccaggtct gcggtttgct ggcatgttga   10920
aacttgtgct cgttacgcan ggcttcaaga aacacgcact ggagaatgtc atccacatca   10980
tcagggttca tacccgcttt ttggataaac gccctgagca tctgaatctg atcgggcggc   11040
atttggcgaa ataccgcgga cnaaaatggc tgacngggct gggttgagtc nangatcaca   11100
atcttttgaa acatgggctt accctgatta atggngtaca aaccctatag cgataaccat   11160
gccnncttaa aaaaanaaaa aactggntga tttatnaaaa aattttaaaa anngaaattt   11220
tttgtataca aaacttgggc naccgntttt gcccaaaact tttgggcaaa aanatnggan   11280
ctttcanggg antgatccng gaccgnaacc cttannggaa taatccggtt aaancggcta   11340
tnaaanagng ttccnctata tggnaaaatt cgggggccca cccnttngaa ccttttggna   11400
acccttcaa tgttgatttg ncaaataagg gattnnccca aaaggtttng ctttnggg     11458
```

Several undefined nucleotides exist in SEQ. ID. No. 18, however these appear to be present in intergenic regions. The EEL of *Pseudomonas syringae* pv. *tomato* DC3000 contains a number of ORFs. One of the products encoded by the EEL is a homolog of TnpA' from *P. stutzeri*. An additional four products are produced by ORF1-4, respectively. The nucleotide sequences for a number of these ORFs and their encoded protein or polypeptide products are provided below.

The DNA molecule of ORF1 from the *Pseudomonas syringae* pv. *tomato* DC3000 EEL has a nucleotide sequence (SEQ. ID. No. 19) as follows:

```
atgagacccg tcggtggacc ggctccaggc tattatccgc caacctatga agctgagcgt    60
cccactgcgc aagctgcagg aaacgatcgc gcccgatctt cacaggccag ttcctctcca   120
gcagccagcg ttgcgccaga gactccaatg ctgggggacc tgaagcgctt tccagccggg   180
```

-continued

```
cgctatccgg atatgaaggt agaaaatatc cggctgaaaa tcgaggggca ggagcctggc    240

ggaaaggatg gcgtaaagca caccagaagg cgtaagccgg acgcagcagg cagcagtcat    300

gtgcacggcg gccagagcgt ggcctcgacc tcggcttcag ctcaaagcaa agcattgcag    360

gatacgaact tcaaggcgag cgatcttgcc gagctcgcgc gctggtgtga gagcccgcac    420

ccctatgcgc tggcaccctc aaaagcagcg gggaaaagca gccaactgtc tgcaaatgtt    480

gtgagcatcc tgttgcaaga aggcaagcac gcccttgaac agcgccttga ggctcaaggt    540

ctcaagctgg ccgacgttgt tgtctcggaa ggtcgggacc accttcatat aaatctcaat    600

taccttgaaa tggacagttg tctggggacg tccaagggtt tatgggcacc tgacagtaat    660

gacaagaaac tgattgccaa ggcagcgcgt tattttgatg atttcaacgc gcaaaagtta    720

cctgagctgg cgccgttgac gaagatgaaa agcaaggaca gtctcggtgt catgcgcgag    780

ctgttacgtg atgcgccggg gcttgttatt ggtgagggtc acaattcaac gtccagcaag    840

cgtgaactga tcaataacat gaagagcttg aaggccagtg gcgtgaccac gctttttatg    900

gagcacctct gcgccgagtc acatgacaag gcgctcaata attacctgag cgcgcccaaa    960

ggcagtccga tgcctgccag gctgaaaaac tacctcgatt tgcagagtca gggtcatcag   1020

gccccggaag agctccacac gaaatataac ttcaccacct tggtggaagc ggccaagcac   1080

gccgggttgc gcgttgtctc gctggataca acgtccacct atatggcccc ggagaaagct   1140

gagataaagc gtgcccaagc catgaattac tacgcagcag aaaaaaataag gctgagcaaa   1200

ccggaaggta agtgggtcgc ttttgtcggg gcaacgcacg ccacttcctg tgacggagtc   1260

ccagggttgg cagagttgca tggggtacgc agtctggtga tcgatgatct gggcctcaag   1320

tcccgagcga ccgtcgatat caatgtgaaa aactacggcg gcaagctgaa tccagacgtg   1380

aggctttcct ataaggtctg a                                              1401
```

The protein or polypeptide encoded by Pto DC3000 EEL ORF1 has an amino acid sequence (SEQ. ID. No. 20) as follows:

```
Met Arg Pro Val Gly Gly Pro Ala Pro Gly Tyr Tyr Pro Pro Thr Tyr
  1               5                  10                  15

Glu Ala Glu Arg Pro Thr Ala Gln Ala Ala Gly Asn Asp Arg Ala Arg
             20                  25                  30

Ser Ser Gln Ala Ser Ser Ser Pro Ala Ala Ser Val Ala Pro Glu Thr
         35                  40                  45

Pro Met Leu Gly Asp Leu Lys Arg Phe Pro Ala Gly Arg Tyr Pro Asp
     50                  55                  60

Met Lys Val Glu Asn Ile Arg Leu Lys Ile Glu Gly Gln Glu Pro Gly
 65                  70                  75                  80

Gly Lys Asp Gly Val Lys His Thr Arg Arg Arg Lys Pro Asp Ala Ala
                 85                  90                  95

Gly Ser Ser His Val His Gly Gly Gln Ser Val Ala Ser Thr Ser Ala
            100                 105                 110

Ser Ala Gln Ser Lys Ala Leu Gln Asp Thr Asn Phe Lys Ala Ser Asp
        115                 120                 125

Leu Ala Glu Leu Ala Arg Trp Cys Glu Ser Pro His Pro Tyr Ala Leu
    130                 135                 140

Ala Pro Ser Lys Ala Ala Gly Lys Ser Ser Gln Leu Ser Ala Asn Val
145                 150                 155                 160
```

-continued

```
Val Ser Ile Leu Leu Gln Glu Gly Lys His Ala Leu Glu Gln Arg Leu
                165                 170                 175

Glu Ala Gln Gly Leu Lys Leu Ala Asp Val Val Val Ser Glu Gly Arg
            180                 185                 190

Asp His Leu His Ile Asn Leu Asn Tyr Leu Glu Met Asp Ser Cys Leu
        195                 200                 205

Gly Thr Ser Lys Gly Leu Trp Ala Pro Asp Ser Asn Asp Lys Lys Leu
    210                 215                 220

Ile Ala Lys Ala Ala Arg Tyr Phe Asp Asp Phe Asn Ala Gln Lys Leu
225                 230                 235                 240

Pro Glu Leu Ala Pro Leu Thr Lys Met Lys Ser Lys Asp Ser Leu Gly
                245                 250                 255

Val Met Arg Glu Leu Leu Arg Asp Ala Pro Gly Leu Val Ile Gly Glu
            260                 265                 270

Gly His Asn Ser Thr Ser Ser Lys Arg Glu Leu Ile Asn Asn Met Lys
        275                 280                 285

Ser Leu Lys Ala Ser Gly Val Thr Thr Leu Phe Met Glu His Leu Cys
    290                 295                 300

Ala Glu Ser His Asp Lys Ala Leu Asn Asn Tyr Leu Ser Ala Pro Lys
305                 310                 315                 320

Gly Ser Pro Met Pro Ala Arg Leu Lys Asn Tyr Leu Asp Leu Gln Ser
                325                 330                 335

Gln Gly His Gln Ala Pro Glu Glu Leu His Thr Lys Tyr Asn Phe Thr
            340                 345                 350

Thr Leu Val Glu Ala Ala Lys His Ala Gly Leu Arg Val Val Ser Leu
        355                 360                 365

Asp Thr Thr Ser Thr Tyr Met Ala Pro Glu Lys Ala Glu Ile Lys Arg
    370                 375                 380

Ala Gln Ala Met Asn Tyr Tyr Ala Ala Glu Lys Ile Arg Leu Ser Lys
385                 390                 395                 400

Pro Glu Gly Lys Trp Val Ala Phe Val Gly Ala Thr His Ala Thr Ser
                405                 410                 415

Cys Asp Gly Val Pro Gly Leu Ala Glu Leu His Gly Val Arg Ser Leu
            420                 425                 430

Val Ile Asp Asp Leu Gly Leu Lys Ser Arg Ala Thr Val Asp Ile Asn
        435                 440                 445

Val Lys Asn Tyr Gly Gly Lys Leu Asn Pro Asp Val Arg Leu Ser Tyr
    450                 455                 460

Lys Val
465
```

The DNA molecule of ORF2 from the *Pseudomonas syringae* pv. *tomato* DC3000 EEL has a nucleotide sequence (SEQ. ID. No. 21) as follows:

```
atgcaaaaga cgaccctatg ggctttagcc tttgcaatgt tggcagggtg tggggtttcg   60

gggccggcgc cgggaagtga tattcagggt gcccaggcag agatgaaaac acccgttaaa  120

ctaaatctgg atgcctacac ctcaaaaaaa ctggatgctg tgctggaagc ccgcaccaac  180

aaaagttata tgaataaagg tcagctgatc gaccttgtat caggagcgtt tttaggaaca  240

ccgtaccgct caaacatgtt ggtgggctca gcgaatgtac ctgaacaatt agtcatcgac  300

ttcagaggtc tggattgttt tgcttatctg gattacgtcg aagcgtttcg aagatcaaca  360
```

-continued

```
tcgcagcagg attttgtgag gaatctcgtt caggttcgtt acaagggtgg cgatgttgac  420

tttttgaatc gcaagcactt tttcacggat tgggcttacg gaacggcata ccctgtggcg  480

gatgacatta ccgcgcagat aagccccggt gcggtaagtg tcagaaaacg ccttaatgaa  540

agggccaaag gcaaagtcta tctgccaggg ttgcctgtgg ttgagcgtag catgacgtat  600

atcccgagcc gccttgtcga cagtcaggtg gtgagccacc tgcgcaccgg tgattacatt  660

ggcatttaca cccccgcttc ccgggctgga tgtgacacac gtcggtttct ttatcgtgac  720

ggataa                                                              726
```

The protein or polypeptide encoded by Pto DC3000 EEL ORF2 has amino acid sequence (SEQ. ID. No. 22) as follows:

```
Met Gln Lys Thr Thr Leu Trp Ala Leu Ala Phe Ala Met Leu Ala Gly
  1               5                  10                  15

Cys Gly Val Ser Gly Pro Ala Pro Gly Ser Asp Ile Gln Gly Ala Gln
             20                  25                  30

Ala Glu Met Lys Thr Pro Val Lys Leu Asn Leu Asp Ala Tyr Thr Ser
         35                  40                  45

Lys Lys Leu Asp Ala Val Leu Glu Ala Arg Thr Asn Lys Ser Tyr Met
     50                  55                  60

Asn Lys Gly Gln Leu Ile Asp Leu Val Ser Gly Ala Phe Leu Gly Thr
 65                  70                  75                  80

Pro Tyr Arg Ser Asn Met Leu Val Gly Ser Ala Asn Val Pro Glu Gln
                 85                  90                  95

Leu Val Ile Asp Phe Arg Gly Leu Asp Cys Phe Ala Tyr Leu Asp Tyr
            100                 105                 110

Val Glu Ala Phe Arg Arg Ser Thr Ser Gln Gln Asp Phe Val Arg Asn
        115                 120                 125

Leu Val Gln Val Arg Tyr Lys Gly Gly Asp Val Asp Phe Leu Asn Arg
    130                 135                 140

Lys His Phe Phe Thr Asp Trp Ala Tyr Gly Thr Ala Tyr Pro Val Ala
145                 150                 155                 160

Asp Asp Ile Thr Ala Gln Ile Ser Pro Gly Ala Val Ser Val Arg Lys
                165                 170                 175

Arg Leu Asn Glu Arg Ala Lys Gly Lys Val Tyr Leu Pro Gly Leu Pro
            180                 185                 190

Val Val Glu Arg Ser Met Thr Tyr Ile Pro Ser Arg Leu Val Asp Ser
        195                 200                 205

Gln Val Val Ser His Leu Arg Thr Gly Asp Tyr Ile Gly Ile Tyr Thr
    210                 215                 220

Pro Ala Ser Arg Ala Gly Cys Asp Thr Arg Arg Phe Leu Tyr Arg Asp
225                 230                 235                 240

Gly
```

The DNA molecule of ORF3 from the *Pseudomonas syringae* pv. *tomato* DC3000 EEL has a nucleotide sequence (SEQ. ID. No. 23) as follows:

```
atgcgcgcgt ataaaaacct gacggcaaag atcggcggct ttctgcttgc gctgacgatc   60

attggcactt cgctacctgc atttgccgta aacgattgtg atctggacaa cgacaacagc  120
```

-continued

```
accggtgcca cgtgtggcgg caacgacaag gatctggata acgacaacgt gactgacgcg  180

gcatttggcg gcaacgacaa ggatatggac aatgaccacc acaccgacgc ggcatttggg  240

ggtaacgaca aggacctgga caacgatcac catacggatg cagcgtttgg cggtaacgac  300

aaagatctcg acaacgacaa caaaaccgat gcggctttcg gtggaaatga ccgcgatctt  360

gataacgaca acaacaccga caactacaac ggcacgccgt ctgccgctaa aaagtag     417
```

The protein or polypeptide encoded by Pto DC3000 EEL ORF3 has an amino acid sequence (SEQ. ID. No. 24) as follows:

```
Met Arg Ala Tyr Lys Asn Leu Thr Ala Lys Ile Gly Gly Phe Leu Leu
  1               5                  10                  15

Ala Leu Thr Ile Ile Gly Thr Ser Leu Pro Ala Phe Ala Val Asn Asp
             20                  25                  30

Cys Asp Leu Asp Asn Asp Asn Ser Thr Gly Ala Thr Cys Gly Gly Asn
         35                  40                  45

Asp Lys Asp Leu Asp Asn Asp Asn Val Thr Asp Ala Ala Phe Gly Gly
     50                  55                  60

Asn Asp Lys Asp Met Asp Asn Asp His His Thr Asp Ala Ala Phe Gly
 65                  70                  75                  80

Gly Asn Asp Lys Asp Leu Asp Asn Asp His His Thr Asp Ala Ala Phe
                 85                  90                  95

Gly Gly Asn Asp Lys Asp Leu Asp Asn Asp Asn Lys Thr Asp Ala Ala
            100                 105                 110

Phe Gly Gly Asn Asp Arg Asp Leu Asp Asn Asp Asn Asn Thr Asp Asn
        115                 120                 125

Tyr Asn Gly Thr Pro Ser Ala Ala Lys Lys
    130                 135
```

*P.s. syringae* pv. *tomato* DC3000 EEL ORF3 has now been shown to significantly reduce virulence when mutated. Perhaps more interestingly, overexpression strongly increases lesion size. Hence, this effector is biologically active and appears to have a key role in symptom production.

The DNA molecule of ORF4 from the *Pseudomonas syringae* pv. *tomato* DC3000 EEL has a nucleotide sequence (SEQ. ID. No. 25) as follows:

```
atgaacaaga tcgtctacgt aaaagcttac ttcaaaccca ttggggagga agtctcggtt   60

aaagtaccta caggcgaaat taaaaagggc tttttcggcg acaaggaaat catgaaaaaa  120

gagacccagt ggcagcaaac cgggtggtct gattgtcaga tagacggtga acggctatcg  180

aaagacgtcg aagacgcagt ggcgcaactc aatgctgacg gttatgagat tcaaacggta  240

ttgcctatat tgtccggggc ttatgattat gcgctcaaat accgatacga aatacgtcac  300

aatagaactg aactaagccc aggagaccag tcctatgtct tcggctatgg ctacagcttc  360

accgaaggcg tgacgctggt ggcgaaaaaa tttcagtcgt ctgcaagctg a           411
```

The protein or polypeptide encoded by Pto DC3000 EEL ORF4 has an amino acid sequence (SEQ. ID. No. 26) as follows:

```
Met Asn Lys Ile Val Tyr Val Lys Ala Tyr Phe Lys Pro Ile Gly Glu
  1               5                  10                  15

Glu Val Ser Val Lys Val Pro Thr Gly Glu Ile Lys Lys Gly Phe Phe
             20                  25                  30

Gly Asp Lys Glu Ile Met Lys Lys Glu Thr Gln Trp Gln Gln Thr Gly
         35                  40                  45

Trp Ser Asp Cys Gln Ile Asp Gly Glu Arg Leu Ser Lys Asp Val Glu
     50                  55                  60

Asp Ala Val Ala Gln Leu Asn Ala Asp Gly Tyr Glu Ile Gln Thr Val
 65                  70                  75                  80

Leu Pro Ile Leu Ser Gly Ala Tyr Asp Tyr Ala Leu Lys Tyr Arg Tyr
                 85                  90                  95

Glu Ile Arg His Asn Arg Thr Glu Leu Ser Pro Gly Asp Gln Ser Tyr
            100                 105                 110

Val Phe Gly Tyr Gly Tyr Ser Phe Thr Glu Gly Val Thr Leu Val Ala
        115                 120                 125

Lys Lys Phe Gln Ser Ser Ala Ser
    130                 135
```

The EEL of *Pseudomonas syringae* pv. *syringae* B728a contains a number of ORFs. Two of the open reading frames appear to be mobile genetic elements without comparable homologs in EELs of other *Pseudomonas syringae* variants. An additional four products are produced by ORF1-2 and ORF5-6, respectively. The nucleotide sequences for a number of these ORFs and their encoded protein or polypeptide products are provided below.

The DNA molecule of ORF1 from the *Pseudomonas syringae* pv. *syringae* B728a EEL has a nucleotide sequence (SEQ. ID. No. 27) as follows:

```
atgggttgcg tatcgtcaaa agcatctgtc atttcttcgg acagctttcg cgcatcatat   60

acaaactctc cagaggcatc ctcagtccat caacgagcca ggacgccaag gtgcggtgag  120

cttcaggggc cccaagtgag cagattgatg ccttaccagc aggcgttagt aggtgtggcc  180

cgatggccta atccgcattt taacagggac gatgcgcccc accagatgga gtatggagaa  240

tcgttctacc ataaaagccg agagcttggt gcgtcggtcg ccaatggaga gatagaaacg  300

tttcaggagc tctggagtga agctcgtgat tggagagctt ccagagcagg ccaagatgct  360

cggcttttta gttcatcgcg tgatcccaac tcttcacggg cgtttgttac gcctataact  420

ggaccatacg aatttttaaa agatagattc gcaaaccgta aagatggaga aaagcataag  480

atgatggatt ttctcccaca cagcaatacg tttaggtttc atgggaaaat tgacggtgag  540

cgacttcctc tcacctggat ctcgataagt tctgatcgtc gtgccgacag aacaaaggat  600

ccttaccaaa ggttgcgcga ccaaggcatg aacgatgtgg gtgagcctaa tgtgatgttg  660

cacacccaag ccgagtatgt gcccaaaatt atgcaacatg tggagcatct ttataaggcc  720

gctacggatg ctgcattgtc cgatgccaat gcgctgaaaa aactcgcaga gatacattgg  780

tggacggtac aagctgttcc cgactttcgt ggaagtgcag ctaaggctga gctctgcgtg  840

cgctccattg cccaggcaag gggcatggac ctgccgccga tgagactcgg catcgtgccg  900

gatctggaag cgcttacgat gcctttgaaa gactttgtga aaagttacga agggttcttc  960

gaacataact ga                                                      972
```

The protein or polypeptide encoded by Psy B728a EEL ORF1 has an amino acid sequence (SEQ. ID. No. 28) as follows:

```
Met Gly Cys Val Ser Ser Lys Ala Ser Val Ile Ser Ser Asp Ser Phe
  1             5                  10                  15

Arg Ala Ser Tyr Thr Asn Ser Pro Glu Ala Ser Ser Val His Gln Arg
            20                  25                  30

Ala Arg Thr Pro Arg Cys Gly Glu Leu Gln Gly Pro Gln Val Ser Arg
        35                  40                  45

Leu Met Pro Tyr Gln Gln Ala Leu Val Gly Val Ala Arg Trp Pro Asn
    50                  55                  60

Pro His Phe Asn Arg Asp Asp Ala Pro His Gln Met Glu Tyr Gly Glu
 65                  70                  75                  80

Ser Phe Tyr His Lys Ser Arg Glu Leu Gly Ala Ser Val Ala Asn Gly
                85                  90                  95

Glu Ile Glu Thr Phe Gln Glu Leu Trp Ser Glu Ala Arg Asp Trp Arg
            100                 105                 110

Ala Ser Arg Ala Gly Gln Asp Ala Arg Leu Phe Ser Ser Ser Arg Asp
        115                 120                 125

Pro Asn Ser Ser Arg Ala Phe Val Thr Pro Ile Thr Gly Pro Tyr Glu
    130                 135                 140

Phe Leu Lys Asp Arg Phe Ala Asn Arg Lys Asp Gly Glu Lys His Lys
145                 150                 155                 160

Met Met Asp Phe Leu Pro His Ser Asn Thr Phe Arg Phe His Gly Lys
                165                 170                 175

Ile Asp Gly Glu Arg Leu Pro Leu Thr Trp Ile Ser Ile Ser Ser Asp
            180                 185                 190

Arg Arg Ala Asp Arg Thr Lys Asp Pro Tyr Gln Arg Leu Arg Asp Gln
        195                 200                 205

Gly Met Asn Asp Val Gly Glu Pro Asn Val Met Leu His Thr Gln Ala
    210                 215                 220

Glu Tyr Val Pro Lys Ile Met Gln His Val Glu His Leu Tyr Lys Ala
225                 230                 235                 240

Ala Thr Asp Ala Ala Leu Ser Asp Ala Asn Ala Leu Lys Lys Leu Ala
                245                 250                 255

Glu Ile His Trp Trp Thr Val Gln Ala Val Pro Asp Phe Arg Gly Ser
            260                 265                 270

Ala Ala Lys Ala Glu Leu Cys Val Arg Ser Ile Ala Gln Ala Arg Gly
        275                 280                 285

Met Asp Leu Pro Pro Met Arg Leu Gly Ile Val Pro Asp Leu Glu Ala
    290                 295                 300

Leu Thr Met Pro Leu Lys Asp Phe Val Lys Ser Tyr Glu Gly Phe Phe
305                 310                 315                 320

Glu His Asn
```

As indicated in Table 1 (see Example 2), the DNA molecule encoding this protein or polypeptide bears significant homology to the nucleotide sequence from *Pseudomonas syringae* pv. *phaseolicola* which encodes AvrPphC.

The DNA molecule of ORF2 from the *Pseudomonas syringae* pv. *syringae* B728a EEL has a nucleotide sequence (SEQ. ID. No. 29) as follows:

```
atgagaattc acagttccgg tcatggcatc tccggaccag tatcctctgc agaaaccgtt   60
gaaaaggccg tgcaatcatc ggcccaagcg cagaatgaag cgtctcacag cggtccatca  120
gaacatcctg aatcccgctc ctgtcaggca cgcccgaact acccttattc gtcagtcaaa  180
acacggttac cccctgttgc gtctgcaggg cagtcgctgt ctgagacacc ctcttcattg  240
cctggctacc tgctgttacg tcggcttgat cgtcgtccgc tggaccagga cgcaataaag  300
gggcttattc ctgctgatga agcagtgggc gaagcgcgcc gcgcgttgcc cttcggcagg  360
ggcaacattg atgtggatgc gcaacgctcc aacctggaaa gcggggcccg cacgctcgcc  420
gcaagacgcc tgagaaaaga cgccgagacg gcgggtcatg agccgatgcc cgagaacgaa  480
gacatgaact ggcatgtgct ggttgccatg tcgggtcagg tgttcggggc tggcaactgt  540
ggcgaacatg cccgtatagc gagctttgcc tacggtgcat cggctcagga aaaaggacgc  600
gctggcgatg aaaatattca tctggctgcg cagagcgggg aagatcatgt ctgggctgaa  660
acggatgatt ccagcgctgg ctcttcgcct attgtcatgg acccctggtc aaacggtcct  720
gccgtttttg cagaggacag tcggtttgct aaagataggc gcgcggtaga gcgaacggat  780
tcgttcacgc tttcaaccgc tgccaaagca ggcaagatta cacgagagac agccgagaag  840
gcgctgaccc aagcgaccag ccgtttgcag caacgtcttg ctgatcagca ggcgcaagtc  900
tcgccggttg aaggtggtcg ctatcggcaa gaaaactcgg tgcttgatga tgcgttcgcc  960
cgacgagtca gtgacatgtt gaacaatgcc gatccacggc gtgcattgca ggtggaaatc 1020
gaggcgtccg gagttgcaat gtcgctgggt gcccaaggcg tcaagacggt cgtccgacag 1080
gcgccaaaag tggtcaggca agccagaggc gtcgcatctg ctaaaggtat gtctccgcga 1140
gcaacctga                                                         1149
```

The protein or polypeptide encoded by psy B728a EEL ORF2 has an amino acid sequence (SEQ. ID. No. 30) as follows:

```
Met Arg Ile His Ser Ser Gly His Gly Ile Ser Gly Pro Val Ser Ser
  1               5                  10                  15

Ala Glu Thr Val Glu Lys Ala Val Gln Ser Ser Ala Gln Ala Gln Asn
             20                  25                  30

Glu Ala Ser His Ser Gly Pro Ser Glu His Pro Glu Ser Arg Ser Cys
         35                  40                  45

Gln Ala Arg Pro Asn Tyr Pro Tyr Ser Ser Val Lys Thr Arg Leu Pro
     50                  55                  60

Pro Val Ala Ser Ala Gly Gln Ser Leu Ser Glu Thr Pro Ser Ser Leu
 65                  70                  75                  80

Pro Gly Tyr Leu Leu Leu Arg Arg Leu Asp Arg Arg Pro Leu Asp Gln
                 85                  90                  95

Asp Ala Ile Lys Gly Leu Ile Pro Ala Asp Glu Ala Val Gly Glu Ala
            100                 105                 110

Arg Arg Ala Leu Pro Phe Gly Arg Gly Asn Ile Asp Val Asp Ala Gln
        115                 120                 125

Arg Ser Asn Leu Glu Ser Gly Ala Arg Thr Leu Ala Ala Arg Arg Leu
    130                 135                 140

Arg Lys Asp Ala Glu Thr Ala Gly His Glu Pro Met Pro Glu Asn Glu
145                 150                 155                 160

Asp Met Asn Trp His Val Leu Val Ala Met Ser Gly Gln Val Phe Gly
```

-continued

```
                165                 170                 175

Ala Gly Asn Cys Gly Glu His Ala Arg Ile Ala Ser Phe Ala Tyr Gly
            180                 185                 190

Ala Ser Ala Gln Glu Lys Gly Arg Ala Gly Asp Glu Asn Ile His Leu
        195                 200                 205

Ala Ala Gln Ser Gly Glu Asp His Val Trp Ala Glu Thr Asp Asp Ser
    210                 215                 220

Ser Ala Gly Ser Ser Pro Ile Val Met Asp Pro Trp Ser Asn Gly Pro
225                 230                 235                 240

Ala Val Phe Ala Glu Asp Ser Arg Phe Ala Lys Asp Arg Arg Ala Val
                245                 250                 255

Glu Arg Thr Asp Ser Phe Thr Leu Ser Thr Ala Ala Lys Ala Gly Lys
            260                 265                 270

Ile Thr Arg Glu Thr Ala Glu Lys Ala Leu Thr Gln Ala Thr Ser Arg
        275                 280                 285

Leu Gln Gln Arg Leu Ala Asp Gln Gln Ala Gln Val Ser Pro Val Glu
    290                 295                 300

Gly Gly Arg Tyr Arg Gln Glu Asn Ser Val Leu Asp Asp Ala Phe Ala
305                 310                 315                 320

Arg Arg Val Ser Asp Met Leu Asn Asn Ala Asp Pro Arg Arg Ala Leu
                325                 330                 335

Gln Val Glu Ile Glu Ala Ser Gly Val Ala Met Ser Leu Gly Ala Gln
            340                 345                 350

Gly Val Lys Thr Val Val Arg Gln Ala Pro Lys Val Val Arg Gln Ala
        355                 360                 365

Arg Gly Val Ala Ser Ala Lys Gly Met Ser Pro Arg Ala Thr
    370                 375                 380
```

As indicated in Table 1 (see Example 2), the DNA molecule encoding this protein or polypeptide bears significant homology to the nucleotide sequence from *Pseudomonas syringae* pv. *phaseolicola* which encodes AvrPphE.

The DNA molecule of ORF5 from the *Pseudomonas syringae* pv. *syringae* B728a EEL has a nucleotide sequence (SEQ. ID. No. 31) as follows:

```
atgaatatct caggtccgaa cagacgtcag gggactcagg cagagaacac tgaaagcgct      60

tcgtcatcat cggtaactaa cccaccgcta cagcgtggcg agggcagacg tctgcgacgt     120

caggatgcgc tgccaacgga tatcagatac aacgccaacc agacagcgac atcaccgcaa     180

aacgcgcgcg cggcaggaag atatgaatca ggggccagct catccggcgc gaatgatact     240

ccgcaggctg aaggttcaat gccttcgtcg tccgcccttt tacaatttcg cctcgccggc     300

gggcggaacc attctgagct ggaaaatttt catactatga tgctgaactc accgaaagca     360

tcacggggag atgctatacc tgagaagccc gaagcaatac ctaagcgcct actggagaag     420

atggaaccga ttaacctggc ccagttagct ttgcgtgata aggatctgca tgaatatgcc     480

gtaatggtct gtaaccaagt gaaaaagggt gaaggtccga actccaatat tacgcaagga     540

gatatcaagt tactgccgct gttcgccaaa gcggaaaata caagaaatcc cggcttgaat     600

ctgcatacat tcaaaagtca taaagactgt taccaggcga taaaagagca aaacagggat     660

attcaaaaaa acaagcaatc gctgagtatg cgggttgttt accccccatt caaaaagatg     720

ccagaccacc atatagcctt ggatatccaa ctgagatacg gccatcgacc gtcgattgtc     780
```

-continued

```
ggctttgagt ctgcccctgg gaacattata gatgctgcag aaagggaaat actttcagca     840

ttaggcaacg tcaaaatcaa aatggtagga aattttcttc aatactcgaa aactgactgc     900

accatgtttg cgcttaataa cgccctgaaa gcttttaaac atcacgaaga atataccgcc     960

cgtctgcaca atggagaaaa gcaggtgcct atcccggcga ccttcttgaa acatgctcag    1020

tcaaaaagct tagtggagaa tcacccggaa aaagatacca ccgtcactaa agaccagggc    1080

ggtctgcata tggaaacgct attacacaga aaccgtgcct accgggcgca acgatctgcc    1140

ggtcagcacg ttacctctat tgaaggtttc agaatgcagg aaataaagag agcaggtgac    1200

ttccttgccg caaacagggt ccgggccaag ccttga                              1236
```

The protein or polypeptide encoded by Psy B728a EEL ORF5 has an amino acid sequence (SEQ. ID. No. 32) as follows:

```
Met Asn Ile Ser Gly Pro Asn Arg Arg Gln Gly Thr Gln Ala Glu Asn
  1               5                  10                  15

Thr Glu Ser Ala Ser Ser Ser Ser Val Thr Asn Pro Pro Leu Gln Arg
             20                  25                  30

Gly Glu Gly Arg Arg Leu Arg Arg Gln Asp Ala Leu Pro Thr Asp Ile
         35                  40                  45

Arg Tyr Asn Ala Asn Gln Thr Ala Thr Ser Pro Gln Asn Ala Arg Ala
     50                  55                  60

Ala Gly Arg Tyr Glu Ser Gly Ala Ser Ser Ser Gly Ala Asn Asp Thr
 65                  70                  75                  80

Pro Gln Ala Glu Gly Ser Met Pro Ser Ser Ser Ala Leu Leu Gln Phe
                 85                  90                  95

Arg Leu Ala Gly Gly Arg Asn His Ser Glu Leu Glu Asn Phe His Thr
            100                 105                 110

Met Met Leu Asn Ser Pro Lys Ala Ser Arg Gly Asp Ala Ile Pro Glu
        115                 120                 125

Lys Pro Glu Ala Ile Pro Lys Arg Leu Leu Glu Lys Met Glu Pro Ile
    130                 135                 140

Asn Leu Ala Gln Leu Ala Leu Arg Asp Lys Asp Leu His Glu Tyr Ala
145                 150                 155                 160

Val Met Val Cys Asn Gln Val Lys Lys Gly Glu Gly Pro Asn Ser Asn
                165                 170                 175

Ile Thr Gln Gly Asp Ile Lys Leu Leu Pro Leu Phe Ala Lys Ala Glu
            180                 185                 190

Asn Thr Arg Asn Pro Gly Leu Asn Leu His Thr Phe Lys Ser His Lys
        195                 200                 205

Asp Cys Tyr Gln Ala Ile Lys Glu Gln Asn Arg Asp Ile Gln Lys Asn
    210                 215                 220

Lys Gln Ser Leu Ser Met Arg Val Val Tyr Pro Pro Phe Lys Lys Met
225                 230                 235                 240

Pro Asp His His Ile Ala Leu Asp Ile Gln Leu Arg Tyr Gly His Arg
                245                 250                 255

Pro Ser Ile Val Gly Phe Glu Ser Ala Pro Gly Asn Ile Ile Asp Ala
            260                 265                 270

Ala Glu Arg Glu Ile Leu Ser Ala Leu Gly Asn Val Lys Ile Lys Met
        275                 280                 285

Val Gly Asn Phe Leu Gln Tyr Ser Lys Thr Asp Cys Thr Met Phe Ala
    290                 295                 300
```

-continued

```
Leu Asn Asn Ala Leu Lys Ala Phe Lys His His Glu Glu Tyr Thr Ala
305                 310                 315                 320

Arg Leu His Asn Gly Glu Lys Gln Val Pro Ile Pro Ala Thr Phe Leu
                325                 330                 335

Lys His Ala Gln Ser Lys Ser Leu Val Glu Asn His Pro Glu Lys Asp
            340                 345                 350

Thr Thr Val Thr Lys Asp Gln Gly Gly Leu His Met Glu Thr Leu Leu
        355                 360                 365

His Arg Asn Arg Ala Tyr Arg Ala Gln Arg Ser Ala Gly Gln His Val
    370                 375                 380

Thr Ser Ile Glu Gly Phe Arg Met Gln Glu Ile Lys Arg Ala Gly Asp
385                 390                 395                 400

Phe Leu Ala Ala Asn Arg Val Arg Ala Lys Pro
                405                 410
```

The DNA molecule of ORF6 from the *pseudomonas syringae* pv. *syringae* B728a EEL has a nucleotide sequence (SEQ. ID. No. 33) as follows:

```
atgacgctgg aacggattga acagcaaaat acgctgtttg tttatctgtg cgtgggcacg    60

ctttctactc cagccagcag cacacttctg agcgatattc tggccgccaa cctctttcat   120

tatgggtcca gcgatggggc ggccttcggg ctggacgaaa aaaataatga agtgctgctt   180

tttcagcggt ttgatccgtt acggattgat gaggatcact ttgtcagcgc ctgcgttcag   240

atgatcgaag tggcgaaaat atggcgggca aagttactgc atggccattc tgctccgctc   300

gcctcctcaa ccaggctgac gaaagccggt ttaatgctaa ccatggcggg gactattcga   360

tga                                                                 363
```

The protein or polypeptide encoded by Psy B728a EEL ORF6 has an amino acid sequence (SEQ. ID. No. 34) as follows:

```
Met Thr Leu Glu Arg Ile Glu Gln Gln Asn Thr Leu Phe Val Tyr Leu
  1               5                  10                  15

Cys Val Gly Thr Leu Ser Thr Pro Ala Ser Ser Thr Leu Leu Ser Asp
             20                  25                  30

Ile Leu Ala Ala Asn Leu Phe His Tyr Gly Ser Ser Asp Gly Ala Ala
         35                  40                  45

Phe Gly Leu Asp Glu Lys Asn Asn Glu Val Leu Leu Phe Gln Arg Phe
     50                  55                  60

Asp Pro Leu Arg Ile Asp Glu Asp His Phe Val Ser Ala Cys Val Gln
 65                  70                  75                  80

Met Ile Glu Val Ala Lys Ile Trp Arg Ala Lys Leu Leu His Gly His
                 85                  90                  95

Ser Ala Pro Leu Ala Ser Ser Thr Arg Leu Thr Lys Ala Gly Leu Met
            100                 105                 110

Leu Thr Met Ala Gly Thr Ile Arg
        115                 120
```

The EEL of *Pseudomonas syringae* pv. *syringae* 61 contains a number of ORFs. One of the open reading frames encodes the outer membrane protein HopPsyA. The DNA molecule which encodes HopPsyA has a nucleotide sequence (SEQ. ID. No. 35) as follows:

```
gtgaacccta tccatgcacg cttctccagc gtagaagcgc tcagacattc aaacgttgat     60

attcaggcaa tcaaatccga gggtcagttg gaagtcaacg gcaagcgtta cgagattcgt    120

gcggccgctg acggctcaat cgcggtcctc agacccgatc aacagtccaa agcagacaag    180

ttcttcaaag gcgcagcgca tcttattggc ggacaaagcc agcgtgccca aatagcccag    240

gtactcaacg agaaagcggc ggcagttcca cgcctggaca gaatgttggg cagacgcttc    300

gatctggaga agggcggaag tagcgctgtg ggcgccgcaa tcaaggctgc cgacagccga    360

ctgacatcaa aacagacatt tgccagcttc cagcaatggg ctgaaaaagc tgaggcgctc    420

gggcgatacc gaaatcggta tctacatgat ctacaagagg gacacgccag acacaacgcc    480

tatgaatgcg gcagagtcaa gaacattacc tggaaacgct acaggctctc gataacaaga    540

aaaaccttat catacgcccc gcagatccat gatgatcggg aagaggaaga gcttgatctg    600

ggccgataca tcgctgaaga cagaaatgcc agaaccggct tttttagaat ggttcctaaa    660

gaccaacgcg cacctgagac aaactcggga cgacttacca ttggtgtaga acctaaatat    720

ggagcgcagt tggccctcgc aatggcaacc ctgatggaca agcacaaatc tgtgacacaa    780

ggtaaagtcg tcggtccggc aaaatatggc cagcaaactg actctgccat tctttacata    840

aatggtgatc ttgcaaaagc agtaaaactg ggcgaaaagc tgaaaaagct gagcggtatc    900

cctcctgaag gattcgtcga acatacaccg ctaagcatgc agtcgacggg tctcggtctt    960

tcttatgccg agtcggttga agggcagcct tccagccacg gacaggcgag aacacacgtt   1020

atcatggatg ccttgaaagg ccagggcccc atggagaaca gactcaaaat ggcgctggca   1080

gaaagaggct atgacccgga aaatccggcg ctcagggcgc gaaactga                1128
```

HopPsyA has an amino acid sequence (SEQ. ID. No. 36) as follows:

```
Val Asn Pro Ile His Ala Arg Phe Ser Ser Val Glu Ala Leu Arg His
  1               5                  10                  15

Ser Asn Val Asp Ile Gln Ala Ile Lys Ser Glu Gly Gln Leu Glu Val
             20                  25                  30

Asn Gly Lys Arg Tyr Glu Ile Arg Ala Ala Ala Asp Gly Ser Ile Ala
         35                  40                  45

Val Leu Arg Pro Asp Gln Gln Ser Lys Ala Asp Lys Phe Phe Lys Gly
     50                  55                  60

Ala Ala His Leu Ile Gly Gly Gln Ser Gln Arg Ala Gln Ile Ala Gln
 65                  70                  75                  80

Val Leu Asn Glu Lys Ala Ala Ala Val Pro Arg Leu Asp Arg Met Leu
                 85                  90                  95

Gly Arg Arg Phe Asp Leu Glu Lys Gly Gly Ser Ser Ala Val Gly Ala
            100                 105                 110

Ala Ile Lys Ala Ala Asp Ser Arg Leu Thr Ser Lys Gln Thr Phe Ala
        115                 120                 125

Ser Phe Gln Gln Trp Ala Glu Lys Ala Glu Ala Leu Gly Arg Tyr Arg
    130                 135                 140

Asn Arg Tyr Leu His Asp Leu Gln Glu Gly His Ala Arg His Asn Ala
```

-continued

```
145                 150                 155                 160

Tyr Glu Cys Gly Arg Val Lys Asn Ile Thr Trp Lys Arg Tyr Arg Leu
                165                 170                 175

Ser Ile Thr Arg Lys Thr Leu Ser Tyr Ala Pro Gln Ile His Asp Asp
            180                 185                 190

Arg Glu Glu Glu Glu Leu Asp Leu Gly Arg Tyr Ile Ala Glu Asp Arg
        195                 200                 205

Asn Ala Arg Thr Gly Phe Phe Arg Met Val Pro Lys Asp Gln Arg Ala
    210                 215                 220

Pro Glu Thr Asn Ser Gly Arg Leu Thr Ile Gly Val Glu Pro Lys Tyr
225                 230                 235                 240

Gly Ala Gln Leu Ala Leu Ala Met Ala Thr Leu Met Asp Lys His Lys
                245                 250                 255

Ser Val Thr Gln Gly Lys Val Val Gly Pro Ala Lys Tyr Gly Gln Gln
            260                 265                 270

Thr Asp Ser Ala Ile Leu Tyr Ile Asn Gly Asp Leu Ala Lys Ala Val
        275                 280                 285

Lys Leu Gly Glu Lys Leu Lys Lys Leu Ser Gly Ile Pro Pro Glu Gly
    290                 295                 300

Phe Val Glu His Thr Pro Leu Ser Met Gln Ser Thr Gly Leu Gly Leu
305                 310                 315                 320

Ser Tyr Ala Glu Ser Val Glu Gly Gln Pro Ser Ser His Gly Gln Ala
                325                 330                 335

Arg Thr His Val Ile Met Asp Ala Leu Lys Gly Gln Gly Pro Met Glu
            340                 345                 350

Asn Arg Leu Lys Met Ala Leu Ala Glu Arg Gly Tyr Asp Pro Glu Asn
        355                 360                 365

Pro Ala Leu Arg Ala Arg Asn
    370                 375
```

The remaining open reading frame, designated shcA, is a DNA molecule having a nucleotide sequence (SEQ. ID. No. 37) as follows:

```
atggagatgc ccgccttggc gtttgacgat aagggtgcgt gcaacatgat catcgacaag   60

gcattcgctc tgacgctgtt gcgcgacgac acgcatcaac gtttgttgct gattggtctg  120

cttgagccac acgaggatct acccttgcag cgcctgttgg ctggcgctct caaccccctt  180

gtgaatgccg gccccggcat tggctgggat gagcaaagcg gcctgtacca cgcttaccaa  240

agcatcccgc gggaaaaagt cagcgtggag atgctgaagc tcgaaattgc aggattggtc  300

gaatggatga agtgttggcg agaagcccgc acgtga                            336
```

The encoded protein or polypeptide, ShcA, has an amino acid sequence (SEQ. ID. No. 38) as follows:

```
Met Glu Met Pro Ala Leu Ala Phe Asp Asp Lys Gly Ala Cys Asn Met
  1               5                  10                  15

Ile Ile Asp Lys Ala Phe Ala Leu Thr Leu Leu Arg Asp Asp Thr His
            20                  25                  30

Gln Arg Leu Leu Leu Ile Gly Leu Leu Glu Pro His Glu Asp Leu Pro
        35                  40                  45

Leu Gln Arg Leu Leu Ala Gly Ala Leu Asn Pro Leu Val Asn Ala Gly
     50                  55                  60
```

-continued

```
Pro Gly Ile Gly Trp Asp Glu Gln Ser Gly Leu Tyr His Ala Tyr Gln
 65                 70                  75                  80

Ser Ile Pro Arg Glu Lys Val Ser Val Glu Met Leu Lys Leu Glu Ile
                85                  90                  95

Ala Gly Leu Val Glu Trp Met Lys Cys Trp Arg Glu Ala Arg Thr
            100                 105                 110
```

In addition to the above DNA molecules and proteins or polypeptides, the present invention also relates to homologs of various DNA molecules of the present invention which have been isolated from other *Pseudomonas syringae* pathovars. For example, a number of AvrPphE, AvrPphF, and HopPsyA homologs have been identified from *Pseudomonas syringae* pathovars.

The DNA molecule from *Pseudomonas syringae* pv. *angulata* which encodes an AvrPphE homolog has a nucleotide sequence (SEQ. ID. No. 39) as follows:

```
atgagaattc acagtgctgg tcacagcctg cctgcgccag gccctagcgt ggaaaccact    60

gaaaaggctg ttcaatcatc atcggcccag aaccccgctt cttacagttc acaaacagaa   120

cgtcctgaag ccggttcgac tcaagtgcga ctgaactacc cttactcatc agtcaagaca   180

cgcttgccac ccgtttcttc tacagggcag gccatttctg ccacgccatc ttcattgccc   240

ggttacctgc tgttacgtcg gctcgaccga cgtccactgg atgaagacag tatcaaggct   300

ctggttccgg cagacgaagc ggtgcgtgaa gcacgccgcg cgttgccctt cggcaggggc   360

aacattgatg tggatgcaca acgtacccac ctgcaaagcg gcgctcgcgc agtcgctgca   420

aagcgcttga gaaaagatgc cgagcgcgct ggccatgagc cgatgcccgg gaatgatgag   480

atgaactggc atgttcttgt cgccatgtca gggcaggtgt ttggcgctgg caactgtggc   540

gaacatgctc gtatagcaag cttcgcttac ggggccctgg ctcaggaaag cgggcgtagt   600

ccccgcgaaa agattcattt ggccgagcag cccggaaaag atcacgtctg ggctgaaacg   660

gataattcca gcgctggctc ttcgcccatc gtcatggacc cgtggtctaa cggcgcagcc   720

attttggcgg aggacagccg gtttgccaaa gatcgcagta cggtagagcg aacatattca   780

ttcacccttg caatggcagc tgaagccggc aaggttacgc gtgaaaccgc cgagaacgtt   840

ctgacccaca cgacaagccg tctgcagaaa cgtcttgctg atcagttgcc gaacgtctca   900

ccgcttgaag gaggccgcta tcagcaggaa aagtcggtgc ttgatgaggc gttcgcccga   960

cgagtgagcg acaagttgaa tagtgacgat ccacggcgtg cgttgcagat ggaaattgaa  1020

gctgttggtg ttgcaatgtc gctgggtgcc gaaggcgtca agacggtcgc ccgacaggcg  1080

ccaaaggtgg tcaggcaagc cagaagcgtc gcgtcgtcta aaggcatgcc tccacgaaga  1140

taa                                                                1143
```

The amino acid sequence (SEQ. ID. No. 40) for the AvrPphE homolog of *Pseudomonas syringae* pv. *angulata* is as follows:

```
Met Arg Ile His Ser Ala Gly His Ser Leu Pro Ala Pro Gly Pro Ser
 1               5                  10                  15

Val Glu Thr Thr Glu Lys Ala Val Gln Ser Ser Ser Ala Gln Asn Pro
            20                  25                  30

Ala Ser Tyr Ser Ser Gln Thr Glu Arg Pro Glu Ala Gly Ser Thr Gln
        35                  40                  45

Val Arg Leu Asn Tyr Pro Tyr Ser Ser Val Lys Thr Arg Leu Pro Pro
    50                  55                  60
```

-continued

```
Val Ser Ser Thr Gly Gln Ala Ile Ser Ala Thr Pro Ser Ser Leu Pro
 65                  70                  75                  80

Gly Tyr Leu Leu Leu Arg Arg Leu Asp Arg Arg Pro Leu Asp Glu Asp
                 85                  90                  95

Ser Ile Lys Ala Leu Val Pro Ala Asp Glu Ala Val Arg Glu Ala Arg
            100                 105                 110

Arg Ala Leu Pro Phe Gly Arg Gly Asn Ile Asp Val Asp Ala Gln Arg
        115                 120                 125

Thr His Leu Gln Ser Gly Ala Arg Ala Val Ala Ala Lys Arg Leu Arg
    130                 135                 140

Lys Asp Ala Glu Arg Ala Gly His Glu Pro Met Pro Gly Asn Asp Glu
145                 150                 155                 160

Met Asn Trp His Val Leu Val Ala Met Ser Gly Gln Val Phe Gly Ala
                165                 170                 175

Gly Asn Cys Gly Glu His Ala Arg Ile Ala Ser Phe Ala Tyr Gly Ala
            180                 185                 190

Leu Ala Gln Glu Ser Gly Arg Ser Pro Arg Glu Lys Ile His Leu Ala
        195                 200                 205

Glu Gln Pro Gly Lys Asp His Val Trp Ala Glu Thr Asp Asn Ser Ser
    210                 215                 220

Ala Gly Ser Ser Pro Ile Val Met Asp Pro Trp Ser Asn Gly Ala Ala
225                 230                 235                 240

Ile Leu Ala Glu Asp Ser Arg Phe Ala Lys Asp Arg Ser Thr Val Glu
                245                 250                 255

Arg Thr Tyr Ser Phe Thr Leu Ala Met Ala Ala Glu Ala Gly Lys Val
            260                 265                 270

Thr Arg Glu Thr Ala Glu Asn Val Leu Thr His Thr Thr Ser Arg Leu
        275                 280                 285

Gln Lys Arg Leu Ala Asp Gln Leu Pro Asn Val Ser Pro Leu Glu Gly
    290                 295                 300

Gly Arg Tyr Gln Gln Glu Lys Ser Val Leu Asp Glu Ala Phe Ala Arg
305                 310                 315                 320

Arg Val Ser Asp Lys Leu Asn Ser Asp Asp Pro Arg Arg Ala Leu Gln
                325                 330                 335

Met Glu Ile Glu Ala Val Gly Val Ala Met Ser Leu Gly Ala Glu Gly
            340                 345                 350

Val Lys Thr Val Ala Arg Gln Ala Pro Lys Val Val Arg Gln Ala Arg
        355                 360                 365

Ser Val Ala Ser Ser Lys Gly Met Pro Pro Arg Arg
    370                 375                 380
```

This protein or polypeptide has GC content of about 57 percent, an estimated isoelectric point of about 9.5, and an estimated molecular weight of about 41 kDa.

The DNA molecule from *Pseudomonas syringae* pv. *glycinea* which encodes an AvrPphE homolog has a nucleotide sequence (SEQ. ID. No. 41) as follows:

```
atgagaattc acagtgctgg tcacagcctg cccgcgccag gccctagcgt ggaaaccact      60

gaaaaggctg ttcaatcatc atcggcccag aaccccgctt cttgcagttc acaaacagaa     120

cgtcctgaag ccggttcgac tcaagtgcga ccgaactacc cttactcatc agtcaagaca     180

cgcttgccac ccgtttcttc cacagggcag gccatttctg acacgccatc ttcattgtcc     240

ggttacctgc tgttacgtcg gctcgaccga cgtccactgg atgaagacag tatcaaggct     300

ctggttccgg cagacgaagc gttgcgtgaa gcacgccgcg cgttgccctt cggcaggggc     360
```

-continued aacattgatg tggatgcaca acgtacccac ctgcaaagcg gcgctcgcgc agtcgctgca 420
aagcgcttga gaaaagatgc cgagcgcgct ggccatgagc cgatgcccga gaatgatgag 480
atgaactggc atgttcttgt cgccatgtca gggcaggtgt ttggcgctgg caactgtggc 540
gaacatgctc gtatagcaag cttcgcttac ggggccctgg ctcaggaaag cgggcgtagt 600
ccccgcgaaa agattcattt ggccgagcag cccggaaaag atcacgtctg ggctgaaacg 660
gataattcca gcgctggctc ttcgcccatc gtcatggacc cgtggtctaa cggcgtagcc 720
attttggcgg aggacagccg gtttgccaaa gatcgcagtg cggtagagcg aacatattca 780
ttcacccttg caatggcagc tgaagccggc aaggttgcgc gtgaaaccgc cgagaacgtt 840
ctgacccaca cgacaagccg tctgcagaaa cgtcttgctg atcagttgcc gaacgtctca 900
ccgcttgaag gaggccgcta tcagccggaa aagtcggtgc ttgatgaggc gttcgcccga 960
cgagtgagcg acaagttgaa tagtgacgat ccacggcgtg cgttgcagat ggaaattgaa 1020
gctgttggtg ttgcaatgtc gctgggtgcc gaaggcgtca agacggtcgc ccgacaggcg 1080
ccaaaggtgg tcaggcaagc cagaagcgtc gcgtcgtcta aaggcatgcc tccacgaaga 1140
taa 1143

The amino acid sequence (SEQ. ID. No. 42) for the AvrPphE homolog of *Pseudomonas syringae* pv. *glycinea* is as follows:

Met Arg Ile His Ser Ala Gly His Ser Leu Pro Ala Pro Gly Pro Ser
1 5 10 15

Val Glu Thr Thr Glu Lys Ala Val Gln Ser Ser Ser Ala Gln Asn Pro
20 25 30

Ala Ser Cys Ser Ser Gln Thr Glu Arg Pro Glu Ala Gly Ser Thr Gln
35 40 45

Val Arg Pro Asn Tyr Pro Tyr Ser Ser Val Lys Thr Arg Leu Pro Pro
50 55 60

Val Ser Ser Thr Gly Gln Ala Ile Ser Asp Thr Pro Ser Ser Leu Ser
65 70 75 80

Gly Tyr Leu Leu Leu Arg Arg Leu Asp Arg Arg Pro Leu Asp Glu Asp
85 90 95

Ser Ile Lys Ala Leu Val Pro Ala Asp Glu Ala Leu Arg Glu Ala Arg
100 105 110

Arg Ala Leu Pro Phe Gly Arg Gly Asn Ile Asp Val Asp Ala Gln Arg
115 120 125

Thr His Leu Gln Ser Gly Ala Arg Ala Val Ala Ala Lys Arg Leu Arg
130 135 140

Lys Asp Ala Glu Arg Ala Gly His Glu Pro Met Pro Glu Asn Asp Glu
145 150 155 160

Met Asn Trp His Val Leu Val Ala Met Ser Gly Gln Val Phe Gly Ala
165 170 175

Gly Asn Cys Gly Glu His Ala Arg Ile Ala Ser Phe Ala Tyr Gly Ala
180 185 190

Leu Ala Gln Glu Ser Gly Arg Ser Pro Arg Glu Lys Ile His Leu Ala
195 200 205

Glu Gln Pro Gly Lys Asp His Val Trp Ala Glu Thr Asp Asn Ser Ser
210 215 220

Ala Gly Ser Ser Pro Ile Val Met Asp Pro Trp Ser Asn Gly Val Ala
225 230 235 240

-continued

```
Ile Leu Ala Glu Asp Ser Arg Phe Ala Lys Asp Arg Ser Ala Val Glu
                245                 250                 255

Arg Thr Tyr Ser Phe Thr Leu Ala Met Ala Ala Glu Ala Gly Lys Val
            260                 265                 270

Ala Arg Glu Thr Ala Glu Asn Val Leu Thr His Thr Thr Ser Arg Leu
        275                 280                 285

Gln Lys Arg Leu Ala Asp Gln Leu Pro Asn Val Ser Pro Leu Glu Gly
    290                 295                 300

Gly Arg Tyr Gln Pro Glu Lys Ser Val Leu Asp Glu Ala Phe Ala Arg
305                 310                 315                 320

Arg Val Ser Asp Lys Leu Asn Ser Asp Asp Pro Arg Arg Ala Leu Gln
                325                 330                 335

Met Glu Ile Glu Ala Val Gly Val Ala Met Ser Leu Gly Ala Glu Gly
            340                 345                 350

Val Lys Thr Val Ala Arg Gln Ala Pro Lys Val Val Arg Gln Ala Arg
        355                 360                 365

Ser Val Ala Ser Ser Lys Gly Met Pro Pro Arg Arg
    370                 375                 380
```

This protein or polypeptide has GC content of about 57 percent, an estimated isoelectric point of about 9.1, and an estimated molecular weight of about 41 kDa.

The DNA molecule from *Pseudomonas syringae* pv. *tabaci* which encodes an AvrPphE homolog has a nucleotide sequence (SEQ. ID. No. 43) as follows:

```
atgagaattc acagtgctgg tcacagcctg cctgcgccag gccctagcgt ggaaaccact      60

gaaaaggctg ttcaatcatc atcggcccag aaccccgctt cttgcagttc acaaacagaa     120

cgtcctgaag ccggttcgac tcaagtgcga ccgaactacc cttactcatc agtcaagaca     180

cgcttgccac ccgtttcttc tacagggcag gccatttctg acacgccatc ttcattgccc     240

ggttacctgc tgttacgtcg gctcgaccga cgtccactgg atgaagacag tatcaaggct     300

ctggttccgg cagacgaagc ggtgcgtgaa gcacgccgcg cgttgccctt cggcaggggc     360

aacattgatg tggatgcaca acgtacccac ctgcaaagcg gcgctcgcgc agtcgctgca     420

aagcgcttga gaaaagatgc cgagcgcgct ggccatgagc cgatgcccgg gaatgatgag     480

atgaactggc atgttcttgt cgccatgtca gggcaggtgt ttggcgctgg caactgtggc     540

gaacatgctc gtatagcaag cttcgcttac ggggccctgg ctcaggaaag cgggcgtagt     600

ccccgcgaaa agattcattt ggccgagcag cccggaaaag atcacgtctg ggctgaaacg     660

gataattcca gcgctggctc ttcgcccatc gtcatggacc cgtggtctaa cggcgcagcc     720

attttggcgg aggacagccg gtttgccaaa gatcgcagtg cggtagagcg aacatattca     780

ttcacccttg caatggcagc tgaagccggc aaggttacgc gtgaaactgc cgagaacgtt     840

ctgacccaca cgacaagccg tctgcagaaa cgtcttgctg atcagttgcc gaacgtctca     900

ccgcttgaag gaggccgcta tcagcaggaa aagtcggtgc ttgatgaggc gttcgcccga     960

cgagtgagcg acaagttgaa tagtgacgat ccacggcgtg cgttgcagat ggaaattgaa    1020

gctgttggtg ttgcaatgtc gctgggtgcc gaaggcgtca agacggtcgc ccgacaggcg    1080

ccaaaggtgg tcaggcaagc cagaagcgtc gcgtcgtcta aaggcatgcc tccacgaaga    1140

taa                                                                  1143
```

The amino acid sequence (SEQ. ID. No. 44) for the AvrPphE homolog of *Pseudomonas syringae* pv. *tabaci* is as follows:

```
Met Arg Ile His Ser Ala Gly His Ser Leu Pro Ala Pro Gly Pro Ser
  1               5                  10                  15

Val Glu Thr Thr Glu Lys Ala Val Gln Ser Ser Ser Ala Gln Asn Pro
             20                  25                  30

Ala Ser Cys Ser Ser Gln Thr Glu Arg Pro Glu Ala Gly Ser Thr Gln
         35                  40                  45

Val Arg Pro Asn Tyr Pro Tyr Ser Ser Val Lys Thr Arg Leu Pro Pro
     50                  55                  60

Val Ser Ser Thr Gly Gln Ala Ile Ser Asp Thr Pro Ser Ser Leu Pro
 65                  70                  75                  80

Gly Tyr Leu Leu Leu Arg Arg Leu Asp Arg Arg Pro Leu Asp Glu Asp
                 85                  90                  95

Ser Ile Lys Ala Leu Val Pro Ala Asp Glu Ala Val Arg Glu Ala Arg
            100                 105                 110

Arg Ala Leu Pro Phe Gly Arg Gly Asn Ile Asp Val Asp Ala Gln Arg
        115                 120                 125

Thr His Leu Gln Ser Gly Ala Arg Ala Val Ala Ala Lys Arg Leu Arg
    130                 135                 140

Lys Asp Ala Glu Arg Ala Gly His Glu Pro Met Pro Gly Asn Asp Glu
145                 150                 155                 160

Met Asn Trp His Val Leu Val Ala Met Ser Gly Gln Val Phe Gly Ala
                165                 170                 175

Gly Asn Cys Gly Glu His Ala Arg Ile Ala Ser Phe Ala Tyr Gly Ala
            180                 185                 190

Leu Ala Gln Glu Ser Gly Arg Ser Pro Arg Glu Lys Ile His Leu Ala
        195                 200                 205

Glu Gln Pro Gly Lys Asp His Val Trp Ala Glu Thr Asp Asn Ser Ser
    210                 215                 220

Ala Gly Ser Ser Pro Ile Val Met Asp Pro Trp Ser Asn Gly Ala Ala
225                 230                 235                 240

Ile Leu Ala Glu Asp Ser Arg Phe Ala Lys Asp Arg Ser Ala Val Glu
                245                 250                 255

Arg Thr Tyr Ser Phe Thr Leu Ala Met Ala Ala Glu Ala Gly Lys Val
            260                 265                 270

Thr Arg Glu Thr Ala Glu Asn Val Leu Thr His Thr Thr Ser Arg Leu
        275                 280                 285

Gln Lys Arg Leu Ala Asp Gln Leu Pro Asn Val Ser Pro Leu Glu Gly
    290                 295                 300

Gly Arg Tyr Gln Gln Glu Lys Ser Val Leu Asp Glu Ala Phe Ala Arg
305                 310                 315                 320

Arg Val Ser Asp Lys Leu Asn Ser Asp Asp Pro Arg Arg Ala Leu Gln
                325                 330                 335

Met Glu Ile Glu Ala Val Gly Val Ala Met Ser Leu Gly Ala Glu Gly
            340                 345                 350

Val Lys Thr Val Ala Arg Gln Ala Pro Lys Val Val Arg Gln Ala Arg
        355                 360                 365

Ser Val Ala Ser Ser Lys Gly Met Pro Pro Arg Arg
    370                 375                 380
```

This protein or polypeptide has GC content of about 57 percent, an estimated isoelectric point of about 9.3, and an estimated molecular weight of about 41 kDa.

Another DNA molecule from *Pseudomonas syringae* pv. *tabaci* which encodes a AvrPphE homolog has a nucleotide sequence (SEQ. ID. No. 45) as follows:

```
atgagaattc acagtgctgg tcacagcctg cctgcgccag gccctagcgt ggaaaccact     60
gaaaaggctg ttcaatcatc atcggcccag aacccccgctt cttgcagttc acaaacagaa  120
cgtcctgaag ccggttcgac tcaagtgcga ccgaactacc cttactcatc agtcaagaca    180
cgcttgccac ccgtttcttc tacagggcag gccatttctg acacgccatc ttcattgccc    240
ggttacctgc tgttacgtcg gctcgaccga cgtccactgg atgaagacag tatcaaggct    300
ctggttccgg cagacgaagc ggtgcgtgaa gcacgccgcg cgttgccctt cggcaggggc    360
aacattgatg tggatgcaca acgtacccac ctgcaaagcg gcgctcgcgc agtcgctgca    420
aagcgcttga gaaaagatgc cgagcgcgct ggccatgagc cgatgcccgg gaatgatgag    480
atgaactggc atgttcttgt cgccatgtca gggcaggtgt ttggcgctgg caactgtggc    540
gaacatgctc gtatagcaag cttcgcttac ggggccctgg ctcaggaaag cgggcgtagt    600
ccccgcgaaa agattcattt ggccgagcag cccggaaaag atcacgtctg ggctgaaacg    660
gataattcca gcgctggctc ttcgcccatc gtcatggacc cgtggtctaa cggcgcagcc    720
attttggcgg aggacagccg gtttgccaaa gatcgcagtg cggtagagcg aacatattca    780
ttcacccttg caatggcagc tgaagccggc aaggttacgc gtgaaactgc cgagaacgtt    840
ctgacccaca cgacaagccg tctgcagaaa cgtcttgctg atcagttgcc gaacgtctca    900
ccgcttgaag gaggccgcta tcagcaggaa aagtcggtgc ttgatgaggc gttcgcccga    960
cgagtgagcg acaagttgaa tagtgacgat ccacggcgtg cgttgcagat ggaaattgaa   1020
gctgttggtg ttgcaatgtc gctgggtgcc gaaggcgtca agacggtcgc ccgacaggcg   1080
ccaaaggtgg tcaggcaagc cagaagcgtc gcgtcgtcta aaggcatgcc tccacgaaga   1140
taa                                                                 1143
```

The encoded AvrPphE homolog has an amino acid sequence according to SEQ. ID. No. 46 as follows:

```
Met Arg Ile His Ser Ala Gly His Ser Leu Pro Ala Pro Gly Pro Ser
  1               5                  10                  15

Val Glu Thr Thr Glu Lys Ala Val Gln Ser Ser Ser Ala Gln Asn Pro
             20                  25                  30

Ala Ser Cys Ser Ser Gln Thr Glu Arg Pro Glu Ala Gly Ser Thr Gln
         35                  40                  45

Val Arg Pro Asn Tyr Pro Tyr Ser Ser Val Lys Thr Arg Leu Pro Pro
     50                  55                  60

Val Ser Ser Thr Gly Gln Ala Ile Ser Asp Thr Pro Ser Ser Leu Pro
 65                  70                  75                  80

Gly Tyr Leu Leu Leu Arg Arg Leu Asp Arg Arg Pro Leu Asp Glu Asp
                 85                  90                  95

Ser Ile Lys Ala Leu Val Pro Ala Asp Glu Ala Val Arg Glu Ala Arg
            100                 105                 110

Arg Ala Leu Pro Phe Gly Arg Gly Asn Ile Asp Val Asp Ala Gln Arg
        115                 120                 125

Thr His Leu Gln Ser Gly Ala Arg Ala Val Ala Ala Lys Arg Leu Arg
    130                 135                 140

Lys Asp Ala Glu Arg Ala Gly His Glu Pro Met Pro Gly Asn Asp Glu
145                 150                 155                 160

Met Asn Trp His Val Leu Val Ala Met Ser Gly Gln Val Phe Gly Ala
                165                 170                 175
```

-continued

```
Gly Asn Cys Gly Glu His Ala Arg Ile Ala Ser Phe Ala Tyr Gly Ala
            180                 185                 190

Leu Ala Gln Glu Ser Gly Arg Ser Pro Arg Glu Lys Ile His Leu Ala
        195                 200                 205

Glu Gln Pro Gly Lys Asp His Val Trp Ala Glu Thr Asp Asn Ser Ser
    210                 215                 220
Ala Gly Ser Ser Pro Ile Val Met Asp Pro Trp Ser Asn Gly Ala Ala
225                 230                 235                 240

Ile Leu Ala Glu Asp Ser Arg Phe Ala Lys Asp Arg Ser Ala Val Glu
                245                 250                 255

Arg Thr Tyr Ser Phe Thr Leu Ala Met Ala Ala Glu Ala Gly Lys Val
            260                 265                 270

Thr Arg Glu Thr Ala Glu Asn Val Leu Thr His Thr Thr Ser Arg Leu
        275                 280                 285

Gln Lys Arg Leu Ala Asp Gln Leu Pro Asn Val Ser Pro Leu Glu Gly
    290                 295                 300

Gly Arg Tyr Gln Gln Glu Lys Ser Val Leu Asp Glu Ala Phe Ala Arg
305                 310                 315                 320

Arg Val Ser Asp Lys Leu Asn Ser Asp Asp Pro Arg Arg Ala Leu Gln
                325                 330                 335

Met Glu Ile Glu Ala Val Gly Val Ala Met Ser Leu Gly Ala Glu Gly
            340                 345                 350

Val Lys Thr Val Ala Arg Gln Ala Pro Lys Val Val Arg Gln Ala Arg
        355                 360                 365

Ser Val Ala Ser Ser Lys Gly Met Pro Pro Arg Arg
    370                 375                 380
```

A DNA molecule from *Pseudomonas syringae* pv. *glycinea* race 4 which encodes an avrPphE homolog has a nucleotide sequence (SEQ. ID. No. 47) as follows:

```
atgagaattc acagtgctgg tcacagcctg cccgcgccag gccctagcgt ggaaaccact     60

gaaaaggctg ttcaatcatc atcggcccag aaccccgctt cttgcagttc acaaacagaa    120

cgtcctgaag ccggttcgac tcaagtgcga ccgaactacc cttactcatc agtcaagaca    180

cgcttgccac ccgtttcttc cacagggcag gccatttctg acacgccatc ttcattgtcc    240

ggttacctgc tgttacgtcg gctcgaccga cgtccactgg atgaagacag tatcaaggct    300

ctggttccgg cagacgaagc gttgcgtgaa gcacgccgcg cgttgccctt cggcaggggc    360

aacattgatg tggatgcaca acgtacccac ctgcaaagcg gcgctcgcgc agtcgctgca    420

aagcgcttga gaaaagatgc cgagcgcgct ggccatgagc cgatgcccga gaatgatgag    480

atgaactggc atgttcttgt cgccatgtca gggcaggtgt ttggcgctgg caactgtggc    540

gaacatgctc gtatagcaag cttcgcttac ggggccctgg ctcaggaaag cgggcgtagt    600

ccccgcgaaa agattcattt ggccgagcag cccggaaaag atcacgtctg ggctgaaacg    660

gataattcca gcgctggctc ttcgcccatc gtcatggacc cgtggtctaa cggcgtagcc    720

attttggcgg aggacagccg gtttgccaaa gatcgcagtg cggtagagcg aacatattca    780

ttcacccttg caatggcagc tgaagccggc aaggttgcgc gtgaaaccgc cgagaacgtt    840

ctgacccaca cgacaagccg tctgcagaaa cgtcttgctg atcagttgcc gaacgtctca    900

ccgcttgaag gaggccgcta tcagccggaa aagtcggtgc ttgatgaggc gttcgcccga    960

cgagtgagcg acaagttgaa tagtgacgat ccacggcgtg cgttgcagat ggaaattgaa   1020
```

-continued

```
gctgttggtg ttgcaatgtc gctgggtgcc gaaggcgtca agacggtcgc ccgacaggcg   1080

ccaaaggtgg tcaggcaagc cagaagcgtc gcgtcgtcta aaggcatgcc tccacgaaga   1140

taa                                                                 1143
```

The encoded AvrPphE homolog has an amino acid sequence according to SEQ. ID. No. 48 as follows:

```
Met Arg Ile His Ser Ala Gly His Ser Leu Pro Ala Pro Gly Pro Ser
  1               5                  10                  15

Val Glu Thr Thr Glu Lys Ala Val Gln Ser Ser Ser Ala Gln Asn Pro
             20                  25                  30

Ala Ser Cys Ser Ser Gln Thr Glu Arg Pro Glu Ala Gly Ser Thr Gln
         35                  40                  45

Val Arg Pro Asn Tyr Pro Tyr Ser Ser Val Lys Thr Arg Leu Pro Pro
     50                  55                  60

Val Ser Ser Thr Gly Gln Ala Ile Ser Asp Thr Pro Ser Ser Leu Ser
 65                  70                  75                  80

Gly Tyr Leu Leu Leu Arg Arg Leu Asp Arg Arg Pro Leu Asp Glu Asp
                 85                  90                  95

Ser Ile Lys Ala Leu Val Pro Ala Asp Glu Ala Leu Arg Glu Ala Arg
            100                 105                 110

Arg Ala Leu Pro Phe Gly Arg Gly Asn Ile Asp Val Asp Ala Gln Arg
        115                 120                 125

Thr His Leu Gln Ser Gly Ala Arg Ala Val Ala Ala Lys Arg Leu Arg
    130                 135                 140

Lys Asp Ala Glu Arg Ala Gly His Glu Pro Met Pro Glu Asn Asp Glu
145                 150                 155                 160

Met Asn Trp His Val Leu Val Ala Met Ser Gly Gln Val Phe Gly Ala
                165                 170                 175

Gly Asn Cys Gly Glu His Ala Arg Ile Ala Ser Phe Ala Tyr Gly Ala
            180                 185                 190

Leu Ala Gln Glu Ser Gly Arg Ser Pro Arg Glu Lys Ile His Leu Ala
        195                 200                 205

Glu Gln Pro Gly Lys Asp His Val Trp Ala Glu Thr Asp Asn Ser Ser
    210                 215                 220

Ala Gly Ser Ser Pro Ile Val Met Asp Pro Trp Ser Asn Gly Val Ala
225                 230                 235                 240

Ile Leu Ala Glu Asp Ser Arg Phe Ala Lys Asp Arg Ser Ala Val Glu
                245                 250                 255

Arg Thr Tyr Ser Phe Thr Leu Ala Met Ala Ala Glu Ala Gly Lys Val
            260                 265                 270

Ala Arg Glu Thr Ala Glu Asn Val Leu Thr His Thr Thr Ser Arg Leu
        275                 280                 285

Gln Lys Arg Leu Ala Asp Gln Leu Pro Asn Val Ser Pro Leu Glu Gly
    290                 295                 300

Gly Arg Tyr Gln Pro Glu Lys Ser Val Leu Asp Glu Ala Phe Ala Arg
305                 310                 315                 320

Arg Val Ser Asp Lys Leu Asn Ser Asp Asp Pro Arg Arg Ala Leu Gln
                325                 330                 335

Met Glu Ile Glu Ala Val Gly Val Ala Met Ser Leu Gly Ala Glu Gly
            340                 345                 350

Val Lys Thr Val Ala Arg Gln Ala Pro Lys Val Val Arg Gln Ala Arg
```

-continued 355 360 365

Ser Val Ala Ser Ser Lys Gly Met Pro Pro Arg Arg
370 375 380

A DNA molecule from *Pseudomonas syringae* pv. *phaseolicola* strain B130 which encodes AvrPphE has a nucleotide sequence (SEQ. ID. No. 49) as follows:

atgagaattc acagtgctgg tcacagcctg cccgcgccag gccctagcgt ggaaaccact 60
gaaaaggctg ttcaatcatc atcggcccag aacccccgctt cttgcagttc acaaacagaa 120
cgtcctgaag ccggttcgac tcaagtgcga ccgaactacc cttactcatc agtcaagaca 180
cgcttgccac ccgtttcttc cacagggcag gccatttctg acacgccatc ttcattgccc 240
ggttacctgc tgttacgtcg gctcgaccga cgtccactgg atgaagacag tatcaaggct 300
ctggttccgg cagacgaagc gttgcgtgaa gcacgccgcg cgttgccctt cggcaggggc 360
aacattgatg tggatgcaca acgtacccac ctgcaaagcg gcgctcgcgc agtcgctgca 420
aagcgcttga gaaaagatgc cgagcgcgct ggccatgagc cgatgcccga gaatgatgag 480
atgaactggc atgttcttgt cgccatgtca gggcaggtgt ttggcgctgg caactgtggc 540
gaacatgctc gtatagcaag cttcgcttac ggggccctgg ctcaggaaag cgggcgtagt 600
ccccgcgaaa agattcattt ggccgagcag cccggaaaag atcacgtctg ggctgaaacg 660
gataattcca gcgctggctc ttcgcccatc gtcatggacc cgtggtctaa cggcgcagcc 720
attttggcgg aggacagccg gtttgccaaa gatcgcagtg cggtagagcg aacatattca 780
ttcacccttg caatggcagc tgaagccggc aaggttgcgc gtgaaaccgc cgagaacgtt 840
ctgacccaca cgacaagccg tctgcagaag cgtcttgctg atcagttgcc gaacgtctca 900
ccgcttgaag gaggccgcta tcagccggaa aagtcggtgc ttgatgaggc gttcgcccga 960
cgagtgagcg acaagttgaa tagtgacgat ccacggcgtg cgttgcagat ggaaattgaa 1020
gctgttggtg ttgcaatgtc gctgggtgcc gaaggcgtca agacggtcgc ccgacaggcg 1080
ccaaaggtgg tcaggcaagc cagaagcgtc gcgtcgtcta aaggcatgcc tccacgaaga 1140
taa 1143

The encoded AvrPphE homolog has an amino acid sequence according to SEQ. ID. No. 50 as follows:

Met Arg Ile His Ser Ala Gly His Ser Leu Pro Ala Pro Gly Pro Ser
1 5 10 15

Val Glu Thr Thr Glu Lys Ala Val Gln Ser Ser Ser Ala Gln Asn Pro
20 25 30

Ala Ser Cys Ser Ser Gln Thr Glu Arg Pro Glu Ala Gly Ser Thr Gln
35 40 45

Val Arg Pro Asn Tyr Pro Tyr Ser Ser Val Lys Thr Arg Leu Pro Pro
50 55 60

Val Ser Ser Thr Gly Gln Ala Ile Ser Asp Thr Pro Ser Ser Leu Pro
65 70 75 80

Gly Tyr Leu Leu Leu Arg Arg Leu Asp Arg Arg Pro Leu Asp Glu Asp
85 90 95

Ser Ile Lys Ala Leu Val Pro Ala Asp Glu Ala Leu Arg Glu Ala Arg
100 105 110

-continued

```
Arg Ala Leu Pro Phe Gly Arg Gly Asn Ile Asp Val Asp Ala Gln Arg
        115                 120                 125

Thr His Leu Gln Ser Gly Ala Arg Ala Val Ala Ala Lys Arg Leu Arg
    130                 135                 140

Lys Asp Ala Glu Arg Ala Gly His Glu Pro Met Pro Glu Asn Asp Glu
145                 150                 155                 160

Met Asn Trp His Val Leu Val Ala Met Ser Gly Gln Val Phe Gly Ala
                165                 170                 175

Gly Asn Cys Gly Glu His Ala Arg Ile Ala Ser Phe Ala Tyr Gly Ala
            180                 185                 190

Leu Ala Gln Glu Ser Gly Arg Ser Pro Arg Glu Lys Ile His Leu Ala
        195                 200                 205

Glu Gln Pro Gly Lys Asp His Val Trp Ala Glu Thr Asp Asn Ser Ser
    210                 215                 220

Ala Gly Ser Ser Pro Ile Val Met Asp Pro Trp Ser Asn Gly Ala Ala
225                 230                 235                 240

Ile Leu Ala Glu Asp Ser Arg Phe Ala Lys Asp Arg Ser Ala Val Glu
                245                 250                 255

Arg Thr Tyr Ser Phe Thr Leu Ala Met Ala Ala Glu Ala Gly Lys Val
            260                 265                 270

Ala Arg Glu Thr Ala Glu Asn Val Leu Thr His Thr Thr Ser Arg Leu
        275                 280                 285

Gln Lys Arg Leu Ala Asp Gln Leu Pro Asn Val Ser Pro Leu Glu Gly
    290                 295                 300

Gly Arg Tyr Gln Pro Glu Lys Ser Val Leu Asp Glu Ala Phe Ala Arg
305                 310                 315                 320

Arg Val Ser Asp Lys Leu Asn Ser Asp Asp Pro Arg Arg Ala Leu Gln
                325                 330                 335

Met Glu Ile Glu Ala Val Gly Val Ala Met Ser Leu Gly Ala Glu Gly
            340                 345                 350

Val Lys Thr Val Ala Arg Gln Ala Pro Lys Val Val Arg Gln Ala Arg
        355                 360                 365

Ser Val Ala Ser Ser Lys Gly Met Pro Pro Arg Arg
    370                 375                 380
```

A DNA molecule from *Pseudomonas syringae* pv. *angulata* strain Pa9 which encodes AvrPphE homolog has a nucleotide sequence (SEQ. ID. No. 51) as follows:

```
atgagaattc acagtgctgg tcacagcctg cctgcgccag gccctagcgt ggaaaccact    60

gaaaaggctg ttcaatcatc atcggcccag aaccccgctt cttacagttc acaaacagaa   120

cgtcctgaag ccggttcgac tcaagtgcga ctgaactacc cttactcatc agtcaagaca   180

cgcttgccac ccgtttcttc tacagggcag gccatttctg ccacgccatc ttcattgccc   240

ggttacctgc tgttacgtcg gctcgaccga cgtccactgg atgaagacag tatcaaggct   300

ctggttccgg cagacgaagc ggtgcgtgaa gcacgccgcg cgttgccctt cggcaggggc   360

aacattgatg tggatgcaca acgtacccac ctgcaaagcg gcgctcgcgc agtcgctgca   420

aagcgcttga gaaaagatgc cgagcgcgct ggccatgagc cgatgcccgg gaatgatgag   480

atgaactggc atgttcttgt cgccatgtca gggcaggtgt ttggcgctgg caactgtggc   540

gaacatgctc gtatagcaag cttcgcttac ggggccctgg ctcaggaaag cgggcgtagt   600
```

-continued

```
ccccgcgaaa agattcattt ggccgagcag cccggaaaag atcacgtctg ggctgaaacg    660

gataattcca gcgctggctc ttcgcccatc gtcatggacc cgtggtctaa cggcgcagcc    720

attttggcgg aggacagccg gtttgccaaa gatcgcagta cggtagagcg aacatattca    780

ttcacccttg caatggcagc tgaagccggc aaggttacgc gtgaaaccgc cgagaacgtt    840

ctgacccaca cgacaagccg tctgcagaaa cgtcttgctg atcagttgcc gaacgtctca    900

ccgcttgaag gaggccgcta tcagcaggaa aagtcggtgc ttgatgaggc gttcgcccga    960

cgagtgagcg acaagttgaa tagtgacgat ccacggcgtg cgttgcagat ggaaattgaa   1020

gctgttggtg ttgcaatgtc gctgggtgcc gaaggcgtca agacggtcgc ccgacaggcg   1080

ccaaaggtgg tcaggcaagc cagaagcgtc gcgtcgtcta aaggcatgcc tccacgaaga   1140

taa                                                                 1143
```

The encoded AvrPphE homolog has an amino acid sequence according to SEQ. ID. No. 52 as follows:

```
Met Arg Ile His Ser Ala Gly His Ser Leu Pro Ala Pro Gly Pro Ser
  1               5                  10                  15

Val Glu Thr Thr Glu Lys Ala Val Gln Ser Ser Ser Ala Gln Asn Pro
             20                  25                  30

Ala Ser Tyr Ser Ser Gln Thr Glu Arg Pro Glu Ala Gly Ser Thr Gln
         35                  40                  45

Val Arg Leu Asn Tyr Pro Tyr Ser Ser Val Lys Thr Arg Leu Pro Pro
     50                  55                  60

Val Ser Ser Thr Gly Gln Ala Ile Ser Ala Thr Pro Ser Ser Leu Pro
 65                  70                  75                  80

Gly Tyr Leu Leu Leu Arg Arg Leu Asp Arg Arg Pro Leu Asp Glu Asp
                 85                  90                  95

Ser Ile Lys Ala Leu Val Pro Ala Asp Glu Ala Val Arg Glu Ala Arg
            100                 105                 110

Arg Ala Leu Pro Phe Gly Arg Gly Asn Ile Asp Val Asp Ala Gln Arg
        115                 120                 125

Thr His Leu Gln Ser Gly Ala Arg Ala Val Ala Ala Lys Arg Leu Arg
    130                 135                 140

Lys Asp Ala Glu Arg Ala Gly His Glu Pro Met Pro Gly Asn Asp Glu
145                 150                 155                 160

Met Asn Trp His Val Leu Val Ala Met Ser Gly Gln Val Phe Gly Ala
                165                 170                 175

Gly Asn Cys Gly Glu His Ala Arg Ile Ala Ser Phe Ala Tyr Gly Ala
            180                 185                 190

Leu Ala Gln Glu Ser Gly Arg Ser Pro Arg Glu Lys Ile His Leu Ala
        195                 200                 205

Glu Gln Pro Gly Lys Asp His Val Trp Ala Glu Thr Asp Asn Ser Ser
    210                 215                 220

Ala Gly Ser Ser Pro Ile Val Met Asp Pro Trp Ser Asn Gly Ala Ala
225                 230                 235                 240

Ile Leu Ala Gln Asp Ser Arg Phe Ala Lys Asp Arg Ser Thr Val Glu
                245                 250                 255

Arg Thr Tyr Ser Phe Thr Leu Ala Met Ala Ala Glu Ala Gly Lys Val
            260                 265                 270

Thr Arg Glu Thr Ala Glu Asn Val Leu Thr His Thr Thr Ser Arg Leu
        275                 280                 285
```

-continued

```
Gln Lys Arg Leu Ala Asp Gln Leu Pro Asn Val Ser Pro Leu Glu Gly
    290                 295                 300

Gly Arg Tyr Gln Gln Glu Lys Ser Val Leu Asp Glu Ala Phe Ala Arg
305                 310                 315                 320

Arg Val Ser Asp Lys Leu Asn Ser Asp Asp Pro Arg Arg Ala Leu Gln
                325                 330                 335

Met Glu Ile Glu Ala Val Gly Val Ala Met Ser Leu Gly Ala Glu Gly
            340                 345                 350

Val Lys Thr Val Ala Arg Gln Ala Pro Lys Val Val Arg Gln Ala Arg
        355                 360                 365

Ser Val Ala Ser Ser Lys Gly Met Pro Pro Arg Arg
    370                 375                 380
```

A DNA molecule from *Pseudomonas syringae* pv. *delphinii* strain PDDCC529 which encodes a AvrPphE homolog has a nucleotide sequence (SEQ. ID. No. 53) as follows:

```
atgaaaatac ataacgctgg cccaagcatt ccgatgcccg ctccatcgat tgagagcgct    60

ggcaagactg cgcaatcatc attggctcaa ccgcagagcc aacgagccac ccccgtctcg   120

ccatcagaga cttctgatgc ccgtccgtcc agtgtgcgta cgaactaccc ttattcatca   180

gtcaaaacac ggttgcctcc cgttgcgtct gcagggcagc cactgtccgg gatgccgtct   240

tcattacccg gctacttgct gttacgtcgg cttgaccatc gtccactgga tcaagacggt   300

atcaaaggtt tgattccagc agatgaagcg gtgggtgaag cacgtcgcgc gttgcctttc   360

ggcaggggca atatcgacgt ggatgcgcaa cgctccaact tggaaagcgg agcccgcaca   420

ctcgcggcta ggcgtttgag aaaagatgcc gaggccgcgg gtcacgaacc aatgcctgca   480

aatgaagata tgaactggca tgttcttgtt gcgatgtcag gacaggtttt tggcgcaggt   540

aactgcgggg aacatgcccg catagcgagt ttcgcctacg gtgcactggc tcaggaaaaa   600

gggcggaacg ccgatgagac tattcatttg gctgcgcaac gcggtaaaga ccacgtctgg   660

gctgaaacgg acaattcaag cgctggatct tcaccggttg tcatggatcc gtggtcgaac   720

ggtcctgcca tttttgcgga ggatagtcgg tttgccaaag atcgaagtac ggtagaacga   780

acggattcct tcacgcttgc aactgctgct gaagcaggca agatcacgcg agagacggcc   840

gagaatgctt tgacacaggc gaccagccgt ttgcagaaac gtcttgctga tcagaaaacg   900

caagtctcgc cgcttgcagg agggcgctat cggcaagaaa attcggtgct tgatgacgcg   960

ttcgcccgac gggcaagtgg caagttgagc aacaaggatc cgcggcatgc attacaggtg  1020

gaaatcgagg cggccgcagt tgcaatgtcg ctgggcgccc aaggcgtaaa agcggttgcg  1080

gaacaggccc ggacggtagt tgaacaagcc aggaaggtcg catctcccca aggcacgcct  1140

cagcgagata cgtga                                                    1155
```

The encoded avrPphE homolog has an amino acid sequence according to SEQ. ID. No. 54 as follows:

```
Met Lys Ile His Asn Ala Gly Pro Ser Ile Pro Met Pro Ala Pro Ser
  1               5                  10                  15

Ile Glu Ser Ala Gly Lys Thr Ala Gln Ser Ser Leu Ala Gln Pro Gln
             20                  25                  30
```

-continued

```
Ser Gln Arg Ala Thr Pro Val Ser Pro Ser Gln Thr Ser Asp Ala Arg
        35                  40                  45

Pro Ser Ser Val Arg Thr Asn Tyr Pro Tyr Ser Ser Val Lys Thr Arg
    50                  55                  60

Leu Pro Pro Val Ala Ser Ala Gly Gln Pro Leu Ser Gly Met Pro Ser
 65                 70                  75                  80

Ser Leu Pro Gly Tyr Leu Leu Leu Arg Arg Leu Asp His Arg Pro Leu
                85                  90                  95

Asp Gln Asp Gly Ile Lys Gly Leu Ile Pro Ala Asp Glu Ala Val Gly
            100                 105                 110

Glu Ala Arg Arg Ala Leu Pro Phe Gly Arg Gly Asn Ile Asp Val Asp
        115                 120                 125

Ala Gln Arg Ser Asn Leu Glu Ser Gly Ala Arg Thr Leu Ala Ala Arg
    130                 135                 140

Arg Leu Arg Lys Asp Ala Glu Ala Ala Gly His Glu Pro Met Pro Ala
145                 150                 155                 160

Asn Glu Asp Met Asn Trp His Val Leu Val Ala Met Ser Gly Gln Val
                165                 170                 175

Phe Gly Ala Gly Asn Cys Gly Glu His Ala Arg Ile Ala Ser Phe Ala
            180                 185                 190

Tyr Gly Ala Leu Ala Gln Glu Lys Gly Arg Asn Ala Asp Glu Thr Ile
        195                 200                 205

His Leu Ala Ala Gln Arg Gly Lys Asp His Val Trp Ala Glu Thr Asp
    210                 215                 220

Asn Ser Ser Ala Gly Ser Ser Pro Val Val Met Asp Pro Trp Ser Asn
225                 230                 235                 240

Gly Pro Ala Ile Phe Ala Glu Asp Ser Arg Phe Ala Lys Asp Arg Ser
                245                 250                 255

Thr Val Glu Arg Thr Asp Ser Phe Thr Leu Ala Thr Ala Ala Glu Ala
            260                 265                 270

Gly Lys Ile Thr Arg Glu Thr Ala Glu Asn Ala Leu Thr Gln Ala Thr
        275                 280                 285

Ser Arg Leu Gln Lys Arg Leu Ala Asp Gln Lys Thr Gln Val Ser Pro
    290                 295                 300

Leu Ala Gly Gly Arg Tyr Arg Gln Glu Asn Ser Val Leu Asp Asp Ala
305                 310                 315                 320

Phe Ala Arg Arg Ala Ser Gly Lys Leu Ser Asn Lys Asp Pro Arg His
                325                 330                 335

Ala Leu Gln Val Glu Ile Glu Ala Ala Ala Val Ala Met Ser Leu Gly
            340                 345                 350

Ala Gln Gly Val Lys Ala Val Ala Glu Gln Ala Arg Thr Val Val Glu
        355                 360                 365

Gln Ala Arg Lys Val Ala Ser Pro Gln Gly Thr Pro Gln Arg Asp Thr
    370                 375                 380
```

A DNA molecule from *Pseudomonas syringae* pv. *delphinii* strain PDDCC529 which encodes a homolog of *P. syringae* pv. *tomato* DC3000 EEL ORF2 has a nucleotide sequence (SEQ. ID. No. 55) as follows:

```
gtggttgagc gaaccggcac tgcatatcga aggcgtggag cagcctgctc gcgtatcacg    60

agccaaaatc aggtccgacg acgctttgga attacggtga atcagatgca aaagacgtcc   120
```

-continued

```
ctattggctt tggcctttgc aatcctggca gggtgtgggg gttcggggca ggcgccgggg   180

agtgatattc agggtgccca ggcagagatg aaaacaccca ttaaagtaga tctggatgcc   240

tacacctcaa aaaaacttga tgctgtgttg gaagctcggg ccaataaaag ctatgtgaat   300

aaaggtcaac tgatcgacct tgtgtcaggg gcgtttttgg gaacaccgta ccgctcaaac   360

atgttggtgg gcacagagga aatacctgaa cagttagtca tcgactttag aggtctggat   420

tgttttgctt atctggatta cgtagaggcg ttgcgaagat caacatcgca gcaggatttt   480

gtgaggaatc tcgttcaggt tcgttacaag ggtggtgatg ttgacttttt gaatcgcaag   540

cactttttca cggattgggc ttatggcact acacacccgg tggcggatga catcaccacg   600

cagataagcc ccggtgcggt aagtgtcaga aaacgcctta atgaaagggc caaaggcaaa   660

gtctatctgc caggtttgcc tgtggttgag cgcagcatga cctatatccc gagccgcctt   720

gtcgacagtc aggtggtaag ccacttgcgc acaggtgatt acatcggcat ttacaccccg   780

cttcccgggc tggatgtgac gcacgtcggt ttctttatca tgacggataa aggccctgtc   840

ttgcgaaatg catcttcacg aaaagaaaac agaaaggtaa tggatttgcc ttttctggac   900

tatgtatcgg aaaagccagg gattgttgtt ttcagggcaa aagacaattg a            951
```

The encoded protein or polypeptide has an amino acid sequence according to SEQ. ID. No. 56 as follows:

```
Val Val Glu Arg Thr Gly Thr Ala Tyr Arg Arg Arg Gly Ala Ala Cys
  1               5                  10                  15

Ser Arg Ile Thr Ser Gln Asn Gln Val Arg Arg Arg Phe Gly Ile Thr
             20                  25                  30

Val Asn Gln Met Gln Lys Thr Ser Leu Leu Ala Leu Ala Phe Ala Ile
         35                  40                  45

Leu Ala Gly Cys Gly Gly Ser Gly Gln Ala Pro Gly Ser Asp Ile Gln
     50                  55                  60

Gly Ala Gln Ala Glu Met Lys Thr Pro Ile Lys Val Asp Leu Asp Ala
 65                  70                  75                  80

Tyr Thr Ser Lys Lys Leu Asp Ala Val Leu Glu Ala Arg Ala Asn Lys
                 85                  90                  95

Ser Tyr Val Asn Lys Gly Gln Leu Ile Asp Leu Val Ser Gly Ala Phe
            100                 105                 110

Leu Gly Thr Pro Tyr Arg Ser Asn Met Leu Val Gly Thr Glu Glu Ile
        115                 120                 125

Pro Glu Gln Leu Val Ile Asp Phe Arg Gly Leu Asp Cys Phe Ala Tyr
    130                 135                 140

Leu Asp Tyr Val Glu Ala Leu Arg Arg Ser Thr Ser Gln Gln Asp Phe
145                 150                 155                 160

Val Arg Asn Leu Val Gln Val Arg Tyr Lys Gly Gly Asp Val Asp Phe
                165                 170                 175

Leu Asn Arg Lys His Phe Phe Thr Asp Trp Ala Tyr Gly Thr Thr His
            180                 185                 190

Pro Val Ala Asp Asp Ile Thr Thr Gln Ile Ser Pro Gly Ala Val Ser
        195                 200                 205

Val Arg Lys Arg Leu Asn Glu Arg Ala Lys Gly Lys Val Tyr Leu Pro
    210                 215                 220

Gly Leu Pro Val Val Glu Arg Ser Met Thr Tyr Ile Pro Ser Arg Leu
225                 230                 235                 240
```

-continued

```
Val Asp Ser Gln Val Val Ser His Leu Arg Thr Gly Asp Tyr Ile Gly
                245                 250                 255

Ile Tyr Thr Pro Leu Pro Gly Leu Asp Val Thr His Val Gly Phe Phe
            260                 265                 270

Ile Met Thr Asp Lys Gly Pro Val Leu Arg Asn Ala Ser Ser Arg Lys
        275                 280                 285

Glu Asn Arg Lys Val Met Asp Leu Pro Phe Leu Asp Tyr Val Ser Glu
    290                 295                 300

Lys Pro Gly Ile Val Val Phe Arg Ala Lys Asp Asn
305                 310                 315
```

A DNA molecule from *Pseudomonas syringae* pv. *delphinii* strain PDDCC529 ORF1 encodes a homolog of AvrPphF and has a nucleotide sequence (SEQ. ID. No. 57) as follows:

```
atgaaaaact catttgatct tcttgtcgac ggtttggcga aagactacag catgccgaat   60

ttgccgaaca agaaacacga caatgaagtc tattgcttca cattccagag cgggctcgaa  120

gtaaacattt atcaggacga ctgtcgatgg gtgcatttct ccgccacaat cggacaattt  180

caagacgcca gcaatgacac gctcagccac gcacttcaac tgaacaattt cagtcttgga  240

aagcccttct tcacctttgg aatgaacgga gaaaaggtcg gcgtacttca cacacgcgtt  300

ccgttgattg aaatgaatac cgttgaaatg cgcaaggtat tcgaggactt gctcgatgta  360

gcaggcggca tcagagcgac attcaagctc agttaa                            396
```

The encoded AvrPphF homolog has an amino acid sequence according to SEQ. ID. No 58 as follows:

```
Met Lys Asn Ser Phe Asp Leu Leu Val Asp Gly Leu Ala Lys Asp Tyr
  1               5                  10                  15

Ser Met Pro Asn Leu Pro Asn Lys Lys His Asp Asn Glu Val Tyr Cys
            20                  25                  30

Phe Thr Phe Gln Ser Gly Leu Glu Val Asn Ile Tyr Gln Asp Asp Cys
        35                  40                  45

Arg Trp Val His Phe Ser Ala Thr Ile Gly Gln Phe Gln Asp Ala Ser
    50                  55                  60

Asn Asp Thr Leu Ser His Ala Leu Gln Leu Asn Asn Phe Ser Leu Gly
 65                  70                  75                  80

Lys Pro Phe Phe Thr Phe Gly Met Asn Gly Glu Lys Val Gly Val Leu
                85                  90                  95

His Thr Arg Val Pro Leu Ile Glu Met Asn Thr Val Glu Met Arg Lys
            100                 105                 110

Val Phe Glu Asp Leu Leu Asp Val Ala Gly Gly Ile Arg Ala Thr Phe
        115                 120                 125

Lys Leu Ser
    130
```

A DNA molecule from *Pseudomonas syringae* pv. *delphinii* strain PDDCC529 ORF1 encodes a homolog of AvrPphF and has a nucleotide sequence (SEQ. ID. No. 59) as follows:

```
atgagtacta tacctggcac ctcgggcgct caccccgattt atagctcaat ttccagccca   60

cgaaatatgt ctggctcgcc cacaccgagt caccgtattg gcggggaaac cctgacctct  120

attcatcagc tctctgccag ccagagagaa caatttctga atactcatga ccccatgaga  180

aaactcagga ttaacaatga tacgccactg tacagaacaa ccgagaagcg ttttatacag  240

gaaggcaaac tggccggcaa tccaaagtct attgcacgtg tcaacttgca cgaagaactg  300

cagcttaatc cgctcgccag tattttaggg aacttacctc acgaggcaag cgcttacttt  360

ccgaaaagcg cccgcgctgc ggatctgaaa gacccttcat tgaatgtaat gacaggctct  420

cgggcaaaaa atgctattcg cggctacgct catgacgacc atgtggcggt caagatgcga  480

ctgggcgact ttcttgaaaa aggcggcaag gtgtacgcgg acacttcatc agtcattgac  540

ggcggagacg aggcgagcgc gctgatcgtt acattgccta aaggacaaaa agttccagtc  600

gagattatcc ctacccataa cgacaacagc aataaaggca gaggctga              648
```

The encoded AvrPphF homolog has an amino acid sequence according to SEQ. ID. No. 60 as follows:

```
Met Ser Thr Ile Pro Gly Thr Ser Gly Ala His Pro Ile Tyr Ser Ser
  1               5                  10                  15

Ile Ser Ser Pro Arg Asn Met Ser Gly Ser Pro Thr Pro Ser His Arg
             20                  25                  30

Ile Gly Gly Glu Thr Leu Thr Ser Ile His Gln Leu Ser Ala Ser Gln
         35                  40                  45

Arg Glu Gln Phe Leu Asn Thr His Asp Pro Met Arg Lys Leu Arg Ile
     50                  55                  60

Asn Asn Asp Thr Pro Leu Tyr Arg Thr Thr Glu Lys Arg Phe Ile Gln
 65                  70                  75                  80

Glu Gly Lys Leu Ala Gly Asn Pro Lys Ser Ile Ala Arg Val Asn Leu
                 85                  90                  95

His Glu Glu Leu Gln Leu Asn Pro Leu Ala Ser Ile Leu Gly Asn Leu
            100                 105                 110

Pro His Glu Ala Ser Ala Tyr Phe Pro Lys Ser Ala Arg Ala Ala Asp
        115                 120                 125

Leu Lys Asp Pro Ser Leu Asn Val Met Thr Gly Ser Arg Ala Lys Asn
    130                 135                 140

Ala Ile Arg Gly Tyr Ala His Asp Asp His Val Ala Val Lys Met Arg
145                 150                 155                 160

Leu Gly Asp Phe Leu Glu Lys Gly Gly Lys Val Tyr Ala Asp Thr Ser
                165                 170                 175

Ser Val Ile Asp Gly Gly Asp Glu Ala Ser Ala Leu Ile Val Thr Leu
            180                 185                 190

Pro Lys Gly Gln Lys Val Pro Val Glu Ile Ile Pro Thr His Asn Asp
        195                 200                 205

Asn Ser Asn Lys Gly Arg Gly
    210                 215
```

A DNA molecule from *Pseudomonas syringae* pv. *syringae* strain 226 encodes a homolog of HopPsyA and has a nucleotide sequence (SEQ. ID. No. 61) as follows:

```
gtgaacccta tccatgcacg cttctccagc gtagaagcgc tcagacattc aaacgttgat    60

attcaggcaa tcaaatccga gggtcagttg gaagtcaacg gcaagcgtta cgagattcgt   120

gcggccgctg acggctcaat cgcggtcctc agacccgatc aacagtccaa agcagacaag   180

ttcttcaaag gcgcagcgca tcttattggc ggacaaagcc agcgtgccca aatagcccag   240

gtactcaacg agaaagcggc ggcagttcca cgcctggaca gaatgttggg cagacgcttc   300

gatctggaga agggcggaag tagcgctgtg ggcgccgcaa tcaaggctgc cgacagccga   360

ctgacatcaa aacagacatt tgccagcttc cagcaatggg ctgaaaaagc tgaggcgctc   420

gggcgcgata ccgaaatcgg tatctacatg atctacaaga gggacacgcc agacacaacg   480

cctatgaatg cggcagagca agaacattac ctggaaacgc tacaggctct cgataacaag   540

aaaaacctta tcatacgccc gcagatccat gatgatcggg aagaggaaga gcttgatctg   600

ggccgataca tcgctgaaga cagaaatgcc agaaccggct tttttagaat ggttcctaaa   660

gaccaacgcg cacctgagac aaactcggga cgacttacca ttggtgtaga acctaaatat   720

ggagcgcagt tggccctcgc aatggcaacc ctgatggaca agcacaaatc tgtgacacaa   780

ggtaaagtcg tcggtccggc aaaatatggc cagcaaactg actctgccat tctttacata   840

aatggtgatc ttgcaaaagc agtaaaactg ggcgaaaagc tgaaaaagct gagcggtatc   900

cctcctgaag gattcgtcga acatacaccg ctaagcatgc agtcgacggg tctcggtctt   960

tcttatgccg agtcggttga agggcagcct tccagccacg gacaggcgag aacacacgtt  1020

atcatggatg ccttgaaagg ccagggcccc atggagaaca gactcaaaat ggcgctggca  1080

gaaagaggct atgacccgga aaatccggcg ctcagggcgc gaaactga               1128
```

The encoded HopPsyA homolog has an amino acid sequence according to SEQ. ID No. 62 as follows:

```
Val Asn Pro Ile His Ala Arg Phe Ser Ser Val Glu Ala Leu Arg His
  1               5                  10                  15

Ser Asn Val Asp Ile Gln Ala Ile Lys Ser Glu Gly Gln Leu Glu Val
             20                  25                  30

Asn Gly Lys Arg Tyr Glu Ile Arg Ala Ala Ala Asp Gly Ser Ile Ala
         35                  40                  45

Val Leu Arg Pro Asp Gln Gln Ser Lys Ala Asp Lys Phe Phe Lys Gly
     50                  55                  60

Ala Ala His Leu Ile Gly Gly Gln Ser Gln Arg Ala Gln Ile Ala Gln
 65                  70                  75                  80

Val Leu Asn Glu Lys Ala Ala Ala Val Pro Arg Leu Asp Arg Met Leu
                 85                  90                  95

Gly Arg Arg Phe Asp Leu Glu Lys Gly Gly Ser Ser Ala Val Gly Ala
            100                 105                 110

Ala Ile Lys Ala Ala Asp Ser Arg Leu Thr Ser Lys Gln Thr Phe Ala
        115                 120                 125

Ser Phe Gln Gln Trp Ala Glu Lys Ala Glu Ala Leu Gly Arg Asp Thr
    130                 135                 140

Glu Ile Gly Ile Tyr Met Ile Tyr Lys Arg Asp Thr Pro Asp Thr Thr
145                 150                 155                 160

Pro Met Asn Ala Ala Glu Gln Glu His Tyr Leu Glu Thr Leu Gln Ala
                165                 170                 175

Leu Asp Asn Lys Lys Asn Leu Ile Ile Arg Pro Gln Ile His Asp Asp
            180                 185                 190
```

-continued

```
Arg Glu Glu Glu Glu Leu Asp Leu Gly Arg Tyr Ile Ala Glu Asp Arg
        195                 200                 205

Asn Ala Arg Thr Gly Phe Phe Arg Met Val Pro Lys Asp Gln Arg Ala
    210                 215                 220

Pro Glu Thr Asn Ser Gly Arg Leu Thr Ile Gly Val Glu Pro Lys Tyr
225                 230                 235                 240

Gly Ala Gln Leu Ala Leu Ala Met Ala Thr Leu Met Asp Lys His Lys
                245                 250                 255

Ser Val Thr Gln Gly Lys Val Val Gly Pro Ala Lys Tyr Gly Gln Gln
            260                 265                 270

Thr Asp Ser Ala Ile Leu Tyr Ile Asn Gly Asp Leu Ala Lys Ala Val
        275                 280                 285

Lys Leu Gly Glu Lys Leu Lys Lys Leu Ser Gly Ile Pro Pro Glu Gly
    290                 295                 300

Phe Val Glu His Thr Pro Leu Ser Met Gln Ser Thr Gly Leu Gly Leu
305                 310                 315                 320

Ser Tyr Ala Glu Ser Val Glu Gly Gln Pro Ser Ser His Gly Gln Ala
                325                 330                 335

Arg Thr His Val Ile Met Asp Ala Leu Lys Gly Gln Gly Pro Met Glu
            340                 345                 350

Asn Arg Leu Lys Met Ala Leu Ala Glu Arg Gly Tyr Asp Pro Glu Asn
        355                 360                 365

Pro Ala Leu Arg Ala Arg Asn
    370                 375
```

A DNA molecule from *Pseudomonas syringae* pv. *atrofaciens* strain B143 encodes a homolog of HopPsyA and has a nucleotide sequence (SEQ. ID. No. 63) as follows:

```
atgaacccga tacaaacgcg tttctctaac gtcgaagcac ttagacattc agaggtggat     60

gtacaggagc tcaaagcaca cggtcaaata gaagtgggtg gcaaatgcta cgacattcgc    120

gcggctgcca ataacgacct gactgtccag cgttctgaca aacagatggc gatgagcaag    180

tttttcaaaa aagcagggtt aagtgggagt tccggcagtc agtccgatca aattgcgcag    240

gtactgaatg acaagcgcgg ctcttccgtt ccccgtctta tacgccaggg gcagacccat    300

ctgggccgta tgcaattcaa catcgaagag gggcaaggca gttcggccgc cacgtccgtc    360

cagaacagca ggctgcccaa tggccgcttg gtaaacagca gtattttgca atgggtcgaa    420

aaggcgaaag ccaatggcag cacaagtacc agtgctcttt atcagatcta cgcaaaagaa    480

ctcccgcgtg tagaactgct gccacgcact gagcaccggg cgtgtctggc gcatatgtat    540

aagctgaacg gtaaggacgg tatcagtatt tggccgcagt ttctggatgg cgtgcgcggg    600

ttgcagctaa aacatgacac aaaagtgttc atgatgaaca accccaaagc agcggacgag    660

ttctacaaga tcgaacgttc gggcacgcaa tttccggatg aggctgtcaa ggcgcgcctg    720

acgataaatg tcaaacctca attccagaag gccatggtcg acgcagcggt caggttgacc    780

gctgagcgtc acgatatcat tactgccaaa gtggcaggtc ctgcaaagat tggcacgatt    840

acagatgcag cggttttcta tgtaagcgga gatttttccg ctgcgcagac acttgcaaaa    900

gagcttcagg cactgctccc tgacgatgcg tttatcaatc atacgccagc tggaatgcaa    960

tccatgggca aggggctgtg ttacgccgag cgtacaccgc aggacaggac aagccacgga   1020

atgtcgcgcg ccagcataat cgagtcggca ctggcagaca ccagcaggtc gtcactggag   1080
```

-continued

```
aagaagctgc gcaatgcttt caagagcgcc ggatacaatc ccgacaaccc ggcattcagg   1140

ttggaatga                                                           1149
```

The encoded HopPsyA homolog has an amino acid sequence according to SEQ. ID. No. 64 as follows:

```
Met Asn Pro Ile Gln Thr Arg Phe Ser Asn Val Glu Ala Leu Arg His
  1               5                  10                  15

Ser Glu Val Asp Val Gln Glu Leu Lys Ala His Gly Gln Ile Glu Val
             20                  25                  30

Gly Gly Lys Cys Tyr Asp Ile Arg Ala Ala Ala Asn Asn Asp Leu Thr
         35                  40                  45

Val Gln Arg Ser Asp Lys Gln Met Ala Met Ser Lys Phe Phe Lys Lys
     50                  55                  60

Ala Gly Leu Ser Gly Ser Ser Gly Ser Gln Ser Asp Gln Ile Ala Gln
 65                  70                  75                  80

Val Leu Asn Asp Lys Arg Gly Ser Ser Val Pro Arg Leu Ile Arg Gln
                 85                  90                  95

Gly Gln Thr His Leu Gly Arg Met Gln Phe Asn Ile Glu Glu Gly Gln
            100                 105                 110

Gly Ser Ser Ala Ala Thr Ser Val Gln Asn Ser Arg Leu Pro Asn Gly
        115                 120                 125

Arg Leu Val Asn Ser Ser Ile Leu Gln Trp Val Glu Lys Ala Lys Ala
    130                 135                 140

Asn Gly Ser Thr Ser Thr Ser Ala Leu Tyr Gln Ile Tyr Ala Lys Glu
145                 150                 155                 160

Leu Pro Arg Val Glu Leu Leu Pro Arg Thr Glu His Arg Ala Cys Leu
                165                 170                 175

Ala His Met Tyr Lys Leu Asn Gly Lys Asp Gly Ile Ser Ile Trp Pro
            180                 185                 190

Gln Phe Leu Asp Gly Val Arg Gly Leu Gln Leu Lys His Asp Thr Lys
        195                 200                 205

Val Phe Met Met Asn Asn Pro Lys Ala Ala Asp Glu Phe Tyr Lys Ile
    210                 215                 220

Glu Arg Ser Gly Thr Gln Phe Pro Asp Glu Ala Val Lys Ala Arg Leu
225                 230                 235                 240

Thr Ile Asn Val Lys Pro Gln Phe Gln Lys Ala Met Val Asp Ala Ala
                245                 250                 255

Val Arg Leu Thr Ala Glu Arg His Asp Ile Ile Thr Ala Lys Val Ala
            260                 265                 270

Gly Pro Ala Lys Ile Gly Thr Ile Thr Asp Ala Ala Val Phe Tyr Val
        275                 280                 285

Ser Gly Asp Phe Ser Ala Ala Gln Thr Leu Ala Lys Glu Leu Gln Ala
    290                 295                 300

Leu Leu Pro Asp Asp Ala Phe Ile Asn His Thr Pro Ala Gly Met Gln
305                 310                 315                 320

Ser Met Gly Lys Gly Leu Cys Tyr Ala Glu Arg Thr Pro Gln Asp Arg
                325                 330                 335

Thr Ser His Gly Met Ser Arg Ala Ser Ile Ile Glu Ser Ala Leu Ala
            340                 345                 350

Asp Thr Ser Arg Ser Ser Leu Glu Lys Lys Leu Arg Asn Ala Phe Lys
        355                 360                 365
```

-continued

```
Ser Ala Gly Tyr Asn Pro Asp Asn Pro Ala Phe Arg Leu Glu
    370                 375                 380
```

A DNA molecule from *pseudomonas syringae* pv. *tomato* strain DC3000 encodes a homolog of HopPtoA, identified herein as HopPtoA2, and has a nucleotide sequence (SEQ. ID. No. 65) as follows:

```
atgcacatca accaatccgc ccaacaaccg cctggcgttg caatggagag ttttcggaca     60
gcttccgacg cgtcccttgc ttcgagttct gtgcggtctg tcagcactac ctcgtgccgc    120
gatctacaag ctattaccga ttatctgaaa catcacgtgt tcgctgcgca caggttttcg    180
gtaataggct caccggatga gcgtgatgcc gctcttgcac acaacgagca gatcgatgcg    240
ttggtagaga cacgcgccaa ccgcctgtac tccgaagggg agacccccgc aaccatcgcc    300
gaaacattcg ccaaggcgga aaagttcgac cgtttggcga cgaccgcatc aagtgctttt    360
gagaacacgc catttgccgc tgcctcggtg cttcagtaca tgcagcctgc gatcaacaag    420
ggcgattggc tagcaacgcc gctcaagccg ctgacccccgc tcatttccgg agcgctgtcg   480
ggagccatgg accaggtggg caccaaaatg atggatcgtg cgaggggtga tctgcattac    540
ctgagcactt cgccggacaa gttgcatgat gcgatggccg tatcggtgaa gcgccactcg    600
cctgcgcttg gtcgacaggt tgtggacatg gggattgcag tgcagacgtt ctcggcgcta    660
aatgtggtgc gtaccgtatt ggctccagca ctagcgtcca gaccgtcggt gcagggtgct    720
gttgattttg gcgtatctac ggcgggtggc ttggttgcga atgcaggctt tggcgaccgc    780
atgctcagtg tgcaatcgcg cgatcaactg cgtggggggg cattcgtact tggcatgaaa    840
gataaagagc ccaaggccgc gttgagtgaa gaaactgatt ggcttgatgc ttacaaagcg    900
atcaagtcgg ccagctactc aggtgcggcg ctcaatgcgg gcaagcggat ggccggcctg    960
ccactggacg tcgcgaccga cgggctcaag gcggtgagaa gtctggtgtc ggccaccagc   1020
ctgacaaaaa atggcctggc cctagccggt ggttacgccg gggtaagtaa gttgcagaaa   1080
atggcgacga aaaatatcac tgattcggcg accaaggctg cggttagtca gctgagcaac   1140
ctggtgggtt cggtaggcgt tttcgcaggc tggaccaccg ctggactggc gactgaccct   1200
gcggttaaga aagccgagtc gtttatacag gataaggtga aatcgaccgc atctagtacc   1260
acaagctatg ttgccgacca gaccgtcaaa ctggcgaaaa cagtcaagga catgagcggg   1320
gaggcgatct ccagcaccgg tgccagctta cgcagtactg tcaataacct gcgtcatcgc   1380
tccgctccgg aagctgatat cgaagaaggt gggatttcgg cgttttctcg aagtgaaaca   1440
ccgtttcagc tcaggcgttt gtaa                                          1464
```

Although hopPtoA2 does not lie within the CEL, it is included here as a homolog of hopPtoA, which corresponds to CEL ORF5 as noted above. The encoded HopPtoA2 protein or polypeptide has an amino acid sequence according to SEQ. ID. No. 66 as follows:

```
Met His Ile Asn Gln Ser Ala Gln Gln Pro Pro Gly Val Ala Met Glu
  1               5                  10                  15

Ser Phe Arg Thr Ala Ser Asp Ala Ser Leu Ala Ser Ser Ser Val Arg
             20                  25                  30
```

-continued

```
Ser Val Ser Thr Thr Ser Cys Arg Asp Leu Gln Ala Ile Thr Asp Tyr
        35                  40                  45

Leu Lys His His Val Phe Ala Ala His Arg Phe Ser Val Ile Gly Ser
    50                  55                  60

Pro Asp Glu Arg Asp Ala Ala Leu Ala His Asn Glu Gln Ile Asp Ala
65                  70                  75                  80

Leu Val Glu Thr Arg Ala Asn Arg Leu Tyr Ser Glu Gly Glu Thr Pro
                85                  90                  95

Ala Thr Ile Ala Glu Thr Phe Ala Lys Ala Glu Lys Phe Asp Arg Leu
            100                 105                 110

Ala Thr Thr Ala Ser Ser Ala Phe Glu Asn Thr Pro Phe Ala Ala Ala
        115                 120                 125

Ser Val Leu Gln Tyr Met Gln Pro Ala Ile Asn Lys Gly Asp Trp Leu
    130                 135                 140

Ala Thr Pro Leu Lys Pro Leu Thr Pro Leu Ile Ser Gly Ala Leu Ser
145                 150                 155                 160

Gly Ala Met Asp Gln Val Gly Thr Lys Met Met Asp Arg Ala Arg Gly
                165                 170                 175

Asp Leu His Tyr Leu Ser Thr Ser Pro Asp Lys Leu His Asp Ala Met
            180                 185                 190

Ala Val Ser Val Lys Arg His Ser Pro Ala Leu Gly Arg Gln Val Val
        195                 200                 205

Asp Met Gly Ile Ala Val Gln Thr Phe Ser Ala Leu Asn Val Val Arg
    210                 215                 220

Thr Val Leu Ala Pro Ala Leu Ala Ser Arg Pro Ser Val Gln Gly Ala
225                 230                 235                 240

Val Asp Phe Gly Val Ser Thr Ala Gly Gly Leu Val Ala Asn Ala Gly
                245                 250                 255

Phe Gly Asp Arg Met Leu Ser Val Gln Ser Arg Asp Gln Leu Arg Gly
            260                 265                 270

Gly Ala Phe Val Leu Gly Met Lys Asp Lys Glu Pro Lys Ala Ala Leu
        275                 280                 285

Ser Glu Glu Thr Asp Trp Leu Asp Ala Tyr Lys Ala Ile Lys Ser Ala
    290                 295                 300

Ser Tyr Ser Gly Ala Ala Leu Asn Ala Gly Lys Arg Met Ala Gly Leu
305                 310                 315                 320

Pro Leu Asp Val Ala Thr Asp Gly Leu Lys Ala Val Arg Ser Leu Val
                325                 330                 335

Ser Ala Thr Ser Leu Thr Lys Asn Gly Leu Ala Leu Ala Gly Gly Tyr
            340                 345                 350

Ala Gly Val Ser Lys Leu Gln Lys Met Ala Thr Lys Asn Ile Thr Asp
        355                 360                 365

Ser Ala Thr Lys Ala Ala Val Ser Gln Leu Ser Asn Leu Val Gly Ser
    370                 375                 380

Val Gly Val Phe Ala Gly Trp Thr Thr Ala Gly Leu Ala Thr Asp Pro
385                 390                 395                 400

Ala Val Lys Lys Ala Glu Ser Phe Ile Gln Asp Lys Val Lys Ser Thr
                405                 410                 415
```

-continued

```
Ala Ser Ser Thr Thr Ser Tyr Val Ala Asp Gln Thr Val Lys Leu Ala
            420                 425                 430

Lys Thr Val Lys Asp Met Ser Gly Glu Ala Ile Ser Ser Thr Gly Ala
        435                 440                 445

Ser Leu Arg Ser Thr Val Asn Asn Leu Arg His Arg Ser Ala Pro Glu
    450                 455                 460

Ala Asp Ile Glu Glu Gly Gly Ile Ser Ala Phe Ser Arg Ser Glu Thr
465                 470                 475                 480

Pro Phe Gln Leu Arg Arg Leu
                485
```

Fragments of the above-identified proteins or polypeptides as well as fragments of full length proteins from the EELs and CELs of other bacteria, in particular Gram-negative pathogens, can also be used according to the present invention.

Suitable fragments can be produced by several means. Subclones of the gene encoding a known protein can be produced using conventional molecular genetic manipulation for subcloning gene fragments, such as described by Sambrook et al., 1989, and Ausubel et al., 1994. The subclones then are expressed in vitro or in vivo in bacterial cells to yield a smaller protein or polypeptide that can be tested for activity, e.g., as a product required for pathogen virulence.

In another approach, based on knowledge of the primary structure of the protein, fragments of the protein-coding gene may be synthesized using the PCR technique together with specific sets of primers chosen to represent particular portions of the protein (Erlich et al., 1991). These can then be cloned into an appropriate vector for expression of a truncated protein or polypeptide from bacterial cells as described above.

As an alternative, fragments of a protein can be produced by digestion of a full-length protein with proteolytic enzymes like chymotrypsin or *Staphylococcus* proteinase A, or trypsin. Different proteolytic enzymes are likely to cleave different proteins at different sites based on the amino acid sequence of the particular protein. Some of the fragments that result from proteolysis may be active virulence proteins or polypeptides.

Chemical synthesis can also be used to make suitable fragments. Such a synthesis is carried out using known amino acid sequences for the polyppetide being produced. Alternatively, subjecting a full length protein to high temperatures and pressures will produce fragments. These fragments can then be separated by conventional procedures (e.g., chromatography, SDS-PAGE).

Variants may also (or alternatively) be modified by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

The proteins or polypeptides used in accordance with the present invention are preferably produced in purified form (preferably at least about 80%, more preferably 90%, pure) by conventional techniques. Typically, the protein or polypeptide of the present invention is secreted into the growth medium of recombinant host cells (discussed infra). Alternatively, the protein or polypeptide of the present invention is produced but not secreted into growth medium. In such cases, to isolate the protein, the host cell (e.g., *E. coli*) carrying a recombinant plasmid is propagated, lysed by sonication, heat, or chemical treatment, and the homogenate is centrifuged to remove bacterial debris. The supernatant is then subjected to sequential ammonium sulfate precipitation. The fraction containing the protein or polypeptide of interest is subjected to gel filtration in an appropriately sized dextran or polyacrylamide column to separate the proteins. If necessary, the protein fraction may be further purified by HPLC.

DNA molecules encoding other EEL and CEL protein or polypeptides can be identified using a PCR-based methodology for cloning portions of the pathogenicity islands of a bacterium. Basically, the PCR-based strategy involves the use of conserved sequences from the hrpK and $tRNA^{leu}$ genes (or other conserved border sequences) as primers for cloning EEL intervening regions of the pathogenicity island. As shown in FIGS. 2B–C, the hrpK and $tRNA^{leu}$ genes are highly conserved among diverse *Pseudomonas syringae* variants. Depending upon the size of EEL, additional primers can be prepared from the originally obtained cDNA sequence, allowing for recovery of clones and walking through the EEL in a step-wise fashion. If full-length coding sequences are not obtained from the PCR steps, contigs can be assembled to prepare full-length coding sequences using suitable restriction enzymes. Similar PCR-based procedures can be used for obtaining clones that encode open reading frames in the CEL. As shown in FIG. 3, the CEL of diverse *Pseudomonas syringae* pathovars contain numerous conserved domains. Moreover, known sequences of the hrp/hrc domain, hrp W, AvrE, or gstA can be used to prepare primers.

Using the above-described PCR-based methods, a number of DNA sequences were utilized as the source for primers. One such DNA molecule is isolated from the $tRNA^{leu}$ gene of *Pseudomonas syringae* pv. *tomato* DC3000, which has a nucleotide sequence (SEQ. ID. No. 67) as follows:

```
gccctgatgg cggaattggt agacgcggcg gattcaaaat ccgttttcga aagaagtggg 60
```

-continued

```
agttcgattc tccctcgggg caccacca                                    88
```

An additional DNA molecule which can be used to supply suitable primers is from the tRNA$^{leu}$ gene of *Pseudomonas syringae* pv. *syringae* B728a, which has a nucleotide sequence (SEQ. ID. No. 68) as follows:

```
gccctgatgg cggaattggt agacgcggcg gattcaaaat ccgttttcga aagaagtggg  60
agttcgattc tccctcgggg cacca                                         85
```

Another DNA molecule is isolated from the queA gene of *Pseudomonas syringae* pv. *tomato* DC3000, which has a nucleotide sequence (SEQ. ID. No. 69) as follows:

```
atgcgcgtcg ctgactttac cttcgaactc cccgattccc tgattgctcg tcacccgttg     60
gccgagcgtc gcagcagtcg tctgttgacc cttgatgggc cgacgggcgc gctggcacat    120
cgtcaattca ccgatttgct cgagcatttg cgctcgggcg acttgatggt gttcaacaat    180
acccgtgtca ttcccgcacg tttgttcggg cagaaggcgt ccggcggcaa gctggagatt    240
ctggtcgagc gcgtgctgga cagccatcgt gtgctggcgc acgtgcgtgc cagcaagtcg    300
ccaaagccgg gctcgtcgat cctgatcgat ggcggcggcg aggccgagat ggtggcgcgg    360
catgacgcgc tgttcgagtt gcgctttgcc gaagaagtgc tgccgttgct ggatcgtgtc    420
ggccatatgc cgttgcctcc ttatatagac cgcccggacg aaggtgccga ccgcgagcgt    480
tatcagaccg tttacgccca gcgcgccggt gctgtggcgg cgccgactgc cggcctgcat    540
ttcgaccagc cgttgatgga agcaattgcc gccaagggcg tcgagactgc ttttgtcact    600
ctgcacgtcg gcgcgggtac gttccagccg gtgcgtgtcg agcagatcga agatcaccac    660
atgcacagcg aatggctgga agtcagccag gacgtggtcg atgccgtggc ggcgtgccgt    720
gcgcggggcg ggcgggtgat tgcggtcggg accaccagcg tgcgttcgct ggagagtgcc    780
gcgcgtgatg gccagttgaa gccgtttagc ggcgacaccg acatcttcat ctatccgggg    840
cggccgtttc atgtggtcga tgccctggtg actaattttc atttgcctga atccacgctg    900
ttgatgctgg tttcggcgtt cgccggttat cccgaaacca tggcggccta cgcggcggcc    960
atcgaacacg ggtaccgctt cttcagttac ggtgatgcca tgttcatcac ccgcaatccc   1020
gcgccgacgg ccccacagga atcggcacca gaggatcacg catga                   1065
```

This DNA molecule encodes QueA, which has an amino acid sequence (SEQ. ID. No. 70) as follows:

```
Met Arg Val Ala Asp Phe Thr Phe Glu Leu Pro Asp Ser Leu Ile Ala
  1               5                  10                  15

Arg His Pro Leu Ala Glu Arg Arg Ser Ser Arg Leu Leu Thr Leu Asp
             20                  25                  30

Gly Pro Thr Gly Ala Leu Ala His Arg Gln Phe Thr Asp Leu Leu Glu
         35                  40                  45

His Leu Arg Ser Gly Asp Leu Met Val Phe Asn Asn Thr Arg Val Ile
     50                  55                  60

Pro Ala Arg Leu Phe Gly Gln Lys Ala Ser Gly Gly Lys Leu Glu Ile
 65                  70                  75                  80
```

-continued

```
Leu Val Glu Arg Val Leu Asp Ser His Arg Val Leu Ala His Val Arg
                85                  90                  95

Ala Ser Lys Ser Pro Lys Pro Gly Ser Ser Ile Leu Ile Asp Gly Gly
            100                 105                 110

Gly Glu Ala Glu Met Val Ala Arg His Asp Ala Leu Phe Glu Leu Arg
        115                 120                 125

Phe Ala Glu Glu Val Leu Pro Leu Leu Asp Arg Val Gly His Met Pro
    130                 135                 140

Leu Pro Pro Tyr Ile Asp Arg Pro Asp Glu Gly Ala Asp Arg Glu Arg
145                 150                 155                 160

Tyr Gln Thr Val Tyr Ala Gln Arg Ala Gly Ala Val Ala Ala Pro Thr
                165                 170                 175

Ala Gly Leu His Phe Asp Gln Pro Leu Met Glu Ala Ile Ala Ala Lys
            180                 185                 190

Gly Val Glu Thr Ala Phe Val Thr Leu His Val Gly Ala Gly Thr Phe
        195                 200                 205

Gln Pro Val Arg Val Glu Gln Ile Glu Asp His His Met His Ser Glu
    210                 215                 220

Trp Leu Glu Val Ser Gln Asp Val Val Asp Ala Val Ala Ala Cys Arg
225                 230                 235                 240

Ala Arg Gly Gly Arg Val Ile Ala Val Gly Thr Thr Ser Val Arg Ser
                245                 250                 255

Leu Glu Ser Ala Ala Arg Asp Gly Gln Leu Lys Pro Phe Ser Gly Asp
            260                 265                 270

Thr Asp Ile Phe Ile Tyr Pro Gly Arg Pro Phe His Val Val Asp Ala
        275                 280                 285

Leu Val Thr Asn Phe His Leu Pro Glu Ser Thr Leu Leu Met Leu Val
    290                 295                 300

Ser Ala Phe Ala Gly Tyr Pro Glu Thr Met Ala Ala Tyr Ala Ala Ala
305                 310                 315                 320

Ile Glu His Gly Tyr Arg Phe Phe Ser Tyr Gly Asp Ala Met Phe Ile
                325                 330                 335

Thr Arg Asn Pro Ala Pro Thr Ala Pro Gln Glu Ser Ala Pro Glu Asp
            340                 345                 350

His Ala
```

DNA molecules encoding other EEL and CEL proteins or polypeptides can also be identified by determining whether such DNA molecules hybridize under stringent conditions to a DNA molecule as identified above. An example of suitable stringency conditions is when hybridization is carried out at a temperature of about 37° C. using a hybridization medium that includes 0.9M sodium citrate ("SSC") buffer, followed by washing with 0.2×SSC buffer at 37° C. Higher stringency can readily be attained by increasing the temperature for either hybridization or washing conditions or decreasing the sodium concentration of the hybridization or wash medium. Nonspecific binding may also be controlled using any one of a number of known techniques such as, for example, blocking the membrane with protein-containing solutions, addition of heterologous RNA, DNA, and SDS to the hybridization buffer, and treatment with RNase. Wash conditions are typically performed at or below stringency. Exemplary high stringency conditions include carrying out hybridization at a temperature of about 42° C. to about 65° C. for up to about 20 hours in a hybridization medium containing 1M NaCl, 50 mM Tris-HCl, pH 7.4, 10 mM EDTA, 0.1% sodium dodecyl sulfate (SDS), 0.2% ficoll, 0.2% polyvinylpyrrolidone, 0.2% bovine serum albumin, and 50 μg/ml *E. coli* DNA, followed by washing carried out at between about 42° C. to about 65° C. in a 0.2×SSC buffer.

Also encompassed by the present invention are nucleic acid molecules which contain conserved substitutions as compared to the above identified DNA molecules and, thus, encode the same protein or polypeptides identified above. Further, complementary sequences are also encompassed by the present invention.

The nucleic acid of the present invention can be either DNA or RNA, which can readily be prepared using the above identified DNA molecules of the present invention.

The delivery of effector proteins or polypeptides can be achieved in several ways, depending upon the host being treated and the materials being used: (1) as a stable or plasmid-encoded transgene; (2) transiently expressed via *Agrobacterium* or viral vectors; (3) delivered by the type III secretion systems of disarmed pathogens or recombinant nonpathogenic bacteria which express a functional, heterologous type III secretion system; or (4) delivered via topical application followed by TAT protein transduction domain-mediated spontaneous uptake into cells. Each of these is discussed infra.

The DNA molecule encoding the protein or polypeptide can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference), pQE, pIH821, pGEX, pET series (see Studier et al., 1990). Recombinant molecules can be introduced into cells via transformation, particularly transduction, conjugation, mobilization, or electroporation. The DNA sequences are cloned into the vector using standard cloning procedures in the art, as described by Sambrook et al., 1989.

A variety of host-vector systems may be utilized to express the protein-encoding sequence(s). Primarily, the vector system must be compatible with the host cell used. Host-vector systems include, but are not limited to, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Eukaryotic promoters and accompanying genetic signals may not be recognized in or may not function in a prokaryotic system and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, 1979.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires an SD sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

Because it is desirable for recombinant host cells to secrete the encoded protein or polypeptide, it is preferable that the host cell also possess a functional type III secretion system. The type III secretion system can be heterologous to host cell (Ham et al., 1998) or the host cell can naturally possess a type III secretion system. Host cells which naturally contain a type III secretion system include many pathogenic Gram-negative bacterium, such as numerous *Erwinia* species, *Pseudomonas* species, *Xanthomonas* species, etc. Other type III secretion systems are known and still others are continually being identified. Pathogenic bacteria that can be utilized to deliver effector proteins or polypeptides are preferably disarmed according to known techniques, i.e., as described above. Alternatively, isolation of the effector protein or polypeptide from the host cell or growth medium can be carried out as described above.

Another aspect of the present invention relates to a transgenic plant which express a protein or polypeptide of the present invention and methods of making the same.

In order to express the DNA molecule in isolated plant cells or tissue or whole plants, a plant expressible promoter is needed. Any plant-expressible promoter can be utilized regardless of its origin, i.e., viral, bacterial, plant, etc. Without limitation, two suitable promoters include the nopaline synthase promoter (Fraley et al., 1983) and the cauliflower mosaic virus 35S promoter (O'Dell et al., 1985). Both of these promoters yield constitutive expression of coding sequences under their regulatory control.

While constitutive expression is generally suitable for expression of the DNA molecule, it should be apparent to those of skill in the art that temporally or tissue regulated expression may also be desirable, in which case any regulated promoter can be selected to achieve the desired expression. Typically, the temporally or tissue regulated promoters will be used in connection with the DNA molecule that are expressed at only certain stages of development or only in certain tissues.

In some plants, it may also be desirable to use promoters which are responsive to pathogen infiltration or stress. For example, it may be desirable to limit expression of the protein or polypeptide in response to infection by a particular pathogen of the plant. One example of a pathogen-inducible promoter is the gst1 promoter from potato, which is described in U.S. Pat. Nos. 5,750,874 and 5,723,760 to Strittmayer et al., which are hereby incorporated by reference.

Expression of the DNA molecule in isolated plant cells or tissue or whole plants also requires appropriate transcription termination and polyadenylation of mRNA. Any 3' regulatory region suitable for use in plant cells or tissue can be operably linked to the first and second DNA molecules. A number of 3' regulatory regions are known to be operable in plants. Exemplary 3' regulatory regions include, without limitation, the nopaline synthase 3' regulatory region (Fraley et al., 1983) and the cauliflower mosaic virus 3' regulatory region (Odell et al., 1985).

The promoter and a 3' regulatory region can readily be ligated to the DNA molecule using well known molecular cloning techniques described in Sambrook et al., 1989.

One approach to transforming plant cells with a DNA molecule of the present invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford, et al. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Another method of introducing the DNA molecule into plant cells is fusion of protoplasts with other entities, either minicells, cells, lysosomes, or other fusible lipid-surfaced bodies that contain the DNA molecule (Fraley et al., 1982).

The DNA molecule may also be introduced into the plant cells by electroporation (Fromm, et al., 1985). In this technique, plant protoplasts are electroporated in the presence of plasmids containing the DNA molecule. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *Agrobacterium rhizogenes* previously transformed with the DNA molecule. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

*Agrobacterium* is a representative genus of the Gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences such as a DNA molecule of the present invention can be introduced into appropriate plant cells by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome (Schell, 1987).

Plant tissue suitable for transformation include leaf tissue, root tissue, meristems, zygotic and somatic embryos, and anthers.

After transformation, the transformed plant cells can be selected and regenerated.

Preferably, transformed cells are first identified using, e.g., a selection marker simultaneously introduced into the host cells along with the DNA molecule of the present invention. Suitable selection markers include, without limitation, markers coding for antibiotic resistance, such as kanamycin resistance (Fraley et al., 1983). A number of antibiotic-resistance markers are known in the art and other are continually being identified. Any known antibiotic-resistance marker can be used to transform and select transformed host cells in accordance with the present invention. Cells or tissues are grown on a selection media containing an antibiotic, whereby generally only those transformants expressing the antibiotic resistance marker continue to grow.

Once a recombinant plant cell or tissue has been obtained, it is possible to regenerate a full-grown plant therefrom. Thus, another aspect of the present invention relates to a transgenic plant that includes a DNA molecule of the present invention, wherein the promoter induces transcription of the first DNA molecule in response to infection of the plant by an oomycete. Preferably, the DNA molecule is stably inserted into the genome of the transgenic plant of the present invention.

Plant regeneration from cultured protoplasts is described in Evans et al., 1983, and Vasil, 1984 and 1986.

It is known that practically all plants can be regenerated from cultured cells or tissues, including but not limited to, all major species of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the DNA molecule is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field.

Diseases caused by the vast majority of bacterial pathogens result in limited lesions. That is, even when everything is working in the pathogen's favor (e.g., no triggering of the hypersensitive response because of R-gene detection of one of the effectors), the parasitic process still triggers defenses after a couple of days, which then stops the infection from spreading. Thus, the very same effectors that enable parasitism to proceed must also eventually trigger defenses. Therefore, premature expression of these effectors is believed to "turn on" plant defenses earlier (i.e., prior to infection) and make the plant resistant to either the specific bacteria from which the effector protein was obtained or many pathogens. An advantage of this approach is that it involves natural products and plants seem highly sensitive to pathogen effector proteins.

According to one embodiment, a transgenic plant is provided that contains a heterologous DNA molecule of the present invention. Preferably, the heterologous DNA molecule is derived from a plant pathogen EEL. When the heterologous DNA molecule is expressed in the transgenic plant, plant defenses are activated, imparting disease resistance to the transgenic plant. The transgenic plant can also contain an R-gene which is activated by the protein or polypeptide product of the heterologous DNA molecule. The R gene can be naturally occurring in the plant or heterologously inserted therein. A number of R genes have been identified in various plant species, including without limitation: RPS2, RPM1, and RPP5 from *Arabidopsis thaliana*; Cf2, Cf9, I2, Pto, and Prf from tomato; N from tobacco; L6 and M from flax; Xa2l from rice; and Hs1pro-1 from sugar beet. In addition to imparting disease resistance, it is believed that stimulation of plant defenses in transgenic plants of the present invention will also result in a simultaneous enhancement in growth and resistance to insects.

According to another embodiment, a plant, transgenic or non-transgenic, is treated with a protein or polypeptide of the present invention. By treating, it is intended to include various forms of applying the protein or polypeptide to the plant. The embodiments of the present invention where the effector polypeptide or protein is applied to the plant can be carried out in a number of ways, including: 1) application of an isolated protein (or composition containing the same) or 2) application of bacteria which do not cause disease and are transformed with a gene encoding the effector protein of the present invention. In the latter embodiment, the effector protein can be applied to plants by applying bacteria containing the DNA molecule encoding the effector protein. Such bacteria are preferably capable of secreting or exporting the protein so that the protein can contact plant cells. In these embodiments, the protein is produced by the bacteria in planta.

Such topical application is typically carried out using an effector fusion protein which includes a transduction domain, which will afford transduction domain-mediated spontaneous uptake of the effector protein into cells. Basically, this is carried out by fusing an 11-amino acid peptide (YGRKKRRQRRR, SEQ. ID. No. 91) by standard rDNA techniques to the N-terminus of the effector protein, and the resulting tagged protein is taken up into cells by a poorly understood process. This peptide is the protein transduction domain (PTD) of the human immunodeficiency virus (HIV) TAT protein (Schwarze et al., 2000). Other PTDs are known and may possibly be used for this purpose (Prochiantz, 2000).

When the effector protein is topically applied to plants, it can be applied as a composition, which includes a carrier in the form, e.g., of water, aqueous solutions, slurries, or dry powders. In this embodiment, the composition contains greater than about 5 nM of the protein of the present invention.

Although not required, this composition may contain additional additives including fertilizer, insecticide, fungicide, nematicide, and mixtures thereof. Suitable fertilizers include $(NH_4)_2NO_3$. An example of a suitable insecticide is Malathion. Useful fungicides include Captan.

Other suitable additives include buffering agents, wetting agents, coating agents, and, in some instances, abrading agents. These materials can be used to facilitate the process of the present invention.

According to another aspect of the present invention, a transgenic plant is provided that contains a heterologous DNA molecule that encodes a transcript or a protein or polypeptide capable of disrupting function of a plant pathogen CEL product. Because the genes in the CEL are particularly important in pathogenesis, disrupting the function of their products in plants can result in broad resistance since CEL genes are highly conserved among Gram negative pathogens, particularly along species lines. An exemplary protein or polypeptide which can disrupt function of a CEL product is an antibody, polyclonal or monoclonal, raised against the CEL product using conventional techniques. Once isolated, the antibody can be sequenced and nucleic acids synthesized for encoding the same. Such nucleic acids, e.g., DNA, can be used to transform plants.

Transgenic plants can also be engineered so that they are hypersusceptible and, therefore, will support the growth of nonpathogenic bacteria for biotechnological purposes. It is known that many plant pathogenic bacteria can alter the environment inside plant leaves so that nonpathogenic bacteria can grow. This ability is presumably based on changes in the plant caused by pathogen effector proteins. Thus, transgenic plants expressing the appropriate effector genes can be used for these purposes.

According to one embodiment, a transgenic plant including a heterologous DNA molecule of the present invention expresses one or more effector proteins, wherein the transgenic plant is capable of supporting growth of compatible nonpathogenic bacteria (i.e., non-pathogenic endophytes such as various *Clavibacter* ssp.). The compatible nonpathogenic bacteria can be naturally occurring or it can be recombinant. Preferably, the nonpathogenic bacteria is recombinant and expresses one or more useful products. Thus, the transgenic plant becomes a green factory for producing desirable products. Desirable products include, without limitation, products that can enhance the nutritional quality of the plant or products that are desirable in isolated form. If desired in isolated form, the product can be isolated from plant tissues. To prevent competition between the non-pathogenic bacteria which express the desired product and those that do not, it is possible to tailor the needs of recombinant, non-pathogenic bacteria so that only they are capable of living in plant tissues expressing a particular effector protein or polypeptide of the present invention.

The effector proteins or polypeptides of the present invention are believed to alter the plant physiology by shifting metabolic pathways to benefit the parasite and by activating or suppressing cell death pathways. Thus, they may also provide useful tools for efficiently altering the nutrient content of plants and delaying or triggering senescence. There are agricultural applications for all of these possible effects.

A further aspect of the present invention relates to diagnostic uses of the CEL and EEL. The CEL genes are universal to species of Gram negative bacteria, particularly pathogenic Gram negative bacteria (such as *P. syringae*), whereas the EEL sequences are strain-specific and provide a "virulence gene fingerprint" that could be used to track the presence, origins, and movement (and restrict the spread through quarantines) of strains that are particularly threatening. Although the CEL and EEL have been identified in various pathovars of *Pseudomonas syringae*, it is expected that most all Gram-negative pathogens can be identified, distinguished, and classified based upon the homology of the CEL and EEL genes.

According to one embodiment, a method of determining relatedness between two bacteria is carried out by comparing a nucleic acid alignment or amino acid alignment for a CEL of the two bacteria and then determining the relatedness of the two bacteria, wherein a higher sequence identity indicates a closer relationship. The CEL is particularly useful for determining the relatedness of two distinct bacterial species.

According to another embodiment, a method of determining relatedness between two bacteria which is carried out by comparing a nucleic acid alignment or amino acid alignment for an EEL of the two bacteria and then determining the relatedness of the two bacteria, wherein a higher sequence identity indicates a closer relationship. The EEL is particularly useful for determining the relatedness of two pathovars of a single bacterial species.

Given the methods of determining relatedness of bacteria species and/or pathovars, these methods can be utilized in conjunction with plant breeding programs. By detecting the "virulence gene fingerprint" of pathogens which are prevalent in a particular growing region, it is possible either to develop transgenic cultivars as described above or to identify existing plant cultivars which are resistant to the prevalent pathogens.

In addition to the above described uses, another aspect of the present invention relates to gene- and protein-based therapies for animals, preferably mammals including, without limitation, humans, dogs, mice, rats. The *P. syringae* pv. *syringae* B728a EEL ORF5 protein (SEQ. ID. No. 32) is a member of the AvrRxv/YopJ protein family. YopJ is injected into human cells by the *Yersinia* type III secretion system, where it disrupts the function of certain protein kinases to inhibit cytokine release and promote programmed cell death. It is believed that the targets of many pathogen effector proteins (i.e., *P. syringae* effector proteins) will be universal to eukaryotes and therefore have a variety of potentially useful functions. In fact, two of the proteins in the *P. syringae* Hrp pathogenicity islands are toxic when expressed in yeast. They are HopPsyA from the *P. syringae* pv. *syringae* EEL and HopPtoA from the *P. syringae* pv. *tomato* DC3000 CEL. This supports the concept of universal eukaryote targets.

Thus, a further aspect of the present invention relates to a method of causing eukaryotic cell death which is carried out by introducing into a eukaryotic cell a cytotoxic *Pseudomonas* protein. The cytotoxic *Pseudomonas* protein is preferably HopPsyA (e.g., SEQ. ID. Nos. 36 (Psy 61), 62 (Psy 226), or 64 (Psy B143)) HopPtoA (SEQ. ID. No. 7), or HopPtoA2 (SEQ. ID. No. 66). The eukaryotic cell which is treated can be either in vitro or in vivo. When treating eukaryotic cells in vivo, a number of different protein- or DNA-delivery systems can be employed to introduce the effector protein into the target eukaryotic cell.

Without being bound by theory, it is believed that at least the HopPsyA effector proteins exert their cytotoxic effects through Mad2 interactions, disrupting cell checkpoint of spindle formation (see infra).

The protein- or DNA-delivery systems can be provided in the form of pharmaceutical compositions which include the delivery system in a pharmaceutically acceptable carrier, which may include suitable excipients or stabilizers. The dosage can be in solid or liquid form, such as powders, solutions, suspensions, or emulsions. Typically, the composition will contain from about 0.01 to 99 percent, preferably from about 20 to 75 percent of active compound(s), together with the carrier, excipient, stabilizer, etc.

The compositions of the present invention are preferably administered in injectable or topically-applied dosages by solution or suspension of these materials in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

Alternatively, the effector proteins can also be delivered via solution or suspension packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Depending upon the treatment being effected, the compounds of the present invention can be administered orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Compositions within the scope of this invention include all compositions wherein the compound of the present invention is contained in an amount effective to achieve its intended purpose. While individual needs vary, determination of optimal ranges of effective amounts of each component is within the skill of the art.

One approach for delivering an effector protein into cells involves the use of liposomes. Basically, this involves providing a liposome which includes that effector protein to be delivered, and then contacting the target cell with the liposome under conditions effective for delivery of the effector protein into the cell.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., *Proc. Natl. Acad. Sci. USA* 84:7851 (1987); *Biochemistry* 28:908 (1989), which are hereby incorporated by reference). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane which slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

This liposome delivery system can also be made to accumulate at a target organ, tissue, or cell via active targeting (e.g., by incorporating an antibody or hormone on the surface of the liposomal vehicle). This can be achieved according to known methods.

Different types of liposomes can be prepared according to Bangham et al., (1965); U.S. Pat. No. 5,653,996 to Hsu et al., U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al.

An alternative approach for delivery of effector proteins involves the conjugation of the desired effector protein to a polymer that is stabilized to avoid enzymatic degradation of the conjugated effector protein. Conjugated proteins or polypeptides of this type are described in U.S. Pat. No. 5,681,811 to Ekwuribe.

Yet another approach for delivery of proteins or polypeptides involves preparation of chimeric proteins according to U.S. Pat. No. 5,817,789 to Heartlein et al. The chimeric protein can include a ligand domain and, e.g., an effector protein of the present invention. The ligand domain is specific for receptors located on a target cell. Thus, when the chimeric protein is delivered intravenously or otherwise introduced into blood or lymph, the chimeric protein will adsorb to the targeted cell, and the targeted cell will internalize the chimeric protein, which allows the effector protein to de-stabilize the cell checkpoint control mechanism, affording its cytotoxic effects.

When it is desirable to achieve heterologous expression of an effector protein of the present invention in a target cell, DNA molecules encoding the desired effector protein can be delivered into the cell. Basically, this includes providing a nucleic acid molecule encoding the effector protein and then introducing the nucleic acid molecule into the cell under conditions effective to express the effector protein in the cell. Preferably, this is achieved by inserting the nucleic acid molecule into an expression vector before it is introduced into the cell.

When transforming mammalian cells for heterologous expression of an effector protein, an adenovirus vector can be employed. Adenovirus gene delivery vehicles can be readily prepared and utilized given the disclosure provided in Berkner, 1988, and Rosenfeld et al., 1991. Adeno-associated viral gene delivery vehicles can be constructed and used to deliver a gene to cells. The use of adeno-associated viral gene delivery vehicles in vitro is described in Chatterjee et al. 1992; Walsh et al. 1992; Walsh et al., 1994; Flotte et al., 1993a; Ponnazhagan et al., 1994; Miller et al., 1994; Einerhand et al., 1995; Luo et al., 1995; and Zhou et al., 1996. In vivo use of these vehicles is described in Flotte et al., 1993b and Kaplitt et al., 1994. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel.

Retroviral vectors which have been modified to form infective transformation systems can also be used to deliver nucleic acid encoding a desired effector protein into a target cell. One such type of retroviral vector is disclosed in U.S. Pat. No. 5,849,586 to Kriegler et al.

Regardless of the type of infective transformation system employed, it should be targeted for delivery of the nucleic acid to a specific cell type. For example, for delivery of the nucleic acid into tumor cells, a high titer of the infective transformation system can be injected directly within the tumor site so as to enhance the likelihood of tumor cell infection. The infected cells will then express the desired effector protein, e.g., HopPtoA, HopPsyA, or HopPtoA2, disrupting cellular functions and producing cytotoxic effects.

Particularly preferred is use of the effector proteins of the present invention to treat a cancerous condition (i.e., the eukaryotic cell which is affected is a cancer cell). This can be carried out by introducing a cytotoxic *Pseudomonas* protein into cancer cells of a patient under conditions effective to inhibit cancer cell division, thereby treating the cancerous condition.

By introducing, it is intended that the effector protein is administered to the patient, preferably in the form of a composition which will target delivery to the cancer cells.

Alternatively, when using DNA-based therapies, it is intended that the introducing be carried out by administering a target DNA delivery system to the patient such that the cancer cells are targeted and the effector protein is expressed therein.

EXAMPLES

The following Examples are intended to be illustrative and in no way are intended to limit the scope of the present invention.

Materials and Methods

Bacterial Strains, Culture Conditions, Plasmids, and DNA Manipulation Techniques Three experimentally amenable strains that represent different levels of diversity in *P. syringae* were investigated: Psy 61, Psy B728a, and Pto DC3000. (i) Psy 61 is a weak pathogen of bean whose hrp gene cluster, cloned on cosmid pHIR11, contains all of the genes necessary for nonpathogenic bacteria like *Pseudomonas fluorescens* and *Escherichia coli* to elicit the HR in tobacco and to secrete in culture the HrpZ harpin, a protein with unknown function that is secreted abundantly by the Hrp system (Alfano et al., 1996). The pHIR11 hip cluster has been completely sequenced (FIG. 1) (Alfano and Collmer, 1997), and the hopPsyA gene in the hypervariable region at the left edge of the cluster was shown to encode a protein that has an Avr phenotype, travels the Hrp pathway, and elicits cell death when expressed in tobacco cells (Alfano and Collmer, 1997; Alfano et al., 1997; van Dijk et al., 1999). (ii) Psy B728a is in the same pathovar as strain 61 but is highly virulent and is a model for studying the role of the Hrp system in epiphytic fitness and pathogenicity (brown spot of bean) in the field (Hirano et al., 1999). (iii) Pto DC3000 is a well-studied pathogen of *Arabidopsis* and *tomato* (causing bacterial speck) that is highly divergent from pathovar syringae strains. Analysis of rRNA operon RFLP patterns has indicated that Pto and Psy are distantly related and could be considered separate species (Manceau and Horvais, 1997). Thus, we were able to compare two strains in the same pathovar with a strain from a highly divergent pathovar.

Conditions for culturing *E. coli* and *P. syringae* strains have been described (van Dijk et al., 1999), as have the sources for Psy 61 (Preston et al., 1995), Psy B728a (Hirano et al., 1999), and Pto DC3000 (Preston et al., 1995). Cloning and DNA manipulations were done in *E. coli* DH5α using pBluescript II (Stratagene, La Jolla, Calif.), pRK415 (Keen et al., 1988), and cosmid pCPP47 (Bauer and Collmer, 1997), according to standard procedures (Ausubel et al., 1994). Cosmid libraries of Pto DC3000 and Psy B728a genomic DNA were previously constructed (Charkowski et al., 1998). Oligonucleotide synthesis and DNA sequencing were performed at the Cornell Biotechnology Center. The nucleotide sequence of the Pto DC3000 hrp/hrc cluster was determined using subclones of pCPP2473, a cosmid selected from a genomic cosmid library based on hybridization with the hrpK gene of Psy 61. The nucleotide sequence of the Psy B728a hrp/hrc cluster was determined using subclones of pCPP2346 and pCPP3017. These cosmids were selected from a genomic library based on hybridization with the hrpC operon of 61. The left side of the Psy 61 EEL region was cloned by PCR into pBSKSII+ XhoI and EcoRI sites using the following primers:

SEQ. ID. NO. 71, which primes within queA and contains an XhoI site:

SEQ. ID. NO. 72, which primes within hopPsyA and contains an EcoRI site:

Pfu polymerase was used for all PCR experiments. DNA sequence data were managed and analyzed with the DNAStar Program (Madison, Wis.), and databases were searched with the BLASTX, BLASTP, and BLASTN programs (Altschul et al., 1997).

Mutant Construction and Analysis

Large deletions in the Pto DC3000 Hrp Pai were constructed by subcloning border fragments into restriction sites on either side of an $\Omega Sp^R$ cassette in pRK415, electroporating the recombinant plasmids into DC3000, and then selecting and screening for marker exchange mutants as described (Alfano et al., 1996). The following left and right side (FIGS. 2 and 3) deletion border fragments were used (with residual gene fragments indicated): for CUCPB5110 left tgt-gueA-tRNA-$^{Leu}$-ORF4' (27 bp of ORF4) and right ORF1'-hrpK (396 bp of ORF1); and for CUCPB5115 left hrpS'-avrE' (2569 bp of avrE) and right ORF6 (156 bp upstream of ORF6 start codon). The later fragment was PCR-amplified using the following primers:

SEQ. ID. NO. 73, which primes in the ORF5-ORF6 intergenic region and contains an XbaI site:

SEQ. ID. NO. 74, which primes in ORF6 and contains a HindIII site:

Mutant constructions were confirmed by Southern hybridizations using previously described conditions (Charkowski et al., 1998). The ability of mutants to secrete AvrPto was determined with anti-AvrPto antibodies and immunoblot analysis of cell fractions as previously described (van Dijk et al., 1999). Mutant CUCPB5 115 was complemented with pCPP3016, which carries ORF2 through ORF10 in cosmid pCPP47, and was introduced from *E. coli* DH5α by triparental mating using helper strain *E. coli* DH5α (pRK600), as described (Charkowski et al., 1998).

T7 Expression Analysis

Protein products of the Pto DC3000 EEL were analyzed by T7 polymerase-dependent expression using vector pET21 and *E. coli* BL21(DE3) as previously described (Huang et al., 1995). The following primer sets were used to PCR each ORF from pCPP3091, which carries in pBSKSII+ a BamH1 fragment containing tgt to hrcV:

ORF1, SEQ. ID. Nos. 75 and 76, respectively:

```
agtaggatcc tgaaatgtag gggcccgg        28
agtaaagctt atgatgctgt ttccagta        28
```

ORF2, SEQ. ID. Nos. 77 and 78, respectively:

```
agtaggatcc tctcgaagga atggagca        28
agtaaagctt cgtgaagatg catttcgc        28
```

ORF3, SEQ. ID. Nos. 79 and 80, respectively:

```
agtaggatcc tagtcactga tcgaacgt        28
agtactcgag ccacgaaata acacggta        28
```

ORF4, SEQ. ID. Nos. 81 and 82, respectively:

```
agtaggatcc caggactgcc ttccagcg        28

agtactcgag cagagcggcg tccgtggc        28
```

tnpA, SEQ. ID. Nos. 83 and 84, respectively:

```
agtaggatcc agaattgttg aagaaatc        28

agtaaagctt tgcgctgtta actcatcg        28
```

Plant Bioassays

Tobacco (*Nicotiana tabacum* L. cv. *Xanthi*) and tomato (*Lycopersicon esculentum* Mill. cvs. Moneymaker and Rio Grande) were grown under greenhouse conditions and then maintained at 25° C. with daylight and supplemental halide illumination for HR and virulence assays. Bacteria were grown overnight on King's medium B agar supplemented with appropriate antibiotics, suspended in 5 mM MES pH 5.6, and then infiltrated with a needleless syringe into the leaves of test plants at $10^8$ cfu/ml for HR assays and $10^4$ cfu/ml for pathogenicity assays (Charkowski et al., 1998). All assays were repeated at least four times on leaves from different plants. Bacterial growth in tomato leaves was assayed by excising disks from infiltrated areas with a cork borer, comminuting the tissue in 0.5 ml of 5 mM MES, pH 5.6, with a Kontes Pellet Pestle (Fisher Scientific, Pittsburgh, Pa.), and then dilution plating the homogenate on King's medium B agar with 50 μg/ml rifampicin and 2 μg/ml cycloheximide to determine bacterial populations. The mean and SD from three leaf samples were determined for each time point. The relative growth in planta of DC3000 and CUCPB5110 was similarly assayed in 4 independent experiments and the relative growth of DC3000, CUCPB5115, and CUCPB5115(pCPP3016) in 3 independent experiments. Although the final population levels achieved by DC3000 varied between experiments, the populations levels of the mutants relative to the wild type were the same as in the representative experiments presented below.

Example 1

Comparison of hrp/hrc Gene Clusters of Psy 61, Psy B728a, and Pto DC3000

To determine if the hrp/hrc clusters from Psy B728a and Pto DC3000 were organized similarly to the previously characterized hrp/hrc cluster of Psy 61, two cosmids carrying hrp/hrc inserts were partially characterized. pCPP2346 carries the entire hrp/hrc cluster of B728a, and pCPP2473 carries the left half of the hrp/hrc cluster of DC3000. The right half of the DC3000 hrp/hrc cluster had been characterized previously (Preston et al., 1995). Sequencing the ends of several subclones derived from these cosmids provided fingerprints of the B728a and DC3000 hrp/hrc clusters, which indicated that both are arranged like that of strain 61 (FIG. 1). However, B728a contains between hrcU and hrpV a 3.6-kb insert with homologs of bacteriophage lambda genes Ea59 (23% amino-acid identity; E=2e-7) and Ea3l (30% amino-acid identity; E=6e-8) (Hendrix et al., 1983), and the B728a hrcU ORF has 36 additional codons. A possible insertion of this size in several Psy strains that are highly virulent on bean was suggested by a previous RFLP analysis (Legard et al., 1993). Cosmid pCPP2346, which contains the B728a hrp/hrc region and flanking sequences (4 kb on the left and 13 kb on the right), enabled *P. fluorescens* to secrete the B728a HrpZ harpin in culture and to elicit the HR in tobacco leaves, however, confluent necrosis developed more slowly than with *P. fluorescens* (pHIR11) (data not shown). To further test the relatedness of the Psy 61 and B728a hrp/hrc gene clusters using an internal reference, the B728a hrpA gene was sequenced. Of the hrp/hrc genes that have been sequenced in Psy and Pto, hrpA, which encodes the major subunit of the Hrp pilus (Roine et al., 1997), is the least conserved (28% amino-acid identity) (Preston et al., 1995). However, the hrpA genes of strains 61 and B728a were 100% identical, which further supports the close relationship of these strains and their Hrp systems.

Example 2

Figure 2:
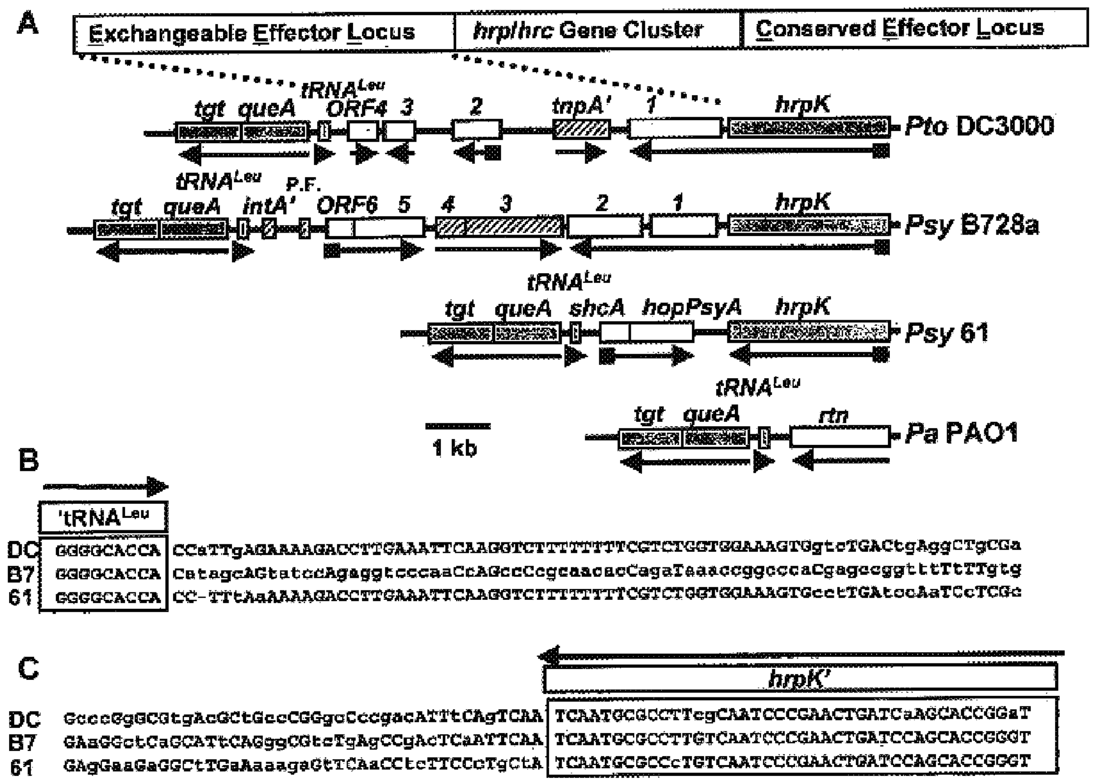
FIGS. 2A–C show the EEL of Pto DC3000, Psy B728a, and Psy 61, the tgt-queA-tRNA$^{Leu}$ locus in *P. aeruginosa* (*Pa*), and EEL border sequences.

Identification of an Exchangeable Effector Locus (EEL) in the Hrp Pai between hrpK and $tRNA^{Leu}$ Sequence analysis of the left side of the Psy 61, Psy B728a, and Pto DC3000 Hrp Pais revealed that the high percentage identity in hrpK sequences in these strains abruptly terminates three nucleotides after the hrpK stop codon and then is restored near $tRNA^{Leu}$, queA, and tgt sequences after 2.5 kb (Psy 61), 7.3 kb (Psy B728a), or 5.9 kb (Pto DC3000) of dissimilar, intervening DNA (FIG. 2). The difference between Psy strains 61 and B728a in this region was particularly surprising. This region of the *P. syringae* Hrp Pai was given the EEL designation because it contained completely different effector protein genes (Table 1 below), which appear to be exchanged at this locus at a high frequency. In this regard, it is noteworthy that (i) ORF2 in the B728a EEL is a homolog of avrPphE, which is in a different location, immediately downstream of hrpK (hrpY), in Pph 1302A (Mansfield et al., 1994), (ii) hopPsyA (hrmA) is present in only a few Psy strains (Heu and Hutcheson, 1993; Alfano et al., 1997), (iii) and ORF5 in the B728a EEL predicts a protein that is similar to *Xanthomonas* AvrBsT and possesses multiple motifs characteristic of the AvrRxv family (Ciesiolka et al., 1999). G+C content different from the genomic average is a hallmark of horizontally transferred genes, and the G+C contents of the ORFs in the three EELs are considerably lower than the average of 59–61% for *P. syringae* (Palleroni et al., 1984) (Table 1 below). They are also lower than hrpK (60%) and queA (63–64%). The ORFs in the Pto DC3000 EEL predict no products with similarity to known effector proteins, however T7 polymerase-dependent expression revealed products in the size range predicted for ORF 1, ORF3, and ORF4. Furthermore, the ORF1 protein is secreted in a hrp-dependent manner by *E. coli*(pCPP2156), which expresses an *Erwinia chrysanthemi* Hrp system that secretes *P. syringae* Avr proteins (Ham et al., 1998). Several ORFs in these EELs are preceded by Hrp boxes indicative of HrpL-activated promoters (FIG. 1) (Xiao and Hutcheson, 1994), and the lack of intervening Rho-independent terminator sequences or promoters suggests that ORF1 in DC3000 and ORF1 and ORF2 in B728a are expressed from HrpL-activated promoters upstream of the respective hrpK genes.

The EELs of these three strains also contain sequences homologous to insertion sequences, transposases, phage integrase genes, and plasmids (FIG. 2 and Table 1 below). The Psy B728a ORF5 and ORF6 operon is bordered on the left side linked to any type III secretion system genes or other genes in the Hrp Pai (FIG. 2). Thus, this is the apparent point of insertion of the Hrp Pai in the ancestral *Pseudomonas* genome.

Example 3

Identification of a Conserved Effector Locus (CEL) Located on the Right Side of the Hrp Pai in Psy B728a and Pto DC3000

Previous studies of the region to the right of hrpR in DC3000 had revealed the existence of the avrE locus, which is comprised of two transcriptional units (Lorang and Keen, 1995), the 5' sequences for the first 4 transcriptional units beyond hrpR (Lorang and Keen, 1995), and the identity of the fourth transcriptional unit as the hrpW gene encoding a second harpin (Charkowski et al., 1998). The DNA sequence of the first 14 ORFs to the right of hrpR in Pto DC3000 was completed in this investigation and the corresponding region in Psy B728a was partially sequenced (FIG. 3). Like the EEL, this region contains putative effector genes, e.g., avrE (Lorang and Keen, 1995). Unlike the EEL, the ORFs in this region have an average G+C content of 58.0%, which is close to that of the hrp/hrc genes, the region contains no sequences similar to known mobile genetic elements, and it appears conserved between Psy and Pto (FIG. 3). Comparison of the regions sequenced in B728a and DC3000 revealed that the first 7 ORFs are arranged identically and have an average DNA sequence identity of 78%. Hence, this region was given the CEL designation.

The precise border of the CEL remains undefined, and no sequences that were repeated in the EEL border of the Hrp Pai were found. ORF7 and ORF8 are likely to be part of the CEL, based on the presence of an upstream Hrp box (FIG. 3). However, the region beyond ORF10 probably is not in the CEL because the product of the next ORF shows homology to a family of bacterial GstA proteins (e.g., 28% identity with *E. coli* GstA over 204 amino acids; E=1e-8) (Blattner et al., 1997), and glutathione-S-transferase activity is common in nonpathogenic fluorescent pseudomonads (Zablotowicz et al., 1995). The presence of a galP homolog (38% identity over 256 amino acids, based on incomplete sequence, to *E. coli* GalP; E=2e-42) (Blattner et al., 1997) in this region further suggests that it is beyond the CEL.

Several other features of this region in B728a and DC3000 are noteworthy. (i) Both strains have a 1-kb intergenic region between hrpR and ORF1 that is distinguished by low sequence identity (44%) but which contains three inverted repeats that could form stem loop structures affecting expression of the hrpRS operon. (ii) ORF1 is most similar to *E. coli* murein lytic transglycosylase MltD (38% identity over 324 amino acids; E=4e-56). (iii) ORF2 is 42% identical over 130 amino acids with *E. amylovora* DspF (E=9e-24), a candidate chaperone (Bogdanove et al., 1998a; Gaudriault et al., 1997). (iv) The ORF5 protein is secreted in a hrp-dependent manner by *E. coli*(pCPP2156), but mutation with an $\Omega Sp^r$ cassette has little effect on either HR elicitation in tobacco or pathogenicity in tomato (Charkowski, unpublished). (v) Finally, six operons in this region are preceded by Hrp boxes (Lorang and Keen, 1995) (FIG. 3), which is characteristic of known avr genes in *P. syringae* (Alfano et al., 1996). Thus, the CEL carries multiple candidate effectors.

Example 4

Investigation of EEL and CEL Roles in Pathogenicity

A mutation was constructed in DC3000 that replaced all of the ORFs between hrpK and $tRNA^{Leu}$ (EEL) with an $\Omega Sp^r$ cassette (FIG. 2). This Pto mutant, CUCPB5110, was tested for its ability to elicit the HR in tobacco and to cause disease in tomato. The mutant retained the ability to elicit the HR and to produce disease symptoms, but it failed to reach population levels as high as the parental strain in tomato (FIG. 4A).

A mutation was constructed in DC3000 that replaced avrE through ORF5 (CEL) with an $\Omega Sp^r$ cassette. This deleted all of the CEL ORFs that were both partially characterized and likely to encode effectors. This Pto mutant, CUCPB5115, still elicited the HR in tobacco, but tissue collapse was delayed ca. 5 h (FIG. 4C). The mutant no longer elicited disease symptoms in tomato when infiltrated at a concentration of $10^4$ cfu/ml, and growth in planta was strongly reduced (FIG. 4B). However, the mutant elicited an HR dependent on the tomato Pto R gene that was indistinguishable from the wild-type in tests involving PtoS (susceptible) and PtoR (resistant) Rio Grande tomato lines. Plasmid pCPP3016, which carries ORF2 through ORF10, fully restored the ability of CUCPB5115 to cause disease symptoms and partially restored the ability of the mutant to multiply in tomato leaves (FIGS. 4B and 4E). Deletion of the hrp/hrc cluster abolishes HR and pathogenicity phenotypes in Pto DC3000 (Collmer et al., 2000). To confirm that the large deletions in Pto mutants CUCPB5110 and CUCPB5115 did not disrupt Hrp secretion functions, we compared the ability of these mutants, the DC3000 hrp/hrc deletion mutant, and wild-type DC3000 to make and secrete AvrPto in culture while retaining a cytoplasmic marker comprised of β-lactamase lacking its signal peptide. AvrPto provided an ideal subject for this test because it is a well-studied effector protein that is secreted in culture and injected into host cells in planta (Alfano and Collmer, 1997; van Dijk et al., 1999). Only the hrp/hrc deletion cluster mutant was impaired in AvrPto production and secretion (FIG. 5).

Based on the above studies, the *P. syringae* hrp/hrc genes are part of a Hrp Pai that has three distinct loci: an EEL, the hrp/hrc gene cluster, and a CEL. The EEL harbors exchangeable effector genes and makes only a quantitative contribution to parasitic fitness in host plants. The hrp/hrc locus encodes the Hrp secretion system and is required for effector protein delivery, parasitism, and pathogenicity. The CEL makes no discernible contribution to Hrp secretion functions but contributes strongly to parasitic fitness and is required for Pto pathogenicity in tomato. The Hrp Pai of *P. syringae* has several properties of Pais possessed by animal pathogens (Hacker et al., 1997), including the presence of many virulence-associated genes (several with relatively low G+C content) in a large (ca. 50-kb) chromosomal region linked to a tRNA locus and absent from the corresponding locus in a closely related species. In addition, the EEL portion of the Hrp Pai is unstable and contains many sequences related to mobile genetic elements.

The EEL is a novel feature of known Pais, which is likely involved in fine-tuning the parasitic fitness of *P. syringae* strains with various plant hosts. By comparing closely- and distantly-related strains of *P. syringae*, we were able to establish the high instability of this locus and the contrasting high conservation of its border sequences. No single mechanism can explain the high instability, as we found fragments related to phages, insertion sequences, and plasmids in the Psy and Pto EELs, and insertion sequences were recently reported in the corresponding region of three other *P. syringae* strains (Inoue and Takikawa, 1999). The mechanism or significance of the localization of the EELs between $tRNA^{Leu}$ and hrpK sequences in the Hrp Pais also is unclear. Pto DC3000 carries at least one other effector gene, avrPto, that is located elsewhere in the genome (Ronald et al., 1992), many *P. syringae* avr genes are located on plasmids (Leach and White, 1996), and the EEL ORFs represent a mix of widespread, (e.g., avrRxv family) and seemingly rare (e.g., hopPsyA), effector genes. The G+C content of the EEL ORFs is significantly lower than that of the rest of the Hrp Pai and the *P. syringae* genome. Although certain genes in the non-EEL portions of the Hrp Pai, such as hrpA, are highly divergent, they have a high G+C content, and there is no evidence that they have been horizontally transferred separately from the rest of the Hrp Pai. The relatively low G+C content of the ORFs in the EELs (and of other *P. syringae* avr genes) suggests that these genes may be horizontally acquired from a wider pool of pathogenic bacteria than just *P. syringae* (Kim et al., 1998). Indeed, the avrRxv family of genes is found in a wide range of plant and animal pathogens (Ciesiolka et al., 1999). The weak effect on parasitic fitness of deleting the Pto DC3000 EEL, or of mutating hopPsyA (hrmA) in Psy 61 (Huang et al., 1991), is typical of mutations in individual avr genes and presumably results from redundancy in the effector protein system (Leach and White, 1996).

The functions of hrpK and of the CEL ORF1 are unclear but warrant discussion. These two ORFs reside just outside the hrpL and hrpR delimited cluster of operons containing both hrp and hrc genes and thereby spatially separate the three regions of the Hrp Pai (FIGS. 1–3). hrpK mutants have a variable Hrp phenotype (Mansfield et al., 1994; Bozso et al., 1999), and a Psy B728a hrpK mutant still secretes HrpZ (Alfano, unpublished), which suggests that HrpK may be an effector protein. Nevertheless, the HrpK proteins of Psy 61 and Pto DC3000 are 79% identical and therefore are more conserved than many Hrp secretion system components. It is also noteworthy that hrpK appears to be in an operon with other effector genes in Psy B728a and Pto DC3000. In contrast, the CEL ORF1 may contribute (weakly or redundantly) to Hrp secretion functions by promoting penetration of the system through the bacterial peptidoglycan layer. The ORF1 product has extensive homology with *E. coli* MltD and shares a lysozyme-like domain with the product of ipgF (Mushegian et al., 1996), a *Shigella flexneri* gene that is also located between loci encoding a type III secretion system and effector proteins (Allaoui et al., 1993). Mutations in these genes in Pto and *S. flexneri* have no obvious phenotype (Lorang and Keen, 1995; Allaoui et al., 1993), as is typical for genes encoding peptidoglycan hydrolases (Dijkstra and Keck, 1996).

The loss of pathogenicity in Pto mutant CUCPB5115, with an avrE-ORF5 deletion in the CEL, was surprising because pathogenicity is retained in DC3000 mutants in which the corresponding operons are individually disrupted (Lorang and Keen, 1995; Charkowski et al., 1998). In assessing the possible function of this region and the conservation of its constituent genes, it should be noted that avrE is unlike other avr genes found in Pto in that it confers avirulence to *P. syringae* pv *glycinea* on all tested soybean cultivars and it has a homolog (dspE) in *E. amylovora* that is required for pathogenicity (Lorang and Keen, 1995; Bogdanove et al., 1998b). Although the CEL is required for pathogenicity, it is not essential for type III effector protein secretion because the mutant still secretes AvrPto. It also appears to play no essential role in type III translocation of effector proteins into plant cells because the mutant still elicits the HR in nonhost tobacco and in a PtoR-resistance tomato line, and pHIR11, which lacks this region, appears capable of translocating several Avr proteins (Gopalan et al., 1996; Pirhonen et al., 1996). The conservation of this region in the divergent pathovars Psy and Pto, and its importance in disease, suggests that the products of the CEL may be redundantly involved in a common, essential aspect of pathogenesis.

The similar G+C content and codon usage of the hrp/hrc genes, the genes in the CEL, and total *P. syringae* genomic DNA suggests that the Hrp Pai was acquired early in the evolution of *P. syringae*. Although, the EEL region may have similarly developed early in the radiation of *P. syringae* into its many pathovars, races, and strains, the apparent instability that is discussed above suggests ongoing rapid evolution at this locus. Indeed, many *P. syringae* avr genes are associated with mobile genetic elements, regardless of their location (Kim et al., 1998). Thus, it appears that Hrp-mediated pathogenicity in *P. syringae* is collectively dependent on a set of genes that are universal among divergent pathovars and on another set that varies among strains even in the same pathovar. The latter are presumably acquired and lost in response to opposing selection pressures to promote parasitism while evading host R-gene surveillance systems.

Example 5

Role of ShcA as a Type III Chaperone for the HopPsyA Effector

The ORF upstream of hopPsyA, tentatively named shcA, encodes a protein product of the predicted molecular mass. The ORF upstream of the hopPsyA gene in *P. s. syringae* 61 (originally designated ORF1) shares sequence identity with exsC and ORF7, which are genes adjacent to type III effector genes in *P. aeruginosa* and *Yersinia pestis*, respectively (Frank and Iglewski, 1991; Perry et al., 1998). Although neither of these ORFs have been shown experimentally to encode chaperones, they have been noted to share properties that type III chaperones often possess (Cornellis et al., 1998). One of these properties is the location of the chaperone gene itself (FIGS. 1 and 6). Chaperone genes are often adjacent to a gene that encodes the effector protein with which the chaperone interacts. Furthermore, shcA also shares other common characteristics of type III chaperones: its protein product is relatively small (about 14 kDa), it has an acidic pI, and it has a C-terminal region that is predicted to be an amphipathic α-helix. To begin assessing the function of shcA, it was first determined whether shcA encodes a protein product. A construct was prepared using PCR that fused shcA in-frame to a sequence encoding the FLAG epitope. This construct, pLV26, contains the nucleotide sequence upstream of shcA, including a putative ribosome binding site (RBS). DH5αF'IQ(pLV26) cultures were grown in rich media and induced at the appropriate density with IPTG. Whole cell lysates were separated by SDS-PAGE and analyzed with immunoblots using anti-FLAG antibodies. By comparing the ShcA-FLAG encoded by pLV26 to a construct that made ShcA-FLAG from a vector RBS, it was concluded that the native RBS upstream of shcA was competent for translation (FIG. 7). Thus, the shcA ORF is a legitimate gene that encodes a protein product.

Figure 8:
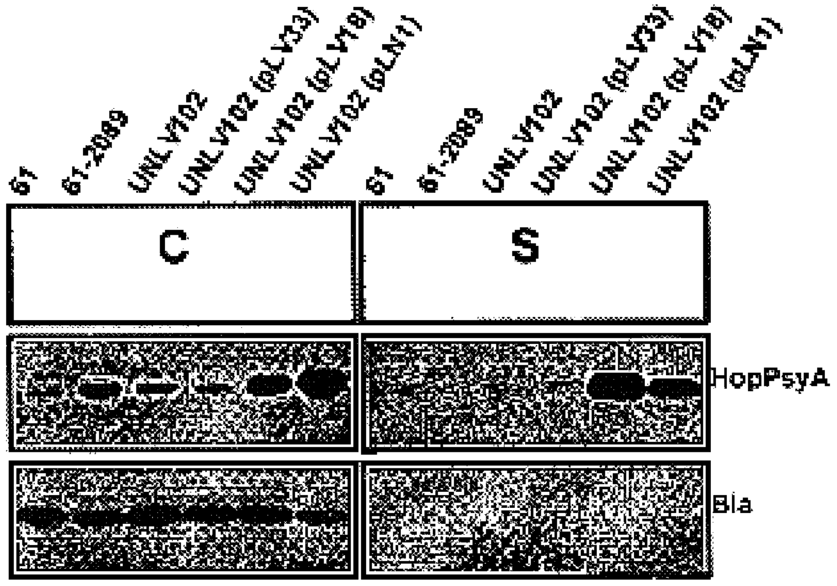
FIG. 8 is an image of an immunoblot showing that Psy 61 shcA mutant UNLV102 does not secrete HopPsyA and shcA provided in trans complements this defect. Psy 61 cultures were grown at 22° C. in hrp-derepressing medium and separated into cell-bound (C) and supernatant fractions (S). The cell-bound fractions were concentrated 13.4-fold and the supernatant fractions were concentrated 100-fold relative to the initial culture volumes. The samples were subjected to SDS-PAGE and immunoblot analysis, and HopPsyA and β-lactamase (Bla) were detected with either anti-HopPsyA or anti-β-lactamase antibodies followed by secondary antibodies conjugated to alkaline phosphatase as described in the experimental procedures. The image of the immunoblot was captured using the Bio-Rad Gel Doc 2000 UV fluorescent gel documentation system with the accompanying Quantity 1 software.
Figure 9:
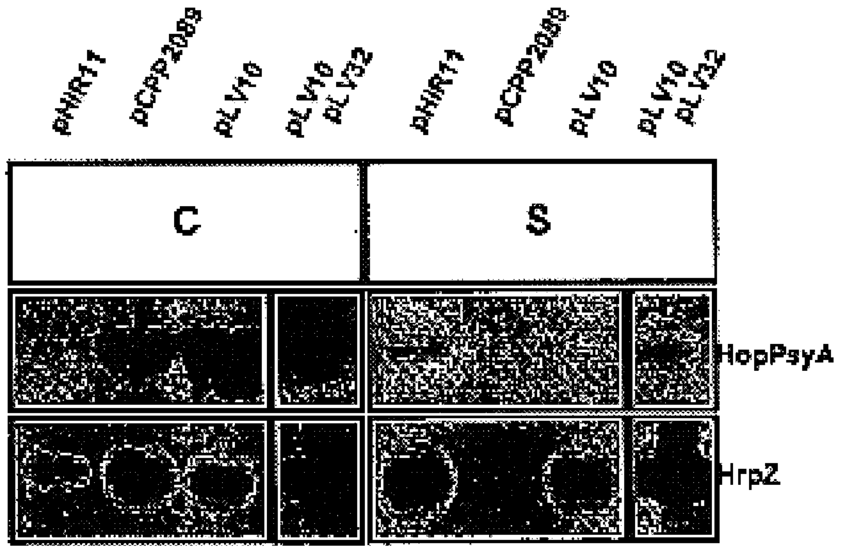
FIG. 9 is an image of an immunoblot showing that shcA is required for the type III secretion of HopPsyA, but not secretion of HrpZ. *P. fluorescens* 55 cultures were grown in hrp-derepressing medium and separated into cell-bound (C) and supernatant (S) fractions. The cell-bound fractions were concentrated 13.4-fold and the supernatant fractions were concentrated 100-fold relative to the initial culture volumes. The samples were subjected to SDS-PAGE and immunoblot analysis, and HopPsyA and HrpZ were detected with either anti-HopPsyA or anti-HrpZ antibodies followed by secondary antibodies conjugated to alkaline phosphatase as described in experimental procedures. The image of the immunoblot was captured using the Bio-Rad Gel Doc 2000 UV fluorescent gel documentation system with the accompanying Quantity 1 software.
Figure 10:
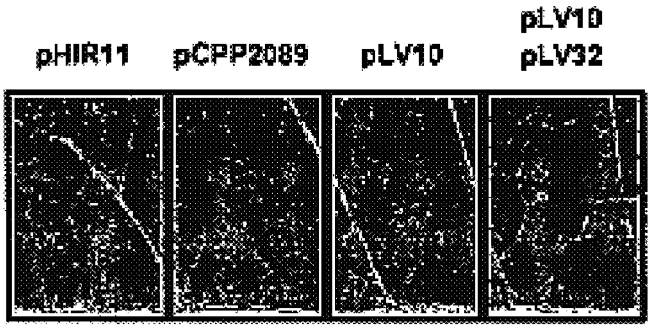
FIG. 10 is a series of four images of tobacco leaves showing that *P. fluorescens* 55 carrying a pHIR11 derivative with a functionally nonpolar shcA mutation is impaired in its ability to translocate HopPsyA into plant cells. *P. fluorescens* 55 cultures were grown overnight in King's B and suspended in 5 mM MES pH 5.6 to an $OD_{600}$ of 1.0, and infiltrated into tobacco leaf panels. Because the pHIR11-induced HR is due to the translocation of HopPsyA inside plant cells, a reduced HR indicates that HopPsyA is not delivered well enough to induce a typical HR. The leaf panels were photographed with incident light 24 hours later.
Figure 11:
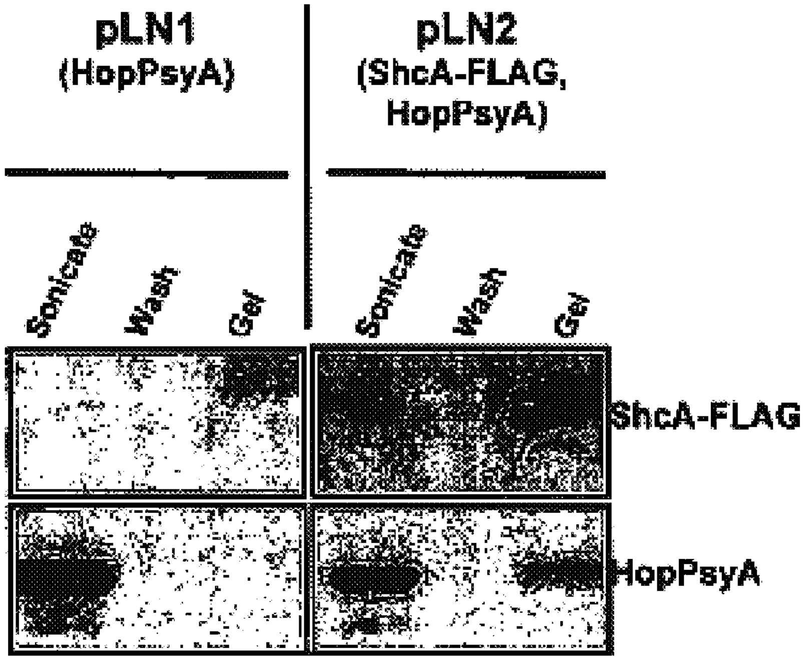
FIG. 11 is an image of an immunoblot showing that ShcA binds to HopPsyA. Soluble protein samples from sonicated cultures (Sonicate) of Psy 61 shcA mutant UNLV102 carrying pLN1 (HopPsyA) or pLN2 (ShcA-FLAG, HopPsyA) were mixed with anti-FLAG M2 affinity gel (Gel). The gel was washed (Wash) with TBS buffer, mixed with SDS-PAGE buffer, and subjected to SDS-PAGE and immunoblot analysis along with the sonicate and wash samples. HopPsyA and ShcA-FLAG were detected with anti-HopPsyA or anti-FLAG antibodies followed by secondary antibodies conjugated to alkaline phosphatase as described in experimental procedures.

To test the effects of shcA on bacterial-plant interactions, an shcA mutation was constructed in the minimalist hrp/hrc cluster carried on cosmid pHIR11. There are distinct advantages to having the shcA mutation marker-exchanged into pHIR11. The main one is that the HR assay can be used as a screen to determine if HopPsyA is being translocated into plant cells because the pHIR11-dependent HR requires the delivery of HopPsyA into plant cells (Alfano et al., 1996; Alfano et al., 1997). With the chromosomal shcA mutant, other Hop proteins would probably be delivered to the interior of plant cells. Some of these proteins would be recognized by the R gene-based plant surveillance system and initiate an HR masking any defect in HopPsyA delivery. *E. coli* MC4100 carrying pLV10, a pHIR11 derivative, which contains a nonpolar nptII cartridge within shcA, was unable to elicit an HR on tobacco (FIG. 8). This indicates that shcA is required for the translocation of HopPsyA into plant cells. To determine if HopPsyA was secreted in culture, cultures of the nonpathogen *P. fluorescens* 55 were grown. This bacterium carried either pHIR11, pCPP2089 (a pHIR11 derivative defective in type III secretion), or pLV10. The representative results can be seen in FIG. 8. shcA was required for the in-culture type III secretion of the HopPsyA effector protein, but not for HrpZ secretion, another protein secreted by the pHIR11 encoded Hrp system. These results indicate that the defect in type III secretion is specific to HopPsyA and are consistent with shcA encoding a chaperone for HopPsyA. It was after these results that the ORF upstream of the hopPsyA gene was named shcA for specific hop chaperone for HopPsyA, a naming system consistent with the naming system researchers have employed for chaperones in the archetypal *Yersinia* type III system.

Example 6

Cytotoxic Effects of hopPsyA Expressed in Plants

Transient expression of hopPsyA DNA in planta induces cell death in *Nicotiana tabacum*, but not in *N. benthamiana*, bean, or in *Arabidopsis*. To determine whether HopPsyA induced cell death on tobacco leaves as it did when produced in tobacco suspension cells, a transformation system that delivers the hopPsyA gene on T-DNA of *Agrobacterium tumefaciens* was used (Rossi et al., 1993; van den Ackerveken et al., 1996). This delivery system works better than biolistics for transiently transforming whole plant leaves. For these experiments, vector pTA7002, kindly provided by Nam-Hai Chua and his colleagues at Rockefeller University, was used. The unique property of this vector is that it contains an inducible expression system that uses the regulatory mechanism of the glucocorticoid receptor (Picard et al., 1988; Aoyama and Chua, 1997; McNellis et al., 1998). pTA7002 encodes a chimeric transcription factor consisting of the DNA-binding domain of GAL4, the transactivating domain of the herpes viral protein VP16, and the receptor domain of the rat glucocorticoid receptor. Also contained on this vector is a promoter containing GAL4 upstream activating sequences (UAS) upstream of a multiple cloning site. Thus, any gene cloned downstream of the promoter containing the GAL4-UAS is induced by glucocorticoids, of which a synthetic glucocorticoid, dexamethasone (DEX), is available commercially. hopPsyA was PCR-cloned downstream of the GAL4-UAS. Plant leaves from several different test plants were infiltrated with *Argrobacterium* carrying pTA7002::hopPsyA and after 48 hours these plants were sprayed with DEX. Only *N. tabacum* elicited an HR in response to the DEX-induced transient expression of hopPsyA (FIG. 13A). In contrast, *N. benthamiana* produced no obvious response after DEX induction (FIG. 13B). Moreover, transient expression of hopPsyA in bean plants (*Phaseolus vulgaris* L. 'Eagle')(data not shown) and *Arabidopsis thaliana* ecotype Col-1 (FIG. 13) did not result in a HR. These results suggest that bean cv. Eagle, *Arabidopsis* Col-1, and *N. benthamiana* lack a resistance protein that can recognize HopPsyA. The lack of an apparent defense response for HopPsyA transiently expressed in bean was predicted, because HopPsyA is normally produced in *P. s. syringae* 61, a pathogen of bean. But, it was somewhat unknown how transient expression of HopPsyA would effect *Arabidopsis*. However, since *P. s. tomato* DC3000, a pathogen of *Arabidopsis*, appears to have a hopPsyA homolog based on DNA gel blots using hopPsyA as a probe, it was expected that HopPsyA would not to be recognized by an R protein in *Arabidopsis* (i.e., no HR produced) (Alfano et al., 1997). Thus, these plants (bean, *Arabidopsis*, and *N. benthamiana*) should represent ideal plants to explore the bacterial-intended role of HopPsyA in plant pathogenicity.

Figure 14:
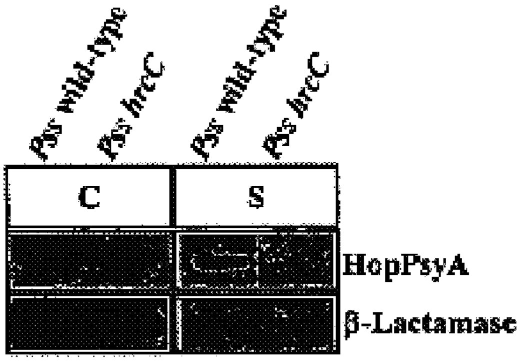
FIG. 14 is an image of an SDS-PAGE which shows the distribution of HopPsyA and β-lactamase in cultures of Psy 61 (pCPP2318) or a hrp mutant, Psy 61-4 2089 (pCPP2318). Bacterial cultures were grown at 22° C. in hrp-depressing medium and separated into cell-bound (C) and supernatant fractions (S). The cell-bound fractions were concentrated 13.4 fold, and the supernatant fractions were concentrated 100 fold relative to initial culture volumes. The samples were subjected to SDS-PAGE and immunoblot analysis and HopPsyA and β-lactamase were detected with either anti-HopPsyA or anti-β-lactamase antibodies followed by secondary antibodies conjugated to alkaline phosphatase. Pss wild-type=*Pseudomonas syringae* pv. *syringae* 61 (pCPP2318); Pss hrcC=*Pseudomonas syringae* pv. *syringae* 61-2089 (pCPP2318).

P.s. pv. *syringae* 61 secretes HopPsyA in culture via the Hrp (type III) protein secretion system. Because the *P. syringae* Avr proteins AvrB and AvrPto were found to be secreted by the type III secretion system encoded by the functional *E. chrysanthemi* hrp cluster carried on cosmid pCPP2 156 expressed in *E. coli* (Ham et al., 1998), detection of HopPsyA secretion in culture directly via the native Hrp system carried in *P. s. syringae* 61 was tested. *P. s. syringae* 61 cultures grown in hrp-derepressing fructose minimal medium at 22° C. were separated into cell-bound and supernatant fractions by centrifugation. Proteins present in the supernatant fractions were concentrated by TCA precipitation, and the cell-bound and supernatant samples were resolved with SDS-PAGE and analyzed with immunoblots using anti-HopPsyA antibodies. A HopPsyA signal was detected in supernatant fractions from wild type *P. s. syringae* 61 (FIG. 14). Importantly, HopPsyA was not detected in supernatant fractions from *P. s. syringae* 61-2089, which is defective in Hrp secretion, indicating that the HopPsyA signal in the supernatant was due specifically to type III protein secretion (FIG. 14). As a second control, both strains contained pCPP2318, which encodes the mature β-lactamase lacking its N-terminal signal peptide, and provides a marker for cell lysis. β-lactamase was detected only in the cell-bound fractions of these samples, clearly showing that cell lysis did not occur at a significant level (FIG. 14). The fact that HopPsyA is secreted via the type III secretion system in culture and that the avirulence activity of HopPsyA occurs only when it is expressed in plant cells strongly support that HopPsyA is delivered into plant cells via the type III pathway.

Figure 15:
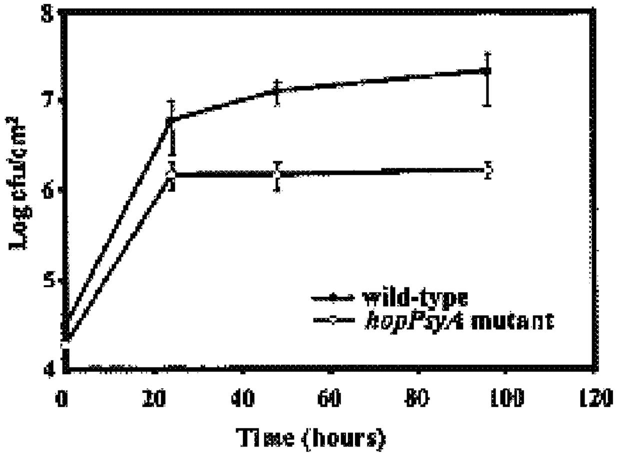
FIG. 15 is a graph illustrating the ability of wild-type *Pseudomonas syringae* pv. *syringae* and a hopPsyA mutant to multiply in bean leaves. Values represent the average plate counts from crushed plant leaves of two independent inoculations. Wild-type (●), *Pseudomonas syringae* pv. *syringae* 61; hopPsyA mutant (○), *Pseudomonas syringae* pv. *syringae* 61-2070.

HopPsyA contributes in a detectable, albeit minor, way to growth of *P. s. syringae* 61 in bean. The effect of a HopPsyA mutation on the multiplication of *P. s. syringae* 61 in bean tissue has been reported (Huang et al., 1991). These data essentially indicate that HopPsyA contributes little to the ability of *P. s. syringae* 61 to multiply in bean. The *P. s. syringae* 61 hopPsyA mutant does not grow as well in bean leaves as the wild-type strain (FIG. 15). This was unexpected, because these results are in direct conflict with previously reported data. One rationale for the discrepancy is that the previous reports focused primarily on the major phenotype that a hrp mutant exhibits on in planta growth and predated the discovery that HopPsyA was a type III-secreted protein. Thus, it is quite possible that the earlier experiments missed the more subtle effect that HopPsyA appears to have on the multiplication of *P. s. syringae* 61 in bean tissue (Huang et al., 1991). The data presented here supports that HopPsyA contributes to the pathogenicity of *P. s. syringae* and are consistent with the hypothesis that the majority of Hops from *P. syringae* contribute subtly to pathogenicity. The lack of strong pathogenicity phenotypes for mutants defective in different avr and hop genes may be due to possible avr/hop gene redundancy or a decreased dependence on any one Hop protein through coevolution with the plant. Indeed, the type III-delivered proteins of plant pathogens that are delivered into plant cells may not be virulence proteins per se, but rather they may suppress responses of the plant that are important for pathogenicity to proceed (Jakobek et al., 1993). These responses may be defense responses or other more general processes that maintain the status quo within the plant (e.g., the cell cycle).

Example 7

Molecular Interactions of HopPsyA

HopPsyA interacts with the *Arabidopsis* Mad2 protein in the yeast 2-hybrid system. To determine a pathogenic target for HopPsyA, the yeast 2-hybrid system was used with cDNA libraries made from *Arabidopsis* (Fields and Song, 1989; Finley and Brent, 1994). In the yeast 2-hybrid system, a fusion between the protein of interest (the "bait") and the LexA DNA-binding domain was transformed into a yeast tester strain. A cDNA expression library was constructed in a vector that creates fusions to a transcriptional activator domain. This library was transformed into the tester strain en masse, and clones encoding partners for the "bait" are selected via their ability to bring the transcriptional activator domain into proximity with the DNA binding domain, thus initiating transcription of the LEU2 selectable marker gene. A second round screening of candidates, that activate the LEU2 marker, relies on their ability to also activate a lacZ reporter gene. Bait constructs were initially made with hopPsyA in the yeast vector pEG202 that corresponded to a full-length HopPsyA-LexA fusion, the carboxy-terminal half of HopPsyA fused to LexA, and the amino-terminal half of HopPsyA fused to LexA, and named these constructs pLV23, pLV24, and pLV25, respectively. However, pLV23 was lethal to yeast and pLV25 activated the lacZ reporter gene in relatively high amounts on its own (i.e., without the activation domain present). Thus, both pLV23 and pLV25 were not used to screen for protein interactors via the yeast 2-hybrid system. pLV24, which contains the 3' portion of hopPsyA fused to lexA, proved to be an appropriate construct to use for bait in the yeast 2-hybrid system, because it did not autoactivate the lacZ reporter gene and, based on the lacZ repression assay using pJK101, the 'HopPsyA-LexA fusion produced by pLV24 appeared to localize to the nucleus. In addition, it was confirmed that pLV24 made a protein of the appropriate size that corresponds to HopPsyA by performing immunoblots with anti-HopPsyA antibodies on yeast cultures carrying this vector.

Initial screens with pLV24 and *Arabidopsis* cDNA libraries in the yeast 2-hybrid vector pJG4-5. From three independent screens, several hundred by sequences similar to those in a Pph plasmid that carries several avr genes (Jackson et al., 1999) and by a sequence homologous to insertion elements that are typically found on plasmids, suggesting plasmid integration via an IS element in this region (Szabo and Mills, 1984). Psy B728a ORF3 and ORF4 show similarity to sequences implicated in the horizontal acquisition of the LEE Pai by pathogenic *E. coli* strains (Perna et al., 1998). These Psy B728a ORFs are not preceded by Hrp boxes and are unlikely to encode effector proteins.

TABLE 1

ORFs and fragments of genetic elements in the EELs of Pto DC3000, Psy B728a, and Psy 61 and similarities with known avr genes and mobile genetic elements.

| ORF or sequence | % G + C | Size | BLAST E value with representative similar sequence(s) in database, or relevant feature |
|---|---|---|---|
| Pto DC3000[a] | | | |
| ORF1 | 55 | 466 aa | Hrp-secreted (Alfano, unpublished) |
| TnpA' | 55 | 279 aa | 1e-125 *P. stutzeri* TnpA1 (Bosch et al., 1999) |
| ORF2 | 51 | 241 aa | None |
| ORF3 | 53 | 138 aa | None |
| ORF4 | 47 | 136 aa | None |

TABLE 1-continued

ORFs and fragments of genetic elements in the EELs of Pto DC3000, Psy B728a, and Psy 61 and similarities with known avr genes and mobile genetic elements.

| ORF or sequence | % G + C | Size | BLAST E value with representative similar sequence(s) in database, or relevant feature |
|---|---|---|---|
| Psy B728a | | | |
| ORF1 | 51 | 323 aa | 9e-40 Pph AvrPphC (Yucel et al., 1994) |
| ORF2 | 58 | 382 aa | 1e-154 Pph AvrPphE (Mansfield et al., 1994) |
| ORF3 | 55 | 507 aa | 2e-63 *E. coli* L0015 (Perna et al., 1998) |
| ORF4 | 55 | 118 aa | 9e-9 *E. coli* L0014 (Perna et al., 1998) |
| ORF5 | 49 | 411 aa | 1e-4 Xcv AvrBsT (Ciesiolka et al., 1999) |
| ORF6 | 52 | 120 aa | None |
| B plasmid | 46 | 96 nt | 1e-25 Pph pAV511 (Jackson et al., 1999) |
| IntA' | 59 | 49 aa | 3e-5 *E. coli* CP4-like integrase (Perna et al., 1998) |
| Psy 61 | | | |
| HopPsyA | 53 | 375 aa | Hrp-secreted Avr (Alfano et al., 1997; van Dijk et al., 1999) |
| ShcA | 57 | 112 aa | 6e-4 Y0008 (Perry et al., 1998) |

[a]Pathovar abbreviations correspond to the recommendations of Vivian and Mansfield (1993) for uniform avr nomenclature.

The left border of the EELs contains sequences similar to many $tRNA^{Leu}$ genes and to *E. coli* queA and tgt queuosine biosynthesis genes (ca. 70% amino-acid identity in predicted products). The EEL sequences terminate at the 3' end of the *P. syringae* tRNA sequences, as is typical for Pais (Hou, 1999). Virtually identical tgt-queA-$tRNA^{Leu}$ sequences are found in the genome of *P. aeruginosa* PAO1 (www.*pseudomonas*.com), which is also in the fluorescent pseudomonad group. But PAO1 is not a plant pathogen, and this $tRNA^{Leu}$ in *P. aeruginosa* is not putative interactors with HopPsyA were identified, each activating the two reporter systems to varying degrees. When these putative positive yeast strains were rescreened and criteria were limited to interactors that strongly induced both the lacZ reporter and LEU2 gene in the presence of galactose, about 50 yeast strains were identified that appeared to contain pJG4-5 derivatives that encoded proteins that could interact with the C-terminal half of HopPsyA. DNA gel blots using PCR-amplified inserts from selected pJG4-5 derivatives as probes allowed each of these putative positives to be grouped. Approximately 50% of the pJG4-5 derivatives that encoded strong HopPsyA interactors belonged to the same group. A pJG4-5 derivative containing this insert, pLV116 was sequenced. The predicted amino acid sequence of the insert contained within pLV116 shared high amino acid identity to Mad2 homologs (for mitotic arrest deficient) found in yeast, humans, frogs, and corn. Moreover, based on amino acid comparison with the other Mad2 proteins, pLV116 contains a cDNA insert that corresponds to the full-length mad2 mRNA. Table 2 below shows the amino acid percent identity of all of the Mad2 homologs currently in the databases.

TABLE 2

Percent Amino Acid Sequence Identity Between Different Mad2 Homologs*

| Mad2 Homolog | Arabidopsis | Corn | Human | Mouse | Frog | Fission Yeast | Budding Yeast |
|---|---|---|---|---|---|---|---|
| Arabidopsis | — | | | | | | |
| Corn | 81.3 | — | | | | | |

TABLE 2-continued

Percent Amino Acid Sequence Identity Between Different Mad2 Homologs*

| Mad2 Homolog | Arabidopsis | Corn | Human | Mouse | Frog | Fission Yeast | Budding Yeast |
|---|---|---|---|---|---|---|---|
| Human | 44.4 | 44.9 | — | | | | |
| Mouse | 45.4 | 45.9 | 94.6 | — | | | |
| Frog | 43.3 | 42.9 | 78.3 | 77.3 | — | | |
| Fission Yeast | 40.4 | 41.9 | 43.8 | 43.8 | 46.3 | — | |
| Budding Yeast | 38.3 | 38.8 | 39.3 | 39.3 | 39.8 | 45.4 | — |

*Comparisons were made with the MEGALIGN program at DNAStar (Madison, WI) using sequences present in Genbank. Abbreviations and accession numbers are as follows: Arabidopsis, *A. thaliana* Col-0 (this work); Corn, *Zea mays* (AAD30555); Human, *Homo sapiens* (NP_002349); Mouse, *Mus musculus* (AAD09238); Frog, *Xenopus laevis*, (AAB41527); Fission yeast, *Schizosaccharomyces pombe* (AAB68597); Budding yeast, *Saccharamoyces cerevisiae* (P40958).

Not unexpectedly, the sequence of the *Arabidopsis* Mad2 protein is more closely related to the corn Mad2, the only plant Mad2 homolog represented in the databases.

The corn Mad2 is about 82% identical to the *Arabidopsis* Mad2. FIGS. 16A–B show yeast strains containing either pLV24 and pJG4-5, pEG202 and pLV116, or pLV24 and pLV116 on leucine drop-out plates and plates containing X-Gal, showing that only when both HopPsyA and Mad2 are present, β-galactosidase and LEU2 activity are induced. It is important to note that the cDNA library that yielded mad2 has been used for many different yeast 2-hybrid screens and a mad2 clone has never been isolated from it before. Thus, the results shown in FIGS. 16A–B are unlikely to represent an artifact produced by the nature of the cDNA library. Moreover, different Mad2 homologs are known to interact with specific proteins and one of these homologs was isolated with a yeast 2-hybrid screen using a protein of the spindle checkpoint as bait (Kim et al., 1998). This is reassuring for two reasons. First, other Mad2 homologs do not appear to be nonspecifically "sticky" proteins. Second, they appear to modulate cellular processes through protein-protein interactions.

The above results are very promising, because Mad2 is a regulator controlling the transition from metaphase to anaphase during mitosis, a key step in the cell cycle of eukaryotes. The eukaryotic cell cycle is dependent on the completion of earlier events before another phase of the cell cycle can be initiated. For example, before mitosis can occur DNA replication has to be completed. Some of these dependencies in the cell cycle can be relieved by mutations and represent checkpoints that insure the cell cycle is proceeding normally (Hartwell and Weinert, 1989). In pioneering work, Hoyt et al. and Li and Murray independently discovered that there is a checkpoint in place in *Saccharomyces cerevisiae* to monitor whether the spindle assembly required for chromosome segregation is completed (Hoyt et al., 1991; Li and Murray, 1991). This so-called spindle checkpoint was discovered when the observation was made that wild-type yeast cells plated onto media containing drugs that disrupt microtubule polymerization arrested in mitosis, whereas certain mutants proceeded into anaphase. These initial reports identified 6 different nonessential genes that are involved in the spindle checkpoint: bub1-3 named for budding uninhibited by benzimidazole and mad1-3 for mitotic arrest deficient. Mutations in these genes ignore spindle assembly abnormalities and attempt mitosis regardless. In the years since, the spindle checkpoint has been shown to be conserved in other eukaryotes and many advances have occurred resulting in a better picture of what is taking place at the spindle checkpoint (Glotzer, 1996; Rudner and Murray, 1996).

Required for the transition from metaphase to anaphase (as well as other cell cycle transitions) is the ubiquitin proteolysis pathway. Proteins that inhibit entry into anaphase (e.g., Pds1 in *S. cerevisiae*) are tagged for degradation via the ubiquitin pathway by the anaphase-promoting complex (APC) (King et al., 1996). Only when these proteins are degraded by the 26S proteosome are the cells allowed to cycle to anaphase. Although it is not well understood how the APC knows when to tag the anaphase inhibitors for degradation, there have been several important advances (Elledge, 1996; Elledge, 1998; Hardwick, 1998). The Mad2 protein and the Bub1 protein kinase have been shown to bind to kinetochores when these regions are not attached to microtubules (Chen et al., 1996; Li and Benezra, 1996; Taylor and McKeon, 1997; Yu et al., 1999). Thus, these proteins appear to somehow relay a signal that all of the chromosomes are not bound to spindle fibers ready to separate. Mad1 encodes a phosphoprotein, which becomes hyperphosphorylated when the spindle checkpoint is activated and the hyperphosphorylation of Mad1 is dependent on functional Bub1, Bub3, and Mad2 proteins (Hardwick and Murray, 1995). Another required protein in this checkpoint is Mps1, a protein kinase that activates the spindle checkpoint when overexpressed in a manner that is dependent on all of the Bub and Mad proteins, indicating that Mps1 acts very early in the spindle checkpoint (Hardwick et al., 1996).

Figure 12:
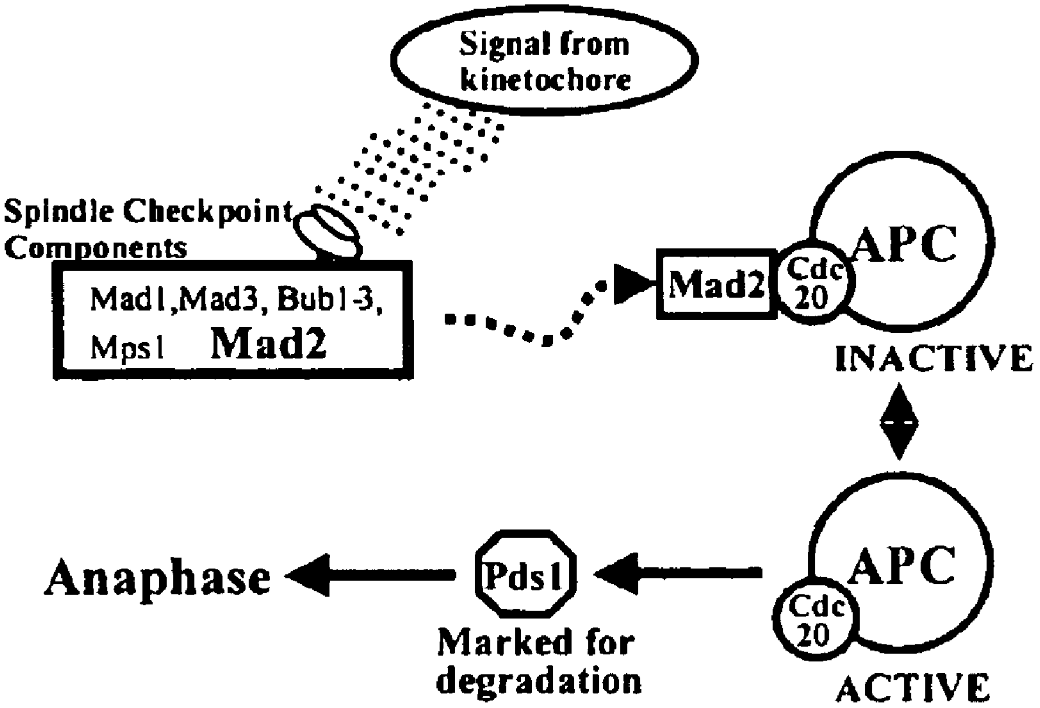
FIG. 12 is a diagram illustrating the spindle checkpoint in *S. cerevisiae*. The spindle checkpoint is activated by a signal emitted from the kinetochores when there are abnormalities with the microtubules. This signal is somehow received by the spindle checkpoint components, which respond in a variety of ways. Mad2 is thought to bind to Cdc20 at the APC inhibiting its ubiquitin ligase activity. In the absence of Mad2 (and presumably damage to the spindle), the APC is active and it marks Pds1 and other inhibitors of anaphase for degradation via the ubiquitin proteolysis pathway; anaphase ensues.

Based on data from the different Mad2 homologs that have been studied, Mad2 appears to have a central role in the spindle checkpoint. Addition of Mad2 to *Xenopus* egg extracts results in inhibition of cyclin B degradation and mitotic arrest due to the inhibition of the ubiquitin ligase activity of the APC (Li et al., 1997). The overexpression of Mad2 from fission yeast causes mitotic arrest by activating the spindle checkpoint (He et al., 1997). Whereas, introducing anti-Mad2 antibodies into mammalian cell cultures causes early transition to anaphase in the absence of microtubule drugs, indicating that Mad2 is involved in the normal cell cycle. Several reports suggest that different Mad2 homologs directly interact with the APC (Li et al., 1997; Fang et al., 1998; Kallio et al., 1998). Another protein called Cdc20 in *S. cerevisiae* binds to the APC, is required for activation of the APC during certain cell cycles, and Mad2 binds to it (Hwang et al., 1998; Kim et al., 1998; Lorca et al., 1998; Wassmann and Benezra, 1998). The picture that is emerging from all of these exciting findings is that Mad2 acts as an inhibitor of the APC, probably by binding to Cdc20. When Mad2 is not present, the Cdc20 binds to the APC, which activates the APC to degrade inhibitors of the transition to anaphase. FIG. 12 shows a summary of the spindle checkpoint focusing on Mad2's involvement and using the names of the spindle checkpoint proteins from *S. cerevisiae.*

The plant spindle checkpoint: A possible target of bacterial pathogens. Many of the cell cycle proteins from animals have homologs in plants (Mironov et al., 1999). In fact, one of the early clues that there existed a spindle checkpoint was first made in plants. The observation noted was that chromosomes that lagged behind in their attachment to the spindle caused a delay in the transition to anaphase (Bajer and Mole-Bajer, 1956). Moreover, mad2 has been recently isolated from corn and the Mad2 protein localization in plant cells undergoing mitosis is consistent with the localization of Mad2 in other systems (Yu et al., 1999). Based on a published meeting report, genes that encode components of the APC from *Arabidopsis* have been recently cloned (Inze et al., 1999). Thus, it appears that a functional spindle checkpoint probably is conserved in plants. The data presented above shows that the *P. syringae* HopPsyA protein interacts with the *Arabidopsis* Mad2 protein in the yeast 2-hybrid system.

It is possible that a pathogenic strategy of a bacterial plant pathogen is to alter the plant cell cycle. Duan et al. recently reported that pthA, a member of the avrBs3 family of avr genes from *X. citri*, is expressed in citrus and causes cell enlargement and cell division, which may implicate the plant cell cycle (Duan et al., 1999). If HopPsyA does target Mad2, at least two possible benefits to pathogenicity can be envisioned. Since plant cells in mature leaves are quiescent, one benefit of delivering HopPsyA into these cells may be that it may trigger cell division through its interaction with Mad2. This is consistent with the observation that anti-Mad2 antibodies cause an early onset of anaphase in mammalian cells (Gorbsky et al., 1998). More plant cells near the pathogen may increase the nutrients available in the apoplast. A second possible benefit may occur if HopPsyA is delivered into plant cells actively dividing in young leaves. Delivery of HopPsyA into plant cells of these leaves may derail the spindle checkpoint through its interaction with Mad2. These cells would be prone to more mistakes segregating their chromosomes; in some cells this would result in death and the cellular contents would ultimately leak into the apoplast providing nutrients for the pathogen.

Example 8

Cytotoxic Effects of HopPtoA and HopPsyA Expressed in Yeast

Both hopPtoA (SEQ. ID. No. 6) and hopPsyA (SEQ. ID. No. 35) were first cloned into pFLAG-CTC (Kodak) to generate an in-frame fusion with the FLAG epitope, which permitted monitoring of protein production with anti-FLAG monoclonal antibodies. The FLAG-tagged genes were then cloned under the control of the GALL promoter in the yeast shuttle vector p415GAL1(Mumberg et al., 1994). These regulatable promoters of *Saccharomyces cerevisiae* allowed comparison of transcriptional activity and heterologous expression. The recombinant plasmids were transformed into uracil auxotrophic yeast strains FY833/4, selecting for growth on SC-Ura (synthetic complete medium lacking uracil) based on the presence of the URA3 gene on the plasmid. The transformants were then streaked onto SC-Ura medium plates containing either 2% galactose (which will induce expression of HopPsyA and HopPtoA) or 2% glucose. No growth was observed on the plates supplemented with 2% galactose. This effect was observed with repeated testing and was not observed with empty vector controls, with four other effectors similarly cloned into p415GAL1, or when raffinose was used instead of galactose. FLAG-tagged nontoxic Avr proteins were used to confirm that the genes were differentially expressed, as expected, on plates containing galactose. Importantly, the toxic effect with HopPsyA was observed when the encoding gene was recloned into p416GALS, which expresses foreign genes at a substantially lower level than p415GAL1.

References

Each of the references cited herein or otherwise listed below are expressly incorporated by reference in their entirety into this specification.

Alfano et al., (1996) *Mol. Microbiol.* 19:715–728.

Alfano et al., (1997) *Mol. Plant-Microbe Interact.* 10:580–588.

Alfano and Collmer, (1997) *J. Bacteriol.* 169:5655–5662.

Allaoui et al., (1993) *Infect. Immun.* 61:1707–1714.

Altschul et al., (1997) *Nucleic Acids Res.* 25:3389–3402.

Aoyama and Chua, (1997) *Plant Journal* 11(3):605–612.

Ausubel et al., (1994) *Current Protocols in Molecular Biology.* (John Wiley and Sons, New York).

Bajer and Mole-Bajer, (1956) *Chromosoma* (*Berl.*) 7:558–607.

Bangham et al., (1965) *J. Mol. Biol.* 13:238–252.

Berkner, (1988) *Biotechniques* 6:616–627.

Blattner et al., (1997) *Science* 277:1453–1474.

Bogdanove et al., (1997) *Mol. Microbiol.* 26:1057–1069.

Bogdanove et al., (1998) *Proc. Natl. Acad. Sci. USA* 95:1325–1330.

Bosch et al., (1999) *Gene* 236:149–157.

Bozso et al., (1999) *Physiol. Mol. Plant Pathol.* 55:215–223.

Charkowski et al., (1998) *J. Bacteriol.* 180:5211–5217.

Chatterjee et al., (1992) *Science* 258:1485–1488.

Chen et al., (1996) *Science* 274:242–245.

Ciesiolka et al., (1999) *Mol. Plant Microbe Interact.* 12:35–44.

Collmer et al., (2000) in *Biology of Plant-Microbe Interactions*, vol. 2. ed. de Wit, P. J. G. M., Bisseling, T., and Stiekema, W. (International Society for Molecular Plant-Microbe Interactions, St. Paul), pp. 65–70.

Cornelis et al., (1998) *Microbiol. Mol. Biol. Rev.* 62:1315–1352.

Dijkstra and Keck, (1996) *J. Bacteriol.* 178:5555–5562.

Duan et al., (1999) *Mol. Plant-Microbe Interact.* 12:556–560.

Ehrlich et al., (1991) *Science* 252:1643–1651.

Einerhand et al., (1995) *Gene Ther.* 2:336–343.

Elledge, (1996) *Science* 274:1664–1672.

Elledge, (1998) *Science* 279:999–1000.

Evans et al., (1983) *Handbook of Plant Cell Cultures*, Vol. 1, MacMillan Publ. Co., New York.

Fang et al., (1998) *Genes Dev.* 12:1871–1883.

Fields and Song (1989) *Nature* 340:245–246.

Finley and Brent (1994) *Proc. Natl. Acad. Sci. USA* 91:12980–12984.

Flotte et al., (1993a) *J. Biol. Chem.* 268:3781–3790.

Flotte et al., (1993b) *Proc. Natl. Acad. Sci.* 90:10613–10617.

Fraley et al., (1982) *Proc. Natl. Acad. Sci. USA* 79:1859–1863.

Fraley et al., (1983) *Proc. Natl. Acad. Sci. USA* 80:4803–4807.

Frank and Iglewski, (1991) *J. Bacteriol.* 173:6460–6468.

Fromm et al. (1985) *Proc. Natl. Acad. Sci. USA* 82:5824.

Glotzer, (1996) *Curr. Biol.* 6:1592–1594.

Gopalan et al., (1996) *Plant Cell* 8:1095–1105.

Gorbsky et al., (1998) *J. Cell Biology* 141:1193–1205.

Hacker et al., (1997) *Mol. Microbiol.* 23:1089–1097.

Ham et al., (1998) *Proc. Natl. Acad. Sci. USA* 95:10206–10211.

Hardwick, (1998) *Trends Genetics* 14:1–4.

Hardwick and Murray, (1995) *J. Cell Biol.* 131:3.

Hardwick et al., (1996) *Science* 273:953–956.

Hartwell and Weinert, (1989) *Science* 246:629–634.

He et al., (1997) *Proc. Natl. Acad. Sci. USA* 94:7965–7970.

Hendrix et al., (1983) *Lambda II.* (Cold Spring Harbor Laboratory, Cold Spring Harbor).

Hensel et al., (1999) *Mol. Microbiol.* 31:489–498.

Heu and Hutcheson, (1993) *Mol. Plant-Microbe Interact.* 6:553–564.

Hirano and Upper, (1990) *Annu. Rev. Phytopathol.* 28:155–177.

Hirano et al., (1999) *Proc. Natl. Acad. Sci. USA* 96:9851–9856.

Hou, (1999) *Trends Biochem. Sci.* 24:295–298.

Hoyt et al., (1991) *Cell* 66:507–517.

Huang et al., (1991) *Mol. Plant-Microbe Interact.* 4:469–476.

Huang et al., (1995) *Mol. Plant-Microbe Interact.* 8:733–746.

Hueck, (1998) *Microbiol. Mol. Biol. Rev.* 62:379–433.

Hwang et al., (1998) *Science* 279:1041–1044.

Inoue and Takikawa, (1999) *Ann. Phytopathol. Soc. Japan* 65:100–109.

Inze et al., (1999) *Plant Cell* 11:991–994.

Jackson et al., (1999) *Proc. Natl. Acad. Sci. USA* 96:10875–10880.

Jakobek et al., (1993) *Plant Cell* 5:57–63.

Kallio et al., (1998) *J. Cell Biol.* 141:1393–1406.

Kaplitt et al., (1994) *Nature Genet.* 8:148–153.

Keen, (1990) *Annu. Rev. Genet.* 24:447–463.

Keen et al., (1997) *Mol. Plant-Microbe Interact.* 10:369–379.

Kim et al., (1998) *Mol. Plant-Microbe Interact.* 11:1247–1252.

Kim et al., (1998) *Science* 279:1045–1047.

King et al., (1996) *Science* 274:1652–1659.

Leach and White, (1996) *Annu. Rev. Phytopathol.* 34:153–179.

Legard et al., (1993) *Appl. Environ. Microbiol.* 59:4180–4188.

Li and Murray, (1991) *Cell* 66:519–531.

Li and Benezra, (1996) *Science* 274:246–248.

Li et al., (1997) *Proc. Natl. Acad. Sci. USA* 94:12431–12436.

Lorang and Keen, (1995) *Mol. Plant-Microbe Interact.* 8:49–57.

Lorca et al., (1998). *EMBO* 17:3565–3575.

Luo et al., (1995) *Exp. Hematol.* 23:1261–1267.

Manceau and Horvais, (1997) *Appl. Environ. Microbiol.* 63:498–505.

Mansfield, et al., (1994) *Mol. Plant-Microbe Interact.* 7:726–739.

McNellis et al., (1998) *Plant J.* 14(2):247–257.

Miller et al., (1994) *Proc. Natl. Acad. Sci.* 91:10183–10187.

Mindrinos et al., (1994) *Cell* 78:1089–1099.

Mirold et al., (1999) *Proc. Natl. Acad. Sci. USA* 96:9845–9850.

Mironov et al., (1999). *Plant Cell* 11:509–521.

Mumberg et al., (1994) *Nucleic Acids Res.* 22:5767–5768.

Mushegian et al., (1996) *Proc. Natl. Acad. Sci. USA* 93:7321–7326.

O'dell et al., (1985) *Nature* 313:810–812.

Orth et al., (2000) *Science* 290:1594–1597.

Palleroni, (1984) in *Bergey's Manual of Systematic Bacteriology*. ed. Krieg, N. R. and Holt, J. G. (Williams and Wilkins, Baltimore), pp. 141–199.

Perna et al., (1998) *Infect. Immun.* 66:3810–3817.

Perry et al., (1998) *Infect. Immun.* 66:4611–4623.

Picard et al., (1988). *Cell* 54:1073–1080.

Pirhonen et al., (1996) *Mol. Plant-Microbe Interact.* 9:252–260.

Ponnazhagan et al., (1994) *J. Exp. Med.* 179:733–738.

Preston et al., (1995) *Mol. Plant-Microbe Interact.* 8:717–732.

Prochiantz, (2000) *Curr. Opin. Cell Biol.* 12:400–406.

Roberts and Lauer, (1979) *Methods in Enzymology* 68:473.

Roine et al., (1997) *Proc. Natl. Acad. Sci. USA* 94:3459–3464.

Ronald, et al., (1992) *J. Bacteriol.* 174:1604–1611.

Rosenfeld et al., *Science* 252:431–434 (1991).

Rossi et al., (1993) *Plant Mol. Biol. Reporter* 11:220–229.

Rudner and Murray, (1996) *Curr. Opin. Cell Biol.* 8:773–780.

Sambrook et al., (1989) *Molecular Cloning: A Laboratory Manual*, Cold Springs Laboratory, Cold Springs Harbor, N.Y.

Schell, (1987) *Science* 237:1176–1183.

Schwartz et al., (2000) *Trend Cell Biol.* 10:2990–295.

Studier et. al., (1990) *Gene Expression Technology* vol. 185.

Szabo and Mills, (1984) *J. Bacteriol.* 157:821–827.

Taylor and McKeon, (1997) *Cell* 89:727–735.

van den Ackerveken et al., (1996) *Cell* 87:1307–1316.

van Dijk et al., (1999) *J. Bacteriol.* 181:4790–4797.

Vasil (ed.), (1984, 1986) *Cell Culture and Somatic Cell Genetics of plants*, Acad. Press, Orlando, Vols. I and III.

Vivian and Mansfield, (1993) *Mol. Plant-Microbe Interact.* 6:9–10.

Walsh et al., (1992) *Proc. Nat'l. Acad. Sci.* 89:7257–7261.

Walsh et al., (1994) *J. Clin Invest.* 94:1440–1448.

Wassmann and Benezra, (1998) *Proc. Natl. Acad. Sci. USA* 95:11193–11198.

Wieler et al., (1997) *FEMS Microbiol. Lett.* 156:49–53.

Yu et al., (1999) *J. Cell Biol.* 145: 425–435.

Xiao and Hutcheson, (1994) *J. Bacteriol.* 176:3089–3091. Author's correction. 176:6158.

Yucel et al., (1994) *Mol. Plant-Microbe Interact.* 7:677–679.

Zablotowicz et al., (1995) *Appl. Environ. Microbiol* 61:1054–1060.

Zhou et al., (1996) *Gene Ther.* 3:223–229.

U.S. Pat. No. 4,237,224 to Cohen and Boyer.

U.S. Pat. No. 4,945,050 to Sanford et al.

U.S. Pat. No. 5,036,006 to Sanford et al.

U.S. Pat. No. 5,059,421 to Loughrey et al.

U.S. Pat. No. 5,100,792 to Sanford et al.

U.S. Pat. No. 5,631,237 to Dzau et al.

U.S. Pat. No. 5,643,599 to Lee et al.

U.S. Pat. No. 5,653,996 to Hsu et al.

U.S. Pat. No. 5,681,811 to Ekwuribe.

U.S. Pat. No. 5,723,760 to Strittmayer et al.

U.S. Pat. No. 5,750,874 to Strittmayer et al.

U.S. Pat. No. 5,817,789 to Heartlein et al.

U.S. Pat. No. 5,849,586 to Kriegler et al.

U.S. Pat. No. 5,871,727 to Curiel.

U.S. Pat. No. 5,885,613 to Holland et al.

U.S. Pat. No. 5,885,808 to Spooner et al.

U.S. Pat. No. 5,981,225 to Kochanek et al.

U.S. Pat. No. 5,994,132 to Chamberlain et al.

U.S. Pat. No. 6,001,557 to Wilson et al.

U.S. Pat. No. 6,033,908 to Bout et al.

U.S. Pat. No. 6,057,155 to Wickham et al.

Although the invention has been described in detail for the purposes of illustration, it is understood that such detail is solely for that purpose, and variations can be made therein by those skilled in the art without departing from the spirit and scope of the invention which is defined by the following claims.

---

What is claimed:

1. An isolated protein or polypeptide selected from the group consisting of (i) a protein or polypeptide comprising an amino acid sequence of SEQ ID NO: 7 or SEQ ID NO: 66, and (ii) a protein or polypeptide encoded by a nucleic acid molecule whose complement hybridizes, at a temperature of at least about 37° C. in a medium comprising at most about 0.9M SSC, to a DNA molecule comprising the nucleotide sequence of SEQ ID NO: 6 or SEQ ID NO: 65.

2. The isolated protein or polypeptide according to claim 1, wherein the protein or polypeptide comprises an amino acid sequence of SEQ ID NO: 7 or SEQ ID NO: 66.

3. A composition comprising:

a carrier and a protein or polypeptide according to claim 1.

4. The isolated protein or polypeptide according to claim 1, wherein the protein or polypeptide is a recombinant protein or polypeptide.

5. The isolated protein or polypeptide according to claim 1, wherein the protein or polypeptide is at least about 80% pure.

6. The isolated protein or polypeptide according to claim 1, wherein the protein or polypeptide is at least about 90% pure.

7. The isolated protein or polypeptide according to claim 1, wherein the protein or polypeptide is encoded by a nucleic acid molecule whose complement hybridizes, at a temperature of at least about 37° C. in a medium comprising at most about 0.9M SSC, to a DNA molecule comprising the nucleotide sequence of SEQ ID NO: 6 or SEQ ID NO: 65.

8. The isolated protein or polypeptide according to claim 1, wherein the protein or polypeptide is encoded by a nucleic acid molecule whose complement hybridizes, at a temperature of at least about 42° C. in a medium comprising at most about 0.9M SSC, to a DNA molecule comprising the nucleotide sequence of SEQ ID NO: 6 or SEQ ID NO: 65.

9. The isolated protein or polypeptide according to claim 1, wherein the protein or polypeptide is encoded by a nucleic acid molecule whose complement hybridizes, at a temperature of about 65° C. in a medium comprising at most about 0.9M SSC, to a DNA molecule comprising the nucleotide sequence of SEQ ID NO: 6 or SEQ ID NO: 65.

10. The composition according to claim 3, wherein the protein or polypeptide comprises an amino acid sequence of SEQ ID NO: 7 or SEQ ID NO: 66.

11. The composition according to claim 3, wherein the protein or polypeptide is encoded by a nucleic acid molecule whose complement hybridizes, at a temperature of at least about 37° C. in a medium comprising at most about 0.9M SSC, to a DNA molecule comprising the nucleotide sequence of SEQ ID NO: 6 or SEQ ID NO: 65.

* * * * *

SEQUENCE LISTING

```
<160> NUMBER OF SEQ ID NOS: 91

<210> SEQ ID NO 1
<211> LENGTH: 30365
<212> TYPE: DNA
<213> ORGANISM: Pseudomonas syringae
<220> FEATURE:
<221> NAME/KEY: unsure
<222> LOCATION: (29734)
<223> OTHER INFORMATION: n at any position is undefined

<400> SEQUENCE: 1

ggtaccgggc tctgtgacgc agagcgtcac gcaaggcatt ccactggagc gtgaggaacg     60

ataatcctga cgacaactat cgtgcgacgc tccgcgtcgg catgccgttc tggacgctct    120

gcgtcctgtc ttgagaggtg cgccaagcgc aaagcacggt aagtatcagg gaggggtgta    180

taggagggtt gcaaggcggg aggtgttcat atcaaggcag tgttcatgaa cccgtcttgc    240

ctgggctcat gaacacgttc ggcttacgcg gtcagtgcat ttcctcgctc aaatggtcca    300

gccctgccag catcaactca tgccggtgga tgtcgtccag gctggcgtag gaacccggtt    360

tttcgttgac cgcgtgccac accacaaagt cgcgtcgtac gtccagaaac aggaagtagt    420

gattgaaacg ctctgactcc ataaaacgtc gttgcagtgc atcacgcagt tgatcgggac    480

gcaacgcgcg gccttctatg tgcaaggcga tcccccaatc atggtgttcg cgccgactga    540

caaacgcgac gccattggcc actggccata ctgctgggct ctgggcggca acctgagcgt    600

aaaatgccga cttttccgtt acctcaatca tttctaatcc tttaactgca cgacagtgta    660

atcccgctca tggtcccggt cgtccagacc ttcgcgcatg tcgggcggcc accaaatgac    720

cagctcgcgg ttgttggagt ccgggcgttt gcaagcgttc cccgcacagc cgtgggtggc    780

acaccctgtc agcgtagcaa acagcaagag caagagcgtt aggctacgaa tcatcatggt    840

ttcgctcccc ggagcagtga cggcctgctt tctttggcca ttttagatat ctgcggctgg    900

cgcacagcga tgtacacctc actttcttca cccggctgca gccatgcatg aggccaggcc    960

gcaacgccga tgacccagcg accgccgcat cggctttcgt cgatacgtac cggcttgtcc   1020

gtgttgttac gcgcaaccac cacagcaaca ccccagtctt ttttgacgaa ccactgcgag   1080

cgctgcccat caagcgtcag accttcgccc ggatcacaca gacttcgtgt ttcaaagggc   1140
```

-continued

```
agggtctggc cagcgcgcag gccttccggg gcggggccgt cgatcatttg ggtaaagact   1200
ttctggatgt cgccccgcgt tggcagtcgg cctccgtcac gtcgttcctt gattttcttc   1260
atctggtcat cgacgtcatg gggttgccg ttctgtacat agcgtgctgg attgacctga   1320
tcgccgatca gtcgaggggt cagaatgaac agccgctcgc gctgactcag ttcgcgactg   1380
cgggactgga acagcagctt gccgatatag ggaatgtcgc ccaacagcgg gatcttgtga   1440
atcctgtcat tggcttccag accgtggaag ccgccgatga ccagcgagcc gtgctcggca   1500
atcaccgcct gggtgctgac attgcctcgg cgcacactgg gttgggtgtc attgatcgtc   1560
gacacatcga tctggccatc ctcgatgtcc acgatcattt ggacctgagg cttgccatcg   1620
ttgtccagcg aacgcggaat cacttgaagg ctggtgcccg ccgtgatggg cagaatgtca   1680
gcggcccgct cggaagtggg cgtcaggtat tcggtgcgac tgaggtcgat cactgcaggc   1740
tgattctcca gggtcaggat cgacgggttg gcgatgactg acgcagaacc attgccttca   1800
agcgcatgca attcggcaga aaacttgctg gcgttctgca agaacaacgt tgaactggtg   1860
ccgccatcaa acaggttggc acccacctcc gacgctgccg ggcattgaaa ttccagccga   1920
ctggacagtt cagccagttc attggggtcg atgtcgagaa tgaccgcatc gatttcgatc   1980
aggttgcgcg gaacgtccag ctccttgacc agtttctggt acatggcctt gcgctctggc   2040
aggtcgtaaa tcaatacgga gttgttacgc acatcagcgc ttacgcggat attgccttgc   2100
ctgaggcatg acccttggca gttttttgc tgttgaagtt caatacgcgg tgcaatgccc   2160
ctgttgcagt gctcccgtat cgataccatt ggagcccagg ttgtaaggca ggccggggcc   2220
gcgacacctg tgctgttggc aacactgctg ccctgccccg ccaacaagtt cacgctgtca   2280
atgctttcgc cacgcgaacg gctttccagc agctcttgaa gaatactggc gacaccggcc   2340
accactaact gctggtcacg gtagcgaata gtccgatcag ccgcgttggc gtatttgagt   2400
ggcagcacga caacatcttg cttgtcggcc ttctcgtcgg gcttttcgac tttcttgctg   2460
tagtcgcgca caaactccac gtatttggcc ggaccacgaa ccagaaccac gccttcgtca   2520
ggcagcgagc cccagcccaa acgcttgtca acaagaccga catcggtcag cgccgtttgc   2580
aggtcgtcca ccgcatccgg cgagacttcg atgcgccccg aggtgtgctc gctggaaggg   2640
ctgacataca gcgtgtcgtt atagacgaac cactggaagt ggtattcctg actcagccgc   2700
tcaagaaact cttcagggtt ctgagcacga atacgtccat cgaggtttcc ctggacaggc   2760
gacatgtcga gcgacatacc gaactccctg gcaaagtcag ccagggcagt agacaactcg   2820
gtctgccggg catcataggc gtaggcggtg tgtttccagg cttctggggt gaccgcccac   2880
gtggcaggga tcaccccgat caacaataaa ggcaaccaca ttaaggcctt gcgcatttca   2940
cactcccggt tgccggtgat tgaggatcga acgcccggac aaagtgggcg tcgtgttacg   3000
aatagtggtt tgcatcaggc tgagcatgcc cgcgcgctga ttggccaggc tttccagacg   3060
atcgagcagg tcaccgaggc tgcaggggtt tgccatccag ctgaccagca ctacgcagcg   3120
ggtctgcgga tcgatggcca gcgcgccgtc gcaggcacac gccaggcttg cgccgccctc   3180
gccaagcaag gcttcgagcc gttgcgggtc accggcgtcg tacgggtcga gcagttcgat   3240
actgcaacgc accccgtcgc cgacgaccgc cagccgagca ttggcgtcat cgatccagca   3300
gtccagcggc atcgctggac gctgggcaga ccactggcca acgatctcgg tgaattcact   3360
gaattccatc gatgactgct ttattgatac cgtgcttggc acgcaggcat tcattgacgg   3420
caataccggc gacatcgacc tgctgctggg acatcgtgaa tgcctgcagg tcttcgacgg   3480
```

-continued

```
tgccactctc ggaggcttcc atcgctgcct ggtccatgtt ggtgtgagca cggctcaccg   3540
aattgtcgag atggcgttgc aagctgttga aactgatcat gtcctggtgc tccagcagaa   3600
gggttcaaac cttgagtgga gcaaacccgc cgagcggttc catcatgcga tcaagtgagt   3660
gcagagagtg tgtatcaggc agcaggctcg acacccagca gccccttgcg caggtctgcc   3720
caagcgatat cgaacgcgcc attggcatcg ctcagacgca agctgtccga ggcgatcgtt   3780
gcatcgcgct tgagttgcca gtgctcggaa aaacggctgt ctgccagcca ctcagccacg   3840
gggtcggcta tttgggggtg aacactgagc gtcgcgaccg cttcattgag ctggctggcg   3900
gccaggtttc tggccagcgc ccgcgcacgt tcggccagcg tggtgtcgtc taacaagtgc   3960
cgcagggatt cactcaacag ttcttctacg gcggtcattg cctgctcctg caacgcctcg   4020
cgctgcacct gaagctcgcc gagaaacgcg ttggcgtttt cccagaactg cgccagcgcc   4080
tgctgctgaa ggtgctcggc tttctcttgc tcaagggcca gtatctgcgt ggcctgctgc   4140
cgcgcgtctg ccaggatgtc gcgcgccagc aggctgtcgg cgatgtcttc gcggcgcaag   4200
atcggttcgc gcagcagcgt agcggccgtc agagcaatac tgcgtttggc gagcatgggc   4260
gtattcctga tgcagagaag ctggttcgga ttcaggcagc cgtgacgcgc cacatgatgg   4320
cctgccataa cgcctgaagt ttgttttcgg gtgccttgcc gggggtgtcg ggcacttcat   4380
tgggcgggca ctccagacac agtcgcgacc agtattgcgg cccaagccag gcgcccagca   4440
gaagacgcgc gtcctcgtgt tcaaactcca gccagacacc ggggcgcagc gctttggtca   4500
acccccagca ccattgaccg tcaggtccgt cgctttcgtt acgggagaag cagatgcact   4560
gcgccaggct tagcgcctgc tcacgctgcg agggcgtcag cgccaaccag cgcagcaccg   4620
gttccgcggg cgctggcggc tgagccgggt caatgcccag actctgcaga aacacgccat   4680
gacggctggc catgagcgca tcgcagtcac tgaccgataa cccacgagcg ttggcgaatc   4740
ggtcatgcca ctccgaatgt gcccactgcc aggggttgca ccaccagtga atccagtgat   4800
cctcggcaga aaggctcatc atgcacgtgc cggcagcgtt gaacgaccgc gactgccaaa   4860
cccgatccgt cgcaacagac tggcgcgcca gtcactgcgc accagcagtg caccgatcag   4920
caacaccaac gcaagaccga caggtgccac ccagagcatc aggttccaga acggcaagtt   4980
cgtgctgtcc agcttgaagg gcccgaagct cacccattgc gtggtctctt ggaactctgc   5040
agcaggcaca aacacgatgg aaaacttttt cgaatcgaca gattgcgtgg acataccggg   5100
aatactgctg gcgaccatct gttgaatacg tccgcgcaca ctgtcgggat caagtgcagc   5160
agagtgcttg atgaacaccg cagcagaagc cggttgaaca ggttcgcccg gcgcgatgcg   5220
ctcgggcagc accacatgca ccctggccac aatgactccg tcgatctgcg acagcgtggc   5280
ttcaagttcc tgggacaagg cgtagatgta acgggcacgc tcttcaagcg gcgtcgaaat   5340
cacccccttcc ttcttgaaaa tctcccccag cgtggtgcgc gagcgccgag gcagacccgc   5400
agcgtcgagc acgcgcacgg cgcggttcat ttcgctggtg gcgacagtca cgacaacgcc   5460
ggttttctcc agacgtttac gcgcatcgat atgctgatcg gcgaggcgcg ctacgacctc   5520
attggaatcc tgctcggaca agccagtgaa caaatcagtc tcatcactgc agccgccgag   5580
cagcagcatg cacaacagca gcagccctgc gctcagaaaa ttcacggaaa cctctactgc   5640
aggttggtca acttgtcgag cgcctgagcg ctcttgctca cgaccttggt cgtcaacgcc   5700
atttgcaacg agcactgcga caacgcccga ctcatctgca cgatgtctcc aggatcttcg   5760
gtgttcgaca ctttcttcat ctggcgtaat gcttgctgtg aaagcttctc ggtactgccc   5820
agccgctcgg acagcgcact ggctatccgg tcggacaggt gcgacgctgc tggcccgctg   5880
```

-continued

```
tcagggcgca tcgccgcatt gaataggtcg acatccgcct gaacgggttc ggagccgagc   5940
ccctgatgag cattctgccc aagctccggc gatacacttt tcaaattgct gagttgggaa   6000
atggtcacac tggttctccg tcaggcggct gtcagtcagg ccacagcctg gttagtctgg   6060
ttattggtgc cttgcaacag cgcattgatc agctgagctg ccacttgcgc agcgctcgat   6120
tgcaggtcgg cgccggtgtt gccagcatcc tgaagcgtcg cttccagccc gcgttgacgc   6180
aagccgctca gcagttgacc caggtcctga ttggacacgt tgcccgtcgg gttagccact   6240
ggcgtgccac ctgtcggctg cgtggaattg tcgaccggtg taccaagacc accacccgac   6300
gaaaccgact gcaaaccacg gtcgatgagt tgaccgatca gttgacctac gtcgacgctg   6360
gcattgccat tggccgcggg acctgtgttg gcatcgattg caggattacc cagggagctg   6420
tcactcacgg gcgaacccag accgccgcca ctggtaacgc cactggcatc accttgttgc   6480
tggccgagct gttgaccaat gacgtcgaga gccgaacgaa actgagcggt ttcctgtgca   6540
tccaggccat tgtcttcctt cagctcgttc atccacgagc cgccgtcccg agtagggaac   6600
tgggccttgt tgtcgtccat gaactgggca actttttcca gggtcggcat gtcatcactg   6660
gaaaaggttg ttccgccttc accactcggt gtcagcagat cgtccagcac ggctttgccg   6720
aggccgttca ggacctggct catcagatcg gattgcccgg cacccgcgtc gctgctcaga   6780
ccgccaccga cacccgaacc agaacccgcc ccgccaatgc caccgccacc gccacccgcg   6840
ccgatgccgg cagaggcacc gaaattgtcg ccgagctttt cgtggatcag cttgtcgagc   6900
gatgcagtga tgtcatcgat gctgttagcc gacttgccat ccgcagccat ggccttggcg   6960
agcattttgc cgagcggtga ggtttcatcg agctgcccac tttgggtcag cgcctgaacc   7020
agctgatcga tcacagcctt gagctctttg ctggaagtgc tggtgttggc gctcacatcg   7080
ctgttgagcg acacggggaa caatgatgca gaggtttgca acgaactgat gctgttaagt   7140
gcttgcataa aacgcccatc ccaaggtagc ggccccctct gatgaggggg caatcagaaa   7200
taattagtaa ctgatacctt tagcgttcgt cgctgtggca ctgatcttct tgttggtaga   7260
gtcttctttg ccggcctgga tggcgttgag cacgtccatg gtctgcttct tcattgtttc   7320
ctgggcctgc atcgcgatca gcttcgcgcc gttggcgtcg gactctttac tggccttggc   7380
ttgtgcatca accgacaggc tgtcgccggt gcccaaaaga atgtttttct gaagagtggc   7440
gttggaagca accgtgttga caccctgcaa tgcgccgccg acaccgccaa cggcgctgtt   7500
accaaggttg gtgagtttgg aggttaatcc tgcaaatgcg accatgattt gatgcccctt   7560
aagatttacc agcgtgattg cttggtactc actaggtggc agcagcctgc gatacggttc   7620
cagcgtcttt gcaaaaaatc agatctgcaa ttctttgatg cgtcgataga gcgtacgggc   7680
gtggcagtcc agttccaggc ttaccgaatc caaacaattg tcgtggcgct tgagcgactc   7740
ctgaatcagg gctttttcat caactcgcaa ttgcgatttg agcccacagg ccaagtgctc   7800
ttcgccctgc ggctcggcgc ccagcaaggg gaaacccagc acatggcgtt tggctgcagc   7860
cttgagctca cggatattgc cgggccagtc gtggcccagc agcactttgt gcagcagtgg   7920
gcaaacatcg ggaacgggaa caccgagctc cctcgcggcg gcggccgtaa aacgtgtgaa   7980
caggggaact atgcgatcag actggttacg tagcggagga agcttgagtg tcaggacgtt   8040
caggcgaaaa tacagatcgc gacgaaactg cccccgctcg acggcgtcgt ccagcgagca   8100
ttgggcggag gcgatcacgc agatatccag gttgatcgtc gacgtcgaac ccagccgttc   8160
aagcgctcgg gtttccagca ccctcagcaa tttggcttgc agggccagcg gcatgctatc   8220
```

-continued

```
gatctcatcc aggtacagcg tgccgccctg cgccgcttcg acataaccga ctctggagcg   8280
atcagcgccg gtgtaggcac cgctgaccac gccgaataac tcgctctcgg cgagggactc   8340
cggaatggcc gcgcaattca tcgccaccag gcgccctttg cgggctgaca tctcatgaat   8400
ccgtcgggca atcgtgtctt tgcccgtgcc ggtctcaccc gatagcagca cgtcgatacc   8460
cagttgcgaa atactttcgg caactatccc cagattcgga acccgctcct cgtccagatc   8520
atcctcaaac ctttcatcaa gactcatccc atgacccccca ggacatcaac gttggataac   8580
cacacctgcg tcacagaccc cggacctcgc agagtatcgg cgctgcaact cccagttcct   8640
tcatgcggtg atacagggtg cgtcttggca actccaactc ctgaagcacc gcgtcgaaat   8700
tgtgcctgtg ccgcttcaag gcatcctgga tgagcatttt ctcgatgatg cgcatttgcg   8760
tgcgcagccc cgtggcaggg tcaagcgctt ccacagggtc ggcgcccagc aaggggaagc   8820
cgagtacgaa gcgcttggct gcagacttca attcgcggat gttgcccggc cagtcgtggc   8880
tgagcagcag ctgcacacgc ccgctgtcca gcgcaggagc gggacgtccg aactcggcag   8940
cgataccctg ggtgaactgg tcgaacaatg gcaggatctg ttcacgacgt ttgcgcaagg   9000
ctggcaagtg aagcgtcagc acgttgagcc gaaaaaacag gtcgcgacgg aaaagtcctt   9060
gttccaccag ttcatccagt ggccgctggg ccgaggcaat gatccgcaga tccaccggga   9120
tgaattcggt cgagcccaga cgctcgatac ctcgactctc caacacacgc agcagtttgg   9180
cctgcaggct caacggcatg ctgtcgattt catccaggta caaggtgcca ccactggagg   9240
cctctatgta gccctcgcga gcccggcata cgccggtgaa tgcaccgttg accacaccga   9300
ataactggct ctctgccagc gactcgggaa tggcggcgca gttcatgccc acaaagggtc   9360
ccgacctgct ggacaactcg tgaatgcggt tggccagtgt gtccttgccg gtgccggttt   9420
ccccgcacaa cagcaagtcc atatccagaa acgcgctatt cattgcaatt tgatgacccg   9480
ctgataatgc agttacgccc caacactctc ggacgtcctt atcgatgcct gtactcatcg   9540
ttgcactctc atggtgggtg gcaagcggag tattaatacc acgtcttaca aggcagaaat   9600
atattaattt agttccccgg gaaatgagaa aaagatcaca aagttgagaa ttactatcat   9660
attaatatca ccataccaag acgaccctac cgatagactc aggctcttga gatgattgct   9720
ttaatctatc gttactccaa tgcgaacaag cgcttacagc gtccatgcgc tggctcgccc   9780
cgcaagccat agggcctctc cacacctcaa agcagctgtg atccgggaca agagcaggca   9840
cctttgagca gcaagcgccc caaaatcgcg caatgaaacg caactaactt ctcgtcacta   9900
ctcgagagaa acatataaga cttttccaaa acaactaaag gggtcacaag taaggaagca   9960
gaagaaaacc gaacacacaa aacaagaaaa ccaaacggtt tttagcggcg agcttaaaga  10020
agcgaacaac aataacacga gaaaacaaaa aacagcctga cactaactat ttgcacttta  10080
gaacagtcga taccaaccag cttagttccg ccccacgagc agtcggattt ccgaacaaca  10140
cagaggcttg gatactggca aagcggtcat agccccggtt tttcggcacc actcagtact  10200
ggcatttagt catcatcgca ttcggcaatc cgaacaaaag cccacctgct tagactattt  10260
ccaggcacag ccatctaagg aatcgcggaa aggattcagc gtagcttaat accggaaccg  10320
caggtttagg ttctgtgaac caggcggtta atacgatcga tgatcgcgtg ccatcaccta  10380
gaatgtttct aaatgtgtgt aatctttcac ttacattcgg ctaaaaaagt tcatcaaaat  10440
aatcatatgt agcgctctac atcatatggc taagcgccat ctttagggtc caaaaaacgg  10500
gtaacgctca ataaaagaag ttgtattgag gcagatcaat attgtccgac aacgagaaaa  10560
agcaccaaaa aagtgcgctt ttcaggggtt ttcaatagaa caatcgagta aaaccggggt  10620
```

-continued tattggcgtg gatcactggc aaaaaccacg acgcgcggcc ccgtaggcag ctcgcgcgga 10680
ccgctgcgat actcgtcgtc atcacgcttg cgaggcgacg aacggtcatc cctgatgcgg 10740
ggcaactgta tccggtttgt aagcggatca ggttccacaa caggtgcgga ttgggcgatc 10800
tctaccgccg gcgctgattc agctgcagga gctggctgta acgcctcagg cgcagtgggc 10860
tgctgagcca ccggcaacgg ctgagccgtt ttgggcgaag gcaggttctc ggctaactgg 10920
gccgactgca cgggcttggg cagcggcgga cgctctgcaa cgcgcactgg acgctcagcc 10980
acaggcgcgg gcgcgggcag acgctcagcc gcccgtttca caatggctga aggggtgacc 11040
agcgggatgc tggcagtcac cggggactca ccggtaatgc gcgcgatgct ggtcgtgagc 11100
acgcgattct gggttttagg tatcagcaga cgtcccggtc catcgaaggt ctttttgcgc 11160
aggaatgccg agttcagccg caacaactgg ccctcatcca cacccgccgt ggccgcgagc 11220
tgggtcaggt ctacggcatg gttaagctcg actacgtcaa aatacggcgt gttggcgacc 11280
ggggtcagtt tcacaccgta ggcattgggg ttgcgcacaa ccattgagag cgccaacagt 11340
ctgggcacgt aatcctgggt ttccttgggt aaattcagat tccagtagtc cacaggcaga 11400
ccacgccgtc ggttggcctc aatcgcccga ccgacggtgc cctcccccgc gttataggcg 11460
gccagcgcca gcagccagtc attattgaac tgatcatgca agcgggtcag gtaatccatc 11520
gccgccttgc tggaggccac cacgtcacgg cgagcgtcgt aggtcgcgct ttgatgcaga 11580
ttgaagctgc gccccgtgga tggaatgaat tgccacaaac ctgccgcagc ggccggagag 11640
ttggccatgg ggttataaga gctttcgatc atcggcagca gtgccagctc cagcggcatg 11700
ttgcgctcgt ccaggcgctc gacaataaaa tgcagataag ggctggcccg gacactggct 11760
cccgtgataa atccgcgatt gctcagcaac cagtcgcgct ggcgagcgat acgctcattc 11820
atgccttggc catcgaccag cctgcagcgc tgggcaaccc gctgccacac gtcctcgccg 11880
ttataaacag gcagatcgga gattttgtct gcagcccgcg aaccttcctt atcatctccc 11940
ccccaataga ccagccccga caccagccgc ggcggacggt cctgacgcgg cggcgaatag 12000
tccacagact ggcagcccac acacaaggcg cccatagcga ggactgcgat ttgaacagcg 12060
cgagccagca agcgtgggct cgatacgggg aaggcgacgg cgggcatggg cgggaatgtc 12120
ctgagcgtgt ccaccctacg tggcacgctc gccgttacgg ttccctttttg aaaccgagat 12180
cggcgcacac aacgcattgc tgaatccttt cagccgtaag tttttccgat ggaacccgct 12240
ggcattgcat gccactcatc ctgtgaagga attttcacgt ttggtatcag gcggctatca 12300
gcgataaaat ggacagagag attcaccgtg cagtcaccat cgatccaccg gaacaccgga 12360
agcatcattc agccaaccgt cacccctgac gcacgtgctg caactgacct gcaggaaaga 12420
gccgaacaac ccaggcaacg ctcttcgcac tcgttgagca gtgtcggcaa gcgggcgctg 12480
aaaagcgtcg gtaaattgtt ccagaaatcc aaagcgccgc agcagaaagc tgccacgccg 12540
cccaccgcga aaaacgtcaa gacgcccccg cctgcttcaa atgtggctac gcccagaaac 12600
aaagcccgcg aatccggttt ttccaacagc agcccgcaaa atacccatag ggcacccaag 12660
tggattctgc gtaaccaccc caaccaggcg agcagctcgg gcgcgcagac gcatgaaata 12720
cacccggagg cagccccccg taaaaacctg cgcgtaaggt ttgatctgcc gcaagaccgc 12780
cttgagcgca gcccgtcgta cctcgattca gacaacccga tgaccgatga agaagcggtc 12840
gcaaatgcca ctcgccaatt ccggtcacct gacagtcacc tgcagggctc tgacggtacg 12900
cgcatttcaa tgctggccac agatcctgat cagcccagca gctccggcag caaaatcggt 12960

-continued

```
gattcggacg gaccgattcc gccgcgcgag cccatgctgt ggcgcagcaa cggaggccgt  13020
ttcgagctga aagacgaaaa actggttcgc aactcagagc cacaaggcag cattcagctg  13080
gatgccaagg gaaagcctga cttctccacg ttcaatacgc ccggcctggc tccattgctc  13140
gattccattc ttgccacacc caagcaaacc tacctggccc accaaagcaa agacggcgtg  13200
cacgggcacc agttgctaca ggccaacggg cactttctgc acctggcgca agacgacagc  13260
tcgctggccg tgatccgtag cagcaacgaa gcactcctta tagaaggaaa gaaaccaccg  13320
gccgtgaaaa tggagcgtga agacggcaac attcacatcg acaccgccag cggccgcaaa  13380
acccaagagc tcccaggcaa ggcacacatc gctcacatta ccaatgtgct tctcagtcac  13440
gacggcgagc gtatgcgtgt gcatgaggac cgtctctatc agttcgaccc gataagcact  13500
cgctggaaaa taccggaagg cctggaggat accgctttca acagcctgtc cactggcggc  13560
aacggctcgg tttatgcaaa aagtgacgat gccgtggtcg acttgtcgag cccgttcatg  13620
ccgcacgtgg aagtcgaaga cctgcagtca ttttcagtcg cgccggacaa cagagcagcg  13680
ttgctcagcg gcaaaacgac ccaggcgatc ctactgactg acatgagccc ggtgattggc  13740
gggctgacgc cgaaaaaaac caaaggcctt gagctcgacg gcggcaaggc gcaggcggcg  13800
gcggtcggtt tgagtggcga caagctgttt atcgctgaca ctcagggcag actttacagt  13860
gcggaccgta gcgcattcga gggcgatgac ccgaaattga agctgatgcc cgagcaggca  13920
aactttcagc tggaaggcgt gcccctcgga ggccacaacc gcgtcaccgg attcatcaac  13980
ggggacgacg gcggtgttca cgcgctgatc aaaaaccgtc agggcgagac tcactcccac  14040
gctttagacg agcaaagctc aaaactgcaa agcggctgga acctgaccaa tgcgctggta  14100
ctgaacaaca atcgcggcct gaccatgccc ccgccaccca ccgccgctga ccggctcaac  14160
ctcgatcgtg cgggcctggt tggcctgagt gaaggacgca ttcaacgctg ggacgcaacg  14220
ccagaatgct ggaaagacgc aggcataaaa gatatcgatc gcctgcaacg cggcgccgac  14280
agcaatgctt atgtactcaa gggcggcaag ctgcacgcac tcaagattgc ggccgaacac  14340
cccaacatgg cttttgaccg caacacagca ctggcccaga ccgcacgctc gacaaaagtc  14400
gaaatgggca aagagatcga aggcctcgac gaccgagtga tcaaagcctt tgcaatggtc  14460
agcaacaaac gcttcgtcgc cctcgatgac cagaacaagc tgaccgccca cagtaaggat  14520
cacaaacccg tcacactcga cattcccggg ctggaaggcg atatcaagag cctgtcgctg  14580
gacgaaaaac acaacctgca cgccctcacc agtaccggcg ggctttactg cctgcccaag  14640
gaagcctggc aatcgacaaa gctgggggac cagttgcgag cccgctggac gccggttgcg  14700
ctgcccggag ggcagccggt aaaggcactt ttcaccaacg acgacaacgt gctcagcgcc  14760
cagatcgaag acgccgaggg caagggtctt atgcagctca aggcaggcca atggcaaagg  14820
ttcgaacagc gcccggtaga agaaaacggt ttgaatgatg tgcactcgcg catcacaggt  14880
tcaaacaaga cctggcgaat tccaaaaacc gggctgacgc tcagaatgga cgtcaataca  14940
ttcgggcgca gcggtgtgga gaaatccaaa aaagccagca ccagcgagtt catccgcgcc  15000
aacatctaca aaaacaccgc agaaacgccc cgctggatga agaacgtagg tgaccatatt  15060
cagcatcgct accagggtcg cctgggtctg aaagaggttt atgaaaccga gtcgatgctg  15120
ttcaagcaac tggagctgat ccatgagtcc gggggaaggc ctccggcacg gggtcaagac  15180
ctgaaagcgc gcatcaccgc actggaagca aaactggggc ctcaaggcgc tacgctggtc  15240
aaggaactgg aaaccctgcg cgacgagctg gaaaatcaca gctacaccgc gctgatgtcg  15300
atcggtcaga gctatggcaa ggcgaaaaac cttaaacagc aggacggcat tctcaaccag  15360
```

-continued

```
catggcgagc tggccaagcc gtcggtgcgc atgcagtttg gcaagaagct tgctgatctg  15420
ggcacaaagc tcaacttcaa aagctctgga catgacttgg tcaaggagct gcaggatgcc  15480
ttgactcaag tggctccgtc tgctgaaaac cccaccaaaa agttgctcgg cacgctgaag  15540
catcaagggc tgaaactcag ccaccagaaa gccgacatac ctttgggaca gcgccgcgat  15600
gccagcgagg atcatggcct gagcaaagcg cgcctggcgc tggatctggt cacactgaaa  15660
agccttggcg cgctgctcga ccaggtcgaa cagctaccgc cgcaaagcga catagagccg  15720
ttacaaaaaa agctggcgac gctgcgtgat gtgacttacg gcgaaaaccc ggtcaaggtg  15780
gtcacagaca tgggctttac cgataacaaa gcgctggaaa gcggttacga atcggtcaag  15840
acattcctca agtcgttcaa aaaagcggac catgccgtca gcgtcaatat gcgcgcagcc  15900
acaggcagca aggaccaggc cgagctggcc ggaaaattca aaagcatgct caagcaactg  15960
gagcatggcg acgacgaagt cgggctgcag cgcagctacg gagtgaacct caccaccccg  16020
ttcatcattc ttgccgacaa ggctacaggg ctctggccaa cggcaggtgc caccggtaac  16080
cgtaactaca tactcaatgc cgagcgttgc gagggcggcg ttacgctgta cctcattagc  16140
gaaggtgcgg gaaacgtgag cggcggtttc ggtgccggca aagactactg gccgggcttt  16200
tttgacgcaa ataatcctgc acgcagtgtt gatgtcggca acaaccgcac actgaccccc  16260
aactttcgcc tgggcgtgga cgtgaccgcc accgtcgccg ccagccagcg cgccggggtg  16320
gtcttcaatg ttccggatga agacatcgac gcattcgtcg acgacctgtt tgaaggtcag  16380
ttgaatccat tgcaggtgct gaaaaaagca gtggaccatg agagctacga ggctcggcga  16440
ttcaacttcg acctcacggc aggtggaact gccgatatac gcgccggaat aaacctgacc  16500
gaagaccgag acccgaatgc cgaccccaac agcgattcgt tttctgcggt agtgcgcggc  16560
ggattcgctg cgaacatcac cgttaacctg atgacctaca ccgattattc gttgacccag  16620
aaaaacgaca agaccgaact gaaggaaggc ggtaaaaacc gcccgcgctt tttgaataac  16680
gtgacggccg gcgggcagct tcgcgctcag atcggcggca gccacacggc ccccacaggc  16740
acacccgcct ccgccccagg ccccactccc gcatcacaaa cagccgccaa caacttgggc  16800
ggagcgctca atttcagtgt ggaaaacagg acggtcaaac ggatcaagtt tcgttacaac  16860
gtcgccaagc cgataacgac tgaaggtctg agcaaattgt cgaagggcct tggggaagcg  16920
ttcctggaca acacgaccaa agcaaaactg gcggagctgg ccgaccctct gaatgcacgc  16980
tacacaggca agaaaccgga tgaggttatt caggcgcaac tcgacgggct tgaagaactg  17040
tttgccgaca taccaccgcc caaagacaac gacaagcagt acaaggcatt gcgcgacttg  17100
aaacgcgcgg cggtcgagca tcgggcatca gccaacaagc acagcgtgat ggacaacgca  17160
cgctttgaaa ccagcaaaac caacctctcc ggcctgtcca gtgaaagcat acttaccaaa  17220
ataatgagtt ccgtgcgcga cgcgagcgcc ccgggcaatg cgacaagagt tgccgaattc  17280
atgcgccagg acccgaaact tcgcgccatg ctcaaggaga tggagggcag tatcgggacg  17340
ctggcacgcg tacggctgga accgaaggac tcactggtcg acaagatcga tgaaggcagc  17400
ctcaacggca ccatgactca aagcgacctc tccagcatgc tggaggatcg caacgagatg  17460
cgcatcaagc gtctggtggt attccacacc gcgacccagg ctgaaaactt cacctcacca  17520
acaccgttgg tcagctataa cagtggagcg aatgtgagcg tcactaaaac actggggcgc  17580
atcaacttcg tttatggcgc agaccaggac aagccgattg gttacacctt cgacggcgaa  17640
ttgtcacgac catcggcatc gctcaaggaa gcggctggcg acttgaagaa agaggggttc  17700
```

-continued

```
gaactgaaga gctaataacg aaaacagtaa aaaaagcgcc gcattgaagt ggcgcttttt  17760
tattcaagcc tgtaaaaaag cacgcgcttc acgtgcctgg gaaatgaacc cgcgcgtcac  17820
gtcacaaaac gctggctcat cgagtgaggc cagttcacgc tgcgcgcata gacggacatc  17880
tccctgatcg accgcaaacc agcagccatg caagcgcgct acgtcgaagt tcagactcaa  17940
cagacgcagc aaatcggggg ctcgttccgg gcagcggcca atgcggcaat gaaagatgac  18000
catctcactg tgctcgggca attcaatgat cgccgcttcg ttgttctgac cgtcataaag  18060
agcgcatacg ccgttctgca aggtcagtga cgtgccgagc tgggcgccca gagaattgat  18120
gaagcgggcg aaatcgggtt gcgaagtttt catcgtcata gtcctttaag gttaaaacag  18180
catgaagcat gccggacagc aggcgcctgc agcctgtgtc cggcgccggg attaacgcgg  18240
gtcaagcaag ccctcttcaa gtgccctcaa tgcgtcatcg tcttttgtcg gctgcttaag  18300
cgcctcgcgt gctgacgcga ctgcgttcaa cacaccttca tccacgaccc gaaccgtatc  18360
cacggccatc tgggtaggca actgcaatgc gcctcgtccc atgtgatagg cgttttccgc  18420
gactcgtggg ataccgctca acgtgctctt ctggaacgta tgtggcagag actccctgtt  18480
cggatgacgg atgttattca aagcgtctcg gtacggtcca gcataggtgt tgcaccgccc  18540
atgcctgccg ctttcaacgc cttggcttct gcggtaaccg actggttggt gtacaacgtg  18600
gacagatagg acaccgaacc cgtcgctgcc agggccatgt tgcgcaaaat agccccccgca  18660
ctgagcgtgc cacttgcgcc ttcagcctga gcggtcacag gcggcagtgc cgaggtcagt  18720
gcagaactct gaatacccga aagagccttg ctgtagaacg tggtgcgtac cgacggctcg  18780
cgcaggtcca tacctttgag caggtccttt ttcagatcgc tctcggcgcg gtccggggta  18840
aataccggaa ttttgcgccc ttgcgggtcg acataattcg acttcaattg cagcagcgtt  18900
tgcgaactgg cagacaccgc cccgccaaaa ccggatgcca gagctcttgc actcagcgtc  18960
tgcccattga tctggtgaac atcgttgagc atctggcgca cagcctgaga accaccgaag  19020
gcactgtaag ccatcagctc acctaccgga tgggtggacg aaccctgaac cttcttctgg  19080
ttcagcagcg cgcgttcact tttcacgaac gccttgtcct gagcgacttc ctcgggcgtt  19140
tttttgacca gctcaccgtg ttcgcttttc agctcgaagg ggtcaggaat aaccgtattg  19200
gtatccacag ccttcattgg caccatgttc aggcgttcgt tgaggccagt cttctgcaag  19260
gcggcctgaa acatcggctt gaccacgctg ttgaccgtct cgtgagcaat gcccgccacc  19320
atcccgatta tcgaagcctt gagcatgttg gcgtcgctgc tggtctcggg aatcgtgtct  19380
cgcagcttgt cgctggtgga caaacgcaca taacccaagt gtgtcattga agacaagaac  19440
tgcggaaccg cagccgcgac aatcggccct gcacctttcc agccacccac cgtgttacgg  19500
gcagtgacga gatcgctgac gacgttgtcc agttgcgtat gtgcggcgac cgaagcaagg  19560
cgcttggcct ccggcgactt gacgaaatcg gcgtgcaaac ctaccagggt ggttttggcg  19620
tcgaccagcg cctgcctgtc agcgtgcaga gactccttgt tgccctgttc ggcatcttgc  19680
agagtgagat ccagcgcact gatgtgctca tccagcgacg cgatgctgtt gctcaggcct  19740
tcgccgattg ccttgcttgc acgaccggcg tattcgccaa gggcagtctg actgacggca  19800
agcgtcgcct tgtccgcttt tgcatgctgg cctaccgttg cgggcgaagc gtcatgcatc  19860
agttgaaagt gctccagttg atcagcgacc gactgagcaa aacccttgat cagttgcccg  19920
acctcggctt tatccggtat ctgacccggc tgggcgaatt tttccagccg ctgctgcaag  19980
tccgagccct gaaactgctt cagttgatag cgctcaggag acaatttctc ggccatgact  20040
tcaaaaggca aaggctcggc ctgcagcaga ctaccgatca acaacgcagc acgcgaactg  20100
```

-continued

```
atcatcggcg cgccgctgac cggagccgtc ccatgctcag ccttgaaggc ctgcaaaagc  20160
tgtgtgtgtc gagccgcgac attcagccgc gccgcgccgg cagacgagct ttctgtcgcg  20220
tgtgaccctg actgatcggg agtcagcggc ggattcatgc ctgcagtgac tgcatttggg  20280
tgagctgtct gggcgggaac agtatcgtgc tgctggttta cccggctgag tttgacgcca  20340
ccggccccgc cgatccgcga actgatcatt ggaatctccc aggagccgaa aggctctcgc  20400
gtttggctgc tggggcaaca ggttggtccg tcgaggagcc tgcagttgtg gcctgcccca  20460
tgaatccatg ctcgcgccac tctttggcca ggtcggaaaa cgacttcatc aacaacagca  20520
cgccttcggc agaggctcgt tcaagggcca cagagcccat cagcagcaca cgaccggtct  20580
gcgcattaaa ggaaaatgcc gggctgtggg cgcccgcgaa catgtgaaag ttgatgtcca  20640
tcaacgccag caacgcgctc tcacggccgc gcgcgggcaa cgcgcccatg tcaccgtaga  20700
tcagaacggc acggccttcg tcgcggtcct gaaactgcag ggtgaagtcc acttcgctga  20760
ttttgaaatt ggcagattca tagaaacgtt caggtgtgga aatcaggctg agtgcgcaga  20820
tttcgttgat aagggtgtgg tactggtcat tgttggtcat ttcaaggcct ctgagtgcgg  20880
tgcggacgaa taccagtctt cctgctggcg tgtgcacact gagtcgcagg cataggcatt  20940
tcagttcctt gcgttggttg ggcatataaa aaaaggaact tttaaaaaca gtgcaatgag  21000
atgccggcaa aacgggaacc ggtcgctgcg ctttgccact cacttcgagc aagctcaacc  21060
ccaaacatcc acatccctat cgaacggaca gcgatacggc cacttgctct ggtaaaccct  21120
ggagctggcg tcggtccaat tgcccactta gcgaggtaac gcagcatgag catcggcatc  21180
acaccccggc cgcaacagac caccacgcca ctcgattttt cggcgctaag cggcaagagt  21240
cctcaaccaa acacgttcgg cgagcagaac actcagcaag cgatcgaccc gagtgcactg  21300
ttgttcggca gcgacacaca gaaagacgtc aacttcggca cgcccgacag caccgtccag  21360
aatccgcagg acgccagcaa gcccaacgac agccagtcca acatcgctaa attgatcagt  21420
gcattgatca tgtcgttgct gcagatgctc accaactcca ataaaaagca ggacaccaat  21480
caggaacagc ctgatagcca ggctcctttc cagaacaacg gcgggctcgg tacaccgtcg  21540
gccgatagcg gggcggcggg tacaccggat gcgacaggtg gcggcggcgg tgatacgcca  21600
agcgcaacag gcggtggcgg cggtgatact ccgaccgcaa caggcggtgg cggcagcggt  21660
ggcggcggca cacccactgc aacaggtggc ggcagcggtg gcacacccac tgcaacaggc  21720
ggtggcgagg gtggcgtaac accgcaaatc actccgcagt tggccaaccc taaccgtacc  21780
tcaggtactg gctcggtgtc ggacaccgca ggttctaccg agcaagccgg caagatcaat  21840
gtggtgaaag acaccatcaa ggtcggcgct ggcgaagtct ttgacggcca cggcgcaacc  21900
ttcactgccg acaaatctat gggtaacgga gaccagggcg aaaatcagaa gcccatgttc  21960
gagctggctg aaggcgctac gttgaagaat gtgaacctgg gtgagaacga ggtcgatggc  22020
atccacgtga aagccaaaaa cgctcaggaa gtcaccattg acaacgtgca tgcccagaac  22080
gtcggtgaag acctgattac ggtcaaaggc gagggaggcg cagcggtcac taatctgaac  22140
atcaagaaca gcagtgccaa aggtgcagac gacaaggttg tccagctcaa cgccaacact  22200
cacttgaaaa tcgacaactt caaggccgac gatttcggca cgatggttcg caccaacggt  22260
ggcaagcagt ttgatgacat gagcatcgag ctgaacggca tcgaagctaa ccacggcaag  22320
ttcgccctgg tgaaaagcga cagtgacgat ctgaagctgg caacgggcaa catcgccatg  22380
accgacgtca aacacgccta cgataaaacc caggcatcga cccaacacac cgagctttga  22440
```

-continued

```
atccagacaa gtagcttgaa aaaaggggggt ggactcgtcg agtccacccc ctttttactg  22500
tttagctaca gctcacagat tgcttacgac cgcataggcc gaaacggtat ttcacttgga  22560
gaagccgccg tgcccccctc ttctatatca gcttcacgag ccgggcgttg acgcaggtta  22620
ttgaccgtat tgcgcaagct ggcgccggta tgggtgatcg cctccccgcc catgtctttg  22680
acggtcttcg ccagtttgac ggtctggtcg gctacgtagc ctgtggtact ggatgcagtc  22740
gatttcaccg tgtcctgtat gaacgactcg gctttttttca ccgcgggatc ggttgtcagc  22800
gcggccgtgg tccagcctgc gaaaacggct gccgaacctg ccaggttggt caactgactg  22860
accgcggcct tggtcgccgg gtcggtgata tttttcgtcg ccatctcctg caacttgcct  22920
acccctgcaa agccacccgc cagggccaga ccgttttggg tcaggctgga cgctgacacc  22980
aggcttctta ccgcacccat tgcgtcggtc gccatatcca gtggcagacc ggccatccgc  23040
ttgccagcgt tgagcgccgc acccgagtag ctggccgatt tgattgcttt ataagcctcg  23100
agccagtcgt tttcttcgct cagttgagcc ttgggctctt tatccttcaa accgagcact  23160
aatgcaccgc cacgctggtg atcacgcgac tgcacactga gcaggcggtt gccaaagcct  23220
gcgttggcag ccagaccacc cgccatcgat acaccaaggt ccacagcacc ctgcacggcg  23280
ggtctggacg ccagtgccgg agccaatacg gtacgtacgg cgttgcgcgc cgagtacgtc  23340
tgaaccgcaa cccccgtgtc cagaacctgt cgagcaaggc ttggcgagtg gcgcttcacc  23400
gaagcggcca tcgcatcgtg gagcctgtcc ggcgaggcgc tcaggtaatg cagatcaccc  23460
gtcgcgcggt ccatcatctt ggtgcccacc tggtccatgg cgcccgacag cgctccggaa  23520
atgagcgggg tcagcggttt gagcggagcc ggcagccaat cgcccttgtt gatcgcaggc  23580
tgcatgtact gaagcaacga ggccatggca aagggcgtcg cccgcaacgc gcctgatgta  23640
gtcgtcgcca atcggtcgag cttttccgcc ttggcgaagg tgtcggcgat ggttgccggg  23700
gtttcccctt cgaagtgcag gcggctggcg cgcgtctcga tcagcgcagt gatctgcgca  23760
ttgtgtacgt caactgcagc ttggccatca gccgaatcgg ccggcggcag tttatgcgca  23820
gcgaacacat gatctgtcag gtaatcggca atcgcattta tctcgcgttg ctgatcggag  23880
ctgacagatc gcacagagct ggaggcaaga gacgcgtcgg acgctgtccg aaagctatcc  23940
gtcgcagtca caggcggttg ttggacgcgt cggttgatgt gcatggaaat tccctctcgt  24000
tctacggaag tttgaacagc gcagtgctga agcgggcgtg tccggagcga ctacttgcgt  24060
gaaagcaata cagtgaactg tcgatcaaac agcgccagaa acagcgaaac gtccggtcgt  24120
ccgccggttt aaaaggatcg acgaaggctg tgtggtcccg gatcggttga cggttccact  24180
gaataatctg cgtacgccca ctaccaagga ctgcgccgaa aaatcaccgt cgtttgtgtt  24240
gcagattacg caaattgaaa ttaagcgagc tttaaggatg gcagcgtaag ttcacaacat  24300
ggcttggcgc ttagcgagta agcgccttct tccaaaccag caaaggagtg ccgcaatgtc  24360
tggtcctttc gagaaaaaat ggcggtgttt cacccgaacc gtgacctacg ttggctggtc  24420
gctgttctgg cttctgctct gggacgtggc cgtcaccgtg gacgtcatgc tgatagaagg  24480
caaaggcatc gacttccccc tgatgcccct cacgttgctt tgctcggcac tgatcgtgct  24540
gatcagcttt cgcaactcga gtgcctataa ccgttggtgg gaagcgcgca ccttgtgggg  24600
cgcaatggtc aacacttcac gcagttttgg ccggcaggta ctgacgctga tcgatggcga  24660
acgggatgac ctcaacaacc ctgtcaaagc catactcttt caacgtcatg tggcttactt  24720
gcgtgccctg cgcgcgcacc tcaaaggcga cgtcaaaaca gcaaaactcg acgggttact  24780
gtcgcccgac gagattcagc gcgccagcca gagcaacaac ttccccaatg acatcctcaa  24840
```

-continued

```
tggctctgct gcggttatct cgcaagcctt tgccgccggc cagttcgaca gcatccgtct  24900
gacccgcctg gaatcgacca tggtcgatct gtccaactgt cagggcggca tggagcgcat  24960
cgccaacacg ccactgccct accccctacgt ttatttccca cggctgttca gcacgctgtt  25020
ctgcatcctg atgccgctga gcatggtcac caccctgggc tggttcaccc cggcgatctc  25080
cacggtggta ggctgcatgc tgctggcaat ggaccgcatc ggtacagacc tgcaagcccc  25140
gttcggcaac agtcagcacc ggatccgcat ggaagacctg tgcaacacca tcgaaaagaa  25200
cctgcaatcg atgttctctt cgccagagag gcagccgctg ctggctgacc tgaaaagccc  25260
cgtaccgtgg cgcgtggcca acgcatcaat tggcggtctg agcaggcaga aaaacaggtt  25320
aggggaaggc gcgaggctta tcgcaagtga aagtctgctc tgggcaccat ttcgctcagt  25380
tgcagacgtt gctccgtgcc acgccagtgc gtacctacgt cgcgcttgaa cacatcagca  25440
agaaaatggc tcatgttgct gaagctgtct gcctgaacca cgccaaaaag aggatcaaaa  25500
aaatgcagac atccctgact gtcctgatgc agagccatcg catggctatc actcaaaaac  25560
agaagcatct ggtctttacc gggctgcaac actgctttga gatcgcgatc aaggttttcc  25620
agagcaaccg catagtgcgc gtgctgtgct ctgcccagcc cttttccaag tgtcatgccc  25680
aacttgggaa gtgtgtccag aagcataggt gctgcgttct gcaacttgtt tgaataggcc  25740
tgctgctcga tatgctggaa gcccattacc ctgggtagca atgcatcgcc ctgatagtcc  25800
tccagtttgt gaaagaaggc ctcatccgac tgcccttttg cacggctctg acaccaattt  25860
actgatagcc ccagacaagc gtgcccgtcg ccacccgcgc ggccatagtc agcagcaaac  25920
gctctatcat cgatagtttt ttcaaataga aatttgctct ggtgaaacgg gtggacaagc  25980
tgacagccgt gctcttgggc aatctttctt ttggcttcga tgttcgcagt cgcgcctatg  26040
ctgttgtccg ccatagcctt gattctggtc ttgatgtatt gcgtggcgcc gtcacgtaat  26100
gaggcgatag agaccatcag atccggtagc agggtacgca acgaatgaag ctggggttgt  26160
acctgctcgg gactgggaag atcagcggca tcgaccgacg aaaaggaaga gcgcgcatcg  26220
aaaaagacct cttcatgccc ctccaatggg acaaaggcgc ccgccttttc gggatgaaaa  26280
cgggcgaacg catccgacga accgggggcg agtccggaca atgacgaggg cttatcgtgt  26340
tgcgtcttag cggcaacccc tgattgggcg ccagattgct ggatatacat aaaccgccct  26400
ctgtcaggtc atgaacgttc gtggggtcag atggacagcc ggtaagaacc gaggctcttt  26460
ctgggcggtt tttccggctt gctcctggcg tcgataatct tccagatagc gctgcaacga  26520
gacggccaat gtgctaattc gcgtcatgag gtgatcaagt ccggtctcat ccagatccgc  26580
cattgagtgc acactgcgca acaacagttc ccttgaatca gggttatagc caagcgcagc  26640
gccacctgtg cgagcaggct ccagattcag cgccattgcc agaatcaaaa tgacgttgtc  26700
ctgcggcatc gtcagccttt cgatctgtgt gaagatgaac aacgaagtgt cctgttctgg  26760
caaccagagc agacactcgc ttccattcgc ggtccttacg ttgtggcgtt gaccctcctg  26820
cgcatcgatg cctcgattgc gcagccactg ataaagccga tcttttgcct cgacaggccg  26880
catggaaatt ccccgctcgt ttaacgatga ttttcctctg tggttcaaga cgtgatgcgg  26940
ttccctttag ggtttgcact aatatcaatg cgattcttgt aaaaatcgac tcgtgagtgc  27000
cgccgatggc aaaggtaacg ggatgggcag cgagtttttg gtaacgttgc cgttgttgca  27060
gggttgaatt tgttgggtga cgttaaaacg aaggaatgta tgcttaaaaa atgcctgcta  27120
ctggttatat caatgtcact tggcggctgc tggagcctga tgattcatct ggacggcgag  27180
```

-continued

```
cgttgcatct atcccggcac tcgccaaggt tgggcgtggg gaacccataa cggagggcag  27240
agttggccca tacttataga cgtgccgttt tccctcgcgt tggacacact gctgctgccc  27300
tacgacctca ccgcttttct gcccgaaaat cttggcggtg atgaccgcaa atgtcagttc  27360
agtggaggat tgaacgtgct cggttgatcc atatttttac tgcgacagaa gagtgcggcc  27420
ccgacgcttt tggagagcac accagggatt caaacccgcc ttaaaagctt tatatgcgtg  27480
gcatgcacct cgtcaactgc ctgaaagccg caacgtaagt aaaattttgc tccgctcgga  27540
gtatcagtga acaggcgcac ggcgaaaaat tcctgcgccg catgctccac aagtcgattc  27600
accagagtct ttccaaggcc ttgacctctt gatgcgcttg cgacgtataa ccgtcgtagc  27660
ctgcccatat caccccgggc atgcggatca cgcgaaaggc ctccgatacc tgccagagcg  27720
ccgtccagaa gtacgaccat gaggcattca cccttggcct cgaatcgatt ctttccggac  27780
ctccactcct cgatcaagcg ggtaagaaac ctgaagccct ctgctactgc ctcttgctcc  27840
aggatcagaa cctgacaagg caattcagta atgatctgga cttctacctg tttcatctaa  27900
tgacctcatc cacagtggtc ctgcgctggc gaaaacacga gcaggtctgg acagaatgca  27960
tatgcaacag caaaggctgc aaccagtgca caccaccaga accgggttcg acagttaagc  28020
tgatatcatt caagcacctg caagccgagt agaagcacat gaaccgtcgc aagaaaatac  28080
agcaactgtt aaaggctcat gccaagaaag ccagcgctaa actggcaccg gcaaacaaat  28140
ccagctacgt gagcaaggct gatcggttga agctggcggc agagtccggt aacgacccga  28200
tcagttccgt cgaggactga acagcgacgt ttacgcgcca ccggtatggt caggctgttc  28260
attccgatgg agcgtattgc aaggagcctg ttcaacagct cacttacttc gcaaacgagt  28320
actcaccgcc ctgctccagc gcctggcgat acgcaggtct ttcctggcat cgttgtaccc  28380
aggctgcaag gttaggatgc ggctgcagca ttccctgcat tttggcgaat tcgccaatga  28440
agctcatctg aatatccgcg ccactcaatt cgtcgcccag cagataaggc gtcagcccca  28500
gagcttcatt cagatagccc agatagttgg ccagttcaga gtgaatgcgc ggatgcaaag  28560
gcgcgcccgc gtcacccagg cgaccgacgt acaggttgag catcagcggc agaatggccg  28620
aaccttcggc gaagtgcagc cattgtacgt actcatcgta ggtggcgctg gcaggatccg  28680
gttgcaggcg gccgtcgcca tgacggcgga tcaggtaatc gacgatggcg ccagactcga  28740
taaccacatg ggaccgtct tcgatcaccg gggatttgcc cagcggatga atggccttca  28800
gctcaggcgg cgcgaggttg gttttcgggt cgcgctggta gcgttttatc tcgtacggca  28860
ggccaagttc ttcgagtaac cacagaatgc gctgcgaacg tgagttgttc aggtggtgga  28920
caataatcat gtgggtctcc gctgggtgag agtgggatgt ctagaaaaag actgctgggc  28980
cgccgtagag tgccgtgaat cgaatgtcct ctggcgacct cagacgcgtc tgtcggcgca  29040
gagcgctgcc gactcaccgc gaagctgacg ctccactgcc gctttatcga ttaccgacca  29100
aacgccgatt atcttgccat cgctgaatgt gtagaacaca ttttcggaaa aggtgatgcg  29160
ccgtccctgt gtgtcctgcc ccagaaatcg accctgtggc gagcagttga agaccagccg  29220
ggcagcgacc tgtggtgctt caacgaccag caaatcgatc ttgaaacgca agtcggggat  29280
aatcctgacg tcgttttcca gcattgtttt gtagccggaa aggctgatca gctcaccgtt  29340
gtaatgcaca ttgtcatcga cgaagttgcc caactggtgc caactacggt cattcagaca  29400
ggcgatgtaa gcccgatagt gatcggtcag gttcatggcg cgccctcctt caggtgctca  29460
aagcagtcac tgtcaatcat ccagataacc cgcacagttt taacagagtc atagggaact  29520
cgtgcggccg acatcgccct aagcctcaca tctatgtact ggcgcgacgc tggtttcaag  29580
```

```
cgaaggactt cagattcatg tcttcaagta gcactacagc agcggctgac acgcaaggtc  29640

ggcaaaacgc ctcgcctaac cgactgattt tcatctccgt acttgtggca accatgggcg  29700

cgctcgcgtt tggttatgac accggtatta tcgncggcgc attgcccttc atgacgctgc  29760

cggccgatca gggcgggctg ggtttgaatg cctacagcga agggatgatc acggcttcgc  29820

tgatcgtcgg tgcagccttc ggctcactgg ccagtggcta tatttccgac cgtttcggac  29880

gacgcctgac cctgcgcctc ctgtcggtgc tgttcatcgc gggtgcgctg ggtacggcca  29940

ttgcgccgtc cattccgttc atggtcgccg cgcgcttcct gctgggtatc gcggtgggtg  30000

gcggctcggc gacggtgccg gtgttcattg ccgaaatcgc cggcccctcg cgtcgtgcgc  30060

ggctggtcag ccgcaacgaa ctgatgatcg tcagcggcca gttgctcgcc tatgtgctca  30120

gcgcggtcat ggccgcgctg ctgcacacgc cgggcatctg gcgctatatg ctggcgatcg  30180

cgatggtgcc gggggtgttg ctgctgatcg gcaccttctt cgtacctcct tcgccgngct  30240

ggctggcgtc caaaggccgt tttgacgaag ctcaggatgt gctggagcaa ctgcgcagca  30300

acaaggacga tgcgcancgt gaagtggacg aaatgaaagc tcatgacgag caggcgcgca  30360

atcgt                                                              30365
```

<210> SEQ ID NO 2
<211> LENGTH: 1872
<212> TYPE: DNA
<213> ORGANISM: Pseudomonas syringae

<400> SEQUENCE: 2

```
atgatcagtt cgcggatcgg cggggccggt ggcgtcaaac tcagccgggt aaaccagcag     60

cacgatactg ttcccgccca gacagctcac ccaaatgcag tcactgcagg catgaatccg    120

ccgctgactc ccgatcagtc agggtcacac gcgacagaaa gctcgtctgc cggcgcggcg    180

cggctgaatg tcgcggctcg acacacacag cttttgcagg ccttcaaggc tgagcatggg    240

acggctccgg tcagcggcgc gccgatgatc agttcgcgtg ctgcgttgtt gatcggtagt    300

ctgctgcagg ccgagccttt gccttttgaa gtcatggccg agaaattgtc tcctgagcgc    360

tatcaactga agcagtttca gggctcggac ttgcagcagc ggctggaaaa attcgcccag    420

ccgggtcaga taccggataa agccgaggtc gggcaactga tcaagggttt tgctcagtcg    480

gtcgctgatc aactggagca ctttcaactg atgcatgacg cttcgcccgc aacggtaggc    540

cagcatgcaa aagcggacaa ggcgacgctt gccgtcagtc agactgccct tggcgaatac    600

gccggtcgtg caagcaaggc aatcggcgaa ggcctgagca acagcatcgc gtcgctggat    660

gagcacatca gtgcgctgga tctcactctg caagatgccg aacagggcaa caaggagtct    720

ctgcacgctg acaggcaggc gctggtcgac gccaaaacca ccctggtagg tttgcacgcc    780

gatttcgtca agtcgccgga ggccaagcgc cttgcttcgg tcgccgcaca tacgcaactg    840

gacaacgtcg tcagcgatct cgtcactgcc cgtaacacgg tgggtggctg gaaaggtgca    900

gggccgattg tcgcggctgc ggttccgcag ttcttgtctt caatgacaca cttgggttat    960

gtgcgtttgt ccaccagcga caagctgcga gacacgattc ccgagaccag cagcgacgcc   1020

aacatgctca aggcttcgat aatcgggatg gtggcgggca ttgctcacga gacggtcaac   1080

agcgtggtca agccgatgtt tcaggccgcc ttgcagaaga ctggcctcaa cgaacgcctg   1140

aacatggtgc caatgaaggc tgtggatacc aatacggtta ttcctgaccc cttcgagctg   1200

aaaagcgaac acggtgagct ggtcaaaaaa acgcccgagg aagtcgctca ggacaaggcg   1260
```

-continued

```
ttcgtgaaaa gtgaacgcgc gctgctgaac cagaagaagg ttcagggttc gtccacccat   1320

ccggtaggtg agctgatggc ttacagtgcc ttcggtggtt ctcaggctgt gcgccagatg   1380

ctcaacgatg ttcaccagat caatgggcag acgctgagtg caagagctct ggcatccggt   1440

tttggcgggg cggtgtctgc cagttcgcaa acgctgctgc aattgaagtc gaattatgtc   1500

gacccgcaag ggcgcaaaat tccggtattt accccggacc gcgccgagag cgatctgaaa   1560

aaggacctgc tcaaaggtat ggacctgcgc gagccgtcgg tacgcaccac gttctacagc   1620

aaggctcttt cgggtattca gagttctgca ctgacctcgg cactgccgcc tgtgaccgct   1680

caggctgaag gcgcaagtgg cacgctcagt gcgggggcta ttttgcgcaa catggccctg   1740

gcagcgacgg gttcggtgtc ctatctgtcc acgttgtaca ccaaccagtc ggttaccgca   1800

gaagccaagg cgttgaaagc ggcaggcatg ggcggtgcaa cacctatgct ggaccgtacc   1860

gagacgcttt ga                                                       1872
```

```
<210> SEQ ID NO 3
<211> LENGTH: 623
<212> TYPE: PRT
<213> ORGANISM: Pseudomonas syringae

<400> SEQUENCE: 3

Met Ile Ser Ser Arg Ile Gly Gly Ala Gly Gly Val Lys Leu Ser Arg
  1               5                  10                  15

Val Asn Gln Gln His Asp Thr Val Pro Ala Gln Thr Ala His Pro Asn
             20                  25                  30

Ala Val Thr Ala Gly Met Asn Pro Pro Leu Thr Pro Asp Gln Ser Gly
         35                  40                  45

Ser His Ala Thr Glu Ser Ser Ser Ala Gly Ala Ala Arg Leu Asn Val
     50                  55                  60

Ala Ala Arg His Thr Gln Leu Leu Gln Ala Phe Lys Ala Glu His Gly
 65                  70                  75                  80

Thr Ala Pro Val Ser Gly Ala Pro Met Ile Ser Ser Arg Ala Ala Leu
                 85                  90                  95

Leu Ile Gly Ser Leu Leu Gln Ala Glu Pro Leu Pro Phe Glu Val Met
            100                 105                 110

Ala Glu Lys Leu Ser Pro Glu Arg Tyr Gln Leu Lys Gln Phe Gln Gly
        115                 120                 125

Ser Asp Leu Gln Gln Arg Leu Glu Lys Phe Ala Gln Pro Gly Gln Ile
    130                 135                 140

Pro Asp Lys Ala Glu Val Gly Gln Leu Ile Lys Gly Phe Ala Gln Ser
145                 150                 155                 160

Val Ala Asp Gln Leu Glu His Phe Gln Leu Met His Asp Ala Ser Pro
                165                 170                 175

Ala Thr Val Gly Gln His Ala Lys Ala Asp Lys Ala Thr Leu Ala Val
            180                 185                 190

Ser Gln Thr Ala Leu Gly Glu Tyr Ala Gly Arg Ala Ser Lys Ala Ile
        195                 200                 205

Gly Glu Gly Leu Ser Asn Ser Ile Ala Ser Leu Asp Glu His Ile Ser
    210                 215                 220

Ala Leu Asp Leu Thr Leu Gln Asp Ala Glu Gln Gly Asn Lys Glu Ser
225                 230                 235                 240

Leu His Ala Asp Arg Gln Ala Leu Val Asp Ala Lys Thr Thr Leu Val
                245                 250                 255

Gly Leu His Ala Asp Phe Val Lys Ser Pro Glu Ala Lys Arg Leu Ala
```

-continued

```
            260                 265                 270

Ser Val Ala Ala His Thr Gln Leu Asp Asn Val Val Ser Asp Leu Val
        275                 280                 285

Thr Ala Arg Asn Thr Val Gly Gly Trp Lys Gly Ala Gly Pro Ile Val
    290                 295                 300

Ala Ala Ala Val Pro Gln Phe Leu Ser Ser Met Thr His Leu Gly Tyr
305                 310                 315                 320

Val Arg Leu Ser Thr Ser Asp Lys Leu Arg Asp Thr Ile Pro Glu Thr
                325                 330                 335

Ser Ser Asp Ala Asn Met Leu Lys Ala Ser Ile Ile Gly Met Val Ala
            340                 345                 350

Gly Ile Ala His Glu Thr Val Asn Ser Val Val Lys Pro Met Phe Gln
        355                 360                 365

Ala Ala Leu Gln Lys Thr Gly Leu Asn Glu Arg Leu Asn Met Val Pro
    370                 375                 380

Met Lys Ala Val Asp Thr Asn Thr Val Ile Pro Asp Pro Phe Glu Leu
385                 390                 395                 400

Lys Ser Glu His Gly Glu Leu Val Lys Lys Thr Pro Glu Glu Val Ala
                405                 410                 415

Gln Asp Lys Ala Phe Val Lys Ser Glu Arg Ala Leu Leu Asn Gln Lys
            420                 425                 430

Lys Val Gln Gly Ser Ser Thr His Pro Val Gly Glu Leu Met Ala Tyr
        435                 440                 445

Ser Ala Phe Gly Gly Ser Gln Ala Val Arg Gln Met Leu Asn Asp Val
    450                 455                 460

His Gln Ile Asn Gly Gln Thr Leu Ser Ala Arg Ala Leu Ala Ser Gly
465                 470                 475                 480

Phe Gly Gly Ala Val Ser Ala Ser Ser Gln Thr Leu Leu Gln Leu Lys
                485                 490                 495

Ser Asn Tyr Val Asp Pro Gln Gly Arg Lys Ile Pro Val Phe Thr Pro
            500                 505                 510

Asp Arg Ala Glu Ser Asp Leu Lys Lys Asp Leu Leu Lys Gly Met Asp
        515                 520                 525

Leu Arg Glu Pro Ser Val Arg Thr Thr Phe Tyr Ser Lys Ala Leu Ser
    530                 535                 540

Gly Ile Gln Ser Ser Ala Leu Thr Ser Ala Leu Pro Pro Val Thr Ala
545                 550                 555                 560

Gln Ala Glu Gly Ala Ser Gly Thr Leu Ser Ala Gly Ala Ile Leu Arg
                565                 570                 575

Asn Met Ala Leu Ala Ala Thr Gly Ser Val Ser Tyr Leu Ser Thr Leu
            580                 585                 590

Tyr Thr Asn Gln Ser Val Thr Ala Glu Ala Lys Ala Leu Lys Ala Ala
        595                 600                 605

Gly Met Gly Gly Ala Thr Pro Met Leu Asp Arg Thr Glu Thr Leu
    610                 615                 620

<210> SEQ ID NO 4
<211> LENGTH: 495
<212> TYPE: DNA
<213> ORGANISM: Pseudomonas syringae

<400> SEQUENCE: 4

atgaccaaca atgaccagta ccacaccctt atcaacgaaa tctgcgcact cagcctgatt      60

tccacacctg aacgtttcta tgaatctgcc aatttcaaaa tcagcgaagt ggacttcacc     120
```

ctgcagtttc aggaccgcga cgaaggccgt gccgttctga tctacggtga catgggcgcg 180
ttgcccgcgc gcggccgtga gagcgcgttg ctggcgttga tggacatcaa ctttcacatg 240
ttcgcgggcg cccacagccc ggcattttcc tttaatgcgc agaccggtcg tgtgctgctg 300
atgggctctg tggcccttga acgagcctct gccgaaggcg tgctgttgtt gatgaagtcg 360
ttttccgacc tggccaaaga gtggcgcgag catggattca tggggcaggc cacaactgca 420
ggctcctcga cggaccaacc tgttgcccca gcagccaaac gcgagagcct ttcggctcct 480
gggagattcc aatga 495

<210> SEQ ID NO 5
<211> LENGTH: 164
<212> TYPE: PRT
<213> ORGANISM: Pseudomonas syringae

<400> SEQUENCE: 5

Met Thr Asn Asn Asp Gln Tyr His Thr Leu Ile Asn Glu Ile Cys Ala
1 5 10 15

Leu Ser Leu Ile Ser Thr Pro Glu Arg Phe Tyr Glu Ser Ala Asn Phe
20 25 30

Lys Ile Ser Glu Val Asp Phe Thr Leu Gln Phe Gln Asp Arg Asp Glu
35 40 45

Gly Arg Ala Val Leu Ile Tyr Gly Asp Met Gly Ala Leu Pro Ala Arg
50 55 60

Gly Arg Glu Ser Ala Leu Leu Ala Leu Met Asp Ile Asn Phe His Met
65 70 75 80

Phe Ala Gly Ala His Ser Pro Ala Phe Ser Phe Asn Ala Gln Thr Gly
85 90 95

Arg Val Leu Leu Met Gly Ser Val Ala Leu Glu Arg Ala Ser Ala Glu
100 105 110

Gly Val Leu Leu Leu Met Lys Ser Phe Ser Asp Leu Ala Lys Glu Trp
115 120 125

Arg Glu His Gly Phe Met Gly Gln Ala Thr Thr Ala Gly Ser Ser Thr
130 135 140

Asp Gln Pro Val Ala Pro Ala Ala Lys Arg Glu Ser Leu Ser Ala Pro
145 150 155 160

Gly Arg Phe Gln

<210> SEQ ID NO 6
<211> LENGTH: 1461
<212> TYPE: DNA
<213> ORGANISM: Pseudomonas syringae

<400> SEQUENCE: 6
atgcacatca accgacgcgt ccaacaaccg cctgtgactg cgacggatag ctttcggaca 60
gcgtccgacg cgtctcttgc ctccagctct gtgcgatctg tcagctccga tcagcaacgc 120
gagataaatg cgattgccga ttacctgaca gatcatgtgt tcgctgcgca taaactgccg 180
ccggccgatt cggctgatgg ccaagctgca gttgacgtac acaatgcgca gatcactgcg 240
ctgatcgaga cgcgcgccag ccgcctgcac ttcgaagggg aaaccccggc aaccatcgcc 300
gacaccttcg ccaaggcgga aaagctcgac cgattggcga cgactacatc aggcgcgttg 360
cgggcgacgc cctttgccat ggcctcgttg cttcagtaca tgcagcctgc gatcaacaag 420
ggcgattggc tgccggctcc gctcaaaccg ctgaccccgc tcatttccgg agcgctgtcg 480

-continued

```
ggcgccatgg accaggtggg caccaagatg atggaccgcg cgacgggtga tctgcattac    540

ctgagcgcct cgccggacag gctccacgat gcgatggccg cttcggtgaa gcgccactcg    600

ccaagccttg ctcgacaggt tctggacacg gggttgcgg ttcagacgta ctcggcgcgc    660

aacgccgtac gtaccgtatt ggctccggca ctggcgtcca gacccgccgt gcagggtgct    720

gtggaccttg gtgtatcgat ggcgggtggt ctggctgcca acgcaggctt tggcaaccgc    780

ctgctcagtg tgcagtcgcg tgatcaccag cgtggcggtg cattagtgct cggtttgaag    840

gataaagagc ccaaggctca actgagcgaa gaaaacgact ggctcgaggc ttataaagca    900

atcaaatcgg ccagctactc gggtgcggcg ctcaacgctg gcaagcggat ggccggtctg    960

ccactggata tggcgaccga cgcaatgggt gcggtaagaa gcctggtgtc agcgtccagc   1020

ctgacccaaa acggtctggc cctggcgggt ggctttgcag ggtaggcaa gttgcaggag   1080

atggcgacga aaaatatcac cgacccggcg accaaggccg cggtcagtca gttgaccaac   1140

ctggcaggtt cggcagccgt tttcgcaggc tggaccacgg ccgcgctgac aaccgatccc   1200

gcggtgaaaa aagccgagtc gttcatacag gacacggtga aatcgactgc atccagtacc   1260

acaggctacg tagccgacca gaccgtcaaa ctggcgaaga ccgtcaaaga catgggcggg   1320

gaggcgatca cccataccgg cgccagcttg cgcaatacgg tcaataacct gcgtcaacgc   1380

ccggctcgtg aagctgatat agaagagggg ggcacggcgg cttctccaag tgaaataccg   1440

tttcggccta tgcggtcgta a                                              1461
```

```
<210> SEQ ID NO 7
<211> LENGTH: 486
<212> TYPE: PRT
<213> ORGANISM: Pseudomonas syringae

<400> SEQUENCE: 7

Met His Ile Asn Arg Arg Val Gln Gln Pro Pro Val Thr Ala Thr Asp
  1               5                  10                  15

Ser Phe Arg Thr Ala Ser Asp Ala Ser Leu Ala Ser Ser Ser Val Arg
             20                  25                  30

Ser Val Ser Ser Asp Gln Gln Arg Glu Ile Asn Ala Ile Ala Asp Tyr
         35                  40                  45

Leu Thr Asp His Val Phe Ala Ala His Lys Leu Pro Pro Ala Asp Ser
     50                  55                  60

Ala Asp Gly Gln Ala Ala Val Asp Val His Asn Ala Gln Ile Thr Ala
 65                  70                  75                  80

Leu Ile Glu Thr Arg Ala Ser Arg Leu His Phe Glu Gly Glu Thr Pro
                 85                  90                  95

Ala Thr Ile Ala Asp Thr Phe Ala Lys Ala Glu Lys Leu Asp Arg Leu
            100                 105                 110

Ala Thr Thr Thr Ser Gly Ala Leu Arg Ala Thr Pro Phe Ala Met Ala
        115                 120                 125

Ser Leu Leu Gln Tyr Met Gln Pro Ala Ile Asn Lys Gly Asp Trp Leu
    130                 135                 140

Pro Ala Pro Leu Lys Pro Leu Thr Pro Leu Ile Ser Gly Ala Leu Ser
145                 150                 155                 160

Gly Ala Met Asp Gln Val Gly Thr Lys Met Met Asp Arg Ala Thr Gly
                165                 170                 175

Asp Leu His Tyr Leu Ser Ala Ser Pro Asp Arg Leu His Asp Ala Met
            180                 185                 190

Ala Ala Ser Val Lys Arg His Ser Pro Ser Leu Ala Arg Gln Val Leu
```

-continued

```
        195                 200                 205

Asp Thr Gly Val Ala Val Gln Thr Tyr Ser Ala Arg Asn Ala Val Arg
    210                 215                 220

Thr Val Leu Ala Pro Ala Leu Ala Ser Arg Pro Ala Val Gln Gly Ala
225                 230                 235                 240

Val Asp Leu Gly Val Ser Met Ala Gly Gly Leu Ala Ala Asn Ala Gly
                245                 250                 255

Phe Gly Asn Arg Leu Leu Ser Val Gln Ser Arg Asp His Gln Arg Gly
            260                 265                 270

Gly Ala Leu Val Leu Gly Leu Lys Asp Lys Glu Pro Lys Ala Gln Leu
        275                 280                 285

Ser Glu Glu Asn Asp Trp Leu Glu Ala Tyr Lys Ala Ile Lys Ser Ala
    290                 295                 300

Ser Tyr Ser Gly Ala Ala Leu Asn Ala Gly Lys Arg Met Ala Gly Leu
305                 310                 315                 320

Pro Leu Asp Met Ala Thr Asp Ala Met Gly Ala Val Arg Ser Leu Val
                325                 330                 335

Ser Ala Ser Ser Leu Thr Gln Asn Gly Leu Ala Leu Ala Gly Gly Phe
            340                 345                 350

Ala Gly Val Gly Lys Leu Gln Glu Met Ala Thr Lys Asn Ile Thr Asp
        355                 360                 365

Pro Ala Thr Lys Ala Ala Val Ser Gln Leu Thr Asn Leu Ala Gly Ser
    370                 375                 380

Ala Ala Val Phe Ala Gly Trp Thr Thr Ala Ala Leu Thr Thr Asp Pro
385                 390                 395                 400

Ala Val Lys Lys Ala Glu Ser Phe Ile Gln Asp Thr Val Lys Ser Thr
                405                 410                 415

Ala Ser Ser Thr Thr Gly Tyr Val Ala Asp Gln Thr Val Lys Leu Ala
            420                 425                 430

Lys Thr Val Lys Asp Met Gly Gly Glu Ala Ile Thr His Thr Gly Ala
        435                 440                 445

Ser Leu Arg Asn Thr Val Asn Asn Leu Arg Gln Arg Pro Ala Arg Glu
    450                 455                 460

Ala Asp Ile Glu Glu Gly Gly Thr Ala Ala Ser Pro Ser Glu Ile Pro
465                 470                 475                 480

Phe Arg Pro Met Arg Ser
                485


<210> SEQ ID NO 8
<211> LENGTH: 1074
<212> TYPE: DNA
<213> ORGANISM: Pseudomonas syringae

<400> SEQUENCE: 8

atgtctggtc ctttcgagaa aaaatggcgg tgtttcaccc gaaccgtgac ctacgttggc      60

tggtcgctgt tctggcttct gctctgggac gtggccgtca ccgtggacgt catgctgata     120

gaaggcaaag gcatcgactt ccccctgatg cccctcacgt tgctttgctc ggcactgatc     180

gtgctgatca gctttcgcaa ctcgagtgcc tataaccgtt ggtgggaagc gcgcaccttg     240

tggggcgcaa tggtcaacac ttcacgcagt tttggccggc aggtactgac gctgatcgat     300

ggcgaacggg atgacctcaa caaccctgtc aaagccatac tctttcaacg tcatgtggct     360

tacttgcgtg ccctgcgcgc gcacctcaaa ggcgacgtca aaacagcaaa actcgacggg     420

ttactgtcgc ccgacgagat tcagcgcgcc agccagagca acaacttccc caatgacatc     480
```

-continued

```
ctcaatggct ctgctgcggt tatctcgcaa gcctttgccg ccggccagtt cgacagcatc    540

cgtctgaccc gcctggaatc gaccatggtc gatctgtcca actgtcaggg cggcatggag    600

cgcatcgcca acacgccact gccctacccc tacgtttatt tcccacggct gttcagcacg    660

ctgttctgca tcctgatgcc gctgagcatg gtcaccaccc tgggctggtt caccccggcg    720

atctccacgg tggtaggctg catgctgctg gcaatggacc gcatcggtac agacctgcaa    780

gccccgttcg gcaacagtca gcaccggatc cgcatggaag acctgtgcaa caccatcgaa    840

aagaacctgc aatcgatgtt ctcttcgcca gagaggcagc cgctgctggc tgacctgaaa    900

agccccgtac cgtggcgcgt ggccaacgca tcaattggcg gtctgagcag gcagaaaaac    960

aggttagggg aaggcgcgag gcttatcgca agtgaaagtc tgctctgggc accatttcgc   1020

tcagttgcag acgttgctcc gtgccacgcc agtgcgtacc tacgtcgcgc ttga         1074
```

<210> SEQ ID NO 9
<211> LENGTH: 357
<212> TYPE: PRT
<213> ORGANISM: Pseudomonas syringae

<400> SEQUENCE: 9

```
Met Ser Gly Pro Phe Glu Lys Lys Trp Arg Cys Phe Thr Arg Thr Val
  1               5                  10                  15

Thr Tyr Val Gly Trp Ser Leu Phe Trp Leu Leu Leu Trp Asp Val Ala
             20                  25                  30

Val Thr Val Asp Val Met Leu Ile Glu Gly Lys Gly Ile Asp Phe Pro
         35                  40                  45

Leu Met Pro Leu Thr Leu Leu Cys Ser Ala Leu Ile Val Leu Ile Ser
     50                  55                  60

Phe Arg Asn Ser Ser Ala Tyr Asn Arg Trp Trp Glu Ala Arg Thr Leu
 65                  70                  75                  80

Trp Gly Ala Met Val Asn Thr Ser Arg Ser Phe Gly Arg Gln Val Leu
                 85                  90                  95

Thr Leu Ile Asp Gly Glu Arg Asp Asp Leu Asn Asn Pro Val Lys Ala
            100                 105                 110

Ile Leu Phe Gln Arg His Val Ala Tyr Leu Arg Ala Leu Arg Ala His
        115                 120                 125

Leu Lys Gly Asp Val Lys Thr Ala Lys Leu Asp Gly Leu Leu Ser Pro
    130                 135                 140

Asp Glu Ile Gln Arg Ala Ser Gln Ser Asn Asn Phe Pro Asn Asp Ile
145                 150                 155                 160

Leu Asn Gly Ser Ala Ala Val Ile Ser Gln Ala Phe Ala Ala Gly Gln
                165                 170                 175

Phe Asp Ser Ile Arg Leu Thr Arg Leu Glu Ser Thr Met Val Asp Leu
            180                 185                 190

Ser Asn Cys Gln Gly Gly Met Glu Arg Ile Ala Asn Thr Pro Leu Pro
        195                 200                 205

Tyr Pro Tyr Val Tyr Phe Pro Arg Leu Phe Ser Thr Leu Phe Cys Ile
    210                 215                 220

Leu Met Pro Leu Ser Met Val Thr Thr Leu Gly Trp Phe Thr Pro Ala
225                 230                 235                 240

Ile Ser Thr Val Val Gly Cys Met Leu Leu Ala Met Asp Arg Ile Gly
                245                 250                 255

Thr Asp Leu Gln Ala Pro Phe Gly Asn Ser Gln His Arg Ile Arg Met
            260                 265                 270
```

-continued

```
Glu Asp Leu Cys Asn Thr Ile Glu Lys Asn Leu Gln Ser Met Phe Ser
        275                 280                 285

Ser Pro Glu Arg Gln Pro Leu Leu Ala Asp Leu Lys Ser Pro Val Pro
    290                 295                 300

Trp Arg Val Ala Asn Ala Ser Ile Gly Gly Leu Ser Arg Gln Lys Asn
305                 310                 315                 320

Arg Leu Gly Glu Gly Ala Arg Leu Ile Ala Ser Glu Ser Leu Leu Trp
                325                 330                 335

Ala Pro Phe Arg Ser Val Ala Asp Val Ala Pro Cys His Ala Ser Ala
            340                 345                 350

Tyr Leu Arg Arg Ala
        355
```

<210> SEQ ID NO 10
<211> LENGTH: 1053
<212> TYPE: DNA
<213> ORGANISM: Pseudomonas syringae

<400> SEQUENCE: 10

```
atgtatatcc agcaatctgg cgcccaatca ggggttgccg ctaagacgca acacgataag     60

ccctcgtcat tgtccggact cgccccccggt tcgtcggatg cgttcgcccg ttttcatccc    120

gaaaaggcgg gcgcctttgt cccattggag gggcatgaag aggtcttttt cgatgcgcgc    180

tcttcctttt cgtcggtcga tgccgctgat cttcccagtc ccgagcaggt acaaccccag    240

cttcattcgt tgcgtaccct gctaccggat ctgatggtct ctatcgcctc attacgtgac    300

ggcgccacgc aatacatcaa gaccagaatc aaggctatgg cggacaacag cataggcgcg    360

actgcgaaca tcgaagccaa aagaaagatt gcccaagagc acggctgtca gcttgtccac    420

ccgtttcacc agagcaaatt tctatttgaa aaaactatcg atgatagagc gtttgctgct    480

gactatggcc gcgcgggtgg cgacgggcac gcttgtctgg ggctatcagt aaattggtgt    540

cagagccgtg caaaagggca gtcggatgag gccttctttc acaaactgga ggactatcag    600

ggcgatgcat tgctacccag ggtaatgggc ttccagcata tcgagcagca ggcctattca    660

aacaagttgc agaacgcagc acctatgctt ctggacacac ttcccaagtt gggcatgaca    720

cttggaaaag ggctgggcag agcacagcac gcgcactatg cggttgctct ggaaaacctt    780

gatcgcgatc tcaaagcagt gttgcagccc ggtaaagacc agatgcttct gtttttgagt    840

gatagccatg cgatggctct gcatcaggac agtcagggat gtctgcattt ttttgatcct    900

ctttttggcg tggttcaggc agacagcttc agcaacatga gccattttct tgctgatgtg    960

ttcaagcgcg acgtaggtac gcactggcgt ggcacggagc aacgtctgca actgagcgaa   1020

atggtgccca gagcagactt tcacttgcga taa                                1053
```

<210> SEQ ID NO 11
<211> LENGTH: 350
<212> TYPE: PRT
<213> ORGANISM: Pseudomonas syringae

<400> SEQUENCE: 11

```
Met Tyr Ile Gln Gln Ser Gly Ala Gln Ser Gly Val Ala Ala Lys Thr
  1               5                  10                  15

Gln His Asp Lys Pro Ser Ser Leu Ser Gly Leu Ala Pro Gly Ser Ser
            20                  25                  30

Asp Ala Phe Ala Arg Phe His Pro Glu Lys Ala Gly Ala Phe Val Pro
        35                  40                  45
```

-continued

```
Leu Glu Gly His Glu Glu Val Phe Phe Asp Ala Arg Ser Ser Phe Ser
     50                  55                  60

Ser Val Asp Ala Ala Asp Leu Pro Ser Pro Glu Gln Val Gln Pro Gln
 65                  70                  75                  80

Leu His Ser Leu Arg Thr Leu Leu Pro Asp Leu Met Val Ser Ile Ala
                 85                  90                  95

Ser Leu Arg Asp Gly Ala Thr Gln Tyr Ile Lys Thr Arg Ile Lys Ala
            100                 105                 110

Met Ala Asp Asn Ser Ile Gly Ala Thr Ala Asn Ile Glu Ala Lys Arg
        115                 120                 125

Lys Ile Ala Gln Glu His Gly Cys Gln Leu Val His Pro Phe His Gln
    130                 135                 140

Ser Lys Phe Leu Phe Glu Lys Thr Ile Asp Asp Arg Ala Phe Ala Ala
145                 150                 155                 160

Asp Tyr Gly Arg Ala Gly Gly Asp Gly His Ala Cys Leu Gly Leu Ser
                165                 170                 175

Val Asn Trp Cys Gln Ser Arg Ala Lys Gly Gln Ser Asp Glu Ala Phe
            180                 185                 190

Phe His Lys Leu Glu Asp Tyr Gln Gly Asp Ala Leu Leu Pro Arg Val
        195                 200                 205

Met Gly Phe Gln His Ile Glu Gln Gln Ala Tyr Ser Asn Lys Leu Gln
    210                 215                 220

Asn Ala Ala Pro Met Leu Leu Asp Thr Leu Pro Lys Leu Gly Met Thr
225                 230                 235                 240

Leu Gly Lys Gly Leu Gly Arg Ala Gln His Ala His Tyr Ala Val Ala
                245                 250                 255

Leu Glu Asn Leu Asp Arg Asp Leu Lys Ala Val Leu Gln Pro Gly Lys
            260                 265                 270

Asp Gln Met Leu Leu Phe Leu Ser Asp Ser His Ala Met Ala Leu His
        275                 280                 285

Gln Asp Ser Gln Gly Cys Leu His Phe Phe Asp Pro Leu Phe Gly Val
    290                 295                 300

Val Gln Ala Asp Ser Phe Ser Asn Met Ser His Phe Leu Ala Asp Val
305                 310                 315                 320

Phe Lys Arg Asp Val Gly Thr His Trp Arg Gly Thr Glu Gln Arg Leu
                325                 330                 335

Gln Leu Ser Glu Met Val Pro Arg Ala Asp Phe His Leu Arg
            340                 345                 350
```

<210> SEQ ID NO 12
<211> LENGTH: 480
<212> TYPE: DNA
<213> ORGANISM: Pseudomonas syringae

<400> SEQUENCE: 12

```
atgcggcctg tcgaggcaaa agatcggctt tatcagtggc tgcgcaatcg aggcatcgat     60

gcgcaggagg gtcaacgcca caacgtaagg accgcgaatg gaagcgagtg tctgctctgg    120

ttgccagaac aggacacttc gttgttcatc ttcacacaga tcgaaaggct gacgatgccg    180

caggacaacg tcattttgat tctggcaatg gcgctgaatc tggagcctgc tcgcacaggt    240

ggcgctgcgc ttggctataa ccctgattca agggaactgt tgttgcgcag tgtgcactca    300

atggcggatc tggatgagac cggacttgat cacctcatga cgcgaattag cacattggcc    360

gtctcgttgc agcgctatct ggaagattat cgacgccagg agcaagccgg aaaaaccgcc    420
```

-continued

```
cagaaagagc ctcggttctt accggctgtc catctgaccc cacgaacgtt catgacctga    480


<210> SEQ ID NO 13
<211> LENGTH: 159
<212> TYPE: PRT
<213> ORGANISM: Pseudomonas syringae

<400> SEQUENCE: 13

Met Arg Pro Val Glu Ala Lys Asp Arg Leu Tyr Gln Trp Leu Arg Asn
  1               5                  10                  15

Arg Gly Ile Asp Ala Gln Glu Gly Gln Arg His Asn Val Arg Thr Ala
             20                  25                  30

Asn Gly Ser Glu Cys Leu Leu Trp Leu Pro Glu Gln Asp Thr Ser Leu
         35                  40                  45

Phe Ile Phe Thr Gln Ile Glu Arg Leu Thr Met Pro Gln Asp Asn Val
     50                  55                  60

Ile Leu Ile Leu Ala Met Ala Leu Asn Leu Glu Pro Ala Arg Thr Gly
 65                  70                  75                  80

Gly Ala Ala Leu Gly Tyr Asn Pro Asp Ser Arg Glu Leu Leu Leu Arg
                 85                  90                  95

Ser Val His Ser Met Ala Asp Leu Asp Glu Thr Gly Leu Asp His Leu
            100                 105                 110

Met Thr Arg Ile Ser Thr Leu Ala Val Ser Leu Gln Arg Tyr Leu Glu
        115                 120                 125

Asp Tyr Arg Arg Gln Glu Gln Ala Gly Lys Thr Ala Gln Lys Glu Pro
    130                 135                 140

Arg Phe Leu Pro Ala Val His Leu Thr Pro Arg Thr Phe Met Thr
145                 150                 155


<210> SEQ ID NO 14
<211> LENGTH: 288
<212> TYPE: DNA
<213> ORGANISM: Pseudomonas syringae

<400> SEQUENCE: 14

atgcttaaaa aatgcctgct actggttata tcaatgtcac ttggcggctg ctggagcctg     60

atgattcatc tggacggcga gcgttgcatc tatcccggca ctcgccaagg ttgggcgtgg    120

ggaacccata acggagggca gagttggccc atacttatag acgtgccgtt ttccctcgcg    180

ttggacacac tgctgctgcc ctacgacctc accgcttttc tgcccgaaaa tcttggcggt    240

gatgaccgca aatgtcagtt cagtggagga ttgaacgtgc tcggttga                288


<210> SEQ ID NO 15
<211> LENGTH: 95
<212> TYPE: PRT
<213> ORGANISM: Pseudomonas syringae

<400> SEQUENCE: 15

Met Leu Lys Lys Cys Leu Leu Leu Val Ile Ser Met Ser Leu Gly Gly
  1               5                  10                  15

Cys Trp Ser Leu Met Ile His Leu Asp Gly Glu Arg Cys Ile Tyr Pro
             20                  25                  30

Gly Thr Arg Gln Gly Trp Ala Trp Gly Thr His Asn Gly Gly Gln Ser
         35                  40                  45

Trp Pro Ile Leu Ile Asp Val Pro Phe Ser Leu Ala Leu Asp Thr Leu
     50                  55                  60
```

-continued

```
Leu Leu Pro Tyr Asp Leu Thr Ala Phe Leu Pro Glu Asn Leu Gly Gly
 65                  70                  75                  80

Asp Asp Arg Lys Cys Gln Phe Ser Gly Gly Leu Asn Val Leu Gly
                 85                  90                  95


<210> SEQ ID NO 16
<211> LENGTH: 447
<212> TYPE: DNA
<213> ORGANISM: Pseudomonas syringae

<400> SEQUENCE: 16

atgaaacagg tagaagtcca gatcattact gaattgcctt gtcaggttct gatcctggag      60

caagaggcag tagcagaggg cttcaggttt cttacccgct tgatcgagga gtggaggtcc     120

ggaaagaatc gattcgaggc caagggtgaa tgcctcatgg tcgtacttct ggacggcgct     180

ctggcaggta tcggaggcct ttcgcgtgat ccgcatgccc ggggtgatat gggcaggcta     240

cgacggttat acgtcgcaag cgcatcaaga ggtcaaggcc ttggaaagac tctggtgaat     300

cgacttgtgg agcatgcggc gcaggaattt ttcgccgtgc gcctgttcac tgatactccg     360

agcggagcaa aattttactt acgttgcggc tttcaggcag ttgacgaggt gcatgccacg     420

catataaagc ttttaaggcg ggtttga                                         447


<210> SEQ ID NO 17
<211> LENGTH: 148
<212> TYPE: PRT
<213> ORGANISM: Pseudomonas syringae

<400> SEQUENCE: 17

Met Lys Gln Val Glu Val Gln Ile Ile Thr Glu Leu Pro Cys Gln Val
  1               5                  10                  15

Leu Ile Leu Glu Gln Glu Ala Val Ala Glu Gly Phe Arg Phe Leu Thr
             20                  25                  30

Arg Leu Ile Glu Glu Trp Arg Ser Gly Lys Asn Arg Phe Glu Ala Lys
         35                  40                  45

Gly Glu Cys Leu Met Val Val Leu Leu Asp Gly Ala Leu Ala Gly Ile
     50                  55                  60

Gly Gly Leu Ser Arg Asp Pro His Ala Arg Gly Asp Met Gly Arg Leu
 65                  70                  75                  80

Arg Arg Leu Tyr Val Ala Ser Ala Ser Arg Gly Gln Gly Leu Gly Lys
                 85                  90                  95

Thr Leu Val Asn Arg Leu Val Glu His Ala Ala Gln Glu Phe Phe Ala
            100                 105                 110

Val Arg Leu Phe Thr Asp Thr Pro Ser Gly Ala Lys Phe Tyr Leu Arg
        115                 120                 125

Cys Gly Phe Gln Ala Val Asp Glu Val His Ala Thr His Ile Lys Leu
    130                 135                 140

Leu Arg Arg Val
145


<210> SEQ ID NO 18
<211> LENGTH: 11458
<212> TYPE: DNA
<213> ORGANISM: Pseudomonas syringae
<220> FEATURE:
<221> NAME/KEY: unsure
<222> LOCATION: (10940)
<223> OTHER INFORMATION: n at any position is undefined

<400> SEQUENCE: 18
```

-continued

```
ggatccagcg gcgtattgtc gtggcgatgg aacgcgttac ggattttcag cacaccggta     60
tcgatgaaca ggtggccgtt gcgggcgttg cgggtcggca tgacacaatc gaacatatca    120
acgccacggc gcacaccttc gaccagatct tcgggcttgc ctacacccat caagtaacga    180
ggtttgtctg ctggcataag gcccggcagg taatccagca ccttgatcat ctcgtgcttg    240
ggctcgccca ccgacagacc gccaatcgcc aggccgtcaa agccgatctc atccaggcct    300
tcgagcgaac gcttgcgcag gttctcgtgc atgccaccct gaacaatgcc gaacagcgcg    360
gcagtgtttt cgccgtgcgc gaccttggag cgcttggccc agcgcaacga cagctccatg    420
gagacacgtg ctacgtcttc gtcggccggg tacggcgtgc actcatcgaa aatcatcacg    480
acgtccgaac ccaggtcacg ctggacctgc atcgactctt ccgggcccat gaacaccttg    540
gcaccatcga ccggagaggc gaaggtcacg ccctcctcct tgatcttgcg catggcgccc    600
aggctgaaca cctgaaaacc gccagagtcg gtcagaatcg gccctttcca ctgcatgaaa    660
tcgtgcaggt cgccgtggcc cttgatgacc tcggtgcccg gacgcagcca caagtggaag    720
gtgttgccca gaatcatctg cgcaccggtg gcctcgatat cacgcggcaa catgcccttg    780
accgtgccgt aggtgcccac cggcatgaac gccggggtct cgaccacgcc acgcggaaag    840
gtcaggcgac cgcgacgggc cttgccgtcg gtggccaaca actcgaaaga catacgacag    900
gtgcgactca tgcgtgatcc tctggtgccg attcctgtgg ggccgtcggc gcgggattgc    960
gggtgatgaa catggcatca ccgtaactga agaagcggta cccgtgttcg atggccgccg   1020
cgtaggccgc catggtttcg ggataaccgg cgaacgccga aaccagcatc aacagcgtgg   1080
attcaggcaa atgaaaatta gtcaccaggg catcgaccac atgaaacggc cgccccggat   1140
agatgaagat gtcggtgtcg ccgctaaacg gcttcaactg gccatcacgc gcggcactct   1200
ccagcgaacg cacgctggtg gtcccgaccg caatcacccg cccgccccgc gcacggcacg   1260
ccgccacggc atcgaccacg tcctggctga cttccagcca ttcgctgtgc atgtggtgat   1320
cttcgatctg ctcgacacgc accggctgga acgtacccgc gccgacgtgc agagtgacaa   1380
aagcagtctc gacgcccttg gcggcaattg cttccatcaa cggctggtcg aaatgcaggc   1440
cggcagtcgg cgccgccaca gcaccggcgc gctgggcgta aacggtctga taacgctcgc   1500
ggtcggcacc ttcgtccggg cggtctatat aaggaggcaa cggcatatgg ccgacacgat   1560
ccagcaacgg cagcacttct tcggcaaagc gcaactcgaa cagcgcgtca tgccgcgcca   1620
ccatctcggc ctcgccgccg ccatcgatca ggatcgacga gcccggcttt ggcgacttgc   1680
tggcacgcac gtgcgccagc acacgatggc tgtccagcac gcgctcgacc agaatctcca   1740
gcttgccgcc ggacgccttc tgcccgaaca aacgtgcggg aatgacacgg gtattgttga   1800
acaccatcaa gtcgcccgag cgcaaatgct cgagcaaatc ggtgaattga cgatgtgcca   1860
gcgcgcccgt cggcccatca agggtcaaca gacgactgct gcgacgctcg gccaacgggt   1920
gacgagcaat cagggaatcg gggagttcga aggtaaagtc agcgacgcgc atgatcgggt   1980
tcgtttagca gggccgggaa gtttatccgg tttgacggca ttagtaaaaa acctgcgtaa   2040
atccctgttg accaacggaa aactcatcct tatacttcgc cgccattgag ccctgatggc   2100
ggaattggta gacgcggcgg attcaaaatc cgttttcgaa agaagtggga gttcgattct   2160
ccctcggggc accaccattg agaaaagacc ttgaaattca aggtcttttt tttcgtctgg   2220
tggaaagtgg tctgactgag gctgcgatct accccacctg cccggaattg gccgcggagc   2280
gcccaggact gccttccagc gcagagcgtc ggtacccgga tcacacgacc aaggataacg   2340
```

-continued

```
ctatgaacaa gatcgtctac gtaaaagctt acttcaaacc cattggggag gaagtctcgg   2400
ttaaagtacc tacaggcgaa attaaaaagg gctttttcgg cgacaaggaa atcatgaaaa   2460
aagagaccca gtggcagcaa accgggtggt ctgattgtca gatagacggt gaacggctat   2520
cgaaagacgt cgaagacgca gtggcgcaac tcaatgctga cggttatgag attcaaacgg   2580
tattgcctat attgtccggg gcttatgatt atgcgctcaa ataccgatac gaaatacgtc   2640
acaatagaac tgaactaagc ccaggagacc agtcctatgt cttcggctat ggctacagct   2700
tcaccgaagg cgtgacgctg gtggcgaaaa aatttcagtc gtctgcaagc tgaataatag   2760
tgacctcgtg ccacggacgc cgctctgccc cctgatacga aaacgccttc ctcaacaaga   2820
ggcaggcgta ctaacgtgca caagacctgc ccgtatcagc aagcgcaaga cgctcgcctc   2880
cacgaaataa cacggtaggt cgcgttgcta ctttttagcg gcagacggcg tgccgttgta   2940
gttgtcggtg ttgttgtcgt tatcaagatc gcggtcattt ccaccgaaag ccgcatcggt   3000
tttgttgtcg ttgtcgagat ctttgtcgtt accgccaaac gctgcatccg tatggtgatc   3060
gttgtccagg tccttgtcgt tacccccaaa tgccgcgtcg gtgtggtggt cattgtccat   3120
atccttgtcg ttgccgccaa atgccgcgtc agtcacgttg tcgttatcca gatccttgtc   3180
gttgccgcca cacgtggcac cggtgctgtt gtcgttgtcc agatcacaat cgtttacggc   3240
aaatgcaggt agcgaagtgc caatgatcgt cagcgcaagc agaaagccgc cgatctttgc   3300
cgtcaggttt ttatacgcgc gcatcaggtt ttcccggata agtgaaaatg atgaagcaag   3360
ggttactgaa cacgttcgat cagtgactaa aacagtatgt aactgcagcc ttctgcaaga   3420
ccgacagagg tcgaccaaac tgcagcctgt ttcataccca tcaatttcta tagcgaccgt   3480
tcacacgact ctcctaccga tgctgggagt accaaaaaac ttccgcactg catttttttg   3540
cagtgtcgga tggtttgacc ggttttgggg agaattgctc aaacggagaa cgatgagttt   3600
tttgttgcgt ggcatgctaa tcgatacatt tatcagtgtg tgatgcggta tggcagcttc   3660
atgcctccgt caaatagtgg acgccagtca cgttgcataa aacctgacgt cactccaaaa   3720
aaggctacgc acgaggacat tgctgagatt cggctgggca ttttcgctgt ttacacaggg   3780
atcgagcaga acgcccccat gccagccacc cgttaactca attgtctttt gccctgaaaa   3840
caacaatccc tggcttttcc gatacatagt ccagaaaagg caaatccatc acctttctgt   3900
tttcttttcg tgaagatgca tttcgcaaga cagggccttt atccgtcacg ataaagaaac   3960
cgacgtgtgt cacatccagc ccgggaagcg gggtgtaaa tgccaatgta atcaccggtg   4020
cgcaggtggc tcaccacctg actgtcgaca aggcggctcg ggatatacgt catgctacgc   4080
tcaaccacag gcaaccctgg cagatagact ttgcctttgg ccctttcatt aaggcgtttt   4140
ctgacactta ccgcaccggg gcttatctgc gcggtaatgt catccgccac agggtatgcc   4200
gttccgtaag cccaatccgt gaaaaagtgc ttgcgattca aaaagtcaac atcgccaccc   4260
ttgtaacgaa cctgaacgag attcctcaca aaatcctgct gcgatgttga tcttcgaaac   4320
gcttcgacgt aatccagata agcaaaacaa tccagacctc tgaagtcgat gactaattgt   4380
tcaggtacat tcgctgagcc caccaacatg tttgagcggt acggtgttcc taaaaacgct   4440
cctgatacaa ggtcgatcag ctgaccttta ttcatataac ttttgttggt gcgggcttcc   4500
agcacagcat ccagtttttt tgaggtgtag gcatccagat ttagtttaac gggtgttttc   4560
atctctgcct gggcaccctg aatatcactt cccggcgccg gccccgaaac cccacaccct   4620
gccaacattg caaaggctaa agcccatagg gtcgtctttt gcatctgatt caccgtaatt   4680
ccaaagcgtc gtcggacctg attgtggctc gcgatacgcg agcaggctgc tccattcctt   4740
```

-continued

```
cgagatgccg cattggttag ctcaatcacg gcgcactatt taccacgtgt catcggttgc   4800
gtcatcggct gggagcatca gttggcaatg cattcgcggt ctcggcctca gcagacgctg   4860
gtagtgccca gagtgcagct gaccagcgtg ccgccatcga ggccgccgca gaggccgccc   4920
agcgatacgg attcgtttgc ggcaggggcc atgcccgcta ttgaatcggc tgactggccc   4980
gtgataaagg cctgatgcct cagtacgcca cctggcttac aggcgggttg cattgcaata   5040
ggtctatacc ttttgcaagg ttaacgaact gtcatcaaaa aacatggaag cacaatcaga   5100
aaaaagacct tgagtttcaa ggtctttttt cgtttggtga aaagtgatct gactcaaccc   5160
gcgatcttac cctcctctac tcgggttggc cgttagcacc caaagctacc ttcctgcgcg   5220
aatgcttgtt tcgttatggg catggcgtga tacaagcggt aggcgtacag caggtccatg   5280
agtctcggga acctgattga gagccgctct gcgctgtacc cccctggcct gagccactgt   5340
tcaaggcaac gcttccctga ccttgagcac cacttagctg ggcgccacca tcggcatgca   5400
ccaaaggcat ttgcagagag aggacagcaa agctggccaa tgcaatgaat tttgttttag   5460
agcagatatc tttaagtttc ataacaacca cctttgttga tcagaattgt tgaagaaatc   5520
atgagtcacg cttatgtgtg gcgactcatc gaaatcggtt ccaatgcaag atgggatttt   5580
tacgtccggc ctatccgctg atggcgatgc tgcggattca cctgatgcag aactggtttg   5640
attacagcga tccggcgatg gaggaagcac tttacgagac aacgatcctg cgccagttcg   5700
cagggttgag tctggatcga atcgccgatg aaaccacgat tctcaatttc cggcgcctgc   5760
tggaaaagca tgagttggca ggcgggattt tgcaggtcat caatggctat ctgggtgatc   5820
gaggtttgat gctgcgccaa ggtatggtgg tcgatgcgac gatcattcat gcgccgagct   5880
cgaccaagaa caaggacggc aaacgcgatc ccgaaatgca tcagacgaag aaaggaaacc   5940
agtatttctt cggcatgaaa gcgcatatcg gcgtcgatgc cgagtcgggt ttagtccata   6000
gcctggtggg tactgcggcg aatgtggcgg acgtgactca ggtcgatcaa ctgctgcaca   6060
gtgaggaaac ctatgtcagc ggtgatgcgg gctacaccgg cgtggacaag cgtgcggagc   6120
atcaggatcg ccagatgatc tggtcaattg cggcacgccc aagccgttat aaaaagcatg   6180
gcgagaaaag tttgatcgca cgggtctatc gcaaaatcga gttcacgaaa gcccagttgc   6240
gggcgaaggt tgaacatccg cttcgcgtga tcaagcgcca gtttggttat acgaaagtcc   6300
ggtttcgcgg gctggctaaa aacaccgcgc aacaggctac tctgtttgcc ttgtcgaacc   6360
tttggatggt gcgaaaacgg ctgctggcga tgggagaggt gcgcctgtaa tgcggaaaaa   6420
cgccttggaa aggtgctgtt tgaaggaaaa tcgatgagtt aacagcgcaa aaacgtctga   6480
ctatctgatc gggcgagttt ttttgaacct caggccatga aggcatcaaa aatcgatgct   6540
tacttcagac cttccttaac ctcagtagcg aggccggata aacgagtccc tttctatgat   6600
gctgtttcca gtaaactgac aaatttcatg cactgccgcc cgcgtgttca agcgctcaga   6660
ccttatagga aagcctcacg tctggattca gcttgccgcc gtagtttttc acattgatat   6720
cgacggtcgc tcgggacttg aggcccagat catcgatcac cagactgcgt accccatgca   6780
actctgccaa ccctgggact ccgtcacagg aagtggcgtg cgttgccccg acaaaagcga   6840
cccacttacc ttccggtttg ctcagcctta ttttttctgc tgcgtagtaa ttcatggctt   6900
gggcacgctt tatctcagct ttctccgggg ccatataggt ggacgttgta tccagcgaga   6960
caacgcgcaa cccggcgtgc ttggccgctt ccaccaaggt ggtgaagtta tatttcgtgt   7020
ggagctcttc cggggcctga tgaccctgac tctgcaaatc gaggtagttt ttcagcctgg   7080
```

-continued

```
caggcatcgg actgcctttg ggcgcgctca ggtaattatt gagcgccttg tcatgtgact   7140
cggcgcagag gtgctccata aaaagcgtgg tcacgccact ggccttcaag ctcttcatgt   7200
tattgatcag ttcacgcttg ctggacgttg aattgtgacc ctcaccaata acaagccccg   7260
gcgcatcacg taacagctcg cgcatgacac cgagactgtc cttgcttttc atcttcgtca   7320
acggcgccag ctcaggtaac ttttgcgcgt tgaaatcatc aaaataacgc gctgccttgg   7380
caatcagttt cttgtcatta ctgtcaggtg cccataaacc cttggacgtc cccagacaac   7440
tgtccatttc aaggtaattg agatttatat gaaggtggtc ccgaccttcc gagacaacaa   7500
cgtcggccag cttgagacct tgagcctcaa ggcgctgttc aagggcgtgc ttgccttctt   7560
gcaacaggat gctcacaaca tttgcagaca gttggctgct tttccccgct gcttttgagg   7620
gtgccagcgc ataggggtgc gggctctcac accagcgcgc gagctcggca agatcgctcg   7680
ccttgaagtt cgtatcctgc aatgctttgc tttgagctga agccgaggtc gaggccacgc   7740
tctggccgcc gtgcacatga ctgctgcctg ctgcgtccgg cttacgcctt ctggtgtgct   7800
ttacgccatc ctttccgcca ggctcctgcc cctcgatttt cagccggata ttttctacct   7860
tcatatccgg atagcgcccg gctggaaagc gcttcaggtc ccccagcatt ggagtctctg   7920
gcgcaacgct ggctgctgga gaggaactgg cctgtgaaga tcgggcgcga tcgtttcctg   7980
cagcttgcgc agtgggacgc tcagcttcat aggttggcgg ataatagcct ggagccggtc   8040
caccgacggg tctcatgatt gaatctccgc gtacgaaaaa tagtgccgag cccgggcgtg   8100
acgctgcccg ggccccgaca tttcagtcaa tcaatgcgcc ttcgcaatcc cgaactgatc   8160
aagcaccgga tcaacgttat ggtcgaacgc cttctgcgcc ttatgctttt tcacagcatc   8220
aatgatcatg gaaataccga aacctaccgc cagggcgcca tcgattgccc agccgaccac   8280
tggaatcgcg gcgcctaggg cggcacctgc ggcaaggccg gtggcttcac cggcaaccat   8340
gccgacggcg cgaccgatca tctgtccgcc cagacgccct aggccggctg aggcttcgcg   8400
gcccatcatc ttcgccccgg cgtcgatgcc acctttaatg gcctcggcgc ccatcctcgt   8460
gctgtcgtaa atggcctggg ttgcgccaag cttgtcgcca tgagcgatca ggctggacac   8520
tgaagcaaag cccacgatcg agttgagcgc cttgccgccg acgcccgcct cggcgagctg   8580
agtcaacatg gacggtccgc cctcatcgct tttgccttcc agaagcttgc ggcctttttt   8640
ggagtcttgc agcgtaccca acgtgctgtt catgtagttt tcatgctgat tttcggtgaa   8700
atcagggggc agcacgctgt cgtaaatggc tttctggtta tcggcggttt gcagagactg   8760
gctggcatca gactttttct ggccaagcag ctgcttcagt gcaccgcctt cgctgaagtt   8820
ggtcacgtag gacgtggcaa tcttgtcttg cagatcgggt ttgttttcaa gcacctgatt   8880
ggtagtgggt actttggaat cggggaacag gtctttttgc agttgcaact gggcggacaa   8940
accgctgatg gcgccgctgt aatcggcatt cggattatgt ttgttgacgg ccttgtccgc   9000
cttgtccata tcagtctgca gcgcttgacc gctattgacg tttttcgtct gctcgacgac   9060
tgccttttgc agcgaggcat cactgcggac cagattgcgc tcctgctcgg gaatgctttt   9120
attgaggtac gcttgtacgt caggatcagc ctgtagctgg gaaatccggt cgttcaaacc   9180
ctgctcggtc ttgtcggtgt tgcgcaggct gcgcccggcg ataacgcttt gctgggtctg   9240
ctgcaacttg accatgacgg ccgctttctg tgcaccgctg taagacttgg gtttgtcgaa   9300
tacgtccttg tccagcttgc tgatatcaat cccggccacc gcattgagcg tcgcagaatc   9360
gctgagcatg ctggcgaact ggccgccgtt ggtgggtgcg cttttcttga tccactcact   9420
cagatttttc gcgtcgaaca tcttatcagg gctgtgcgca gccttcttgc gccccgacat   9480
```

-continued gcccgcttcg tctacctgac ccaaaaagcc tggttgcgac caggtgctgc aggactgttt 9540
gagcgctccg gacaaccctg ggttactttg tgccaacccc ttcaggtctt ctgcgtcgac 9600
attaccgtca actttggtct tgtccgctgc atccactgca tgatgtgggt cggcagcaat 9660
cgccagtggc atattggctc gcatcactgc cgcgctgcgc accatttcca gtgactgcgg 9720
gtcagcgtcg ggttgtcct tggtgtagtt ggccaagtcc ttgtcggcac tgtctgcggc 9780
cttttccata ttttttgcga aggtcttgag atctttgttc gtgatcttgc catctgcgtt 9840
gccaccaccc tgagcaacgt ccacggcggt cttcagcgcc gggttggcgt tgatgaaatc 9900
catggccttg ccggcatcgg ggccatcatc acgcgccatc catgccgctg caatcgggcg 9960
attgagctct ttcgccgcct gctcgcgctc ttcgggcggc agatgggcaa ccatcggctc 10020
ccaacgtttc agagcttctg gcgaggagta ttcagaattg tcgagaaagg ctgcgtctgc 10080
ggctttgggg gcgttggaag cgtcggttgc atctgtgttc gtgggagctg cgacctgttc 10140
aaccggagcg gccggggcag tcgcttcagt cggtgcagcc tcggcaggag aatctgcgca 10200
gggttgcggc tggacctgat tattcacatt ggcattggca gctgccccgc cactgccctg 10260
gagcaaaaga gccaggatag acgacgcggt ctgctcggct cctgtcggcg cgccttgcgt 10320
gttgccggcc ggctgaccga actgcacgcc ggcttgccca ccgccaccca caggtgtcgg 10380
caaggctttg gcaagaggcg actcaacagc cagagccagt tcgccaggag tgggttggtt 10440
cacgataacg aagggagaac tggatatacg catggtgagt tgccatccga gagtgagcga 10500
tggcaactgt gtggttgaag gtgcaagttg gttccagaaa aaatgatcga gatcgccatt 10560
caggcgaacg ggtcgatttg ctgcttgagc tgaacccgcg cgcgggacag gcgtgagcga 10620
acggtgccaa tcggcacgcc gaggctgttc gctgtttcct gataattgcc gtccatctcc 10680
agcgacactt ccagcacttt ttgcatgttc gacggcaggc aatcaatggc ctgaatgact 10740
cgcgccagtt gccgatgccc ctctacctga tgactgacat caccgtgccc ttccagctcg 10800
gaatgcactt cgtcttccca gctttcctga tacggctgac gatacatttt gcggaagtga 10860
ttgcggatca ggttcagcgc gatgccacac agccaggtct gcggtttgct ggcatgttga 10920
aacttgtgct cgttacgcan ggcttcaaga aacacgcact ggagaatgtc atccacatca 10980
tcagggttca tacccgcttt ttggataaac gccctgagca tctgaatctg atcgggcggc 11040
atttggcgaa ataccgcgga cnaaaatggc tgacngggct gggttgagtc nangatcaca 11100
atcttttgaa acatgggctt accctgatta atggngtaca aaccctatag cgataaccat 11160
gccnncttaa aaaaanaaaa aactggntga tttatnaaaa aattttaaaa anngaaattt 11220
tttgtataca aaacttgggc naccgntttt gcccaaaact tttgggcaaa aanatnggan 11280
ctttcanggg antgatccng gaccgnaacc cttannggaa taatccggtt aaancggcta 11340
tnaaanagng ttccnctata tggnaaaatt cgggggccca cccnttngaa ccttttggna 11400
accctttcaa tgttgatttg ncaaataagg gattnnccca aaaggtttng ctttnggg 11458

<210> SEQ ID NO 19
<211> LENGTH: 1401
<212> TYPE: DNA
<213> ORGANISM: Pseudomonas syringae

<400> SEQUENCE: 19
atgagacccg tcggtggacc ggctccaggc tattatccgc caacctatga agctgagcgt 60
cccactgcgc aagctgcagg aaacgatcgc gcccgatctt cacaggccag ttcctctcca 120

-continued

```
gcagccagcg ttgcgccaga gactccaatg ctgggggacc tgaagcgctt tccagccggg    180

cgctatccgg atatgaaggt agaaaatatc cggctgaaaa tcgaggggca ggagcctggc    240

ggaaaggatg gcgtaaagca caccagaagg cgtaagccgg acgcagcagg cagcagtcat    300

gtgcacggcg gccagagcgt ggcctcgacc tcggcttcag ctcaaagcaa agcattgcag    360

gatacgaact tcaaggcgag cgatcttgcc gagctcgcgc gctggtgtga gagcccgcac    420

ccctatgcgc tggcaccctc aaaagcagcg gggaaaagca gccaactgtc tgcaaatgtt    480

gtgagcatcc tgttgcaaga aggcaagcac gcccttgaac agcgccttga ggctcaaggt    540

ctcaagctgg ccgacgttgt tgtctcggaa ggtcgggacc accttcatat aaatctcaat    600

taccttgaaa tggacagttg tctggggacg tccaagggtt tatgggcacc tgacagtaat    660

gacaagaaac tgattgccaa ggcagcgcgt tattttgatg atttcaacgc gcaaaagtta    720

cctgagctgg cgccgttgac gaagatgaaa agcaaggaca gtctcggtgt catgcgcgag    780

ctgttacgtg atgcgccggg gcttgttatt ggtgagggtc acaattcaac gtccagcaag    840

cgtgaactga tcaataacat gaagagcttg aaggccagtg gcgtgaccac gctttttatg    900

gagcacctct gcgccgagtc acatgacaag gcgctcaata attacctgag cgcgcccaaa    960

ggcagtccga tgcctgccag gctgaaaaac tacctcgatt tgcagagtca gggtcatcag   1020

gccccggaag agctccacac gaaatataac ttcaccacct tggtggaagc ggccaagcac   1080

gccgggttgc gcgttgtctc gctggataca acgtccacct atatggcccc ggagaaagct   1140

gagataaagc gtgcccaagc catgaattac tacgcagcag aaaaaataag gctgagcaaa   1200

ccggaaggta agtgggtcgc ttttgtcggg gcaacgcacg ccacttcctg tgacggagtc   1260

ccagggttgg cagagttgca tggggtacgc agtctggtga tcgatgatct gggcctcaag   1320

tcccgagcga ccgtcgatat caatgtgaaa aactacggcg gcaagctgaa tccagacgtg   1380

aggctttcct ataaggtctg a                                             1401
```

<210> SEQ ID NO 20
<211> LENGTH: 466
<212> TYPE: PRT
<213> ORGANISM: Pseudomonas syringae

<400> SEQUENCE: 20

```
Met Arg Pro Val Gly Gly Pro Ala Pro Gly Tyr Tyr Pro Pro Thr Tyr
  1               5                  10                  15

Glu Ala Glu Arg Pro Thr Ala Gln Ala Ala Gly Asn Asp Arg Ala Arg
             20                  25                  30

Ser Ser Gln Ala Ser Ser Ser Pro Ala Ala Ser Val Ala Pro Glu Thr
         35                  40                  45

Pro Met Leu Gly Asp Leu Lys Arg Phe Pro Ala Gly Arg Tyr Pro Asp
     50                  55                  60

Met Lys Val Glu Asn Ile Arg Leu Lys Ile Glu Gly Gln Glu Pro Gly
 65                  70                  75                  80

Gly Lys Asp Gly Val Lys His Thr Arg Arg Arg Lys Pro Asp Ala Ala
                 85                  90                  95

Gly Ser Ser His Val His Gly Gly Gln Ser Val Ala Ser Thr Ser Ala
            100                 105                 110

Ser Ala Gln Ser Lys Ala Leu Gln Asp Thr Asn Phe Lys Ala Ser Asp
        115                 120                 125

Leu Ala Glu Leu Ala Arg Trp Cys Glu Ser Pro His Pro Tyr Ala Leu
    130                 135                 140
```

-continued

```
Ala Pro Ser Lys Ala Ala Gly Lys Ser Ser Gln Leu Ser Ala Asn Val
145                 150                 155                 160

Val Ser Ile Leu Leu Gln Glu Gly Lys His Ala Leu Glu Gln Arg Leu
                165                 170                 175

Glu Ala Gln Gly Leu Lys Leu Ala Asp Val Val Val Ser Glu Gly Arg
            180                 185                 190

Asp His Leu His Ile Asn Leu Asn Tyr Leu Glu Met Asp Ser Cys Leu
        195                 200                 205

Gly Thr Ser Lys Gly Leu Trp Ala Pro Asp Ser Asn Asp Lys Lys Leu
    210                 215                 220

Ile Ala Lys Ala Ala Arg Tyr Phe Asp Asp Phe Asn Ala Gln Lys Leu
225                 230                 235                 240

Pro Glu Leu Ala Pro Leu Thr Lys Met Lys Ser Lys Asp Ser Leu Gly
                245                 250                 255

Val Met Arg Glu Leu Leu Arg Asp Ala Pro Gly Leu Val Ile Gly Glu
            260                 265                 270

Gly His Asn Ser Thr Ser Ser Lys Arg Glu Leu Ile Asn Asn Met Lys
        275                 280                 285

Ser Leu Lys Ala Ser Gly Val Thr Thr Leu Phe Met Glu His Leu Cys
    290                 295                 300

Ala Glu Ser His Asp Lys Ala Leu Asn Asn Tyr Leu Ser Ala Pro Lys
305                 310                 315                 320

Gly Ser Pro Met Pro Ala Arg Leu Lys Asn Tyr Leu Asp Leu Gln Ser
                325                 330                 335

Gln Gly His Gln Ala Pro Glu Glu Leu His Thr Lys Tyr Asn Phe Thr
            340                 345                 350

Thr Leu Val Glu Ala Ala Lys His Ala Gly Leu Arg Val Val Ser Leu
        355                 360                 365

Asp Thr Thr Ser Thr Tyr Met Ala Pro Glu Lys Ala Glu Ile Lys Arg
    370                 375                 380

Ala Gln Ala Met Asn Tyr Tyr Ala Ala Glu Lys Ile Arg Leu Ser Lys
385                 390                 395                 400

Pro Glu Gly Lys Trp Val Ala Phe Val Gly Ala Thr His Ala Thr Ser
                405                 410                 415

Cys Asp Gly Val Pro Gly Leu Ala Glu Leu His Gly Val Arg Ser Leu
            420                 425                 430

Val Ile Asp Asp Leu Gly Leu Lys Ser Arg Ala Thr Val Asp Ile Asn
        435                 440                 445

Val Lys Asn Tyr Gly Gly Lys Leu Asn Pro Asp Val Arg Leu Ser Tyr
    450                 455                 460

Lys Val
465
```

<210> SEQ ID NO 21
<211> LENGTH: 726
<212> TYPE: DNA
<213> ORGANISM: Pseudomonas syringae

<400> SEQUENCE: 21

```
atgcaaaaga cgaccctatg ggctttagcc tttgcaatgt tggcagggtg tggggtttcg      60

gggccggcgc cgggaagtga tattcagggt gcccaggcag agatgaaaac acccgttaaa     120

ctaaatctgg atgcctacac ctcaaaaaaa ctggatgctg tgctggaagc ccgcaccaac     180

aaaagttata tgaataaagg tcagctgatc gaccttgtat caggagcgtt tttaggaaca     240
```

-continued

```
ccgtaccgct caaacatgtt ggtgggctca gcgaatgtac ctgaacaatt agtcatcgac    300

ttcagaggtc tggattgttt tgcttatctg gattacgtcg aagcgtttcg aagatcaaca    360

tcgcagcagg attttgtgag gaatctcgtt caggttcgtt acaagggtgg cgatgttgac    420

tttttgaatc gcaagcactt tttcacggat tgggcttacg gaacggcata ccctgtggcg    480

gatgacatta ccgcgcagat aagccccggt gcggtaagtg tcagaaaacg ccttaatgaa    540

agggccaaag gcaaagtcta tctgccaggg ttgcctgtgg ttgagcgtag catgacgtat    600

atcccgagcc gccttgtcga cagtcaggtg gtgagccacc tgcgcaccgg tgattacatt    660

ggcatttaca cccccgcttc ccgggctgga tgtgacacac gtcggtttct ttatcgtgac    720

ggataa                                                               726
```

<210> SEQ ID NO 22
<211> LENGTH: 241
<212> TYPE: PRT
<213> ORGANISM: Pseudomonas syringae

<400> SEQUENCE: 22

```
Met Gln Lys Thr Thr Leu Trp Ala Leu Ala Phe Ala Met Leu Ala Gly
  1               5                  10                  15

Cys Gly Val Ser Gly Pro Ala Pro Gly Ser Asp Ile Gln Gly Ala Gln
             20                  25                  30

Ala Glu Met Lys Thr Pro Val Lys Leu Asn Leu Asp Ala Tyr Thr Ser
         35                  40                  45

Lys Lys Leu Asp Ala Val Leu Glu Ala Arg Thr Asn Lys Ser Tyr Met
     50                  55                  60

Asn Lys Gly Gln Leu Ile Asp Leu Val Ser Gly Ala Phe Leu Gly Thr
 65                  70                  75                  80

Pro Tyr Arg Ser Asn Met Leu Val Gly Ser Ala Asn Val Pro Glu Gln
                 85                  90                  95

Leu Val Ile Asp Phe Arg Gly Leu Asp Cys Phe Ala Tyr Leu Asp Tyr
            100                 105                 110

Val Glu Ala Phe Arg Arg Ser Thr Ser Gln Gln Asp Phe Val Arg Asn
        115                 120                 125

Leu Val Gln Val Arg Tyr Lys Gly Gly Asp Val Asp Phe Leu Asn Arg
    130                 135                 140

Lys His Phe Phe Thr Asp Trp Ala Tyr Gly Thr Ala Tyr Pro Val Ala
145                 150                 155                 160

Asp Asp Ile Thr Ala Gln Ile Ser Pro Gly Ala Val Ser Val Arg Lys
                165                 170                 175

Arg Leu Asn Glu Arg Ala Lys Gly Lys Val Tyr Leu Pro Gly Leu Pro
            180                 185                 190

Val Val Glu Arg Ser Met Thr Tyr Ile Pro Ser Arg Leu Val Asp Ser
        195                 200                 205

Gln Val Val Ser His Leu Arg Thr Gly Asp Tyr Ile Gly Ile Tyr Thr
    210                 215                 220

Pro Ala Ser Arg Ala Gly Cys Asp Thr Arg Arg Phe Leu Tyr Arg Asp
225                 230                 235                 240

Gly
```

<210> SEQ ID NO 23
<211> LENGTH: 417
<212> TYPE: DNA
<213> ORGANISM: Pseudomonas syringae -continued

<400> SEQUENCE: 23
atgcgcgcgt ataaaaacct gacggcaaag atcggcggct ttctgcttgc gctgacgatc 60
attggcactt cgctacctgc atttgccgta aacgattgtg atctggacaa cgacaacagc 120
accggtgcca cgtgtggcgg caacgacaag gatctggata acgacaacgt gactgacgcg 180
gcatttggcg gcaacgacaa ggatatggac aatgaccacc acaccgacgc ggcatttggg 240
ggtaacgaca aggacctgga caacgatcac catacggatg cagcgtttgg cggtaacgac 300
aaagatctcg acaacgacaa caaaaccgat gcggctttcg gtggaaatga ccgcgatctt 360
gataacgaca acaacaccga caactacaac ggcacgccgt ctgccgctaa aaagtag 417

<210> SEQ ID NO 24
<211> LENGTH: 138
<212> TYPE: PRT
<213> ORGANISM: Pseudomonas syringae

<400> SEQUENCE: 24

Met Arg Ala Tyr Lys Asn Leu Thr Ala Lys Ile Gly Gly Phe Leu Leu
1 5 10 15

Ala Leu Thr Ile Ile Gly Thr Ser Leu Pro Ala Phe Ala Val Asn Asp
20 25 30

Cys Asp Leu Asp Asn Asp Asn Ser Thr Gly Ala Thr Cys Gly Gly Asn
35 40 45

Asp Lys Asp Leu Asp Asn Asp Asn Val Thr Asp Ala Ala Phe Gly Gly
50 55 60

Asn Asp Lys Asp Met Asp Asn Asp His His Thr Asp Ala Ala Phe Gly
65 70 75 80

Gly Asn Asp Lys Asp Leu Asp Asn Asp His His Thr Asp Ala Ala Phe
85 90 95

Gly Gly Asn Asp Lys Asp Leu Asp Asn Asp Asn Lys Thr Asp Ala Ala
100 105 110

Phe Gly Gly Asn Asp Arg Asp Leu Asp Asn Asp Asn Asn Thr Asp Asn
115 120 125

Tyr Asn Gly Thr Pro Ser Ala Ala Lys Lys
130 135

<210> SEQ ID NO 25
<211> LENGTH: 411
<212> TYPE: DNA
<213> ORGANISM: Pseudomonas syringae

<400> SEQUENCE: 25
atgaacaaga tcgtctacgt aaaagcttac ttcaaaccca ttggggagga agtctcggtt 60
aaagtaccta caggcgaaat taaaaagggc tttttcggcg acaaggaaat catgaaaaaa 120
gagacccagt ggcagcaaac cgggtggtct gattgtcaga tagacggtga acggctatcg 180
aaagacgtcg aagacgcagt ggcgcaactc aatgctgacg gttatgagat tcaaacggta 240
ttgcctatat tgtccggggc ttatgattat gcgctcaaat accgatacga aatacgtcac 300
aatagaactg aactaagccc aggagaccag tcctatgtct tcggctatgg ctacagcttc 360
accgaaggcg tgacgctggt ggcgaaaaaa tttcagtcgt ctgcaagctg a 411

<210> SEQ ID NO 26
<211> LENGTH: 136
<212> TYPE: PRT
<213> ORGANISM: Pseudomonas syringae -continued

<400> SEQUENCE: 26

```
Met Asn Lys Ile Val Tyr Val Lys Ala Tyr Phe Lys Pro Ile Gly Glu
  1               5                  10                  15

Glu Val Ser Val Lys Val Pro Thr Gly Glu Ile Lys Lys Gly Phe Phe
             20                  25                  30

Gly Asp Lys Glu Ile Met Lys Lys Glu Thr Gln Trp Gln Gln Thr Gly
         35                  40                  45

Trp Ser Asp Cys Gln Ile Asp Gly Glu Arg Leu Ser Lys Asp Val Glu
     50                  55                  60

Asp Ala Val Ala Gln Leu Asn Ala Asp Gly Tyr Glu Ile Gln Thr Val
 65                  70                  75                  80

Leu Pro Ile Leu Ser Gly Ala Tyr Asp Tyr Ala Leu Lys Tyr Arg Tyr
                 85                  90                  95

Glu Ile Arg His Asn Arg Thr Glu Leu Ser Pro Gly Asp Gln Ser Tyr
            100                 105                 110

Val Phe Gly Tyr Gly Tyr Ser Phe Thr Glu Gly Val Thr Leu Val Ala
        115                 120                 125

Lys Lys Phe Gln Ser Ser Ala Ser
    130                 135
```

<210> SEQ ID NO 27
<211> LENGTH: 972
<212> TYPE: DNA
<213> ORGANISM: Pseudomonas syringae

<400> SEQUENCE: 27

```
atgggttgcg tatcgtcaaa agcatctgtc atttcttcgg acagctttcg cgcatcatat     60

acaaactctc cagaggcatc ctcagtccat caacgagcca ggacgccaag gtgcggtgag    120

cttcaggggc cccaagtgag cagattgatg ccttaccagc aggcgttagt aggtgtggcc    180

cgatggccta atccgcattt taacagggac gatgcgcccc accagatgga gtatggagaa    240

tcgttctacc ataaaagccg agagcttggt gcgtcggtcg ccaatggaga gatagaaacg    300

tttcaggagc tctggagtga agctcgtgat tggagagctt ccagagcagg ccaagatgct    360

cggcttttta gttcatcgcg tgatcccaac tcttcacggg cgtttgttac gcctataact    420

ggaccatacg aatttttaaa agatagattc gcaaaccgta aagatggaga aaagcataag    480

atgatggatt ttctcccaca cagcaatacg tttaggtttc atgggaaaat tgacggtgag    540

cgacttcctc tcacctggat ctcgataagt tctgatcgtc gtgccgacag aacaaaggat    600

ccttaccaaa ggttgcgcga ccaaggcatg aacgatgtgg gtgagcctaa tgtgatgttg    660

cacacccaag ccgagtatgt gcccaaaatt atgcaacatg tggagcatct ttataaggcc    720

gctacggatg ctgcattgtc cgatgccaat gcgctgaaaa aactcgcaga gatacattgg    780

tggacggtac aagctgttcc cgactttcgt ggaagtgcag ctaaggctga gctctgcgtg    840

cgctccattg cccaggcaag gggcatggac ctgccgccga tgagactcgg catcgtgccg    900

gatctggaag cgcttacgat gcctttgaaa gactttgtga aaagttacga agggttcttc    960

gaacataact ga                                                         972
```

<210> SEQ ID NO 28
<211> LENGTH: 323
<212> TYPE: PRT
<213> ORGANISM: Pseudomonas syringae

<400> SEQUENCE: 28

-continued

```
Met Gly Cys Val Ser Ser Lys Ala Ser Val Ile Ser Ser Asp Ser Phe
  1               5                  10                  15

Arg Ala Ser Tyr Thr Asn Ser Pro Glu Ala Ser Ser Val His Gln Arg
             20                  25                  30

Ala Arg Thr Pro Arg Cys Gly Glu Leu Gln Gly Pro Gln Val Ser Arg
         35                  40                  45

Leu Met Pro Tyr Gln Gln Ala Leu Val Gly Val Ala Arg Trp Pro Asn
     50                  55                  60

Pro His Phe Asn Arg Asp Asp Ala Pro His Gln Met Glu Tyr Gly Glu
 65                  70                  75                  80

Ser Phe Tyr His Lys Ser Arg Glu Leu Gly Ala Ser Val Ala Asn Gly
                 85                  90                  95

Glu Ile Glu Thr Phe Gln Glu Leu Trp Ser Glu Ala Arg Asp Trp Arg
            100                 105                 110

Ala Ser Arg Ala Gly Gln Asp Ala Arg Leu Phe Ser Ser Ser Arg Asp
        115                 120                 125

Pro Asn Ser Ser Arg Ala Phe Val Thr Pro Ile Thr Gly Pro Tyr Glu
    130                 135                 140

Phe Leu Lys Asp Arg Phe Ala Asn Arg Lys Asp Gly Glu Lys His Lys
145                 150                 155                 160

Met Met Asp Phe Leu Pro His Ser Asn Thr Phe Arg Phe His Gly Lys
                165                 170                 175

Ile Asp Gly Glu Arg Leu Pro Leu Thr Trp Ile Ser Ile Ser Ser Asp
            180                 185                 190

Arg Arg Ala Asp Arg Thr Lys Asp Pro Tyr Gln Arg Leu Arg Asp Gln
        195                 200                 205

Gly Met Asn Asp Val Gly Glu Pro Asn Val Met Leu His Thr Gln Ala
    210                 215                 220

Glu Tyr Val Pro Lys Ile Met Gln His Val Glu His Leu Tyr Lys Ala
225                 230                 235                 240

Ala Thr Asp Ala Ala Leu Ser Asp Ala Asn Ala Leu Lys Lys Leu Ala
                245                 250                 255

Glu Ile His Trp Trp Thr Val Gln Ala Val Pro Asp Phe Arg Gly Ser
            260                 265                 270

Ala Ala Lys Ala Glu Leu Cys Val Arg Ser Ile Ala Gln Ala Arg Gly
        275                 280                 285

Met Asp Leu Pro Pro Met Arg Leu Gly Ile Val Pro Asp Leu Glu Ala
    290                 295                 300

Leu Thr Met Pro Leu Lys Asp Phe Val Lys Ser Tyr Glu Gly Phe Phe
305                 310                 315                 320

Glu His Asn
```

<210> SEQ ID NO 29
<211> LENGTH: 1149
<212> TYPE: DNA
<213> ORGANISM: Pseudomonas syringae

<400> SEQUENCE: 29

```
atgagaattc acagttccgg tcatggcatc tccggaccag tatcctctgc agaaaccgtt      60

gaaaaggccg tgcaatcatc ggcccaagcg cagaatgaag cgtctcacag cggtccatca     120

gaacatcctg aatcccgctc ctgtcaggca cgcccgaact acccttattc gtcagtcaaa     180

acacggttac cccctgttgc gtctgcaggg cagtcgctgt ctgagacacc ctcttcattg     240

cctggctacc tgctgttacg tcggcttgat cgtcgtccgc tggaccagga cgcaataaag     300
```

-continued

```
gggcttattc ctgctgatga agcagtgggc gaagcgcgcc gcgcgttgcc cttcggcagg    360

ggcaacattg atgtggatgc gcaacgctcc aacctggaaa gcggggcccg cacgctcgcc    420

gcaagacgcc tgagaaaaga cgccgagacg gcgggtcatg agccgatgcc cgagaacgaa    480

gacatgaact ggcatgtgct ggttgccatg tcgggtcagg tgttcggggc tggcaactgt    540

ggcgaacatg cccgtatagc gagctttgcc tacggtgcat cggctcagga aaaaggacgc    600

gctggcgatg aaaatattca tctggctgcg cagagcgggg aagatcatgt ctgggctgaa    660

acggatgatt ccagcgctgg ctcttcgcct attgtcatgg acccctggtc aaacggtcct    720

gccgtttttg cagaggacag tcggtttgct aaagataggc gcgcggtaga gcgaacggat    780

tcgttcacgc tttcaaccgc tgccaaagca ggcaagatta cacgagagac agccgagaag    840

gcgctgaccc aagcgaccag ccgtttgcag caacgtcttg ctgatcagca ggcgcaagtc    900

tcgccggttg aaggtggtcg ctatcggcaa gaaaactcgg tgcttgatga tgcgttcgcc    960

cgacgagtca gtgacatgtt gaacaatgcc gatccacggc gtgcattgca ggtggaaatc   1020

gaggcgtccg gagttgcaat gtcgctgggt gcccaaggcg tcaagacggt cgtccgacag   1080

gcgccaaaag tggtcaggca agccagaggc gtcgcatctg ctaaaggtat gtctccgcga   1140

gcaacctga                                                           1149
```

<210> SEQ ID NO 30
<211> LENGTH: 382
<212> TYPE: PRT
<213> ORGANISM: Pseudomonas syringae

<400> SEQUENCE: 30

```
Met Arg Ile His Ser Ser Gly His Gly Ile Ser Gly Pro Val Ser Ser
  1               5                  10                  15

Ala Glu Thr Val Glu Lys Ala Val Gln Ser Ser Ala Gln Ala Gln Asn
             20                  25                  30

Glu Ala Ser His Ser Gly Pro Ser Glu His Pro Glu Ser Arg Ser Cys
         35                  40                  45

Gln Ala Arg Pro Asn Tyr Pro Tyr Ser Ser Val Lys Thr Arg Leu Pro
     50                  55                  60

Pro Val Ala Ser Ala Gly Gln Ser Leu Ser Glu Thr Pro Ser Ser Leu
 65                  70                  75                  80

Pro Gly Tyr Leu Leu Leu Arg Arg Leu Asp Arg Arg Pro Leu Asp Gln
                 85                  90                  95

Asp Ala Ile Lys Gly Leu Ile Pro Ala Asp Glu Ala Val Gly Glu Ala
            100                 105                 110

Arg Arg Ala Leu Pro Phe Gly Arg Gly Asn Ile Asp Val Asp Ala Gln
        115                 120                 125

Arg Ser Asn Leu Glu Ser Gly Ala Arg Thr Leu Ala Ala Arg Arg Leu
    130                 135                 140

Arg Lys Asp Ala Glu Thr Ala Gly His Glu Pro Met Pro Glu Asn Glu
145                 150                 155                 160

Asp Met Asn Trp His Val Leu Val Ala Met Ser Gly Gln Val Phe Gly
                165                 170                 175

Ala Gly Asn Cys Gly Glu His Ala Arg Ile Ala Ser Phe Ala Tyr Gly
            180                 185                 190

Ala Ser Ala Gln Glu Lys Gly Arg Ala Gly Asp Glu Asn Ile His Leu
        195                 200                 205

Ala Ala Gln Ser Gly Glu Asp His Val Trp Ala Glu Thr Asp Asp Ser
```

-continued

```
    210                 215                 220

Ser Ala Gly Ser Ser Pro Ile Val Met Asp Pro Trp Ser Asn Gly Pro
225                 230                 235                 240

Ala Val Phe Ala Glu Asp Ser Arg Phe Ala Lys Asp Arg Arg Ala Val
                245                 250                 255

Glu Arg Thr Asp Ser Phe Thr Leu Ser Thr Ala Ala Lys Ala Gly Lys
            260                 265                 270

Ile Thr Arg Glu Thr Ala Glu Lys Ala Leu Thr Gln Ala Thr Ser Arg
        275                 280                 285

Leu Gln Gln Arg Leu Ala Asp Gln Gln Ala Gln Val Ser Pro Val Glu
    290                 295                 300

Gly Gly Arg Tyr Arg Gln Glu Asn Ser Val Leu Asp Asp Ala Phe Ala
305                 310                 315                 320

Arg Arg Val Ser Asp Met Leu Asn Asn Ala Asp Pro Arg Arg Ala Leu
                325                 330                 335

Gln Val Glu Ile Glu Ala Ser Gly Val Ala Met Ser Leu Gly Ala Gln
            340                 345                 350

Gly Val Lys Thr Val Val Arg Gln Ala Pro Lys Val Val Arg Gln Ala
        355                 360                 365

Arg Gly Val Ala Ser Ala Lys Gly Met Ser Pro Arg Ala Thr
    370                 375                 380


<210> SEQ ID NO 31
<211> LENGTH: 1236
<212> TYPE: DNA
<213> ORGANISM: Pseudomonas syringae

<400> SEQUENCE: 31

atgaatatct caggtccgaa cagacgtcag gggactcagg cagagaacac tgaaagcgct     60

tcgtcatcat cggtaactaa cccaccgcta cagcgtggcg agggcagacg tctgcgacgt    120

caggatgcgc tgccaacgga tatcagatac aacgccaacc agacagcgac atcaccgcaa    180

aacgcgcgcg cggcaggaag atatgaatca ggggccagct catccggcgc gaatgatact    240

ccgcaggctg aaggttcaat gccttcgtcg tccgcccttt tacaatttcg cctcgccggc    300

gggcggaacc attctgagct ggaaaatttt catactatga tgctgaactc accgaaagca    360

tcacggggag atgctatacc tgagaagccc gaagcaatac ctaagcgcct actggagaag    420

atggaaccga ttaacctggc ccagttagct ttgcgtgata aggatctgca tgaatatgcc    480

gtaatggtct gtaaccaagt gaaaaagggt gaaggtccga actccaatat tacgcaagga    540

gatatcaagt tactgccgct gttcgccaaa gcggaaaata caagaaatcc cggcttgaat    600

ctgcatacat tcaaaagtca taaagactgt taccaggcga taaaagagca aaacagggat    660

attcaaaaaa acaagcaatc gctgagtatg cgggttgttt accccccatt caaaaagatg    720

ccagaccacc atatagcctt ggatatccaa ctgagatacg gccatcgacc gtcgattgtc    780

ggctttgagt ctgcccctgg gaacattata gatgctgcag aaagggaaat actttcagca    840

ttaggcaacg tcaaaatcaa aatggtagga aattttcttc aatactcgaa aactgactgc    900

accatgtttg cgcttaataa cgccctgaaa gcttttaaac atcacgaaga atataccgcc    960

cgtctgcaca atggagaaaa gcaggtgcct atcccggcga ccttcttgaa acatgctcag   1020

tcaaaaagct tagtggagaa tcacccggaa aaagatacca ccgtcactaa agaccagggc   1080

ggtctgcata tggaaacgct attacacaga aaccgtgcct accgggcgca acgatctgcc   1140

ggtcagcacg ttacctctat tgaaggtttc agaatgcagg aaataaagag agcaggtgac   1200
```

-continued ttccttgccg caaacagggt ccgggccaag ccttga 1236

<210> SEQ ID NO 32
<211> LENGTH: 411
<212> TYPE: PRT
<213> ORGANISM: Pseudomonas syringae

<400> SEQUENCE: 32

```
Met Asn Ile Ser Gly Pro Asn Arg Arg Gln Gly Thr Gln Ala Glu Asn
  1               5                  10                  15

Thr Glu Ser Ala Ser Ser Ser Ser Val Thr Asn Pro Pro Leu Gln Arg
             20                  25                  30

Gly Glu Gly Arg Arg Leu Arg Arg Gln Asp Ala Leu Pro Thr Asp Ile
         35                  40                  45

Arg Tyr Asn Ala Asn Gln Thr Ala Thr Ser Pro Gln Asn Ala Arg Ala
     50                  55                  60

Ala Gly Arg Tyr Glu Ser Gly Ala Ser Ser Ser Gly Ala Asn Asp Thr
 65                  70                  75                  80

Pro Gln Ala Glu Gly Ser Met Pro Ser Ser Ser Ala Leu Leu Gln Phe
                 85                  90                  95

Arg Leu Ala Gly Gly Arg Asn His Ser Glu Leu Glu Asn Phe His Thr
            100                 105                 110

Met Met Leu Asn Ser Pro Lys Ala Ser Arg Gly Asp Ala Ile Pro Glu
        115                 120                 125

Lys Pro Glu Ala Ile Pro Lys Arg Leu Leu Glu Lys Met Glu Pro Ile
    130                 135                 140

Asn Leu Ala Gln Leu Ala Leu Arg Asp Lys Asp Leu His Glu Tyr Ala
145                 150                 155                 160

Val Met Val Cys Asn Gln Val Lys Lys Gly Glu Gly Pro Asn Ser Asn
                165                 170                 175

Ile Thr Gln Gly Asp Ile Lys Leu Leu Pro Leu Phe Ala Lys Ala Glu
            180                 185                 190

Asn Thr Arg Asn Pro Gly Leu Asn Leu His Thr Phe Lys Ser His Lys
        195                 200                 205

Asp Cys Tyr Gln Ala Ile Lys Glu Gln Asn Arg Asp Ile Gln Lys Asn
    210                 215                 220

Lys Gln Ser Leu Ser Met Arg Val Val Tyr Pro Pro Phe Lys Lys Met
225                 230                 235                 240

Pro Asp His His Ile Ala Leu Asp Ile Gln Leu Arg Tyr Gly His Arg
                245                 250                 255

Pro Ser Ile Val Gly Phe Glu Ser Ala Pro Gly Asn Ile Ile Asp Ala
            260                 265                 270

Ala Glu Arg Glu Ile Leu Ser Ala Leu Gly Asn Val Lys Ile Lys Met
        275                 280                 285

Val Gly Asn Phe Leu Gln Tyr Ser Lys Thr Asp Cys Thr Met Phe Ala
    290                 295                 300

Leu Asn Asn Ala Leu Lys Ala Phe Lys His His Glu Glu Tyr Thr Ala
305                 310                 315                 320

Arg Leu His Asn Gly Glu Lys Gln Val Pro Ile Pro Ala Thr Phe Leu
                325                 330                 335

Lys His Ala Gln Ser Lys Ser Leu Val Glu Asn His Pro Glu Lys Asp
            340                 345                 350

Thr Thr Val Thr Lys Asp Gln Gly Gly Leu His Met Glu Thr Leu Leu
        355                 360                 365
```

-continued

```
His Arg Asn Arg Ala Tyr Arg Ala Gln Arg Ser Ala Gly Gln His Val
    370                 375                 380

Thr Ser Ile Glu Gly Phe Arg Met Gln Glu Ile Lys Arg Ala Gly Asp
385                 390                 395                 400

Phe Leu Ala Ala Asn Arg Val Arg Ala Lys Pro
                405                 410
```

<210> SEQ ID NO 33
<211> LENGTH: 363
<212> TYPE: DNA
<213> ORGANISM: Pseudomonas syringae

<400> SEQUENCE: 33

```
atgacgctgg aacggattga acagcaaaat acgctgtttg tttatctgtg cgtgggcacg     60

ctttctactc cagccagcag cacacttctg agcgatattc tggccgccaa cctctttcat    120

tatgggtcca gcgatggggc ggccttcggg ctggacgaaa aaaataatga agtgctgctt    180

tttcagcggt ttgatccgtt acggattgat gaggatcact ttgtcagcgc ctgcgttcag    240

atgatcgaag tggcgaaaat atggcgggca aagttactgc atggccattc tgctccgctc    300

gcctcctcaa ccaggctgac gaaagccggt ttaatgctaa ccatggcggg gactattcga    360

tga                                                                  363
```

<210> SEQ ID NO 34
<211> LENGTH: 120
<212> TYPE: PRT
<213> ORGANISM: Pseudomonas syringae

<400> SEQUENCE: 34

```
Met Thr Leu Glu Arg Ile Glu Gln Gln Asn Thr Leu Phe Val Tyr Leu
  1               5                  10                  15

Cys Val Gly Thr Leu Ser Thr Pro Ala Ser Ser Thr Leu Leu Ser Asp
             20                  25                  30

Ile Leu Ala Ala Asn Leu Phe His Tyr Gly Ser Ser Asp Gly Ala Ala
         35                  40                  45

Phe Gly Leu Asp Glu Lys Asn Asn Glu Val Leu Leu Phe Gln Arg Phe
     50                  55                  60

Asp Pro Leu Arg Ile Asp Glu Asp His Phe Val Ser Ala Cys Val Gln
 65                  70                  75                  80

Met Ile Glu Val Ala Lys Ile Trp Arg Ala Lys Leu Leu His Gly His
                 85                  90                  95

Ser Ala Pro Leu Ala Ser Ser Thr Arg Leu Thr Lys Ala Gly Leu Met
            100                 105                 110

Leu Thr Met Ala Gly Thr Ile Arg
        115                 120
```

<210> SEQ ID NO 35
<211> LENGTH: 1128
<212> TYPE: DNA
<213> ORGANISM: Pseudomonas syringae

<400> SEQUENCE: 35

```
gtgaacccta tccatgcacg cttctccagc gtagaagcgc tcagacattc aaacgttgat     60

attcaggcaa tcaaatccga gggtcagttg gaagtcaacg gcaagcgtta cgagattcgt    120

gcggccgctg acggctcaat cgcggtcctc agacccgatc aacagtccaa agcagacaag    180

ttcttcaaag gcgcagcgca tcttattggc ggacaaagcc agcgtgccca aatagcccag    240
```

-continued

```
gtactcaacg agaaagcggc ggcagttcca cgcctggaca gaatgttggg cagacgcttc     300

gatctggaga agggcggaag tagcgctgtg ggcgccgcaa tcaaggctgc cgacagccga     360

ctgacatcaa aacagacatt tgccagcttc cagcaatggg ctgaaaaagc tgaggcgctc     420

gggcgatacc gaaatcggta tctacatgat ctacaagagg gacacgccag acacaacgcc     480

tatgaatgcg gcagagtcaa gaacattacc tggaaacgct acaggctctc gataacaaga     540

aaaaccttat catacgcccc gcagatccat gatgatcggg aagaggaaga gcttgatctg     600

ggccgataca tcgctgaaga cagaaatgcc agaaccggct tttttagaat ggttcctaaa     660

gaccaacgcg cacctgagac aaactcggga cgacttacca ttggtgtaga acctaaatat     720

ggagcgcagt tggccctcgc aatggcaacc ctgatggaca agcacaaatc tgtgacacaa     780

ggtaaagtcg tcggtccggc aaaatatggc cagcaaactg actctgccat tctttacata     840

aatggtgatc ttgcaaaagc agtaaaactg ggcgaaaagc tgaaaaagct gagcggtatc     900

cctcctgaag gattcgtcga acatacaccg ctaagcatgc agtcgacggg tctcggtctt     960

tcttatgccg agtcggttga agggcagcct tccagccacg gacaggcgag aacacacgtt    1020

atcatggatg ccttgaaagg ccagggcccc atggagaaca gactcaaaat ggcgctggca    1080

gaaagaggct atgacccgga aaatccggcg ctcagggcgc gaaactga                 1128
```

<210> SEQ ID NO 36
<211> LENGTH: 375
<212> TYPE: PRT
<213> ORGANISM: Pseudomonas syringae

<400> SEQUENCE: 36

```
Val Asn Pro Ile His Ala Arg Phe Ser Ser Val Glu Ala Leu Arg His
  1               5                  10                  15

Ser Asn Val Asp Ile Gln Ala Ile Lys Ser Glu Gly Gln Leu Glu Val
             20                  25                  30

Asn Gly Lys Arg Tyr Glu Ile Arg Ala Ala Ala Asp Gly Ser Ile Ala
         35                  40                  45

Val Leu Arg Pro Asp Gln Gln Ser Lys Ala Asp Lys Phe Phe Lys Gly
     50                  55                  60

Ala Ala His Leu Ile Gly Gly Gln Ser Gln Arg Ala Gln Ile Ala Gln
 65                  70                  75                  80

Val Leu Asn Glu Lys Ala Ala Ala Val Pro Arg Leu Asp Arg Met Leu
                 85                  90                  95

Gly Arg Arg Phe Asp Leu Glu Lys Gly Gly Ser Ser Ala Val Gly Ala
            100                 105                 110

Ala Ile Lys Ala Ala Asp Ser Arg Leu Thr Ser Lys Gln Thr Phe Ala
        115                 120                 125

Ser Phe Gln Gln Trp Ala Glu Lys Ala Glu Ala Leu Gly Arg Tyr Arg
    130                 135                 140

Asn Arg Tyr Leu His Asp Leu Gln Glu Gly His Ala Arg His Asn Ala
145                 150                 155                 160

Tyr Glu Cys Gly Arg Val Lys Asn Ile Thr Trp Lys Arg Tyr Arg Leu
                165                 170                 175

Ser Ile Thr Arg Lys Thr Leu Ser Tyr Ala Pro Gln Ile His Asp Asp
            180                 185                 190

Arg Glu Glu Glu Glu Leu Asp Leu Gly Arg Tyr Ile Ala Glu Asp Arg
        195                 200                 205

Asn Ala Arg Thr Gly Phe Phe Arg Met Val Pro Lys Asp Gln Arg Ala
```

-continued

```
    210                 215                 220

Pro Glu Thr Asn Ser Gly Arg Leu Thr Ile Gly Val Glu Pro Lys Tyr
225                 230                 235                 240

Gly Ala Gln Leu Ala Leu Ala Met Ala Thr Leu Met Asp Lys His Lys
                245                 250                 255

Ser Val Thr Gln Gly Lys Val Val Gly Pro Ala Lys Tyr Gly Gln Gln
            260                 265                 270

Thr Asp Ser Ala Ile Leu Tyr Ile Asn Gly Asp Leu Ala Lys Ala Val
        275                 280                 285

Lys Leu Gly Glu Lys Leu Lys Lys Leu Ser Gly Ile Pro Pro Glu Gly
    290                 295                 300

Phe Val Glu His Thr Pro Leu Ser Met Gln Ser Thr Gly Leu Gly Leu
305                 310                 315                 320

Ser Tyr Ala Glu Ser Val Glu Gly Gln Pro Ser Ser His Gly Gln Ala
                325                 330                 335

Arg Thr His Val Ile Met Asp Ala Leu Lys Gly Gln Gly Pro Met Glu
            340                 345                 350

Asn Arg Leu Lys Met Ala Leu Ala Glu Arg Gly Tyr Asp Pro Glu Asn
        355                 360                 365

Pro Ala Leu Arg Ala Arg Asn
    370                 375
```

<210> SEQ ID NO 37
<211> LENGTH: 336
<212> TYPE: DNA
<213> ORGANISM: Pseudomonas syringae

<400> SEQUENCE: 37

```
atggagatgc ccgccttggc gtttgacgat aagggtgcgt gcaacatgat catcgacaag     60

gcattcgctc tgacgctgtt gcgcgacgac acgcatcaac gtttgttgct gattggtctg    120

cttgagccac acgaggatct acccttgcag cgcctgttgg ctggcgctct caacccccct    180

gtgaatgccg gccccggcat tggctgggat gagcaaagcg gcctgtacca cgcttaccaa    240

agcatcccgc gggaaaaagt cagcgtggag atgctgaagc tcgaaattgc aggattggtc    300

gaatggatga agtgttggcg agaagcccgc acgtga                              336
```

<210> SEQ ID NO 38
<211> LENGTH: 111
<212> TYPE: PRT
<213> ORGANISM: Pseudomonas syringae

<400> SEQUENCE: 38

```
Met Glu Met Pro Ala Leu Ala Phe Asp Asp Lys Gly Ala Cys Asn Met
  1               5                  10                  15

Ile Ile Asp Lys Ala Phe Ala Leu Thr Leu Leu Arg Asp Asp Thr His
            20                  25                  30

Gln Arg Leu Leu Leu Ile Gly Leu Leu Glu Pro His Glu Asp Leu Pro
         35                  40                  45

Leu Gln Arg Leu Leu Ala Gly Ala Leu Asn Pro Leu Val Asn Ala Gly
     50                  55                  60

Pro Gly Ile Gly Trp Asp Glu Gln Ser Gly Leu Tyr His Ala Tyr Gln
 65                  70                  75                  80

Ser Ile Pro Arg Glu Lys Val Ser Val Glu Met Leu Lys Leu Glu Ile
                 85                  90                  95

Ala Gly Leu Val Glu Trp Met Lys Cys Trp Arg Glu Ala Arg Thr
```

-continued 100 105 110

<210> SEQ ID NO 39
<211> LENGTH: 1143
<212> TYPE: DNA
<213> ORGANISM: Pseudomonas syringae pv. angulata

<400> SEQUENCE: 39
atgagaattc acagtgctgg tcacagcctg cctgcgccag gccctagcgt ggaaaccact 60
gaaaaggctg ttcaatcatc atcggcccag aacccgctt cttacagttc acaaacagaa 120
cgtcctgaag ccggttcgac tcaagtgcga ctgaactacc cttactcatc agtcaagaca 180
cgcttgccac ccgtttcttc tacagggcag gccatttctg ccacgccatc ttcattgccc 240
ggttacctgc tgttacgtcg gctcgaccga cgtccactgg atgaagacag tatcaaggct 300
ctggttccgg cagacgaagc ggtgcgtgaa gcacgccgcg cgttgccctt cggcaggggc 360
aacattgatg tggatgcaca acgtacccac ctgcaaagcg gcgctcgcgc agtcgctgca 420
aagcgcttga gaaaagatgc cgagcgcgct ggccatgagc cgatgcccgg gaatgatgag 480
atgaactggc atgttcttgt cgccatgtca gggcaggtgt ttggcgctgg caactgtggc 540
gaacatgctc gtatagcaag cttcgcttac ggggccctgg ctcaggaaag cgggcgtagt 600
ccccgcgaaa agattcattt ggccgagcag cccggaaaag atcacgtctg ggctgaaacg 660
gataattcca gcgctggctc ttcgcccatc gtcatggacc cgtggtctaa cggcgcagcc 720
attttggcgg aggacagccg gtttgccaaa gatcgcagta cggtagagcg aacatattca 780
ttcacccttg caatggcagc tgaagccggc aaggttacgc gtgaaaccgc cgagaacgtt 840
ctgacccaca cgacaagccg tctgcagaaa cgtcttgctg atcagttgcc gaacgtctca 900
ccgcttgaag gaggccgcta tcagcaggaa aagtcggtgc ttgatgaggc gttcgcccga 960
cgagtgagcg acaagttgaa tagtgacgat ccacggcgtg cgttgcagat ggaaattgaa 1020
gctgttggtg ttgcaatgtc gctgggtgcc gaaggcgtca agacggtcgc ccgacaggcg 1080
ccaaaggtgg tcaggcaagc cagaagcgtc gcgtcgtcta aaggcatgcc tccacgaaga 1140
taa 1143

<210> SEQ ID NO 40
<211> LENGTH: 380
<212> TYPE: PRT
<213> ORGANISM: Pseudomonas syringae pv. angulata

<400> SEQUENCE: 40

Met Arg Ile His Ser Ala Gly His Ser Leu Pro Ala Pro Gly Pro Ser
1 5 10 15

Val Glu Thr Thr Glu Lys Ala Val Gln Ser Ser Ser Ala Gln Asn Pro
20 25 30

Ala Ser Tyr Ser Ser Gln Thr Glu Arg Pro Glu Ala Gly Ser Thr Gln
35 40 45

Val Arg Leu Asn Tyr Pro Tyr Ser Ser Val Lys Thr Arg Leu Pro Pro
50 55 60

Val Ser Ser Thr Gly Gln Ala Ile Ser Ala Thr Pro Ser Ser Leu Pro
65 70 75 80

Gly Tyr Leu Leu Leu Arg Arg Leu Asp Arg Arg Pro Leu Asp Glu Asp
85 90 95

Ser Ile Lys Ala Leu Val Pro Ala Asp Glu Ala Val Arg Glu Ala Arg
100 105 110

-continued

```
Arg Ala Leu Pro Phe Gly Arg Gly Asn Ile Asp Val Asp Ala Gln Arg
        115                 120                 125

Thr His Leu Gln Ser Gly Ala Arg Ala Val Ala Ala Lys Arg Leu Arg
    130                 135                 140

Lys Asp Ala Glu Arg Ala Gly His Glu Pro Met Pro Gly Asn Asp Glu
145                 150                 155                 160

Met Asn Trp His Val Leu Val Ala Met Ser Gly Gln Val Phe Gly Ala
                165                 170                 175

Gly Asn Cys Gly Glu His Ala Arg Ile Ala Ser Phe Ala Tyr Gly Ala
            180                 185                 190

Leu Ala Gln Glu Ser Gly Arg Ser Pro Arg Glu Lys Ile His Leu Ala
        195                 200                 205

Glu Gln Pro Gly Lys Asp His Val Trp Ala Glu Thr Asp Asn Ser Ser
    210                 215                 220

Ala Gly Ser Ser Pro Ile Val Met Asp Pro Trp Ser Asn Gly Ala Ala
225                 230                 235                 240

Ile Leu Ala Glu Asp Ser Arg Phe Ala Lys Asp Arg Ser Thr Val Glu
                245                 250                 255

Arg Thr Tyr Ser Phe Thr Leu Ala Met Ala Ala Glu Ala Gly Lys Val
            260                 265                 270

Thr Arg Glu Thr Ala Glu Asn Val Leu Thr His Thr Thr Ser Arg Leu
        275                 280                 285

Gln Lys Arg Leu Ala Asp Gln Leu Pro Asn Val Ser Pro Leu Glu Gly
    290                 295                 300

Gly Arg Tyr Gln Gln Glu Lys Ser Val Leu Asp Glu Ala Phe Ala Arg
305                 310                 315                 320

Arg Val Ser Asp Lys Leu Asn Ser Asp Asp Pro Arg Arg Ala Leu Gln
                325                 330                 335

Met Glu Ile Glu Ala Val Gly Val Ala Met Ser Leu Gly Ala Glu Gly
            340                 345                 350

Val Lys Thr Val Ala Arg Gln Ala Pro Lys Val Val Arg Gln Ala Arg
        355                 360                 365

Ser Val Ala Ser Ser Lys Gly Met Pro Pro Arg Arg
    370                 375                 380
```

<210> SEQ ID NO 41
<211> LENGTH: 1143
<212> TYPE: DNA
<213> ORGANISM: Pseudomonas syringae pv. glycinea

<400> SEQUENCE: 41

```
atgagaattc acagtgctgg tcacagcctg cccgcgccag gccctagcgt ggaaaccact      60
gaaaaggctg ttcaatcatc atcggcccag aaccccgctt cttgcagttc acaaacagaa     120
cgtcctgaag ccggttcgac tcaagtgcga ccgaactacc cttactcatc agtcaagaca     180
cgcttgccac ccgtttcttc cacagggcag gccatttctg acacgccatc ttcattgtcc     240
ggttacctgc tgttacgtcg gctcgaccga cgtccactgg atgaagacag tatcaaggct     300
ctggttccgg cagacgaagc gttgcgtgaa gcacgccgcg cgttgccctt cggcaggggc     360
aacattgatg tggatgcaca acgtacccac ctgcaaagcg gcgctcgcgc agtcgctgca     420
aagcgcttga gaaaagatgc cgagcgcgct ggccatgagc cgatgcccga gaatgatgag     480
atgaactggc atgttcttgt cgccatgtca gggcaggtgt ttggcgctgg caactgtggc     540
gaacatgctc gtatagcaag cttcgcttac ggggccctgg ctcaggaaag cgggcgtagt     600
```

-continued

```
ccccgcgaaa agattcattt ggccgagcag cccggaaaag atcacgtctg ggctgaaacg    660

gataattcca gcgctggctc ttcgcccatc gtcatggacc cgtggtctaa cggcgtagcc    720

attttggcgg aggacagccg gtttgccaaa gatcgcagtg cggtagagcg aacatattca    780

ttcacccttg caatggcagc tgaagccggc aaggttgcgc gtgaaaccgc cgagaacgtt    840

ctgacccaca cgacaagccg tctgcagaaa cgtcttgctg atcagttgcc gaacgtctca    900

ccgcttgaag gaggccgcta tcagccggaa aagtcggtgc ttgatgaggc gttcgcccga    960

cgagtgagcg acaagttgaa tagtgacgat ccacggcgtg cgttgcagat ggaaattgaa   1020

gctgttggtg ttgcaatgtc gctgggtgcc gaaggcgtca agacggtcgc ccgacaggcg   1080

ccaaaggtgg tcaggcaagc cagaagcgtc gcgtcgtcta aaggcatgcc tccacgaaga   1140

taa                                                                 1143
```

<210> SEQ ID NO 42
<211> LENGTH: 380
<212> TYPE: PRT
<213> ORGANISM: Pseudomonas syringae pv. glycinea

<400> SEQUENCE: 42

```
Met Arg Ile His Ser Ala Gly His Ser Leu Pro Ala Pro Gly Pro Ser
  1               5                  10                  15

Val Glu Thr Thr Glu Lys Ala Val Gln Ser Ser Ser Ala Gln Asn Pro
             20                  25                  30

Ala Ser Cys Ser Ser Gln Thr Glu Arg Pro Glu Ala Gly Ser Thr Gln
         35                  40                  45

Val Arg Pro Asn Tyr Pro Tyr Ser Ser Val Lys Thr Arg Leu Pro Pro
     50                  55                  60

Val Ser Ser Thr Gly Gln Ala Ile Ser Asp Thr Pro Ser Ser Leu Ser
 65                  70                  75                  80

Gly Tyr Leu Leu Leu Arg Arg Leu Asp Arg Arg Pro Leu Asp Glu Asp
                 85                  90                  95

Ser Ile Lys Ala Leu Val Pro Ala Asp Glu Ala Leu Arg Glu Ala Arg
            100                 105                 110

Arg Ala Leu Pro Phe Gly Arg Gly Asn Ile Asp Val Asp Ala Gln Arg
        115                 120                 125

Thr His Leu Gln Ser Gly Ala Arg Ala Val Ala Ala Lys Arg Leu Arg
    130                 135                 140

Lys Asp Ala Glu Arg Ala Gly His Glu Pro Met Pro Glu Asn Asp Glu
145                 150                 155                 160

Met Asn Trp His Val Leu Val Ala Met Ser Gly Gln Val Phe Gly Ala
                165                 170                 175

Gly Asn Cys Gly Glu His Ala Arg Ile Ala Ser Phe Ala Tyr Gly Ala
            180                 185                 190

Leu Ala Gln Glu Ser Gly Arg Ser Pro Arg Glu Lys Ile His Leu Ala
        195                 200                 205

Glu Gln Pro Gly Lys Asp His Val Trp Ala Glu Thr Asp Asn Ser Ser
    210                 215                 220

Ala Gly Ser Ser Pro Ile Val Met Asp Pro Trp Ser Asn Gly Val Ala
225                 230                 235                 240

Ile Leu Ala Glu Asp Ser Arg Phe Ala Lys Asp Arg Ser Ala Val Glu
                245                 250                 255

Arg Thr Tyr Ser Phe Thr Leu Ala Met Ala Ala Glu Ala Gly Lys Val
            260                 265                 270
```

-continued

```
Ala Arg Glu Thr Ala Glu Asn Val Leu Thr His Thr Thr Ser Arg Leu
        275                 280                 285

Gln Lys Arg Leu Ala Asp Gln Leu Pro Asn Val Ser Pro Leu Glu Gly
    290                 295                 300

Gly Arg Tyr Gln Pro Glu Lys Ser Val Leu Asp Glu Ala Phe Ala Arg
305                 310                 315                 320

Arg Val Ser Asp Lys Leu Asn Ser Asp Asp Pro Arg Arg Ala Leu Gln
                325                 330                 335

Met Glu Ile Glu Ala Val Gly Val Ala Met Ser Leu Gly Ala Glu Gly
            340                 345                 350

Val Lys Thr Val Ala Arg Gln Ala Pro Lys Val Val Arg Gln Ala Arg
        355                 360                 365

Ser Val Ala Ser Ser Lys Gly Met Pro Pro Arg Arg
    370                 375                 380
```

<210> SEQ ID NO 43
<211> LENGTH: 1143
<212> TYPE: DNA
<213> ORGANISM: Pseudomonas syringae pv. tabaci

<400> SEQUENCE: 43

```
atgagaattc acagtgctgg tcacagcctg cctgcgccag gccctagcgt ggaaaccact      60

gaaaaggctg ttcaatcatc atcggcccag aacccccgctt cttgcagttc acaaacagaa     120

cgtcctgaag ccggttcgac tcaagtgcga ccgaactacc cttactcatc agtcaagaca     180

cgcttgccac ccgtttcttc tacagggcag gccatttctg acacgccatc ttcattgccc     240

ggttacctgc tgttacgtcg gctcgaccga cgtccactgg atgaagacag tatcaaggct     300

ctggttccgg cagacgaagc ggtgcgtgaa gcacgccgcg cgttgccctt cggcaggggc     360

aacattgatg tggatgcaca acgtacccac ctgcaaagcg gcgctcgcgc agtcgctgca     420

aagcgcttga gaaaagatgc cgagcgcgct ggccatgagc cgatgcccgg gaatgatgag     480

atgaactggc atgttcttgt cgccatgtca gggcaggtgt ttggcgctgg caactgtggc     540

gaacatgctc gtatagcaag cttcgcttac ggggccctgg ctcaggaaag cgggcgtagt     600

ccccgcgaaa agattcattt ggccgagcag cccggaaaag atcacgtctg ggctgaaacg     660

gataattcca gcgctggctc ttcgcccatc gtcatggacc cgtggtctaa cggcgcagcc     720

attttggcgg aggacagccg gtttgccaaa gatcgcagtg cggtagagcg aacatattca     780

ttcacccttg caatggcagc tgaagccggc aaggttacgc gtgaaactgc cgagaacgtt     840

ctgacccaca cgacaagccg tctgcagaaa cgtcttgctg atcagttgcc gaacgtctca     900

ccgcttgaag gaggccgcta tcagcaggaa aagtcggtgc ttgatgaggc gttcgcccga     960

cgagtgagcg acaagttgaa tagtgacgat ccacggcgtg cgttgcagat ggaaattgaa    1020

gctgttggtg ttgcaatgtc gctgggtgcc gaaggcgtca agacggtcgc ccgacaggcg    1080

ccaaaggtgg tcaggcaagc cagaagcgtc gcgtcgtcta aaggcatgcc tccacgaaga    1140

taa                                                                   1143
```

<210> SEQ ID NO 44
<211> LENGTH: 380
<212> TYPE: PRT
<213> ORGANISM: Pseudomonas syringae pv. tabaci

<400> SEQUENCE: 44

```
Met Arg Ile His Ser Ala Gly His Ser Leu Pro Ala Pro Gly Pro Ser
  1               5                  10                  15
```

-continued

```
Val Glu Thr Thr Glu Lys Ala Val Gln Ser Ser Ser Ala Gln Asn Pro
            20                  25                  30

Ala Ser Cys Ser Ser Gln Thr Glu Arg Pro Glu Ala Gly Ser Thr Gln
        35                  40                  45

Val Arg Pro Asn Tyr Pro Tyr Ser Ser Val Lys Thr Arg Leu Pro Pro
    50                  55                  60

Val Ser Ser Thr Gly Gln Ala Ile Ser Asp Thr Pro Ser Ser Leu Pro
65                  70                  75                  80

Gly Tyr Leu Leu Leu Arg Arg Leu Asp Arg Arg Pro Leu Asp Glu Asp
                85                  90                  95

Ser Ile Lys Ala Leu Val Pro Ala Asp Glu Ala Val Arg Glu Ala Arg
            100                 105                 110

Arg Ala Leu Pro Phe Gly Arg Gly Asn Ile Asp Val Asp Ala Gln Arg
        115                 120                 125

Thr His Leu Gln Ser Gly Ala Arg Ala Val Ala Ala Lys Arg Leu Arg
    130                 135                 140

Lys Asp Ala Glu Arg Ala Gly His Glu Pro Met Pro Gly Asn Asp Glu
145                 150                 155                 160

Met Asn Trp His Val Leu Val Ala Met Ser Gly Gln Val Phe Gly Ala
                165                 170                 175

Gly Asn Cys Gly Glu His Ala Arg Ile Ala Ser Phe Ala Tyr Gly Ala
            180                 185                 190

Leu Ala Gln Glu Ser Gly Arg Ser Pro Arg Glu Lys Ile His Leu Ala
        195                 200                 205

Glu Gln Pro Gly Lys Asp His Val Trp Ala Glu Thr Asp Asn Ser Ser
    210                 215                 220

Ala Gly Ser Ser Pro Ile Val Met Asp Pro Trp Ser Asn Gly Ala Ala
225                 230                 235                 240

Ile Leu Ala Glu Asp Ser Arg Phe Ala Lys Asp Arg Ser Ala Val Glu
                245                 250                 255

Arg Thr Tyr Ser Phe Thr Leu Ala Met Ala Ala Glu Ala Gly Lys Val
            260                 265                 270

Thr Arg Glu Thr Ala Glu Asn Val Leu Thr His Thr Thr Ser Arg Leu
        275                 280                 285

Gln Lys Arg Leu Ala Asp Gln Leu Pro Asn Val Ser Pro Leu Glu Gly
    290                 295                 300

Gly Arg Tyr Gln Gln Glu Lys Ser Val Leu Asp Glu Ala Phe Ala Arg
305                 310                 315                 320

Arg Val Ser Asp Lys Leu Asn Ser Asp Asp Pro Arg Arg Ala Leu Gln
                325                 330                 335

Met Glu Ile Glu Ala Val Gly Val Ala Met Ser Leu Gly Ala Glu Gly
            340                 345                 350

Val Lys Thr Val Ala Arg Gln Ala Pro Lys Val Val Arg Gln Ala Arg
        355                 360                 365

Ser Val Ala Ser Ser Lys Gly Met Pro Pro Arg Arg
    370                 375                 380
```

<210> SEQ ID NO 45
<211> LENGTH: 1143
<212> TYPE: DNA
<213> ORGANISM: Pseudomonas syringae pv. tabaci

<400> SEQUENCE: 45

```
atgagaattc acagtgctgg tcacagcctg cctgcgccag gccctagcgt ggaaaccact     60
```

-continued

```
gaaaaggctg ttcaatcatc atcggcccag aacccgctt cttgcagttc acaaacagaa    120
cgtcctgaag ccggttcgac tcaagtgcga ccgaactacc cttactcatc agtcaagaca   180
cgcttgccac ccgtttcttc tacagggcag gccatttctg acacgccatc ttcattgccc   240
ggttacctgc tgttacgtcg gctcgaccga cgtccactgg atgaagacag tatcaaggct   300
ctggttccgg cagacgaagc ggtgcgtgaa gcacgccgcg cgttgccctt cggcaggggc   360
aacattgatg tggatgcaca acgtacccac ctgcaaagcg gcgctcgcgc agtcgctgca   420
aagcgcttga gaaaagatgc cgagcgcgct ggccatgagc cgatgcccgg gaatgatgag   480
atgaactggc atgttcttgt cgccatgtca gggcaggtgt ttggcgctgg caactgtggc   540
gaacatgctc gtatagcaag cttcgcttac ggggccctgg ctcaggaaag cgggcgtagt   600
ccccgcgaaa agattcattt ggccgagcag cccggaaaag atcacgtctg ggctgaaacg   660
gataattcca gcgctggctc ttcgcccatc gtcatggacc cgtggtctaa cggcgcagcc   720
attttggcgg aggacagccg gtttgccaaa gatcgcagtg cggtagagcg aacatattca   780
ttcacccttg caatggcagc tgaagccggc aaggttacgc gtgaaactgc cgagaacgtt   840
ctgacccaca cgacaagccg tctgcagaaa cgtcttgctg atcagttgcc gaacgtctca   900
ccgcttgaag gaggccgcta tcagcaggaa aagtcggtgc ttgatgaggc gttcgcccga   960
cgagtgagcg acaagttgaa tagtgacgat ccacggcgtg cgttgcagat ggaaattgaa  1020
gctgttggtg ttgcaatgtc gctgggtgcc gaaggcgtca agacggtcgc ccgacaggcg  1080
ccaaaggtgg tcaggcaagc cagaagcgtc gcgtcgtcta aaggcatgcc tccacgaaga  1140
taa                                                                1143
```

<210> SEQ ID NO 46
<211> LENGTH: 380
<212> TYPE: PRT
<213> ORGANISM: Pseudomonas syringae pv. tabaci

<400> SEQUENCE: 46

```
Met Arg Ile His Ser Ala Gly His Ser Leu Pro Ala Pro Gly Pro Ser
  1               5                  10                  15

Val Glu Thr Thr Glu Lys Ala Val Gln Ser Ser Ser Ala Gln Asn Pro
             20                  25                  30

Ala Ser Cys Ser Ser Gln Thr Glu Arg Pro Glu Ala Gly Ser Thr Gln
         35                  40                  45

Val Arg Pro Asn Tyr Pro Tyr Ser Ser Val Lys Thr Arg Leu Pro Pro
     50                  55                  60

Val Ser Ser Thr Gly Gln Ala Ile Ser Asp Thr Pro Ser Ser Leu Pro
 65                  70                  75                  80

Gly Tyr Leu Leu Leu Arg Arg Leu Asp Arg Arg Pro Leu Asp Glu Asp
                 85                  90                  95

Ser Ile Lys Ala Leu Val Pro Ala Asp Glu Ala Val Arg Glu Ala Arg
            100                 105                 110

Arg Ala Leu Pro Phe Gly Arg Gly Asn Ile Asp Val Asp Ala Gln Arg
        115                 120                 125

Thr His Leu Gln Ser Gly Ala Arg Ala Val Ala Ala Lys Arg Leu Arg
    130                 135                 140

Lys Asp Ala Glu Arg Ala Gly His Glu Pro Met Pro Gly Asn Asp Glu
145                 150                 155                 160

Met Asn Trp His Val Leu Val Ala Met Ser Gly Gln Val Phe Gly Ala
                165                 170                 175
```

-continued

```
Gly Asn Cys Gly Glu His Ala Arg Ile Ala Ser Phe Ala Tyr Gly Ala
            180                 185                 190

Leu Ala Gln Glu Ser Gly Arg Ser Pro Arg Glu Lys Ile His Leu Ala
        195                 200                 205

Glu Gln Pro Gly Lys Asp His Val Trp Ala Glu Thr Asp Asn Ser Ser
    210                 215                 220

Ala Gly Ser Ser Pro Ile Val Met Asp Pro Trp Ser Asn Gly Ala Ala
225                 230                 235                 240

Ile Leu Ala Glu Asp Ser Arg Phe Ala Lys Asp Arg Ser Ala Val Glu
                245                 250                 255

Arg Thr Tyr Ser Phe Thr Leu Ala Met Ala Ala Glu Ala Gly Lys Val
            260                 265                 270

Thr Arg Glu Thr Ala Glu Asn Val Leu Thr His Thr Thr Ser Arg Leu
        275                 280                 285

Gln Lys Arg Leu Ala Asp Gln Leu Pro Asn Val Ser Pro Leu Glu Gly
    290                 295                 300

Gly Arg Tyr Gln Gln Glu Lys Ser Val Leu Asp Glu Ala Phe Ala Arg
305                 310                 315                 320

Arg Val Ser Asp Lys Leu Asn Ser Asp Asp Pro Arg Arg Ala Leu Gln
                325                 330                 335

Met Glu Ile Glu Ala Val Gly Val Ala Met Ser Leu Gly Ala Glu Gly
            340                 345                 350

Val Lys Thr Val Ala Arg Gln Ala Pro Lys Val Val Arg Gln Ala Arg
        355                 360                 365

Ser Val Ala Ser Ser Lys Gly Met Pro Pro Arg Arg
    370                 375                 380
```

<210> SEQ ID NO 47
<211> LENGTH: 1143
<212> TYPE: DNA
<213> ORGANISM: Pseudomonas syringae pv. glycinea

<400> SEQUENCE: 47

```
atgagaattc acagtgctgg tcacagcctg cccgcgccag gccctagcgt ggaaaccact     60

gaaaaggctg ttcaatcatc atcggcccag aacccccgctt cttgcagttc acaaacagaa    120

cgtcctgaag ccggttcgac tcaagtgcga ccgaactacc cttactcatc agtcaagaca    180

cgcttgccac ccgtttcttc cacagggcag gccatttctg acacgccatc ttcattgtcc    240

ggttacctgc tgttacgtcg gctcgaccga cgtccactgg atgaagacag tatcaaggct    300

ctggttccgg cagacgaagc gttgcgtgaa gcacgccgcg cgttgccctt cggcaggggc    360

aacattgatg tggatgcaca acgtacccac ctgcaaagcg gcgctcgcgc agtcgctgca    420

aagcgcttga gaaaagatgc cgagcgcgct ggccatgagc cgatgcccga gaatgatgag    480

atgaactggc atgttcttgt cgccatgtca gggcaggtgt ttggcgctgg caactgtggc    540

gaacatgctc gtatagcaag cttcgcttac ggggccctgg ctcaggaaag cgggcgtagt    600

ccccgcgaaa agattcattt ggccgagcag cccggaaaag atcacgtctg ggctgaaacg    660

gataattcca gcgctggctc ttcgcccatc gtcatggacc cgtggtctaa cggcgtagcc    720

attttggcgg aggacagccg gtttgccaaa gatcgcagtg cggtagagcg aacatattca    780

ttcacccttg caatggcagc tgaagccggc aaggttgcgc gtgaaaccgc cgagaacgtt    840

ctgacccaca cgacaagccg tctgcagaaa cgtcttgctg atcagttgcc gaacgtctca    900

ccgcttgaag gaggccgcta tcagccggaa aagtcggtgc ttgatgaggc gttcgcccga    960
```

-continued

```
cgagtgagcg acaagttgaa tagtgacgat ccacggcgtg cgttgcagat ggaaattgaa   1020

gctgttggtg ttgcaatgtc gctgggtgcc gaaggcgtca agacggtcgc ccgacaggcg   1080

ccaaaggtgg tcaggcaagc cagaagcgtc gcgtcgtcta aaggcatgcc tccacgaaga   1140

taa                                                                 1143
```

```
<210> SEQ ID NO 48
<211> LENGTH: 380
<212> TYPE: PRT
<213> ORGANISM: Pseudomonas syringae pv. glycinea

<400> SEQUENCE: 48

Met Arg Ile His Ser Ala Gly His Ser Leu Pro Ala Pro Gly Pro Ser
  1               5                  10                  15

Val Glu Thr Thr Glu Lys Ala Val Gln Ser Ser Ser Ala Gln Asn Pro
             20                  25                  30

Ala Ser Cys Ser Ser Gln Thr Glu Arg Pro Glu Ala Gly Ser Thr Gln
         35                  40                  45

Val Arg Pro Asn Tyr Pro Tyr Ser Ser Val Lys Thr Arg Leu Pro Pro
     50                  55                  60

Val Ser Ser Thr Gly Gln Ala Ile Ser Asp Thr Pro Ser Ser Leu Ser
 65                  70                  75                  80

Gly Tyr Leu Leu Leu Arg Arg Leu Asp Arg Arg Pro Leu Asp Glu Asp
                 85                  90                  95

Ser Ile Lys Ala Leu Val Pro Ala Asp Glu Ala Leu Arg Glu Ala Arg
            100                 105                 110

Arg Ala Leu Pro Phe Gly Arg Gly Asn Ile Asp Val Asp Ala Gln Arg
        115                 120                 125

Thr His Leu Gln Ser Gly Ala Arg Ala Val Ala Ala Lys Arg Leu Arg
    130                 135                 140

Lys Asp Ala Glu Arg Ala Gly His Glu Pro Met Pro Glu Asn Asp Glu
145                 150                 155                 160

Met Asn Trp His Val Leu Val Ala Met Ser Gly Gln Val Phe Gly Ala
                165                 170                 175

Gly Asn Cys Gly Glu His Ala Arg Ile Ala Ser Phe Ala Tyr Gly Ala
            180                 185                 190

Leu Ala Gln Glu Ser Gly Arg Ser Pro Arg Glu Lys Ile His Leu Ala
        195                 200                 205

Glu Gln Pro Gly Lys Asp His Val Trp Ala Glu Thr Asp Asn Ser Ser
    210                 215                 220

Ala Gly Ser Ser Pro Ile Val Met Asp Pro Trp Ser Asn Gly Val Ala
225                 230                 235                 240

Ile Leu Ala Glu Asp Ser Arg Phe Ala Lys Asp Arg Ser Ala Val Glu
                245                 250                 255

Arg Thr Tyr Ser Phe Thr Leu Ala Met Ala Ala Glu Ala Gly Lys Val
            260                 265                 270

Ala Arg Glu Thr Ala Glu Asn Val Leu Thr His Thr Thr Ser Arg Leu
        275                 280                 285

Gln Lys Arg Leu Ala Asp Gln Leu Pro Asn Val Ser Pro Leu Glu Gly
    290                 295                 300

Gly Arg Tyr Gln Pro Glu Lys Ser Val Leu Asp Glu Ala Phe Ala Arg
305                 310                 315                 320

Arg Val Ser Asp Lys Leu Asn Ser Asp Asp Pro Arg Arg Ala Leu Gln
                325                 330                 335
```

-continued

```
Met Glu Ile Glu Ala Val Gly Val Ala Met Ser Leu Gly Ala Glu Gly
            340                 345                 350

Val Lys Thr Val Ala Arg Gln Ala Pro Lys Val Val Arg Gln Ala Arg
        355                 360                 365

Ser Val Ala Ser Ser Lys Gly Met Pro Pro Arg Arg
    370                 375                 380


<210> SEQ ID NO 49
<211> LENGTH: 1143
<212> TYPE: DNA
<213> ORGANISM: Pseudomonas syringae pv. phaseolicola

<400> SEQUENCE: 49

atgagaattc acagtgctgg tcacagcctg cccgcgccag gccctagcgt ggaaaccact     60

gaaaaggctg ttcaatcatc atcggcccag aaccccgctt cttgcagttc acaaacagaa    120

cgtcctgaag ccggttcgac tcaagtgcga ccgaactacc cttactcatc agtcaagaca    180

cgcttgccac ccgtttcttc cacagggcag gccatttctg acacgccatc ttcattgccc    240

ggttacctgc tgttacgtcg gctcgaccga cgtccactgg atgaagacag tatcaaggct    300

ctggttccgg cagacgaagc gttgcgtgaa gcacgccgcg cgttgccctt cggcaggggc    360

aacattgatg tggatgcaca acgtacccac ctgcaaagcg gcgctcgcgc agtcgctgca    420

aagcgcttga gaaaagatgc cgagcgcgct ggccatgagc cgatgcccga gaatgatgag    480

atgaactggc atgttcttgt cgccatgtca gggcaggtgt ttggcgctgg caactgtggc    540

gaacatgctc gtatagcaag cttcgcttac ggggccctgg ctcaggaaag cgggcgtagt    600

ccccgcgaaa agattcattt ggccgagcag cccggaaaag atcacgtctg ggctgaaacg    660

gataattcca gcgctggctc ttcgcccatc gtcatggacc cgtggtctaa cggcgcagcc    720

attttggcgg aggacagccg gtttgccaaa gatcgcagtg cggtagagcg aacatattca    780

ttcacccttg caatggcagc tgaagccggc aaggttgcgc gtgaaaccgc cgagaacgtt    840

ctgacccaca cgacaagccg tctgcagaag cgtcttgctg atcagttgcc gaacgtctca    900

ccgcttgaag gaggccgcta tcagccggaa aagtcggtgc ttgatgaggc gttcgcccga    960

cgagtgagcg acaagttgaa tagtgacgat ccacggcgtg cgttgcagat ggaaattgaa   1020

gctgttggtg ttgcaatgtc gctgggtgcc gaaggcgtca agacggtcgc ccgacaggcg   1080

ccaaaggtgg tcaggcaagc cagaagcgtc gcgtcgtcta aaggcatgcc tccacgaaga   1140

taa                                                                 1143


<210> SEQ ID NO 50
<211> LENGTH: 380
<212> TYPE: PRT
<213> ORGANISM: Pseudomonas syringae pv. phaseolicola

<400> SEQUENCE: 50

Met Arg Ile His Ser Ala Gly His Ser Leu Pro Ala Pro Gly Pro Ser
  1               5                  10                  15

Val Glu Thr Thr Glu Lys Ala Val Gln Ser Ser Ser Ala Gln Asn Pro
             20                  25                  30

Ala Ser Cys Ser Ser Gln Thr Glu Arg Pro Glu Ala Gly Ser Thr Gln
         35                  40                  45

Val Arg Pro Asn Tyr Pro Tyr Ser Ser Val Lys Thr Arg Leu Pro Pro
     50                  55                  60

Val Ser Ser Thr Gly Gln Ala Ile Ser Asp Thr Pro Ser Ser Leu Pro
```

-continued

```
 65                  70                  75                  80

Gly Tyr Leu Leu Leu Arg Arg Leu Asp Arg Arg Pro Leu Asp Glu Asp
                85                  90                  95

Ser Ile Lys Ala Leu Val Pro Ala Asp Glu Ala Leu Arg Glu Ala Arg
            100                 105                 110

Arg Ala Leu Pro Phe Gly Arg Gly Asn Ile Asp Val Asp Ala Gln Arg
        115                 120                 125

Thr His Leu Gln Ser Gly Ala Arg Ala Val Ala Ala Lys Arg Leu Arg
    130                 135                 140

Lys Asp Ala Glu Arg Ala Gly His Glu Pro Met Pro Glu Asn Asp Glu
145                 150                 155                 160

Met Asn Trp His Val Leu Val Ala Met Ser Gly Gln Val Phe Gly Ala
                165                 170                 175

Gly Asn Cys Gly Glu His Ala Arg Ile Ala Ser Phe Ala Tyr Gly Ala
            180                 185                 190

Leu Ala Gln Glu Ser Gly Arg Ser Pro Arg Glu Lys Ile His Leu Ala
        195                 200                 205

Glu Gln Pro Gly Lys Asp His Val Trp Ala Glu Thr Asp Asn Ser Ser
    210                 215                 220

Ala Gly Ser Ser Pro Ile Val Met Asp Pro Trp Ser Asn Gly Ala Ala
225                 230                 235                 240

Ile Leu Ala Glu Asp Ser Arg Phe Ala Lys Asp Arg Ser Ala Val Glu
                245                 250                 255

Arg Thr Tyr Ser Phe Thr Leu Ala Met Ala Ala Glu Ala Gly Lys Val
            260                 265                 270

Ala Arg Glu Thr Ala Glu Asn Val Leu Thr His Thr Thr Ser Arg Leu
        275                 280                 285

Gln Lys Arg Leu Ala Asp Gln Leu Pro Asn Val Ser Pro Leu Glu Gly
    290                 295                 300

Gly Arg Tyr Gln Pro Glu Lys Ser Val Leu Asp Glu Ala Phe Ala Arg
305                 310                 315                 320

Arg Val Ser Asp Lys Leu Asn Ser Asp Asp Pro Arg Arg Ala Leu Gln
                325                 330                 335

Met Glu Ile Glu Ala Val Gly Val Ala Met Ser Leu Gly Ala Glu Gly
            340                 345                 350

Val Lys Thr Val Ala Arg Gln Ala Pro Lys Val Val Arg Gln Ala Arg
        355                 360                 365

Ser Val Ala Ser Ser Lys Gly Met Pro Pro Arg Arg
    370                 375                 380
```

<210> SEQ ID NO 51
<211> LENGTH: 1143
<212> TYPE: DNA
<213> ORGANISM: Pseudomonas syringae pv. angulata

<400> SEQUENCE: 51

```
atgagaattc acagtgctgg tcacagcctg cctgcgccag gccctagcgt ggaaaccact     60

gaaaaggctg ttcaatcatc atcggcccag aaccccgctt cttacagttc acaaacagaa    120

cgtcctgaag ccggttcgac tcaagtgcga ctgaactacc cttactcatc agtcaagaca    180

cgcttgccac ccgtttcttc tacagggcag gccatttctg ccacgccatc ttcattgccc    240

ggttacctgc tgttacgtcg gctcgaccga cgtccactgg atgaagacag tatcaaggct    300

ctggttccgg cagacgaagc ggtgcgtgaa gcacgccgcg cgttgccctt cggcaggggc    360
```

-continued

```
aacattgatg tggatgcaca acgtacccac ctgcaaagcg gcgctcgcgc agtcgctgca    420

aagcgcttga gaaaagatgc cgagcgcgct ggccatgagc cgatgcccgg gaatgatgag    480

atgaactggc atgttcttgt cgccatgtca gggcaggtgt ttggcgctgg caactgtggc    540

gaacatgctc gtatagcaag cttcgcttac ggggccctgg ctcaggaaag cgggcgtagt    600

ccccgcgaaa agattcattt ggccgagcag cccggaaaag atcacgtctg ggctgaaacg    660

gataattcca gcgctggctc ttcgcccatc gtcatggacc cgtggtctaa cggcgcagcc    720

attttggcgg aggacagccg gtttgccaaa gatcgcagta cggtagagcg aacatattca    780

ttcacccttg caatggcagc tgaagccggc aaggttacgc gtgaaaccgc cgagaacgtt    840

ctgacccaca cgacaagccg tctgcagaaa cgtcttgctg atcagttgcc gaacgtctca    900

ccgcttgaag gaggccgcta tcagcaggaa aagtcggtgc ttgatgaggc gttcgcccga    960

cgagtgagcg acaagttgaa tagtgacgat ccacggcgtg cgttgcagat ggaaattgaa   1020

gctgttggtg ttgcaatgtc gctgggtgcc gaaggcgtca agacggtcgc ccgacaggcg   1080

ccaaaggtgg tcaggcaagc cagaagcgtc gcgtcgtcta aaggcatgcc tccacgaaga   1140

taa                                                                 1143
```

<210> SEQ ID NO 52
<211> LENGTH: 380
<212> TYPE: PRT
<213> ORGANISM: Pseudomonas syringae pv. angulata

<400> SEQUENCE: 52

```
Met Arg Ile His Ser Ala Gly His Ser Leu Pro Ala Pro Gly Pro Ser
  1               5                  10                  15

Val Glu Thr Thr Glu Lys Ala Val Gln Ser Ser Ser Ala Gln Asn Pro
             20                  25                  30

Ala Ser Tyr Ser Ser Gln Thr Glu Arg Pro Glu Ala Gly Ser Thr Gln
         35                  40                  45

Val Arg Leu Asn Tyr Pro Tyr Ser Ser Val Lys Thr Arg Leu Pro Pro
     50                  55                  60

Val Ser Ser Thr Gly Gln Ala Ile Ser Ala Thr Pro Ser Ser Leu Pro
 65                  70                  75                  80

Gly Tyr Leu Leu Leu Arg Arg Leu Asp Arg Arg Pro Leu Asp Glu Asp
                 85                  90                  95

Ser Ile Lys Ala Leu Val Pro Ala Asp Glu Ala Val Arg Glu Ala Arg
            100                 105                 110

Arg Ala Leu Pro Phe Gly Arg Gly Asn Ile Asp Val Asp Ala Gln Arg
        115                 120                 125

Thr His Leu Gln Ser Gly Ala Arg Ala Val Ala Ala Lys Arg Leu Arg
    130                 135                 140

Lys Asp Ala Glu Arg Ala Gly His Glu Pro Met Pro Gly Asn Asp Glu
145                 150                 155                 160

Met Asn Trp His Val Leu Val Ala Met Ser Gly Gln Val Phe Gly Ala
                165                 170                 175

Gly Asn Cys Gly Glu His Ala Arg Ile Ala Ser Phe Ala Tyr Gly Ala
            180                 185                 190

Leu Ala Gln Glu Ser Gly Arg Ser Pro Arg Glu Lys Ile His Leu Ala
        195                 200                 205

Glu Gln Pro Gly Lys Asp His Val Trp Ala Glu Thr Asp Asn Ser Ser
    210                 215                 220

Ala Gly Ser Ser Pro Ile Val Met Asp Pro Trp Ser Asn Gly Ala Ala
```

-continued

```
225                 230                 235                 240

Ile Leu Ala Glu Asp Ser Arg Phe Ala Lys Asp Arg Ser Thr Val Glu
                245                 250                 255

Arg Thr Tyr Ser Phe Thr Leu Ala Met Ala Ala Glu Ala Gly Lys Val
            260                 265                 270

Thr Arg Glu Thr Ala Glu Asn Val Leu Thr His Thr Thr Ser Arg Leu
        275                 280                 285

Gln Lys Arg Leu Ala Asp Gln Leu Pro Asn Val Ser Pro Leu Glu Gly
    290                 295                 300

Gly Arg Tyr Gln Gln Glu Lys Ser Val Leu Asp Glu Ala Phe Ala Arg
305                 310                 315                 320

Arg Val Ser Asp Lys Leu Asn Ser Asp Asp Pro Arg Arg Ala Leu Gln
                325                 330                 335

Met Glu Ile Glu Ala Val Gly Val Ala Met Ser Leu Gly Ala Glu Gly
            340                 345                 350

Val Lys Thr Val Ala Arg Gln Ala Pro Lys Val Val Arg Gln Ala Arg
        355                 360                 365

Ser Val Ala Ser Ser Lys Gly Met Pro Pro Arg Arg
    370                 375                 380
```

<210> SEQ ID NO 53
<211> LENGTH: 1155
<212> TYPE: DNA
<213> ORGANISM: Pseudomonas syringae pv. delphinii

<400> SEQUENCE: 53

```
atgaaaatac ataacgctgg cccaagcatt ccgatgcccg ctccatcgat tgagagcgct     60

ggcaagactg cgcaatcatc attggctcaa ccgcagagcc aacgagccac ccccgtctcg    120

ccatcagaga cttctgatgc ccgtccgtcc agtgtgcgta cgaactaccc ttattcatca    180

gtcaaaacac ggttgcctcc cgttgcgtct gcagggcagc cactgtccgg gatgccgtct    240

tcattacccg gctacttgct gttacgtcgg cttgaccatc gtccactgga tcaagacggt    300

atcaaaggtt tgattccagc agatgaagcg gtgggtgaag cacgtcgcgc gttgcctttc    360

ggcaggggca atatcgacgt ggatgcgcaa cgctccaact tggaaagcgg agcccgcaca    420

ctcgcggcta ggcgtttgag aaaagatgcc gaggccgcgg gtcacgaacc aatgcctgca    480

aatgaagata tgaactggca tgttcttgtt gcgatgtcag gacaggtttt tggcgcaggt    540

aactgcgggg aacatgcccg catagcgagt ttcgcctacg gtgcactggc tcaggaaaaa    600

gggcggaacg ccgatgagac tattcatttg gctgcgcaac gcggtaaaga ccacgtctgg    660

gctgaaacgg acaattcaag cgctggatct tcaccggttg tcatggatcc gtggtcgaac    720

ggtcctgcca tttttgcgga ggatagtcgg tttgccaaag atcgaagtac ggtagaacga    780

acggattcct tcacgcttgc aactgctgct gaagcaggca agatcacgcg agagacggcc    840

gagaatgctt tgacacaggc gaccagccgt ttgcagaaac gtcttgctga tcagaaaacg    900

caagtctcgc cgcttgcagg agggcgctat cggcaagaaa attcggtgct tgatgacgcg    960

ttcgcccgac gggcaagtgg caagttgagc aacaaggatc cgcggcatgc attacaggtg   1020

gaaatcgagg cggccgcagt tgcaatgtcg ctgggcgccc aaggcgtaaa agcggttgcg   1080

gaacaggccc ggacggtagt tgaacaagcc aggaaggtcg catctcccca aggcacgcct   1140

cagcgagata cgtga                                                    1155
```

<210> SEQ ID NO 54

-continued

<211> LENGTH: 384
<212> TYPE: PRT
<213> ORGANISM: Pseudomonas syringae pv. delphinii

<400> SEQUENCE: 54

```
Met Lys Ile His Asn Ala Gly Pro Ser Ile Pro Met Pro Ala Pro Ser
  1               5                  10                  15

Ile Glu Ser Ala Gly Lys Thr Ala Gln Ser Ser Leu Ala Gln Pro Gln
             20                  25                  30

Ser Gln Arg Ala Thr Pro Val Ser Pro Ser Glu Thr Ser Asp Ala Arg
         35                  40                  45

Pro Ser Ser Val Arg Thr Asn Tyr Pro Tyr Ser Ser Val Lys Thr Arg
     50                  55                  60

Leu Pro Pro Val Ala Ser Ala Gly Gln Pro Leu Ser Gly Met Pro Ser
 65                  70                  75                  80

Ser Leu Pro Gly Tyr Leu Leu Leu Arg Arg Leu Asp His Arg Pro Leu
                 85                  90                  95

Asp Gln Asp Gly Ile Lys Gly Leu Ile Pro Ala Asp Glu Ala Val Gly
            100                 105                 110

Glu Ala Arg Arg Ala Leu Pro Phe Gly Arg Gly Asn Ile Asp Val Asp
        115                 120                 125

Ala Gln Arg Ser Asn Leu Glu Ser Gly Ala Arg Thr Leu Ala Ala Arg
    130                 135                 140

Arg Leu Arg Lys Asp Ala Glu Ala Ala Gly His Glu Pro Met Pro Ala
145                 150                 155                 160

Asn Glu Asp Met Asn Trp His Val Leu Val Ala Met Ser Gly Gln Val
                165                 170                 175

Phe Gly Ala Gly Asn Cys Gly Glu His Ala Arg Ile Ala Ser Phe Ala
            180                 185                 190

Tyr Gly Ala Leu Ala Gln Glu Lys Gly Arg Asn Ala Asp Glu Thr Ile
        195                 200                 205

His Leu Ala Ala Gln Arg Gly Lys Asp His Val Trp Ala Glu Thr Asp
    210                 215                 220

Asn Ser Ser Ala Gly Ser Ser Pro Val Val Met Asp Pro Trp Ser Asn
225                 230                 235                 240

Gly Pro Ala Ile Phe Ala Glu Asp Ser Arg Phe Ala Lys Asp Arg Ser
                245                 250                 255

Thr Val Glu Arg Thr Asp Ser Phe Thr Leu Ala Thr Ala Ala Glu Ala
            260                 265                 270

Gly Lys Ile Thr Arg Glu Thr Ala Glu Asn Ala Leu Thr Gln Ala Thr
        275                 280                 285

Ser Arg Leu Gln Lys Arg Leu Ala Asp Gln Lys Thr Gln Val Ser Pro
    290                 295                 300

Leu Ala Gly Gly Arg Tyr Arg Gln Glu Asn Ser Val Leu Asp Asp Ala
305                 310                 315                 320

Phe Ala Arg Arg Ala Ser Gly Lys Leu Ser Asn Lys Asp Pro Arg His
                325                 330                 335

Ala Leu Gln Val Glu Ile Glu Ala Ala Ala Val Ala Met Ser Leu Gly
            340                 345                 350

Ala Gln Gly Val Lys Ala Val Ala Glu Gln Ala Arg Thr Val Val Glu
        355                 360                 365

Gln Ala Arg Lys Val Ala Ser Pro Gln Gly Thr Pro Gln Arg Asp Thr
    370                 375                 380
```

-continued

<210> SEQ ID NO 55
<211> LENGTH: 951
<212> TYPE: DNA
<213> ORGANISM: Pseudomonas syringae pv. delphinii

<400> SEQUENCE: 55

```
gtggttgagc gaaccggcac tgcatatcga aggcgtggag cagcctgctc gcgtatcacg      60
agccaaaatc aggtccgacg acgctttgga attacggtga atcagatgca aaagacgtcc     120
ctattggctt tggcctttgc aatcctggca gggtgtgggg gttcggggca ggcgccgggg     180
agtgatattc agggtgccca ggcagagatg aaaacaccca ttaaagtaga tctggatgcc     240
tacacctcaa aaaaacttga tgctgtgttg gaagctcggg ccaataaaag ctatgtgaat     300
aaaggtcaac tgatcgacct tgtgtcaggg gcgtttttgg gaacaccgta ccgctcaaac     360
atgttggtgg gcacagagga aatacctgaa cagttagtca tcgactttag aggtctggat     420
tgttttgctt atctggatta cgtagaggcg ttgcgaagat caacatcgca gcaggatttt     480
gtgaggaatc tcgttcaggt tcgttacaag ggtggtgatg ttgacttttt gaatcgcaag     540
cactttttca cggattgggc ttatggcact acacacccgg tggcggatga catcaccacg     600
cagataagcc ccggtgcggt aagtgtcaga aaacgcctta atgaaagggc caaaggcaaa     660
gtctatctgc caggtttgcc tgtggttgag cgcagcatga cctatatccc gagccgcctt     720
gtcgacagtc aggtggtaag ccacttgcgc acaggtgatt acatcggcat ttacaccccg     780
cttcccgggc tggatgtgac gcacgtcggt ttctttatca tgacggataa aggccctgtc     840
ttgcgaaatg catcttcacg aaaagaaaac agaaaggtaa tggatttgcc ttttctggac     900
tatgtatcgg aaaagccagg gattgttgtt ttcagggcaa aagacaattg a              951
```

<210> SEQ ID NO 56
<211> LENGTH: 316
<212> TYPE: PRT
<213> ORGANISM: Pseudomonas syringae pv. delphinii

<400> SEQUENCE: 56

```
Val Val Glu Arg Thr Gly Thr Ala Tyr Arg Arg Arg Gly Ala Ala Cys
  1               5                  10                  15

Ser Arg Ile Thr Ser Gln Asn Gln Val Arg Arg Arg Phe Gly Ile Thr
             20                  25                  30

Val Asn Gln Met Gln Lys Thr Ser Leu Leu Ala Leu Ala Phe Ala Ile
         35                  40                  45

Leu Ala Gly Cys Gly Gly Ser Gly Gln Ala Pro Gly Ser Asp Ile Gln
     50                  55                  60

Gly Ala Gln Ala Glu Met Lys Thr Pro Ile Lys Val Asp Leu Asp Ala
 65                  70                  75                  80

Tyr Thr Ser Lys Lys Leu Asp Ala Val Leu Glu Ala Arg Ala Asn Lys
                 85                  90                  95

Ser Tyr Val Asn Lys Gly Gln Leu Ile Asp Leu Val Ser Gly Ala Phe
            100                 105                 110

Leu Gly Thr Pro Tyr Arg Ser Asn Met Leu Val Gly Thr Glu Glu Ile
        115                 120                 125

Pro Glu Gln Leu Val Ile Asp Phe Arg Gly Leu Asp Cys Phe Ala Tyr
    130                 135                 140

Leu Asp Tyr Val Glu Ala Leu Arg Arg Ser Thr Ser Gln Gln Asp Phe
145                 150                 155                 160

Val Arg Asn Leu Val Gln Val Arg Tyr Lys Gly Gly Asp Val Asp Phe
                165                 170                 175
```

-continued

```
Leu Asn Arg Lys His Phe Phe Thr Asp Trp Ala Tyr Gly Thr Thr His
            180                 185                 190

Pro Val Ala Asp Asp Ile Thr Thr Gln Ile Ser Pro Gly Ala Val Ser
        195                 200                 205

Val Arg Lys Arg Leu Asn Glu Arg Ala Lys Gly Lys Val Tyr Leu Pro
    210                 215                 220

Gly Leu Pro Val Val Glu Arg Ser Met Thr Tyr Ile Pro Ser Arg Leu
225                 230                 235                 240

Val Asp Ser Gln Val Val Ser His Leu Arg Thr Gly Asp Tyr Ile Gly
                245                 250                 255

Ile Tyr Thr Pro Leu Pro Gly Leu Asp Val Thr His Val Gly Phe Phe
            260                 265                 270

Ile Met Thr Asp Lys Gly Pro Val Leu Arg Asn Ala Ser Ser Arg Lys
        275                 280                 285

Glu Asn Arg Lys Val Met Asp Leu Pro Phe Leu Asp Tyr Val Ser Glu
    290                 295                 300

Lys Pro Gly Ile Val Val Phe Arg Ala Lys Asp Asn
305                 310                 315
```

<210> SEQ ID NO 57
<211> LENGTH: 396
<212> TYPE: DNA
<213> ORGANISM: Pseudomonas syringae pv. delphinii

<400> SEQUENCE: 57

```
atgaaaaact catttgatct tcttgtcgac ggtttggcga aagactacag catgccgaat      60

ttgccgaaca agaaacacga caatgaagtc tattgcttca cattccagag cgggctcgaa     120

gtaaacattt atcaggacga ctgtcgatgg gtgcatttct ccgccacaat cggacaattt     180

caagacgcca gcaatgacac gctcagccac gcacttcaac tgaacaattt cagtcttgga     240

aagcccttct tcacctttgg aatgaacgga gaaaaggtcg gcgtacttca cacacgcgtt     300

ccgttgattg aaatgaatac cgttgaaatg cgcaaggtat tcgaggactt gctcgatgta     360

gcaggcggca tcagagcgac attcaagctc agttaa                               396
```

<210> SEQ ID NO 58
<211> LENGTH: 131
<212> TYPE: PRT
<213> ORGANISM: Pseudomonas syringae pv. delphinii

<400> SEQUENCE: 58

```
Met Lys Asn Ser Phe Asp Leu Leu Val Asp Gly Leu Ala Lys Asp Tyr
  1               5                  10                  15

Ser Met Pro Asn Leu Pro Asn Lys Lys His Asp Asn Glu Val Tyr Cys
             20                  25                  30

Phe Thr Phe Gln Ser Gly Leu Glu Val Asn Ile Tyr Gln Asp Asp Cys
         35                  40                  45

Arg Trp Val His Phe Ser Ala Thr Ile Gly Gln Phe Gln Asp Ala Ser
     50                  55                  60

Asn Asp Thr Leu Ser His Ala Leu Gln Leu Asn Asn Phe Ser Leu Gly
 65                  70                  75                  80

Lys Pro Phe Phe Thr Phe Gly Met Asn Gly Glu Lys Val Gly Val Leu
                 85                  90                  95

His Thr Arg Val Pro Leu Ile Glu Met Asn Thr Val Glu Met Arg Lys
            100                 105                 110
```

-continued

```
Val Phe Glu Asp Leu Leu Asp Val Ala Gly Gly Ile Arg Ala Thr Phe
        115                 120                 125

Lys Leu Ser
    130


<210> SEQ ID NO 59
<211> LENGTH: 648
<212> TYPE: DNA
<213> ORGANISM: Pseudomonas syringae pv. delphinii

<400> SEQUENCE: 59

atgagtacta tacctggcac ctcgggcgct cacccgattt atagctcaat ttccagccca      60

cgaaatatgt ctggctcgcc cacaccgagt caccgtattg gcggggaaac cctgacctct     120

attcatcagc tctctgccag ccagagagaa caatttctga atactcatga ccccatgaga     180

aaactcagga ttaacaatga tacgccactg tacagaacaa ccgagaagcg ttttatacag     240

gaaggcaaac tggccggcaa tccaaagtct attgcacgtg tcaacttgca cgaagaactg     300

cagcttaatc cgctcgccag tattttaggg aacttacctc acgaggcaag cgcttacttt     360

ccgaaaagcg cccgcgctgc ggatctgaaa gacccttcat tgaatgtaat gacaggctct     420

cgggcaaaaa atgctattcg cggctacgct catgacgacc atgtggcggt caagatgcga     480

ctgggcgact ttcttgaaaa aggcggcaag gtgtacgcgg acacttcatc agtcattgac     540

ggcggagacg aggcgagcgc gctgatcgtt acattgccta aaggacaaaa agttccagtc     600

gagattatcc ctacccataa cgacaacagc aataaaggca gaggctga                  648


<210> SEQ ID NO 60
<211> LENGTH: 215
<212> TYPE: PRT
<213> ORGANISM: Pseudomonas syringae pv. delphinii

<400> SEQUENCE: 60

Met Ser Thr Ile Pro Gly Thr Ser Gly Ala His Pro Ile Tyr Ser Ser
  1               5                  10                  15

Ile Ser Ser Pro Arg Asn Met Ser Gly Ser Pro Thr Pro Ser His Arg
             20                  25                  30

Ile Gly Gly Glu Thr Leu Thr Ser Ile His Gln Leu Ser Ala Ser Gln
         35                  40                  45

Arg Glu Gln Phe Leu Asn Thr His Asp Pro Met Arg Lys Leu Arg Ile
     50                  55                  60

Asn Asn Asp Thr Pro Leu Tyr Arg Thr Thr Glu Lys Arg Phe Ile Gln
 65                  70                  75                  80

Glu Gly Lys Leu Ala Gly Asn Pro Lys Ser Ile Ala Arg Val Asn Leu
                 85                  90                  95

His Glu Glu Leu Gln Leu Asn Pro Leu Ala Ser Ile Leu Gly Asn Leu
            100                 105                 110

Pro His Glu Ala Ser Ala Tyr Phe Pro Lys Ser Ala Arg Ala Ala Asp
        115                 120                 125

Leu Lys Asp Pro Ser Leu Asn Val Met Thr Gly Ser Arg Ala Lys Asn
    130                 135                 140

Ala Ile Arg Gly Tyr Ala His Asp Asp His Val Ala Val Lys Met Arg
145                 150                 155                 160

Leu Gly Asp Phe Leu Glu Lys Gly Gly Lys Val Tyr Ala Asp Thr Ser
                165                 170                 175

Ser Val Ile Asp Gly Gly Asp Glu Ala Ser Ala Leu Ile Val Thr Leu
            180                 185                 190
```

-continued

```
Pro Lys Gly Gln Lys Val Pro Val Glu Ile Ile Pro Thr His Asn Asp
        195                 200                 205

Asn Ser Asn Lys Gly Arg Gly
    210                 215


<210> SEQ ID NO 61
<211> LENGTH: 1128
<212> TYPE: DNA
<213> ORGANISM: Pseudomonas syringae pv. syringae

<400> SEQUENCE: 61

gtgaacccta tccatgcacg cttctccagc gtagaagcgc tcagacattc aaacgttgat     60

attcaggcaa tcaaatccga gggtcagttg gaagtcaacg gcaagcgtta cgagattcgt    120

gcggccgctg acggctcaat cgcggtcctc agacccgatc aacagtccaa agcagacaag    180

ttcttcaaag gcgcagcgca tcttattggc ggacaaagcc agcgtgccca aatagcccag    240

gtactcaacg agaaagcggc ggcagttcca cgcctggaca gaatgttggg cagacgcttc    300

gatctggaga agggcggaag tagcgctgtg ggcgccgcaa tcaaggctgc cgacagccga    360

ctgacatcaa aacagacatt tgccagcttc cagcaatggg ctgaaaaagc tgaggcgctc    420

gggcgcgata ccgaaatcgg tatctacatg atctacaaga gggacacgcc agacacaacg    480

cctatgaatg cggcagagca agaacattac ctggaaacgc tacaggctct cgataacaag    540

aaaaacctta tcatacgccc gcagatccat gatgatcggg aagaggaaga gcttgatctg    600

ggccgataca tcgctgaaga cagaaatgcc agaaccggct tttttagaat ggttcctaaa    660

gaccaacgcg cacctgagac aaactcggga cgacttacca ttggtgtaga acctaaatat    720

ggagcgcagt tggccctcgc aatggcaacc ctgatggaca agcacaaatc tgtgacacaa    780

ggtaaagtcg tcggtccggc aaaatatggc cagcaaactg actctgccat tctttacata    840

aatggtgatc ttgcaaaagc agtaaaactg ggcgaaaagc tgaaaaagct gagcggtatc    900

cctcctgaag gattcgtcga acatacaccg ctaagcatgc agtcgacggg tctcggtctt    960

tcttatgccg agtcggttga agggcagcct tccagccacg gacaggcgag aacacacgtt   1020

atcatggatg ccttgaaagg ccagggcccc atggagaaca gactcaaaat ggcgctggca   1080

gaaagaggct atgacccgga aaatccggcg ctcagggcgc gaaactga                1128


<210> SEQ ID NO 62
<211> LENGTH: 375
<212> TYPE: PRT
<213> ORGANISM: Pseudomonas syringae pv. syringae

<400> SEQUENCE: 62

Val Asn Pro Ile His Ala Arg Phe Ser Ser Val Glu Ala Leu Arg His
  1               5                  10                  15

Ser Asn Val Asp Ile Gln Ala Ile Lys Ser Glu Gly Gln Leu Glu Val
             20                  25                  30

Asn Gly Lys Arg Tyr Glu Ile Arg Ala Ala Ala Asp Gly Ser Ile Ala
         35                  40                  45

Val Leu Arg Pro Asp Gln Gln Ser Lys Ala Asp Lys Phe Phe Lys Gly
     50                  55                  60

Ala Ala His Leu Ile Gly Gly Gln Ser Gln Arg Ala Gln Ile Ala Gln
 65                  70                  75                  80

Val Leu Asn Glu Lys Ala Ala Ala Val Pro Arg Leu Asp Arg Met Leu
                 85                  90                  95
```

-continued

```
Gly Arg Arg Phe Asp Leu Glu Lys Gly Gly Ser Ser Ala Val Gly Ala
            100                 105                 110

Ala Ile Lys Ala Ala Asp Ser Arg Leu Thr Ser Lys Gln Thr Phe Ala
        115                 120                 125

Ser Phe Gln Gln Trp Ala Glu Lys Ala Glu Ala Leu Gly Arg Asp Thr
    130                 135                 140

Glu Ile Gly Ile Tyr Met Ile Tyr Lys Arg Asp Thr Pro Asp Thr Thr
145                 150                 155                 160

Pro Met Asn Ala Ala Glu Gln Glu His Tyr Leu Glu Thr Leu Gln Ala
                165                 170                 175

Leu Asp Asn Lys Lys Asn Leu Ile Ile Arg Pro Gln Ile His Asp Asp
            180                 185                 190

Arg Glu Glu Glu Glu Leu Asp Leu Gly Arg Tyr Ile Ala Glu Asp Arg
        195                 200                 205

Asn Ala Arg Thr Gly Phe Phe Arg Met Val Pro Lys Asp Gln Arg Ala
    210                 215                 220

Pro Glu Thr Asn Ser Gly Arg Leu Thr Ile Gly Val Glu Pro Lys Tyr
225                 230                 235                 240

Gly Ala Gln Leu Ala Leu Ala Met Ala Thr Leu Met Asp Lys His Lys
                245                 250                 255

Ser Val Thr Gln Gly Lys Val Val Gly Pro Ala Lys Tyr Gly Gln Gln
            260                 265                 270

Thr Asp Ser Ala Ile Leu Tyr Ile Asn Gly Asp Leu Ala Lys Ala Val
        275                 280                 285

Lys Leu Gly Glu Lys Leu Lys Lys Leu Ser Gly Ile Pro Pro Glu Gly
    290                 295                 300

Phe Val Glu His Thr Pro Leu Ser Met Gln Ser Thr Gly Leu Gly Leu
305                 310                 315                 320

Ser Tyr Ala Glu Ser Val Glu Gly Gln Pro Ser Ser His Gly Gln Ala
                325                 330                 335

Arg Thr His Val Ile Met Asp Ala Leu Lys Gly Gln Gly Pro Met Glu
            340                 345                 350

Asn Arg Leu Lys Met Ala Leu Ala Glu Arg Gly Tyr Asp Pro Glu Asn
        355                 360                 365

Pro Ala Leu Arg Ala Arg Asn
    370                 375


<210> SEQ ID NO 63
<211> LENGTH: 1149
<212> TYPE: DNA
<213> ORGANISM: Pseudomonas syringae pv. atrofaciens

<400> SEQUENCE: 63

atgaacccga tacaaacgcg tttctctaac gtcgaagcac ttagacattc agaggtggat      60

gtacaggagc tcaaagcaca cggtcaaata gaagtgggtg gcaaatgcta cgacattcgc     120

gcggctgcca ataacgacct gactgtccag cgttctgaca aacagatggc gatgagcaag     180

tttttcaaaa aagcagggtt aagtgggagt tccggcagtc agtccgatca aattgcgcag     240

gtactgaatg acaagcgcgg ctcttccgtt ccccgtctta tacgccaggg gcagacccat     300

ctgggccgta tgcaattcaa catcgaagag gggcaaggca gttcggccgc cacgtccgtc     360

cagaacagca ggctgcccaa tggccgcttg gtaaacagca gtattttgca atgggtcgaa     420

aaggcgaaag ccaatggcag cacaagtacc agtgctcttt atcagatcta cgcaaaagaa     480

ctcccgcgtg tagaactgct gccacgcact gagcaccggg cgtgtctggc gcatatgtat     540
```

-continued

```
aagctgaacg gtaaggacgg tatcagtatt tggccgcagt ttctggatgg cgtgcgcggg    600

ttgcagctaa aacatgacac aaaagtgttc atgatgaaca accccaaagc agcggacgag    660

ttctacaaga tcgaacgttc gggcacgcaa tttccggatg aggctgtcaa ggcgcgcctg    720

acgataaatg tcaaacctca attccagaag gccatggtcg acgcagcggt caggttgacc    780

gctgagcgtc acgatatcat tactgccaaa gtggcaggtc ctgcaaagat tggcacgatt    840

acagatgcag cggttttcta tgtaagcgga gatttttccg ctgcgcagac acttgcaaaa    900

gagcttcagg cactgctccc tgacgatgcg tttatcaatc atacgccagc tggaatgcaa    960

tccatgggca aggggctgtg ttacgccgag cgtacaccgc aggacaggac aagccacgga   1020

atgtcgcgcg ccagcataat cgagtcggca ctggcagaca ccagcaggtc gtcactggag   1080

aagaagctgc gcaatgcttt caagagcgcc ggatacaatc ccgacaaccc ggcattcagg   1140

ttggaatga                                                           1149


<210> SEQ ID NO 64
<211> LENGTH: 382
<212> TYPE: PRT
<213> ORGANISM: Pseudomonas syringae pv. atrofaciens

<400> SEQUENCE: 64

Met Asn Pro Ile Gln Thr Arg Phe Ser Asn Val Glu Ala Leu Arg His
  1               5                  10                  15

Ser Glu Val Asp Val Gln Glu Leu Lys Ala His Gly Gln Ile Glu Val
             20                  25                  30

Gly Gly Lys Cys Tyr Asp Ile Arg Ala Ala Ala Asn Asn Asp Leu Thr
         35                  40                  45

Val Gln Arg Ser Asp Lys Gln Met Ala Met Ser Lys Phe Phe Lys Lys
     50                  55                  60

Ala Gly Leu Ser Gly Ser Ser Gly Ser Gln Ser Asp Gln Ile Ala Gln
 65                  70                  75                  80

Val Leu Asn Asp Lys Arg Gly Ser Ser Val Pro Arg Leu Ile Arg Gln
                 85                  90                  95

Gly Gln Thr His Leu Gly Arg Met Gln Phe Asn Ile Glu Glu Gly Gln
            100                 105                 110

Gly Ser Ser Ala Ala Thr Ser Val Gln Asn Ser Arg Leu Pro Asn Gly
        115                 120                 125

Arg Leu Val Asn Ser Ser Ile Leu Gln Trp Val Glu Lys Ala Lys Ala
    130                 135                 140

Asn Gly Ser Thr Ser Thr Ser Ala Leu Tyr Gln Ile Tyr Ala Lys Glu
145                 150                 155                 160

Leu Pro Arg Val Glu Leu Leu Pro Arg Thr Glu His Arg Ala Cys Leu
                165                 170                 175

Ala His Met Tyr Lys Leu Asn Gly Lys Asp Gly Ile Ser Ile Trp Pro
            180                 185                 190

Gln Phe Leu Asp Gly Val Arg Gly Leu Gln Leu Lys His Asp Thr Lys
        195                 200                 205

Val Phe Met Met Asn Asn Pro Lys Ala Ala Asp Glu Phe Tyr Lys Ile
    210                 215                 220

Glu Arg Ser Gly Thr Gln Phe Pro Asp Glu Ala Val Lys Ala Arg Leu
225                 230                 235                 240

Thr Ile Asn Val Lys Pro Gln Phe Gln Lys Ala Met Val Asp Ala Ala
                245                 250                 255
```

-continued

```
Val Arg Leu Thr Ala Glu Arg His Asp Ile Ile Thr Ala Lys Val Ala
            260                 265                 270

Gly Pro Ala Lys Ile Gly Thr Ile Thr Asp Ala Ala Val Phe Tyr Val
        275                 280                 285

Ser Gly Asp Phe Ser Ala Ala Gln Thr Leu Ala Lys Glu Leu Gln Ala
    290                 295                 300

Leu Leu Pro Asp Asp Ala Phe Ile Asn His Thr Pro Ala Gly Met Gln
305                 310                 315                 320

Ser Met Gly Lys Gly Leu Cys Tyr Ala Glu Arg Thr Pro Gln Asp Arg
                325                 330                 335

Thr Ser His Gly Met Ser Arg Ala Ser Ile Ile Glu Ser Ala Leu Ala
            340                 345                 350

Asp Thr Ser Arg Ser Ser Leu Glu Lys Lys Leu Arg Asn Ala Phe Lys
        355                 360                 365

Ser Ala Gly Tyr Asn Pro Asp Asn Pro Ala Phe Arg Leu Glu
    370                 375                 380


<210> SEQ ID NO 65
<211> LENGTH: 1464
<212> TYPE: DNA
<213> ORGANISM: Pseudomonas syringae pv. tomato

<400> SEQUENCE: 65

atgcacatca accaatccgc ccaacaaccg cctggcgttg caatggagag ttttcggaca      60

gcttccgacg cgtcccttgc ttcgagttct gtgcggtctg tcagcactac ctcgtgccgc     120

gatctacaag ctattaccga ttatctgaaa catcacgtgt tcgctgcgca caggttttcg     180

gtaataggct caccggatga gcgtgatgcc gctcttgcac acaacgagca gatcgatgcg     240

ttggtagaga cacgcgccaa ccgcctgtac tccgaagggg agacccccgc aaccatcgcc     300

gaaacattcg ccaaggcgga aaagttcgac cgtttggcga cgaccgcatc aagtgctttt     360

gagaacacgc catttgccgc tgcctcggtg cttcagtaca tgcagcctgc gatcaacaag     420

ggcgattggc tagcaacgcc gctcaagccg ctgaccccgc tcatttccgg agcgctgtcg     480

ggagccatgg accaggtggg caccaaaatg atggatcgtg cgaggggtga tctgcattac     540

ctgagcactt cgccggacaa gttgcatgat gcgatggccg tatcggtgaa gcgccactcg     600

cctgcgcttg gtcgacaggt tgtggacatg ggattgcag tgcagacgtt ctcggcgcta     660

aatgtggtgc gtaccgtatt ggctccagca ctagcgtcca gaccgtcggt gcagggtgct     720

gttgattttg gcgtatctac ggcgggtggc ttggttgcga atgcaggctt tggcgaccgc     780

atgctcagtg tgcaatcgcg cgatcaactg cgtgggggg cattcgtact tggcatgaaa     840

gataaagagc ccaaggccgc gttgagtgaa gaaactgatt ggcttgatgc ttacaaagcg     900

atcaagtcgg ccagctactc aggtgcggcg ctcaatgcgg gcaagcggat ggccggcctg     960

ccactggacg tcgcgaccga cggctcaag gcggtgagaa gtctggtgtc ggccaccagc    1020

ctgacaaaaa atggcctggc cctagccggt ggttacgccg gggtaagtaa gttgcagaaa    1080

atggcgacga aaaatatcac tgattcggcg accaaggctg cggttagtca gctgagcaac    1140

ctggtgggtt cggtaggcgt tttcgcaggc tggaccaccg ctggactggc gactgaccct    1200

gcggttaaga aagccgagtc gtttatacag gataaggtga aatcgaccgc atctagtacc    1260

acaagctatg ttgccgacca gaccgtcaaa ctggcgaaaa cagtcaagga catgagcggg    1320

gaggcgatct ccagcaccgg tgccagctta cgcagtactg tcaataacct gcgtcatcgc    1380

tccgctccgg aagctgatat cgaagaaggt gggatttcgg cgttttctcg aagtgaaaca    1440
```

ccgtttcagc tcaggcgttt gtaa 1464

<210> SEQ ID NO 66
<211> LENGTH: 487
<212> TYPE: PRT
<213> ORGANISM: Pseudomonas syringae pv. tomato

<400> SEQUENCE: 66

Met His Ile Asn Gln Ser Ala Gln Gln Pro Pro Gly Val Ala Met Glu
1 5 10 15

Ser Phe Arg Thr Ala Ser Asp Ala Ser Leu Ala Ser Ser Ser Val Arg
20 25 30

Ser Val Ser Thr Thr Ser Cys Arg Asp Leu Gln Ala Ile Thr Asp Tyr
35 40 45

Leu Lys His His Val Phe Ala Ala His Arg Phe Ser Val Ile Gly Ser
50 55 60

Pro Asp Glu Arg Asp Ala Ala Leu Ala His Asn Glu Gln Ile Asp Ala
65 70 75 80

Leu Val Glu Thr Arg Ala Asn Arg Leu Tyr Ser Glu Gly Glu Thr Pro
85 90 95

Ala Thr Ile Ala Glu Thr Phe Ala Lys Ala Glu Lys Phe Asp Arg Leu
100 105 110

Ala Thr Thr Ala Ser Ser Ala Phe Glu Asn Thr Pro Phe Ala Ala Ala
115 120 125

Ser Val Leu Gln Tyr Met Gln Pro Ala Ile Asn Lys Gly Asp Trp Leu
130 135 140

Ala Thr Pro Leu Lys Pro Leu Thr Pro Leu Ile Ser Gly Ala Leu Ser
145 150 155 160

Gly Ala Met Asp Gln Val Gly Thr Lys Met Met Asp Arg Ala Arg Gly
165 170 175

Asp Leu His Tyr Leu Ser Thr Ser Pro Asp Lys Leu His Asp Ala Met
180 185 190

Ala Val Ser Val Lys Arg His Ser Pro Ala Leu Gly Arg Gln Val Val
195 200 205

Asp Met Gly Ile Ala Val Gln Thr Phe Ser Ala Leu Asn Val Val Arg
210 215 220

Thr Val Leu Ala Pro Ala Leu Ala Ser Arg Pro Ser Val Gln Gly Ala
225 230 235 240

Val Asp Phe Gly Val Ser Thr Ala Gly Gly Leu Val Ala Asn Ala Gly
245 250 255

Phe Gly Asp Arg Met Leu Ser Val Gln Ser Arg Asp Gln Leu Arg Gly
260 265 270

Gly Ala Phe Val Leu Gly Met Lys Asp Lys Glu Pro Lys Ala Ala Leu
275 280 285

Ser Glu Glu Thr Asp Trp Leu Asp Ala Tyr Lys Ala Ile Lys Ser Ala
290 295 300

Ser Tyr Ser Gly Ala Ala Leu Asn Ala Gly Lys Arg Met Ala Gly Leu
305 310 315 320

Pro Leu Asp Val Ala Thr Asp Gly Leu Lys Ala Val Arg Ser Leu Val
325 330 335

Ser Ala Thr Ser Leu Thr Lys Asn Gly Leu Ala Leu Ala Gly Gly Tyr
340 345 350

Ala Gly Val Ser Lys Leu Gln Lys Met Ala Thr Lys Asn Ile Thr Asp
355 360 365

-continued

```
Ser Ala Thr Lys Ala Ala Val Ser Gln Leu Ser Asn Leu Val Gly Ser
    370                 375                 380

Val Gly Val Phe Ala Gly Trp Thr Thr Ala Gly Leu Ala Thr Asp Pro
385                 390                 395                 400

Ala Val Lys Lys Ala Glu Ser Phe Ile Gln Asp Lys Val Lys Ser Thr
                405                 410                 415

Ala Ser Ser Thr Thr Ser Tyr Val Ala Asp Gln Thr Val Lys Leu Ala
            420                 425                 430

Lys Thr Val Lys Asp Met Ser Gly Glu Ala Ile Ser Ser Thr Gly Ala
        435                 440                 445

Ser Leu Arg Ser Thr Val Asn Asn Leu Arg His Arg Ser Ala Pro Glu
    450                 455                 460

Ala Asp Ile Glu Glu Gly Gly Ile Ser Ala Phe Ser Arg Ser Glu Thr
465                 470                 475                 480

Pro Phe Gln Leu Arg Arg Leu
                485


<210> SEQ ID NO 67
<211> LENGTH: 88
<212> TYPE: DNA
<213> ORGANISM: Pseudomonas syringae pv. tomato

<400> SEQUENCE: 67

gccctgatgg cggaattggt agacgcggcg gattcaaaat ccgttttcga aagaagtggg     60

agttcgattc tccctcgggg caccacca                                        88


<210> SEQ ID NO 68
<211> LENGTH: 85
<212> TYPE: DNA
<213> ORGANISM: Pseudomonas syringae pv. syringae

<400> SEQUENCE: 68

gccctgatgg cggaattggt agacgcggcg gattcaaaat ccgttttcga aagaagtggg     60

agttcgattc tccctcgggg cacca                                           85


<210> SEQ ID NO 69
<211> LENGTH: 1065
<212> TYPE: DNA
<213> ORGANISM: Pseudomonas syringae pv. tomato

<400> SEQUENCE: 69

atgcgcgtcg ctgactttac cttcgaactc cccgattccc tgattgctcg tcacccgttg     60

gccgagcgtc gcagcagtcg tctgttgacc cttgatgggc cgacgggcgc gctggcacat    120

cgtcaattca ccgatttgct cgagcatttg cgctcgggcg acttgatggt gttcaacaat    180

acccgtgtca ttcccgcacg tttgttcggg cagaaggcgt ccggcggcaa gctggagatt    240

ctggtcgagc gcgtgctgga cagccatcgt gtgctggcgc acgtgcgtgc cagcaagtcg    300

ccaaagccgg gctcgtcgat cctgatcgat ggcggcggcg aggccgagat ggtggcgcgg    360

catgacgcgc tgttcgagtt gcgctttgcc gaagaagtgc tgccgttgct ggatcgtgtc    420

ggccatatgc cgttgcctcc ttatatagac cgcccggacg aaggtgccga ccgcgagcgt    480

tatcagaccg tttacgccca gcgcgccggt gctgtggcgg cgccgactgc cggcctgcat    540

ttcgaccagc cgttgatgga agcaattgcc gccaagggcg tcgagactgc ttttgtcact    600

ctgcacgtcg gcgcgggtac gttccagccg gtgcgtgtcg agcagatcga agatcaccac    660
```

-continued

```
atgcacagcg aatggctgga agtcagccag gacgtggtcg atgccgtggc ggcgtgccgt    720

gcgcggggcg ggcgggtgat tgcggtcggg accaccagcg tgcgttcgct ggagagtgcc    780

gcgcgtgatg gccagttgaa gccgtttagc ggcgacaccg acatcttcat ctatccgggg    840

cggccgtttc atgtggtcga tgccctggtg actaattttc atttgcctga atccacgctg    900

ttgatgctgg tttcggcgtt cgccggttat cccgaaacca tggcggccta cgcggcggcc    960

atcgaacacg ggtaccgctt cttcagttac ggtgatgcca tgttcatcac ccgcaatccc   1020

gcgccgacgg ccccacagga atcggcacca gaggatcacg catga                   1065
```

<210> SEQ ID NO 70
<211> LENGTH: 354
<212> TYPE: PRT
<213> ORGANISM: Pseudomonas syringae pv. tomato

<400> SEQUENCE: 70

```
Met Arg Val Ala Asp Phe Thr Phe Glu Leu Pro Asp Ser Leu Ile Ala
  1               5                  10                  15

Arg His Pro Leu Ala Glu Arg Arg Ser Ser Arg Leu Leu Thr Leu Asp
             20                  25                  30

Gly Pro Thr Gly Ala Leu Ala His Arg Gln Phe Thr Asp Leu Leu Glu
         35                  40                  45

His Leu Arg Ser Gly Asp Leu Met Val Phe Asn Asn Thr Arg Val Ile
     50                  55                  60

Pro Ala Arg Leu Phe Gly Gln Lys Ala Ser Gly Gly Lys Leu Glu Ile
 65                  70                  75                  80

Leu Val Glu Arg Val Leu Asp Ser His Arg Val Leu Ala His Val Arg
                 85                  90                  95

Ala Ser Lys Ser Pro Lys Pro Gly Ser Ser Ile Leu Ile Asp Gly Gly
            100                 105                 110

Gly Glu Ala Glu Met Val Ala Arg His Asp Ala Leu Phe Glu Leu Arg
        115                 120                 125

Phe Ala Glu Glu Val Leu Pro Leu Leu Asp Arg Val Gly His Met Pro
    130                 135                 140

Leu Pro Pro Tyr Ile Asp Arg Pro Asp Glu Gly Ala Asp Arg Glu Arg
145                 150                 155                 160

Tyr Gln Thr Val Tyr Ala Gln Arg Ala Gly Ala Val Ala Ala Pro Thr
                165                 170                 175

Ala Gly Leu His Phe Asp Gln Pro Leu Met Glu Ala Ile Ala Ala Lys
            180                 185                 190

Gly Val Glu Thr Ala Phe Val Thr Leu His Val Gly Ala Gly Thr Phe
        195                 200                 205

Gln Pro Val Arg Val Glu Gln Ile Glu Asp His His Met His Ser Glu
    210                 215                 220

Trp Leu Glu Val Ser Gln Asp Val Val Asp Ala Val Ala Ala Cys Arg
225                 230                 235                 240

Ala Arg Gly Gly Arg Val Ile Ala Val Gly Thr Thr Ser Val Arg Ser
                245                 250                 255

Leu Glu Ser Ala Ala Arg Asp Gly Gln Leu Lys Pro Phe Ser Gly Asp
            260                 265                 270

Thr Asp Ile Phe Ile Tyr Pro Gly Arg Pro Phe His Val Val Asp Ala
        275                 280                 285

Leu Val Thr Asn Phe His Leu Pro Glu Ser Thr Leu Leu Met Leu Val
    290                 295                 300
```

-continued

```
Ser Ala Phe Ala Gly Tyr Pro Glu Thr Met Ala Ala Tyr Ala Ala Ala
305                 310                 315                 320

Ile Glu His Gly Tyr Arg Phe Phe Ser Tyr Gly Asp Ala Met Phe Ile
                325                 330                 335

Thr Arg Asn Pro Ala Pro Thr Ala Pro Gln Glu Ser Ala Pro Glu Asp
            340                 345                 350

His Ala


<210> SEQ ID NO 71
<211> LENGTH: 28
<212> TYPE: DNA
<213> ORGANISM: Artificial Sequence
<220> FEATURE:
<223> OTHER INFORMATION: Description of Artificial Sequence:  primer

<400> SEQUENCE: 71

atgactcgag gcgtggattc aggcaaat                                        28


<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence:  primer

<400> SEQUENCE: 72

atgagaattc tgccgccgct ttctcgtt                                        28


<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence:  primer

<400> SEQUENCE: 73

cgctctagac caaggactgc                                                 20


<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence:  primer

<400> SEQUENCE: 74

ccagaagctt ctgtttttga gtc                                             23


<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence:  primer

<400> SEQUENCE: 75

agtaggatcc tgaaatgtag gggcccgg                                        28


<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence:  primer
```

<400> SEQUENCE: 76
agtaaagctt atgatgctgt ttccagta 28

<210> SEQ ID NO 77
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 77
agtaggatcc tctcgaagga atggagca 28

<210> SEQ ID NO 78
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 78
agtaaagctt cgtgaagatg catttcgc 28

<210> SEQ ID NO 79
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 79
agtaggatcc tagtcactga tcgaacgt 28

<210> SEQ ID NO 80
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 80
agtactcgag ccacgaaata acacggta 28

<210> SEQ ID NO 81
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 81
agtaggatcc caggactgcc ttccagcg 28

<210> SEQ ID NO 82
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 82
agtactcgag cagagcggcg tccgtggc 28

<210> SEQ ID NO 83
<211> LENGTH: 28

-continued

<212> TYPE: DNA
<213> ORGANISM: Artificial Sequence
<220> FEATURE:
<223> OTHER INFORMATION: Description of Artificial Sequence: primer

<400> SEQUENCE: 83
agtaggatcc agaattgttg aagaaatc 28

<210> SEQ ID NO 84
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 84
agtaaagctt tgcgctgtta actcatcg 28

<210> SEQ ID NO 85
<211> LENGTH: 82
<212> TYPE: DNA
<213> ORGANISM: Pseudomonas syringae pv. tomato

<400> SEQUENCE: 85
ggggcaccac cattgagaaa agaccttgaa attcaaggtc tttttttcg tctggtggaa 60 agtggtctga ctgaggctgc ga 82

<210> SEQ ID NO 86
<211> LENGTH: 82
<212> TYPE: DNA
<213> ORGANISM: Pseudomonas syringae pv. syringae

<400> SEQUENCE: 86
ggggcaccac atagcagtat ccagaggtcc caaccagccc cgcaacacca gataaaccgg 60
cccacgagcc ggtttttttg tg 82

<210> SEQ ID NO 87
<211> LENGTH: 81
<212> TYPE: DNA
<213> ORGANISM: Pseudomonas syringae pv. syringae

<400> SEQUENCE: 87
ggggcaccac ctttaaaaaa gaccttgaaa ttcaaggtct ttttttcgt ctggtggaaa 60 gtgccttgat ccaatcctcg c 81

<210> SEQ ID NO 88
<211> LENGTH: 82
<212> TYPE: DNA
<213> ORGANISM: Pseudomonas syringae pv. tomato

<400> SEQUENCE: 88
gcccgggcgt gacgctgccc gggccccgac atttcagtca atcaatgcgc cttcgcaatc 60
ccgaactgat caagcaccgg at 82

<210> SEQ ID NO 89
<211> LENGTH: 82
<212> TYPE: DNA
<213> ORGANISM: Pseudomonas syringae pv. syringae

<400> SEQUENCE: 89
gaaggctcag cattcagggc gtctgagccg actcaattca atcaatgcgc cttgtcaatc 60

-continued

```
ccgaactgat ccagcaccgg gt                                              82


<210> SEQ ID NO 90
<211> LENGTH: 82
<212> TYPE: DNA
<213> ORGANISM: Pseudomonas syringae pv. syringae

<400> SEQUENCE: 90

gaggaagagg cttgaaaaag agttcaacct cttccctgct atcaatgcgc cctgtcaatc     60

ccgaactgat ccagcaccgg gt                                              82


<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence:  human
      immunodeficiency virus TAT protein, transduction
      domain

<400> SEQUENCE: 91

Tyr Gly Arg Lys Lys Arg Arg Gln Arg Arg Arg
  1               5                  10
```